United States Patent
Hamel et al.

(10) Patent No.: US 7,128,918 B1
(45) Date of Patent: Oct. 31, 2006

(54) STREPTOCOCCUS ANTIGENS

(75) Inventors: Josee Hamel, Quebec (CA); Bernard R. Brodeur, Quebec (CA); Isabelle Pineau, Quebec (CA); Denis Martin, Quebec (CA); Clement Rioux, Quebec (CA); Nathalie Charland, Quebec (CA)

(73) Assignee: ID Biomedical Corporation, Quebec (CA)

( * ) Notice: Subject to any disclaimer, the term of this patent is extended or adjusted under 35 U.S.C. 154(b) by 0 days.

(21) Appl. No.: 09/471,255

(22) Filed: Dec. 23, 1999

Related U.S. Application Data

(60) Provisional application No. 60/113,800, filed on Dec. 23, 1998.

(51) Int. Cl.
*A61K 39/09* (2006.01)

(52) U.S. Cl. ........... 424/244.1; 530/350; 424/184.1; 424/185.1

(58) Field of Classification Search .......... 514/44; 424/92.1, 234.1, 184.1, 244.1, 185.1, 190.1, 424/237.1, 200.1; 530/350; 435/7.32, 252.3, 435/320.1, 15, 183, 69.3, 6, 69.1, 71.1, 243; 536/23.7, 23.1
See application file for complete search history.

(56) References Cited

U.S. PATENT DOCUMENTS

| | | | |
|---|---|---|---|
| 6,503,511 B1* | 1/2003 | Wizemann et al. | 424/190.1 |
| 6,582,706 B1* | 6/2003 | Johnson et al. | 424/244.1 |
| 6,800,744 B1 | 10/2004 | Doucette-Stamm et al. | |
| 6,833,356 B1* | 12/2004 | Koenig et al. | 514/12 |
| 2003/0077293 A1 | 4/2003 | Hamel et al. | |
| 2003/0138447 A1* | 7/2003 | Wizemann et al. | 424/190.1 |
| 2003/0232976 A1 | 12/2003 | Hamel et al. | |
| 2004/0001836 A1* | 1/2004 | Johnson et al. | 424/165.1 |
| 2004/0005331 A1* | 1/2004 | Johnson et al. | 424/190.1 |
| 2004/0052781 A1* | 3/2004 | Johnson et al. | 424/130.1 |
| 2004/0081662 A1* | 4/2004 | Hermand et al. | 424/190.1 |

FOREIGN PATENT DOCUMENTS

| | | | |
|---|---|---|---|
| WO | 98/18930 | * | 5/1998 |
| WO | 98/18931 | | 5/1998 |
| WO | WO 99/15675 | | 4/1999 |
| WO | WO 00/06737 | | 2/2000 |
| WO | WO 00/06738 | | 2/2000 |
| WO | WO 00/17370 | | 3/2000 |
| WO | 00/37105 | | 6/2000 |
| WO | WO00/39299 | | 7/2000 |
| WO | 00/76540 A2 | | 12/2000 |
| WO | 01/14421 A1 | | 3/2001 |
| WO | WO01/98334 | | 12/2001 |
| WO | WO02/077021 | | 10/2002 |
| WO | WO04/092209 | | 10/2004 |

OTHER PUBLICATIONS

Boslego, John W. et al, Chapter 17, pp. 211-223, Vaccines and Immunotherapy, Pergamon Press, 1991.*
Ellis, Ronald W. Ph.D. Chapter 29, New Technologies for Making Vaccines, Vaccines, WB Saunders Co., 1988, pp. 568-575.*

(Continued)

*Primary Examiner*—Lynette R. F. Smith
*Assistant Examiner*—Ginny Allen Portner
(74) *Attorney, Agent, or Firm*—Seed IP Law Group PLLC

(57) ABSTRACT

*Streptococcus* proteins and polynucleotides encoding them are disclosed. Said proteins are antigenic and therefore useful vaccine components for the prophylaxis or therapy of *streptococcus* infection in animals. Also disclosed are recombinant methods of producing the protein antigens as well as diagnostic assays for detecting *streptococcus* bacterial infection.

19 Claims, 33 Drawing Sheets

```
AEAFLSGREN LSNLRTYRRQ NSDNTPRTNW VPSVSNPGTT NTNTSNNSNT      50
NSQASQSNDI DSLLKQLYKL PLSQRHVESD GLIFDPAQIT SRTARGVAVP     100
HGNHYHFIPY EQMSELEKRI ARIIPLRYRS NHWVPDSRPE EPSPQFTPEP     150
SPSPQPAPNP QPAPSNPIDE KLVKEAVRKV GDGYVFEENG VSRYIPAKNL     200
SAETAAGIDS KLAKQESLSH KLGAKKTDLP SSDREFYNKA YDLLARIHQD     250
LLDNKGRQVD FEALDNLLER LKDVSSDKVK LVDDILAFLA PIRHPERLGK     300
PNAQITYTDD EIQVAKLAGK YTTEDGYIFD PRDITSDEGD AYVTPHMTHS     350
HWIKKDSLSE AERAAAQAYA KEKGLTPPST DHQDSGNTEA KGAEAIYNRV     400
KAAKKVPLDR MPYNLQYTVE VKNGSLIIPH YDHYHNIKFE WFDEGLYEAP     450
KGYTLEDLLA TVKYYVEHPN ERPHSDNGFG NASDHVQRNK NGQADTNQTE     500
KPSEEKPQTE KPEEETPREE KPQSEKPESP KPTEEPEEES PEESEEPQVE     550
TEKVEEKLRE AEDLLGKIQD PIIKSNAKET LTGLKNNLLF GTQDNNTIMA     600
EAEKLLALLK ESK       (SEQ ID NO : 63)                     613
```

OTHER PUBLICATIONS

Adamou, John E et al, Infection and Immunity, Feb. 2001, vol. 69(2), pp. 949-958, Identification and characterization of a Novel Family of *Pneumococcal* proteins that are protective against sepsis.*

Swiss Prot Accession No. Q9ANY1_Strpn.*

Boslego et al. Chapter 17: 'Gonorrhea Vaccines', "*Vaccines And Immunotherapy*". Pergamon Press, 1991, pp. 211-223.

Ellis, et al. Chapter 29: 'New Technologies for Making Vaccines', "*Vaccines*". WB Sanders Co., 1988, Chapter 29, pp. 568-575.

"Lmb, a Protein with Similarities to the LraI Adhesin Family, Mediates Attachment of *Streptococcus agelactiae* to Human Laminin", by R. Spellerberg, et al., Infection and Immunity, vol. 67, No. 2, Feb. 1999, pp. 871-878.

PCT Notification of Transmittal of The International Search Report or The Declaration dated Jul. 24, 2000.

Orihuela, et al., "Organ-Sepcific models of *Streptococcus pneumoniae* Disease," Scandinavian Journal of Infectious Diseases, vol. 35, No. 9, 2003, p. 647-652.

Whittam, et al., "Inferences from whole-genome sequences of bacterial pathogensm," Current Opinion in Genetics and Development, Dec. 2002, vol. 12, No. 6, pp. 719-725.

Sa-Leao, et al., Abstracts of the General Meeting of the American Society for Microbiology, May 20-24, 2001.

Creighton, Thomas E. in his book, "Proteins: Structures and Molecular Principles," 1984, pp. 314-315.

Creighton, Thomas E. in his book, "Protein Structure: A Practical Approach," 1989; pp. 184-186.

Nosoh, et al., in "Protein Stability and Stabilization through Protein Engineering," 1991, pp. 197-217.

Oli, et al., "Redirecting the Humoral Immune Response against *Streptococcus* mutans Antigen P1 with Monoclonal Antibodies," Infection and Immunity, Dec. 2004, p. 6951-6960.

Swildens, et al., "Intestinal translocation of *Streptococcus suis* type 2EF* in pigs," Veterinary Microbiology 103, 2004, pp. 29-33.

Bolton, et al., "Use of the surface proteins GapC and Mig of *Streptococcus dysgalactiae* as potential protective antigens against bovine mastitis," Can J. Microbiol., Jun. 2004, 50(6):423-32 (Abstract only).

Okamoto, et al., "Vaccination with formalin-inactivated influenza vaccine protects mice against lethal influenza *Streptococcus pyogenes* superinfection," Vaccine 22, 2004, pp. 2887-2893.

Briles, et al., "Immunization of Humans with Recombinant *Pneumococcal* Surface Protein A (rPspA) Elicits Antibodies that Passively Protect Mice from Fatal Infection with *Streptococcus pneumoniae* bearing Heterologous PsPA", J. Infectious Disease. 182, Dec. 2000, pp. 1694-1701.

Briles, et al., "Intranasal Immunization of Mice with a Mixture of the *Pneumococcal* Proteins PsaA and PspA is Highly Protective against Nasopharyngeal Carriage of *Streptococcus pneumoniae*", Infection & Immunity, vol. 68, No. 2, Feb. 2000, pp. 796-800.

Zysk, et al, "Detection of 23 Immunogenic *Pneumococcal* Proteins Using Convalescent-Phase Serum", Infection & Immunity, vol. 68, No. 6, Jun. 2000, pp. 3740-3743.

Spellerberg, et al., "Lmb, a Protein with Similarities to the Lral Adhesin Family, Mediates Attachment of *Streptococcus agalactiae* to Human Laminin", Infection and Immunity, Feb. 1999, pp. 871-878.

Adamou, et al., "Identification and Characterization of a Novel Family of *Pneumococcal* Proteins that are Protective Against Sepsis". Infection and Immunity, Feb. 2001, pp. 949-958.

Wizemann, et al., "Use of a Whole Genome Approach to Identify Vaccine Molecules Affording Protection Against *Streptococcus pneumoniae* Infection", Infection and Immunity, Mar. 2001, pp. 1593-1598.

Zhang, et al., "Recominant PhpA Protein, a Unique Histidine Motif-Containing Protein from *Streptococcus pneumoniae*, Protects Mice against Intranasal *Pneumococcal* Challenge", Infection and Immunity, Jun. 2001, pp. 3827-3838.

Hernandez, et al., "Antigenicity of Chimeric Synthetic Peptides Based on HTLV-1 Antigens and the Impact of Epitope Orientation." Biochemical and Biophysical Research Communications, vol. 278, No. 3, pp. 1085-1088.

Partidos et al., "The Influence of orientation and number of copies of T and B cell epitopes on the specificity and affinity of antibodies induced by chimeric peptides." Eur. J. Immunol 1992, 22: pp. 2675-2680.

Oishi, et al., "The effect of amino acid spacers on the antigenicity of dimeric peptide-inducing cross-reacting antibodies to a cell surface protein antigen of *Streptococcus* mutans." Oral Microbiol Immunol 2001: 16: pp. 40-44.

Kurstak, Edward, "Editorial Recent progress in vaccines development and new trends in immunisation." Vaccine 19 (2001) pp. 2198-2200.

* cited by examiner

```
ATGAAATTTA GTAAAAAATA TATAGCAGCT GGATCAGCTG TTATCGTATC CTTGAGTCTA    60
TGTGCCTATG CACTAAACCA GCATCGTTCG CAGGAAAATA AGGACAATAA TCGTGTCTCT   120
TATGTGGATG GCAGCCAGTC AAGTCAGAAA AGTGAAAACT TGACACCAGA CCAGGTTAGC   180
CAGAAAGAAG GAATTCAGGC TGAGCAAATT GTAATCAAAA TTACAGATCA GGGCTATGTA   240
ACGTCACACG GTGACCACTA TCATTACTAT AATGGGAAAG TTCCTTATGA TGCCCTCTTT   300
AGTGAAGAAC TCTTGATGAA GGATCCAAAC TATCAACTTA AAGACGCTGA TATTGTCAAT   360
GAAGTCAAGG GTGGTTATAT CATCAAGGTC GATGGAAAAT ATTATGTCTA CCTGAAAGAT   420
GCAGCTCATG CTGATAATGT TCGAACTAAA GATGAAATCA ATCGTCAAAA ACAAGAACAT   480
GTCAAAGATA ATGAGAAGGT TAACTCTAAT GTTGCTGTAG CAAGGTCTCA GGGACGATAT   540
ACGACAAATG ATGGTTATGT CTTTAATCCA GCTGATATTA TCGAAGATAC GGGTAATGCT   600
TATATCGTTC CTCATGGAGG TCACTATCAC TACATTCCCA AAAGCGATTT ATCTGCTAGT   660
GAATTAGCAG CAGCTAAAGC ACATCTGGCT GGAAAAAATA TGCAACCGAG TCAGTTAAGC   720
TATTCTTCAA CAGCTAGTGA CAATAACACG CAATCTGTAG CAAAAGGATC AACTAGCAAG   780
CCAGCAAATA AATCTGAAAA TCTCCAGAGT CTTTTGAAGG AACTCTATGA TTCACCTAGC   840
GCCCAACGTT ACAGTGAATC AGATGGCCTG GTCTTTGACC CTGCTAAGAT TATCAGTCGT   900
ACACCAAATG GAGTTGCGAT TCCGCATGGC GACCATTACC ACTTTATTCC TTACAGCAAG   960
CTTTCTGCTT TAGAAGAAAA GATTGCCAGA ATGGTGCCTA TCAGTGGAAC TGGTTCTACA  1020
GTTTCTACAA ATGCAAAACC TAATGAAGTA GTGTCTAGTC TAGGCAGTCT TTCAAGCAAT  1080
CCTTCTTCTT TAACGACAAG TAAGGAGCTC TCTTCAGCAT CTGATGGTTA TATTTTTAAT  1140
CCAAAAGATA TCGTTGAAGA AACGGCTACA GCTTATATTG TAAGACATGG TGATCATTTC  1200
CATTACATTC CAAAATCAAA TCAAATTGGG CAACCGACTC TTCCAAACAA TAGTCTAGCA  1260
ACACCTTCTC CATCTCTTCC AATCAATCCA GGAACTTCAC ATGAGAAACA TGAAGAAGAT  1320
GGATACGGAT TTGATGCTAA TCGTATTATC GCTGAAGATG AATCAGGTTT TGTCATGAGT  1380
CACGGAGACC ACAATCATTA TTTCTTCAAG AAGGACTTGA CAGAAGAGCA AATTAAGGCT  1440
GCGCAAAAAC ATTTAGAGGA AGTTAAAACT AGTCATAATG GATTAGATTC TTTGTCATCT  1500
CATGAACAGG ATTATCCAGG TAATGCCAAA GAAATGAAAG ATTTAGATAA AAAAATCGAA  1560
GAAAAAATTG CTGGCATTAT GAAACAATAT GGTGTCAAAC GTGAAAGTAT TGTCGTGAAT  1620
AAAGAAAAAA ATGCGATTAT TTATCCGCAT GGAGATCACC ATCATGCAGA TCCGATTGAT  1680
GAACATAAAC CGGTTGGAAT TGGTCATTCT CACAGTAACT ATGAACTGTT TAAACCCGAA  1740
GAAGGAGTTG CTAAAAAAGA AGGGAATAAA GTTTATACTG GAGAAGAATT AACGAATGTT  1800
GTTAATTTGT TAAAAAATAG TACGTTTAAT AATCAAAACT TTACTCTAGC CAATGGTCAA  1860
AAACGCGTTT CTTTTAGTTT TCCGCCTGAA TTGGAGAAAA AATTAGGTAT CAATATGCTA  1920
GTAAAATTAA TAACACCAGA TGGAAAAGTA TTGGAGAAAG TATCTGGTAA AGTATTTGGA  1980
GAAGGAGTAG GGAATATTGC AAACTTTGAA TTAGATCAAC CTTATTTACC AGGACAAACA  2040
TTAAGTATA CTATCGCTTC AAAAGATTAT CCAGAAGTAA GTTATGATGG TACATTTACA  2100
GTTCCAACCT CTTTAGCTTA CAAAATGGCC AGTCAAACGA TTTTCTATCC TTTCCATGCA  2160
GGGGATACTT ATTTAAGAGT GAACCCTCAA TTTGCAGTGC CTAAAGGAAC TGATAGCTTTA  2220
GTCAGAGTGT TTGATGAATT TCATGGAAAT GCTTATTTAG AAAATAACTA TAAAGTTGGT  2280
GAAATCAAAT TACCGATTCC GAAATTAAAC CAAGGAACAA CCAGAACGGC CGGAAATAAA  2340
ATTCCTGTAA CCTTCATGGC AAATGCTTAT TTGGACAATC AATCGACTTA TATTGTGGAA  2400
GTACCTATCT TGGAAAAAGA AAATCAAACT GATAAACCAA GTATTCTACC ACAATTTAAA  2460
AGGAATAAAG CACAAGAAAA CTCAAAACTT GATGAAAAGG TAGAAGAACC AAAGACTAGT  2520
GAGAAGGTAG AAAAAGAAAA ACTTTCTGAA ACTGGGAATA GTACTAGTAA TTCAACGTTA  2580
GAAGAAGTTC CTACAGTGGA TCCTGTACAA GAAAAGTAG CAAAATTTGC TGAAAGTTAT  2640
GGGATGAAGC TAGAAAATGT CTTGTTTAAT ATGGACGGAA CAATTGAATT ATATTTACCA  2700
TCAGGAGAAG TCATTAAAAA GAATATGGCA GATTTTACAG GAGAAGCACC TCAAGGAAAT  2760
GGTGAAAATA AACCATCTGA AAATGGAAAA GTATCTACTG AACAGTTGA GAACCAACCA  2820
ACAGAAAATA ACCAGCAGA TTCTTTACCA GAGGCACCAA ACGAAAAACC TGTAAAACCA  2880
GAAAACTCAA CGGATAATGG AATGTTGAAT CCAGAAGGGA ATGTGGGGAG TGACCCTATG  2940
TTAGATCCAG CATTAGAGGA AGCTCCAGCA GTAGATCCTG TACAAGAAAA ATTAGAAAAA  3000
TTTACAGCTA GTTACGGATT AGGCTTAGAT AGTGTTATAT TCAATATGGA TGGAACGATT  3060
GAATTAAGAT TGCCAAGTGG AGAAGTGATA AAAAAGAATT TATCTGATTT CATAGCGTAA  3120
(SEQ ID NO: 1)
```

FIG. 1

```
MKFSKKYIAA  GSAVIVSLSL  CAYALNQHRS  QENKDNNRVS  YVDGSQSSQK    50
SENLTPDQVS  QKEGIQAEQI  VIKITDQGYV  TSHGDHYHYY  NGKVPYDALF   100
SEELLMKDPN  YQLKDADIVN  EVKGGYIIKV  DGKYYVYLKD  AAHADNVRTK   150
DEINRQKQEH  VKDNEKVNSN  VAVARSQGRY  TTNDGYVFNP  ADIIEDTGNA   200
YIVPHGGHYH  YIPKSDLSAS  ELAAAKAHLA  GKNMQPSQLS  YSSTASDNNT   250
QSVAKGSTSK  PANKSENLQS  LLKELYDSPS  AQRYSESDGL  VFDPAKIISR   300
TPNGVAIPHG  DHYHFIPYSK  LSALEEKIAR  MVPISGTGST  VSTNAKPNEV   350
VSSLGSLSSN  PSSLTTSKEL  SSASDGYIFN  PKDIVEETAT  AYIVRHGDHF   400
HYIPKSNQIG  QPTLPNNSLA  TPSPSLPINP  GTSHEKHEED  GYGFDANRII   450
AEDESGFVMS  HGDHNHYFFK  KDLTEEQIKA  AQKHLEEVKT  SHNGLDSLSS   500
HEQDYPGNAK  EMKDLDKKIE  EKIAGIMKQY  GVKRESIVVN  KEKNAIIYPH   550
GDHHHADPID  EHKPVGIGHS  HSNYELFKPE  EGVAKKEGNK  VYTGEELTNV   600
VNLLKNSTFN  NQNFTLANGQ  KRVSFSFPPE  LEKKLGINML  VKLITPDGKV   650
LEKVSGKVFG  EGVGNIANFE  LDQPYLPGQT  FKYTIASKDY  PEVSYDGTFT   700
VPTSLAYKMA  SQTIFYPFHA  GDTYLRVNPQ  FAVPKGTDAL  VRVFDEFHGN   750
AYLENNYKVG  EIKLPIPKLN  QGTTRTAGNK  IPVTFMANAY  LDNQSTYIVE   800
VPILEKENQT  DKPSILPQFK  RNKAQENSKL  DEKVEEPKTS  EKVEKEKLSE   850
TGNSTSNSTL  EEVPTVDPVQ  EKVAKFAESY  GMKLENVLFN  MDGTIELYLP   900
SGEVIKKNMA  DFTGEAPQGN  GENKPSENGK  VSTGTVENQP  TENKPADSLP   950
EAPNEKPVKP  ENSTDNGMLN  PEGNVGSDPM  LDPALEEAPA  VDPVQEKLEK  1000
FTASYGLGLD  SVIFNMDGTI  ELRLPSGEVI  KKNLSDFIA  (SEQ ID NO: 2)  1039
```

*FIG. 2*

```
ATGAAAATCA ATAAAAAATA TCTAGCTGGG TCAGTAGCTA CACTTGTTTT AAGTGTCTGT      60
GCTTATGAAC TAGGTTTGCA TCAAGCTCAA ACTGTAAAAG AAAATAATCG TGTTTCCTAT     120
ATAGATGGAA AACAAGCGAC GCAAAAAACG GAGAATTTGA CTCCTGATGA GGTTAGCAAG     180
CGTGAAGGAA TCAACGCCGA ACAAATCGTC ATCAAGATTA CGGATCAAGG TTATGTGACC     240
TCTCATGGAG ACCATTATCA TTACTATAAT GGCAAGGTCC CTTATGATGC CATCATCAGT     300
GAAGAGCTCC TCATGAAAGA TCCGAATTAT CAGTTGAAGG ATTCAGACAT TGTCAATGAA     360
ATCAAGGGTG GTTATGTCAT TAAGGTAAAC GGTAAATACT ATGTTTACCT TAAGGATGCA     420
GCTCATGCGG ATAATGTCCG TACAAAAGAA GAAATCAATC GGCAAAAACA AGAACATAGT     480
CAGCATCGTG AAGGAGGGAC TTCAGCAAAC GATGGTGCGG TAGCCTTTGC ACGTTCACAG     540
GGACGCTACA CCACAGATGA TGGTTATATC TTCAATGCAT CTGATATCAT CGAAGATACG     600
GGCGATGCCT ATATCGTTCC TCATGGAGAT CATTACCATT ACATTCCTAA GAATGAGTTA     660
TCAGCTAGCG AGTTGGCTGC TGCAGAAGCC TTCCTATCTG GTCGGGAAAA TCTGTCAAAT     720
TTAAGAACCT ATCGCCGACA AAATAGCGAT AACACTCCAA GAACAAACTG GGTACCTTCT     780
GTAAGCAATC CAGGAACTAC AAATACTAAC ACAAGCAACA ACAGCAACAC TAACAGTCAA     840
GCAAGTCAAA GTAATGACAT TGATAGTCTC TTGAAACAGC TCTACAAACT GCCTTTGAGT     900
CAACGCCATG TAGAATCTGA TGGCCTTATT TTCGACCCAG CGCAAATCAC AAGTCGAACC     960
GCCAGAGGTG TAGCTGTCCC TCATGGTAAC CATTACCACT TTATCCCTTA TGAACAAATG    1020
TCTGAATTGG AAAAACGAAT TGCTCGTATT ATTCCCCTTC GTTATCGTTC AAACCATTGG    1080
GTACCAGATT CAAGACCAGA AGAACCAAGT CCACAACCGA CTCCAGAACC TAGTCCAAGT    1140
CCGCAACCTG CACCAAATCC TCAACCAGCT CCAAGCAATC AATTGATGA GAAATTGGTC    1200
AAAGAAGCTG TTCGAAAAGT AGGCGATGGT TATGTCTTTG AGGAGAATGG AGTTTCTCGT    1260
TATATCCCAG CCAAGAATCT TTCAGCAGAA ACAGCAGCAG GCATTGATAG CAAACTGGCC    1320
AAGCAGGAAA GTTATCTCA TAAGCTAGGA GCTAAGAAAA CTGACCTCCC ATCTAGTGAT    1380
CGAGAATTTT ACAATAAGGC TTATGACTTA CTAGCAAGAA TTCACCAAGA TTTACTTGAT    1440
AATAAAGGTC GACAAGTTGA TTTTGAGGCT TTGGATAACC TGTTGGAACG ACTCAAGGAT    1500
GTCTCAAGTG ATAAAGTCAA GTTAGTGGAT GATATTCTTG CCTTCTTAGC TCCGATTCGT    1560
CATCCAGAAC GTTTAGGAAA ACCAAATGCG CAAATTACCT ACACTGATGA TGAGATTCAA    1620
GTAGCCAAGT TGGCAGGCAA GTACACAACA GAAGACGGTT ATATCTTTGA TCCTCGTGAT    1680
ATAACCAGTG ATGAGGGGA TGCCTATGTA ACTCCACATA TGACCCATAG CCACTGGATT    1740
AAAAAAGATA GTTTGTCTGA AGCTGAGAGA GCGGCAGCCC AGGCTTATGC TAAAGAGAAA    1800
GGTTTGACCC CTCCTTCGAC AGACCATCAG GATTCAGGAA ATACTGAGGC AAAAGGAGCA    1860
GAAGCTATCT ACAACCGCGT GAAAGCAGCT AAGAAGGTGC CACTTGATCG TATGCCTTAC    1920
AATCTTCAAT ATACTGTAGA AGTCAAAAAC GGTAGTTTAA TCATACCTCA TTATGACCAT    1980
TACCATAACA TCAAATTTGA GTGGTTTGAC GAAGGCCTTT ATGAGGCACC TAAGGGGTAT    2040
ACTCTTGAGG ATCTTTTGGC GACTGTCAAG TACTATGTCG AACATCCAAA CGAACGTCCG    2100
CATTCAGATA ATGGTTTTGG TAACGCTAGC GACCATGTTC AAAGAAACAA AAATGGTCAA    2160
GCTGATACCA ATCAAACGGA AAAACCAAGC GAGGAGAAAC CTCAGACAGA AAAACCTGAG    2220
GAAGAAACCC CTCGAGAAGA GAAACCACAA AGCGAGAAAC CAGAGTCTCC AAAACCAACA    2280
GAGGAACCAG AAGAAGAATC ACCAGAGGAA TCAGAAGAAC CTCAGGTCGA GACTGAAAAG    2340
GTTGAAGAAA AACTGAGAGA GGCTGAAGAT TTACTTGGAA AAATCCAGGA TCCAATTATC    2400
AAGTCCAATG CCAAAGAGAC TCTCACAGGA TTAAAAAATA ATTTACTATT TGGCACCCAG    2460
GACAACAATA CTATTATGGC AGAAGCTGAA AAACTATTGG CTTTATTAAA GGAGAGTAAG    2520
TAA        (SEQ ID NO: 3)                                          2523
```

*FIG. 3*

MKINKKYLAG SVATLVLSVC AYELGLHQAQ TVKENNRVSY IDGKQATQKT         50
ENLTPDEVSK REGINAEQIV IKITDQGYVT SHGDHYHYYN GKVPYDAIIS        100
EELLMKDPNY QLKDSDIVNE IKGGYVIKVN GKYYVYLKDA AHADNVRTKE        150
EINRQKQEHS QHREGGTSAN DGAVAFARSQ GRYTTDDGYI FNASDIIEDT        200
GDAYIVPHGD HYHYIPKNEL SASELAAAEA FLSGRENLSN LRTYRRQNSD        250
NTPRTNWVPS VSNPGTTNTN TSNNSNTNSQ ASQSNDIDSL LKQLYKLPLS        300
QRHVESDGLI FDPAQITSRT ARGVAVPHGN HYHFIPYEQM SELEKRIARI        350
IPLRYRSNHW VPDSRPEEPS PQPTPEPSPS PQPAPNPQPA PSNPIDEKLV        400
KEAVRKVGDG YVFEENGVSR YIPAKNLSAE TAAGIDSKLA KQESLSHKLG        450
AKKTDLPSSD REFYNKAYDL LARIHQDLLD NKGRQVDFEA LDNLLERLKD        500
VSSDKVKLVD DILAFLAPIR HPERLGKPNA QITYTDDEIQ VAKLAGKYTT        550
EDGYIFDPRD ITSDEGDAYV TPHMTHSHWI KKDSLSEAER AAAQAYAKEK        600
GLTPPSTDHQ DSGNTEAKGA EAIYNRVKAA KKVPLDRMPY NLQYTVEVKN        650
GSLIIPHYDH YHNIKFEWFD EGLYEAPKGY TLEDLLATVK YYVEHPNERP        700
HSDNGFGNAS DHVQRNKNGQ ADTNQTEKPS EEKPQTEKPE EETPREEKPQ        750
SEKPESPKPT EEPEEESPEE SEEPQVETEK VEEKLREAED LLGKIQDPII        800
KSNAKETLTG LKNNLLFGTQ DNNTIMAEAE KLLALLKESK (SEQ ID NO: 4)    840

FIG. 4

ATGGAGAATA TAGACATGTT TAAATCAAAT CATGAGCGAA GAATGCGTTA TTCCATTCGT    60
AAATTTAGTG TAGGAGTAGC TAGCGTAGCT GTTGCCAGTC TTTTTATGGG AAGTGTTGTA   120
CATGCGACAG AGAAAGAGGG AAGTACCCAA GCAGCCACTT CTTTTAATAG GGGAAATGGA   180
AGTCAGGCAG AACAACGTGG AGAACTCGAT TTAGAACGAG ATAAGGCAAT GAAAGCGGTC   240
AGTGAATATG TAGGAAAAAT GGTGAGAGAT GCCTATGTAA AATCAGATAG AAAACGACAT   300
AAAAATACTG TAGCTCTAGT TAACCAGTTG GGAAACATTA GAACAGGTA TTTGAATGAA   360
ATAGTTCATT CAACCTCAAA AAGCCAACTA CAGGAACTGA TGATGAAGAG TCAATCAGAA   420
GTAGATGAAG CTGTGTCTAA ATTTGAAAAG GACTCATTTT CTTCGTCAAG TTCAGGATCC   480
TCCACTAAAC CAGAAACTCC GCAGCCGGAA AATCCAGAGC ATCAAAAACC AACAACTCCA   540
TCTCCGGATA CCAAACCAAG CCCTCAACCA GAAGGCAAGA AACCAAGCGT ACCAGACATT   600
AATCAGGAAA AAGAAAAGC TAAGCTTGCT GTAGTAACCT ACATGAGCAA GATTTTAGAT   660
GATATACAAA AACATCATCT GCAGAAAGAA AAACATCGTC AGATTGTTGC TCTTATTAAG   720
GAGCTTGATG AGCTTAAAAA GCAAGCTCTT TCTGAAATTG ATAATGTAAA TACCAAAGTA   780
GAAATTGAAA ATACAGTCCA AAGATATTT GCAGACATGG ATGCAGTTGT GACTAAATTC   840
AAAAAAGGCT TAACTCAGGA CACACCAAAA GAACCAGGTA ACAAAAAACC ATCTGCTCCA   900
AAACCAGGTA TGCAACCAAG TCCTCAACCA GAGGTTAAAC CGCAGCTGGA AAAACCAAAA   960
CCAGAGGTTA AACCGCAACC AGAAAAACCA AAACCAGAGG TTAAACCGCA GCCGGAAAAA  1020
CCAAAACCAG AGGTTAAACC GCAGCCGGAA AAACCAAAAC CAGAGGTTAA ACCGCAGCCG  1080
GAAAAACCAA AACCAGAGGT TAAACCGCAG CCGGAAAAAC CAAAACCAGA GGTTAAACCG  1140
CAGCCGGAAA AACCAGAGGT TAAA CCGCAGCCGG AAAAACCAAA ACCAGAGGTT  1200
AAACCGCAGC CGGAAAAACC AAAACCAGAG GTTAAACCGC AGCCGGAAAA ACCAAAACCA  1260
GAGGTTAAAC CGCAGCCGGA AAAACCAAAA CCAGAGGTTA ACCGCAAACCA AGAAAAACCA  1320
AAACCAGAGG TTAAACCGCA ACCAGAAAAA CCAAAACCAG ATAATAGCAA GCCACAAGCA  1380
GATGATAAGA AGCCATCAAC TACAAATAAT TTAAGCAAGG ACAAGCAACC TTCTAACCAA  1440
GCTTCAACAA ACGAAAAAGC AACAAATAAA CCGAAGAAGT CATTGCCATC AACTGGATCT  1500
ATTTCAAATC TAGCACTTGA AATTGCAGGT CTTCTTACCT TGGCGGGGGC AACCATTCTT  1560
GCTAAGAAAA GAATGAAATA G (SEQ ID NO: 5)                           1581

FIG. 5

| | | | | | |
|---|---|---|---|---|---|
|MENIDMFKSN|HERRMRYSIR|KFSVGVASVA|VASLFMGSVV|HATEKEGSTQ|50|
|AATSFNRGNG|SQAEQRGELD|LERDKAMKAV|SEYVGKMVRD|AYVKSDRKRH|100|
|KNTVALVNQL|GNIKNRYLNE|IVHSTSKSQL|QELMMKSQSE|VDEAVSKFEK|150|
|DSFSSSSSGS|STKPETPQPE|NPEHQKPTTP|SPDTKPSPQP|EGKKPSVPDI|200|
|NQEKEKAKLA|VVTYMSKILD|DIQKHHLQKE|KHRQIVALIK|ELDELKKQAL|250|
|SEIDNVNTKV|EIENTVHKIF|ADMDAVVTKF|KKGLTQDTPK|EPGNKKPSAP|300|
|KPGMQPSPQP|EVKPQLEKPK|PEVKPQPEKP|KPEVKPQPEK|PKPEVKPQPE|350|
|KPKPEVKPQP|EKPKPEVKPQ|PEKPKPEVKP|QPEKPKPEVK|PQPEKPKPEV|400|
|KPQPEKPKPE|VKPQPEKPKP|EVKPQPEKPK|PEVKPQPEKP|KPEVKPQPEK|450|
|PKPDNSKPQA|DDKKPSTTNN|LSKDKQPSNQ|ASTNEKATNK|PKKSLPSTGS|500|
|ISNLALEIAG|LLTLAGATIL|AKKRMK|(SEQ ID NO: 6)| |526|

FIG. 6

| | | | | | |
|---|---|---|---|---|---|
|ATGAAATTTA|GTAAAAAATA|TATAGCAGCT|GGATCAGCTG|TTATCGTATC|CTTGAGTCTA|60|
|TGTGCCTATG|CACTAAACCA|GCATCGTTCG|CAGGAAAATA|AGGACAATAA|TCGTGTCTCT|120|
|TATGTGGATG|GCAGCCAGTC|AAGTCAGAAA|AGTGAAAACT|TGACACCAGA|CCAGGTTAGC|180|
|CAGAAAGAAG|GAATTCAGGC|TGAGCAAATT|GTAATCAAAA|TTACAGATCA|GGGCTATGTA|240|
|ACGTCACACG|GTGACCACTA|TCATTACTAT|AATGGGAAAG|TTCCTTATGA|TGCCCTCTTT|300|
|AGTGAAGAAC|TCTTGATGAA|GGATCCAAAC|TATCAACTTA|AGACGCTGA|TATTGTCAAT|360|
|GAAGTCAAGG|GTGGTTATAT|CATCAAGGTC|GATGGAAAAT|ATTATGTCTA|CCTGAAAGAT|420|
|GCAGCTCATG|CTGATAATGT|TCGAACTAAA|GATGAAATCA|ATCGTCAAAA|ACAAGAACAT|480|
|GTCAAAGATA|ATGAGAAGGT|TAACTCTAAT|GTTGCTGTAG|CAAGGTCTCA|GGGACGATAT|540|
|ACGACAAATG|ATGGTTATGT|CTTTAATCCA|GCTGATATTA|TCGAAGATAC|GGGTAATGCT|600|
|TATATCGTTC|CTCATGGAGG|TCACTATCAC|TACATTCCCA|AAAGCGATTT|ATCTGCTAGT|660|
|GAATTAGCAG|CAGCTAAAGC|ACATCTGGCT|GGAAAAAATA|TGCAACCGAG|TCAGTTAAGC|720|
|TATTCTTCAA|CAGCTAGTGA|CAATAACACG|CAATCTGTAG|CAAAAGGATC|AACTAGCAAG|780|
|CCAGCAAATA|AATCTGAAAA|TCTCCAGAGT|CTTTTGAAGG|AACTCTATGA|TTCACCTAGC|840|
|GCCCAACGTT|ACAGTGAATC|AGATGGCCTG|GTCTTTGACC|CTGCTAAGAT|TATCAGTCGT|900|
|ACACCAAATG|GAGTTGCGAT|TCCGCATGGC|GACCATTACC|ACTTTATTCC|TTACAGCAAG|960|
|CTTTCTGCTT|TAGAAGAAAA|GATTGCCAGA|ATGGTGCCTA|TCAGTGGAAC|TGGTTCTACA|1020|
|GTTTCTACAA|ATGCAAAACC|TAATGAAGTA|GTGTCTAGTC|TAGGCAGTCT|TTCAAGCAAT|1080|
|CCTTCTTCTT|TAACGACAAG|TAAGGAGCTC|TCTTCAGCAT|CTGATGGTTA|TATTTTTAAT|1140|
|CCAAAAGATA|TCGTTGAAGA|AACGGCTACA|GCTTATATTG|TAAGACATGG|TGATCATTTC|1200|
|CATTACATTC|CAAAATCAAA|TCAAATTGGG|CAACCGACTC|TTCCAAACAA|TAGTCTAGCA|1260|
|ACACCTTCTC|CATCTCTTCC|AATCAATCCA|GGAACTTCAC|ATGAGAAACA|TGAAGAAGAT|1320|
|GGATACGGAT|TTGATGCTAA|TCGTATTATC|GCTGAAGATG|AATCAGGTTT|TGTCATGAGT|1380|
|CACGGAGACC|ACAATCATTA|TTTCTTCAAG|AAGGACTTGA|CAGAAGAGCA|AATTAAGGTG|1440|
|CGCAAAAACA|TTTAG|(SEQ ID NO: 7)| | | |1455|

FIG. 7

| | | | | | |
|---|---|---|---|---|---|
| MKFSKKYIAA | GSAVIVSLSL | CAYALNQHRS | QENKDNNRVS | YVDGSQSSQK | 50 |
| SENLTPDQVS | QKEGIQAEQI | VIKITDQGYV | TSHGDHYHYY | NGKVPYDALF | 100 |
| SEELLMKDPN | YQLKDADIVN | EVKGGYIIKV | DGKYYVYLKD | AAHADNVRTK | 150 |
| DEINRQKQEH | VKDNEKVNSN | VAVARSQGRY | TTNDGYVFNP | ADIIEDTGNA | 200 |
| YIVPHGGHYH | YIPKSDLSAS | ELAAAKAHLA | GKNMQPSQLS | YSSTASDNNT | 250 |
| QSVAKGSTSK | PANKSENLQS | LLKELYDSPS | AQRYSESDGL | VFDPAKIISR | 300 |
| TPNGVAIPHG | DHYHFIPYSK | LSALEEKIAR | MVPISGTGST | VSTNAKPNEV | 350 |
| VSSLGSLSSN | PSSLTTSKEL | SSASDGYIFN | PKDIVEETAT | AYIVRHGDHF | 400 |
| HYIPKSNQIG | QPTLPNNSLA | TPSPSLPINP | GTSHEKHEED | GYGFDANRII | 450 |
| AEDESGFVMS | HGDHNHYFFK | KDLTEEQIKV | RKNI | (SEQ ID NO: 8) | 484 |

FIG. 8

| | | | | | |
|---|---|---|---|---|---|
| ATGAAAGATT | TAGATAAAAA | AATCGAAGAA | AAAATTGCTG | GCATTATGAA | ACAATATGGT | 60 |
| GTCAAACGTG | AAAGTATTGT | CGTGAATAAA | GAAAAAAATG | CGATTATTTA | TCCGCATGGA | 120 |
| GATCACCATC | ATGCAGATCC | GATTGATGAA | CATAAACCGG | TTGGAATTGG | TCATTCTCAC | 180 |
| AGTAACTATG | AACTGTTTAA | ACCCGAAGAA | GGAGTTGCTA | AAAAAGAAGG | GAATAAAGTT | 240 |
| TATACTGGAG | AAGAATTAAC | GAATGTTGTT | AATTTGTTAA | AAATAGTAC | GTTTAATAAT | 300 |
| CAAAACTTTA | CTCTAGCCAA | TGGTCAAAAA | CGCGTTTCTT | TTAGTTTTCC | GCCTGAATTG | 360 |
| GAGAAAAAAT | TAGGTATCAA | TATGCTAGTA | AAATTAATAA | CACCAGATGG | AAAAGTATTG | 420 |
| GAGAAAGTAT | CTGGTAAAGT | ATTTGGAGAA | GGAGTAGGGA | ATATTGCAAA | CTTTGAATTA | 480 |
| GATCAACCTT | ATTTACCAGG | ACAAACATTT | AAGTATACTA | TCGCTTCAAA | AGATTATCCA | 540 |
| GAAGTAAGTT | ATGATGGTAC | ATTTACAGTT | CCAACCTCTT | TAGCTTACAA | AATGGCCAGT | 600 |
| CAAACGATTT | TCTATCCTTT | CCATGCAGGG | GATACTTATT | TAAGAGTGAA | CCCTCAATTT | 660 |
| GCAGTGCCTA | AAGGAACTGA | TGCTTTAGTC | AGAGTGTTTG | ATGAATTTCA | TGGAAATGCT | 720 |
| TATTTAGAAA | ATAACTATAA | AGTTGGTGAA | ATCAAATTAC | CGATTCCGAA | ATTAAACCAA | 780 |
| GGAACAACCA | GAACGGCCGG | AAATAAAATT | CCTGTAACCT | TCATGGCAAA | TGCTTATTTG | 840 |
| GACAATCAAT | CGACTTATAT | TGTGGAAGTA | CCTATCTTGG | AAAAAGAAAA | TCAAACTGAT | 900 |
| AAACCAAGTA | TTCTACCACA | ATTTAAAAGG | AATAAAGCAC | AAGAAAACTC | AAAACTTGAT | 960 |
| GAAAAGGTAG | AAGAACCAAA | GACTAGTGAG | AAGGTAGAAA | AAGAAAAACT | TTCTGAAACT | 1020 |
| GGGAATAGTA | CTAGTAATTC | AACGTTAGAA | GAAGTTCCTA | CAGTGGATCC | TGTACAAGAA | 1080 |
| AAAGTAGCAA | AATTTGCTGA | AAGTTATGGG | ATGAAGCTAG | AAAATGTCTT | GTTTAATATG | 1140 |
| GACGGAACAA | TTGAATTATA | TTTACCATCA | GGAGAAGTCA | TTAAAAAGAA | TATGGCAGAT | 1200 |
| TTTACAGGAG | AAGCACCTCA | AGGAAATGGT | GAAAATAAAC | CATCTGAAAA | TGGAAAAGTA | 1260 |
| TCTACTGGAA | CAGTTGAGAA | CCAACCAACA | GAAAATAAAC | CAGCAGATTC | TTTACCAGAG | 1320 |
| GCACCAAACG | AAAAACCTGT | AAAACCAGAA | AACTCAACGG | ATAATGGAAT | GTTGAATCCA | 1380 |
| GAAGGGAATG | TGGGGAGTGA | CCCTATGTTA | GATCCAGCAT | TAGAGGAAGC | TCCAGCAGTA | 1440 |
| GATCCTGTAC | AAGAAAATT | AGAAAAATTT | ACAGCTAGTT | ACGGATTAGG | CTTAGATAGT | 1500 |
| GTTATATTCA | ATATGGATGG | AACGATTGAA | TTAAGATTGC | CAAGTGGAGA | AGTGATAAAA | 1560 |
| AAGAATTTAT | CTGATTTCAT | AGCGTAA | (SEQ ID NO: 9) | | | 1587 |

FIG. 9

```
MKDLDKKIEE  KIAGIMKQYG  VKRESIVVNK  EKNAIIYPHG  DHHHADPIDE      50
HKPVGIGHSH  SNYELFKPEE  GVAKKEGNKV  YTGEELTNVV  NLLKNSTFNN     100
QNFTLANGQK  RVSFSFPPEL  EKKLGINMLV  KLITPDGKVL  EKVSGKVFGE     150
GVGNIANFEL  DQPYLPGQTF  KYTIASKDYP  EVSYDGTFTV  PTSLAYKMAS     200
QTIFYPFHAG  DTYLRVNPQF  AVPKGTDALV  RVFDEFHGNA  YLENNYKVGE     250
IKLPIPKLNQ  GTTRTAGNKI  PVTFMANAYL  DNQSTYIVEV  PILEKENQTD     300
KPSILPQFKR  NKAQENSKLD  EKVEEPKTSE  KVEKEKLSET  GNSTSNSTLE     350
EVPTVDPVQE  KVAKFAESYG  MKLENVLFNM  DGTIELYLPS  GEVIKKNMAD     400
FTGEAPQGNG  ENKPSENGKV  STGTVENQPT  ENKPADSLPE  APNEKPVKPE     450
NSTDNGMLNP  EGNVGSDPML  DPALEEAPAV  DPVQEKLEKF  TASYGLGLDS     500
VIFNMDGTIE  LRLPSGEVIK  KNLSDFIA   (SEQ ID NO: 10)             528
```

FIG. 10

```
BVH3 WU2        1   CAYALNQHRSQENKDNNRVSYVDGSQSSQKSENLTPDQVSQKEGIQAEQIVIKITDQGYV    60
BVH3 RX1        1   CAYALNQHRSQENKDNNRVSYVDGSQSSQKSENLTPDQVSQKEGIQAEQIVIKITDQGYV    60
BVH3 JNR7/87    1   CAYALNQHRSQENKDNNRVSYVDGSQSSQKSENLTPDQVSQKEGIQAEQIVIKITDQGYV    60
BVH3 SP64       1   CAYALNQHRSQENKDNNRVSYVDGSQSSQKSENLTPDQVSQKEGIQAEQIVIKITDQGYV    60
BVH3 P4241      1   CAYALNQHRSQENKDNNRVSYVDGSQSSQKSENLTPDQVSQKEGIQAEQIVIKITDQGYV    60
BVH3 A66        1   CAYALNQHRSQENKDNNRVSYVDGSQSSQKSENLTPDQVSQKEGIQAEQIVIKITDQGYV    60
                    ************************************************************

BVH3 WU2       61   TSHGDHYHYYNGKVPYDALFSEELLMKDPNYQLKDADIVNEVKGGYIIKVDGKYYVYLKD   120
BVH3 RX1       61   TSHGDHYHYYNGKVPYDALFSEELLMKDPNYQLKDADIVNEVKGGYIIKVDGKYYVYLKD   120
BVH3 JNR7/87   61   TSHGDHYHYYNGKVPYDALFSEELLMKDPNYQLKDADIVNEVKGGYIIKVDGKYYVYLKD   120
BVH3 SP64      61   TSHGDHYHYYNGKVPYDALFSEELLMKDPNYQLKDADIVNEVKGGYIIKVDGKYYVYLKD   120
BVH3 P4241     61   TSHGDHYHYYNGKVPYDALFSEELLMKDPNYQLKDADIVNEVKGGYIIKVDGKYYVYLKD   120
BVH3 A66       61   TSHGDHYHYYNGKVPYDALFSEELLMKDPNYQLKDADIVNEVKGGYIIKVDGKYYVYLKD   120
                    ************************************************************

BVH3 WU2      121   AAHADNVRTKDEINRQKQEHVKDNEKVNSNVAVARSQGRYTTNDGYVFNPADIIEDTGNA   180
BVH3 RX1      121   AAHADNVRTKDEINRQKQEHVKDNEKVNSNVAVARSQGRYTTNDGYVFNPADIIEDTGNA   180
BVH3 JNR7/87  121   AAHADNVRTKDEINRQKQEHVKDNEKVNSNVAVARSQGRYTTNDGYVFNPADIIEDTGNA   180
BVH3 SP64     121   AAHADNVRTKDEINRQKQEHVKDNEKVNSNVAVARSQGRYTTNDGYVFNPADIIEDTGNA   180
BVH3 P4241    121   AAHADNVRTKDEINRQKQEHVKDNEKVNSNVAVARSQGRYTTNDGYVFNPADIIEDTGNA   180
BVH3 A66      121   AAHADNVRTKDEINRQKQEHVKDNEKVNSNVAVARSQGRYTTNDGYVFNPADIIEDTGNA   180
                    ************************************************************

BVH3 WU2      181   YIVPHRGHYHYIPKSDLSASELAAAKAHLAGKNMQPSQLSYSSTASDNNTQSVAKGSTSK   240
BVH3 RX1      181   YIVPHGGHYHYIPKSDLSASELAAAKAHLAGKNMQPSQLSYSSTASDNNTQSVAKGSTSK   240
BVH3 JNR7/87  181   YIVPHGGHYHYIPKSDLSASELAAAKAHLAGKNMQPSQLSYSSTASDNNTQSVAKGSTSK   240
BVH3 SP64     181   YIVPHGGHYHYIPKSDLSASELAAAKAHLAGKNMQPSQLSYSSTASDNNTQSVAKGSTSK   240
BVH3 P4241    181   YIVPHRGHYHYIPKSDLSASELAAAKAHLAGKNMQPSQLSYSSTASDNNTQSVAKGSTSK   240
BVH3 A66      181   YIVPHRGHYHYIPKSDLSASELAAAKAHLAGKNMQPSQLSYSSTASDNNTQSVAKGSTSK   240
                    ***** ******************************************************

BVH3 WU2      241   PANKSENLQSLLKELYDSPSAQRYSESDGLVFDPAKIISRTPNGVAIPHGDHYHFIPYSK   300
BVH3 RX1      241   PANKSENLQSLLKELYDSPSAQRYSESDGLVFDPAKIISRTPNGVAIPHGDHYHFIPYSK   300
BVH3 JNR7/87  241   PANKSENLQSLLKELYDSPSAQRYSESDGLVFDPAKIISRTPNGVAIPHGDHYHFIPYSK   300
BVH3 SP64     241   PANKSENLQSLLKELYDSPSAQRYSESDGLVFDPAKIISRTPNGVAIPHGDHYHFIPYSK   300
BVH3 P4241    241   PANKSENLQSLLKELYDSPSAQRYSESDGLVFDPAKIISRTPNGVAIPHGDHYHFIPYSK   300
BVH3 A66      241   PANKSENLQSLLKELYDSPSAQRYSESDGLVFDPAKIISRTPNGVAIPHGDHYHFIPYSK   300
                    ************************************************************

BVH3 WU2      301   LSALEEKIARMVPISGTGSTVSTNAKPNEVVSSLGSLSSNPSSLTTSKELSSASDGYIFN   360
BVH3 RX1      301   LSALEEKIARRVPISGTGSTVSTNAKPNEVVSSLGSLSSNPSSLTTSKELSSASDGYIFN   360
BVH3 JNR7/87  301   LSALEEKIARMVPISGTGSTVSTNAKPNEVVSSLGSLSSNPSSLTTSKELSSASDGYIFN   360
BVH3 SP64     301   LSALEEKIARMVPISGTGSTVSTNAKPNEVVSSLGSLSSNPSSLTTSKELSSASDGYIFN   360
BVH3 P4241    301   LSALEEKIARMVPISGTGSTVSTNAKPNEVVSSLGSLSSNPSSLTTSKELSSASDGYIFN   360
BVH3 A66      301   LSALEEKIARMVPISGTGSTVSTNAKPNEVVSSLGSLSSNPSSLTTSKELSSASDGYIFN   360
                    ********** *************************************************

BVH3 WU2      361   PKDIVEETATAYIVRHGDHFHYIPKSNQIGQPTLPNNSLATPSPSLPINPGTSHEKHEED   420
BVH3 RX1      361   PKDIVEETATAYIVRHGDHFHYIPKSNQIGQPTLPNNSLATPSPSLPINPGISHEKHEED   420
BVH3 JNR7/87  361   PKDIVEETATAYIVRHGDHFHYIPKSNQIGQPTLPNNSLATPSPSLPINPGTSHEKHEED   420
BVH3 SP64     361   PKDIVEETATAYIVRHGDHFHYIPKSNQIGQPTLPNNSLATPSPSLPINPGTSHEKHEED   420
BVH3 P4241    361   PKDIVEETATAYIVRHGDHFHYIPKSNQIGQPTLPNNSLATPSPSLPINPGTSHEKHEED   420
BVH3 A66      361   PKDIVEETATAYIVRHGDHFHYIPKSNQIGQPTLPNNSLATPSPSLPINPGTSHEKHEED   420
                    *************************************************** *******

BVH3 WU2      421   GYGFDANRIIAEDESGFVMSHGDHNHYFFKKDLTEEQIKAAQKHLEEVKTSHNGLDSLSS   480
BVH3 RX1      421   GYGFDANRIIAEDESGFIMSHGNHNHYFFKKDLTEEQIKAAQKHLEEVKTSHNGLDSLSS   480
BVH3 JNR7/87  421   GYGFDANRIIAEDESGFVMSHGDHNHYFFKKDLTEEQIKAAQKHLEEVKTSHNGLDSLSS   480
BVH3 SP64     421   GYGFDANRIIAEDESGFVMSHGDHNHYFFKKDLTEEQIKAAQKHLEEVKTSHNGLDSLSS   480
BVH3 P4241    421   GYGFDANRIIAEDESGFVMSHGDHNHYFFKKDLTEEQIKAAQKHLEEVKTSHNGLDSLSS   480
BVH3 A66      421   GYGFDANRIIAEDESGFVMSHGDHNHYFFKKDLTEEQIKAAQKHLEEVKTSHNGLDSLSS   480
                    ***************** **** *************************************
```

*FIG. 11A*

```
BVH3 WU2      481 HEQDYPSNAKEMKDLDKKIEEKIAGIMKQYGVKRESIVVNKEKNAIIYPHGDHHHADPID 540
BVH3 RX1      481 HEQDYPGNAKEMKDLDKKIEEKIAGIMKQYGVKRESIVVNKEKNAIIYPHGDHHHADPID 540
BVH3 JNR7/87  481 HEQDYPSNAKEMKDLDKKIEEKIAGIMKQYGVKRESIVVNKEKNAIIYPHGDHHHADPID 540
BVH3 SP64     481 HEQDYPGNAKEMKDLDKKIEEKIAGIMKQYGVKRESIVVNKEKNAIIYPHGDHHHADPID 540
BVH3 P4241    481 HEQDYPSNAKEMKDLDKKIEEKIAGIMKQYGVKRESIVVNKEKNAIIYPHGDHHHADPID 540
BVH3 A66      481 HEQDYPSNAKEMKDLDKKIEEKIAGIMKQYGVKRESIVVNKEKNAIIYPHGDHHHADPID 540
                  ****** *****************************************************

BVH3 WU2      541 EHKPVGIGHSHSNYELFKPEEGVAKKEGNKVYTGEELTNVVNLLKNSTFNNQNFTLANGQ 600
BVH3 RX1      541 EHKPVGIGHSHSNYELFKPEEGVAKKEGNKVYTGEELTNVVNLLKNSTFNNQNFTLANGQ 600
BVH3 JNR7/87  541 EHKPVGIGHSHSNYELFKPEEGVAKKEGNKVYTGEELTNVVNLLKNSTFNNQNFTLANGQ 600
BVH3 SP64     541 EHKPVGIGHSHSNYELFKPEEGVAKKEGNKVYTGEELTNVVNLLKNSTFNNQNFTLANGQ 600
BVH3 P4241    541 EHKPVGIGHSHSNYELFKPEEGVAKKEGNKVYTGEELTNVVNLLKNSTFNNQNFTLANGQ 600
BVH3 A66      541 EHKPVGIGHSHSNYELFKPEEGVAKKEGNKVYTGEELTNVVNLLKNSTFNNQNFTLANGQ 600
                  ************************************************************

BVH3 WU2      601 KRVSFSFPPELEKKLGINMLVKLITPDGKVLEKVSGKVFGEGVGNIANFELDQPYLPGQT 660
BVH3 RX1      601 KRVSFSFPPELEKKLGINMLVKLITPDGKVLEKVSGKVFGEGVGNIANFELDQPYLPGQT 660
BVH3 JNR7/87  601 KRVSFSFPPELEKKLGINMLVKLITPDGKVLEKVSGKVFGEGVGNIANFELDQPYLPGQT 660
BVH3 SP64     601 KRVSFSFPPELEKKLGINMLVKLITPDGKVLEKVSGKVFGEGVGNIANFELDQPYLPGQT 660
BVH3 P4241    601 KRVSFSFPPELEKKLGINMLVKLITPDGKVLEKVSGKVFGEGVGNIANFELDQPYLPGQT 660
BVH3 A66      601 KRVSFSFPPELEKKLGINMLVKLITPDGKVLEKVSGKVFGEGVGNIANFELDQPYLPGQT 660
                  ************************************************************

BVH3 WU2      661 FKYTIASKDYPEVSYDGTFTVPTSLAYKMASQTIFYPFHAGDTYLRVNPQFAVPKGTDAL 720
BVH3 RX1      661 FKYTIASKDYPEVSYDGTFTVPTSLAYKMASQTIFYPFHAGDTYLRVNPQFAVPKGTDAL 720
BVH3 JNR7/87  661 FKYTIASKDYPEVSYDGTFTVPTSLAYKMASQTIFYPFHAGDTYLRVNPQFAVPKGTDAL 720
BVH3 SP64     661 FKYTIASKDYPEVSYDGTFTVPTSLAYKMASQTIFYPFHAGDTYLRVNPQFAVPKGTDAL 720
BVH3 P4241    661 FKYTIASKDYPEVSYDGTFTVPTSLAYKMASQTIFYPFHAGDTYLRVNPQFAVPKGTDAL 720
BVH3 A66      661 FKYTIASKDYPEVSYDGTFTVPTSLAYKMASQTIFYPFHAGDTYLRVNPQFAVPKGTDAL 720
                  ************************************************************

BVH3 WU2      721 VRVFDEFHGNAYLENNYKVGEIKLPIPKLNQGTTRTAGNKIPVTFMANAYLDNQSTYIVE 780
BVH3 RX1      721 VRVFDEFHGNAYLENNYKVGEIKLPIPKLNQGTTRTAGNKIPVTFMANAYLDNQSTYIVE 780
BVH3 JNR7/87  721 VRVFDEFHGNAYLENNYKVGEIKLPIPKLNQGTTRTAGNKIPVTFMANAYLDNQSTYIVE 780
BVH3 SP64     721 VRVFDEFHGNAYLENNYKVGEIKLPIPKLNQGTTRTAGNKIPVTFMANAYLDNQSTYIVE 780
BVH3 P4241    721 VRVFDEFHGNAYLENNYKVGEIKLPIPKLNQGTTRTAGNKIPVTFMANAYLDNQSTYIVE 780
BVH3 A66      721 VRVFDEFHGNAYLENNYKVGEIKLPIPKLNQGTTRTAGNKIPVTFMANAYLDNQSTYIVE 780
                  ************************************************************

BVH3 WU2      781 VPILEKENQTDKPSILPQFKRNKAQENSKFDEKVEEPKTSEKVEKEKLSETGNSTSNSTL 840
BVH3 RX1      781 VPILEKENQTDKPSILPQFKRNKAQENSKLDEKVEEPKTSEKVEKEKLSETGNSTSNSTL 840
BVH3 JNR7/87  781 VPILEKENQTDKPSILPQFKRNKAQENLKLDEKVEEPKTSEKVEKEKLSETGNSTSNSTL 840
BVH3 SP64     781 VPILEKENQTDKPSILPQFKRNKAQENSKLDEKVEEPKTSEKVEKEKLSETGNSTSNSTL 840
BVH3 P4241    781 VPILEKENQTDKPSILPQFKRNKAQENSKFDEKVEEPKTSEKVEKEKLSETGNSTSNSTL 840
BVH3 A66      781 VPILEKENQTDKPSILPQFKRNKAQENSKFDEKVEEPKTSEKVEKEKLSETGNSTSNSTL 840
                  *************************** * **********************************

BVH3 WU2      841 EEVPTVDPVQEKVAKFAESYGMKLENVLFNMDGTIELYLPSGEVIKKNMADFTGEAPQGN 900
BVH3 RX1      841 EEVPTVDPVQEKVAKFAESYGMKLENVLFNMDGTIELYLPSGEVIKKNMADFTGEAPQGN 900
BVH3 JNR7/87  841 EEVPTVDPVQEKVAKFAESYGMKLENVLFNMDGTIELYLPSGEVIKKNMADFTGEAPQGN 900
BVH3 SP64     841 EEVPTVDPVQEKVAKFAESYGMKLENVLFNMDGTIELYLPSGEVIKKNMADFTGEAPQGN 900
BVH3 P4241    841 EEVPTVDPVQEKVAKFAESYGMKLENVLFNMDGTIELYLPSGEVIKKNMADFTGEAPQGN 900
BVH3 A66      841 EEVPTVDPVQEKVAKFAESYGMKLENVLFNMDGTIELYLPSGEVIKKNMADFTGEAPQGN 900
                  ************************************************************

BVH3 WU2      901 GENKPSENGKVSTGTVENQPTENKPADSLPEAPNEKPVKPENSTDNGMLNPEGNVGSDPM 960
BVH3 RX1      901 GENKPSENGKVSTGTVENQPTENKPADSLPEAPNEKPVKPENSTDNGMLNPEGNVGSDPM 960
BVH3 JNR7/87  901 GENKPSENGKVSTGTVENQPTENKPADSLPEAPNEKPVKPENSTDNGMLNPEGNVGSDPM 960
BVH3 SP64     901 GENKPSENGKVSTGTVENQPTENKPADSLPEAPNEKPVKPENSTDNGMLNPEGNVGSDPM 960
BVH3 P4241    901 GENKPSENGKVSTGTVENQPTENKPADSLPEAPNEKPVKPENSTDNGMLNPEGNVGSDPM 960
BVH3 A66      901 GENKPSENGKVSTGTVENQPTENKPADSLPEAPNEKPVKPENSTDNGMLNPEGNVGSDPM 960
                  ************************************************************

BVH3 WU2      961 LDPALEEAPAVDPVQEKLEKFTASYGLGLDSVIFNMDGTIELRLPSGEVIKKNLSDLIA 1019
BVH3 RX1      961 LDPALEEAPAVDPVQEKLEKFTASYGLGLDSVIFNMDGTIELRLPSGEVIKKNLSDLIA 1019
BVH3 JNR7/87  961 LDPALEEAPAVDPVQEKLEKFTASYGLGLDSVIFNMDGTIELRLPSGEVIKKNLSDLIA 1019
BVH3 SP64     961 LDPALEEAPAVDPVQEKLEKFTASYGLGLDSVIFNMDGTIELRLPSGEVIKKNLSDFIA 1019
BVH3 P4241    961 LDPALEEAPAVDPVQEKLEKFTASYGLGLDSVIFNMDGTIELRLPSGEVIKKNLSDLIA 1019
BVH3 A66      961 LDPALEEAPAVDPVQEKLEKFTASYGLGLDSVIFNMDGTIELRLPSGEVIKKNLSDLIA 1019
                  ******************************************************** **
```

*FIG. 11B*

```
BVH11-2 SP64     1 CSYELGRHQAGQVKKESNRVSYIDGDQAGQKAENLTPDEVSKREGINAEQIVIKITDQGY 60
BVH11-2 JNR7/87  1 CSYELGRHQAGQVKKESNRVSYIDGDQAGQKAENLTPDEVSKREGINAEQIVIKITDQGY 60
BVH11-2 P4241    1 CSYELGRHQAGQDKKESNRVAYIDGDQAGQKAENLTPDEVSKREGINAEQIVIKITDQGY 60
BVH11-2 A66      1 CSYELGRHQAGQDKKESNRVAYIDGDQAGQKAENLTPDEVSKREGINAEQIVIKITDQGY 60
BVH11-2 WU2      1 CSYELGRHQAGQDKKESNRVAYIDGDQAGQKAENLTPDEVSKREGINAEQIVIKITDQGY 60
BVH11-2 Rx1      1 CSYELGRHQAGQVKKESNRVSYIDGDQAGQKAENLTPDEVSKREGINAEQIVIKITDQGY 60
BVH11   P4241    1 CSYELGRHQAGQDKKESNRVAYIDGDQAGQKAENLTPDEVSKREGINAEQIVIKITDQGY 60
BVH11   WU2      1 CSYELGRHQAGQDKKESNRVAYIDGDQAGQKAENLTPDEVSKREGINAEQIVIKITDQGY 60
BVH11   A66      1 CSYELGRHQAGQDKKESNRVAYIDGDQAGQKAENLTPDEVSKREGINAEQIVIKITDQGY 60
BVH11   Rx1      1 CSYELGRHQAGQVKKESNRVSYIDGDQAGQKAENLTPDEVSKREGINAEQIVIKITDQGY 60
BVH11   JNR7/87  1 CSYELGRHQAGQDKKESNRVAYIDGDQAGQKAENLTPDEVSKREGINAEQIVIKITDQGY 60
BVH11   SP63     1 CSYELGRHQAGQVKKESNRVSYIDGDQAGQKAENLTPDEVSKREGINAEQIVIKITDQGY 60
BVH11   SP64     1 CAYELGLHQA-QTVKENNRVSYIDGKQATQKTENLTPDEVSKREGINAEQIVIKITDQGY 59
                   *.****.***.*..**.***.**** **.************************  *****

BVH11-2 SP64    61 VTSHGDHYHYYNGKVPYDAIISEELLMKDPNYQLKDSDIVNEIKGGYVIKVDGKYYVYLK 120
BVH11-2 JNR7/87 61 VTSHGDHYHYYNGKVPYDAIISEELLMKDPNYQLKDSDIVNEIKGGYVIKVDGKYYVYLK 120
BVH11-2 P4241   61 VTSHGDHYHYYNGKVPYDAIISEELLMKDPNYQLKDSDIVNEIKGGYVIKVNGKYYVYLK 120
BVH11-2 A66     61 VTSHGDHYHYYNGKVPYDAIISEELLMKDPNYQLKDSDIVNEIKGGYVIKVNGKYYVYLK 120
BVH11-2 WU2     61 VTSHGDHYHYYNGKVPYDAIISEELLMKDPNYQLKDSDIVNEIKGGYVIKVNGKYYVYLK 120
BVH11-2 Rx1     61 VTSHGDHYHYYNGKVPYDAIISEELLMKDPNYQLKDSDIVNEIKGGYVIKVDGKYYVYLK 120
BVH11   P4241   61 VTSHGDHYHYYNGKVPYDAIISEELLMKDPNYQLKDSDIVNEIKGGYVIKVNGKYYVYLK 120
BVH11   WU2     61 VTSHGDHYHYYNGKVPYDAIISEELLMKDPNYQLKDSDIVNEIKGGYVIKVNGKYYGYLK 120
BVH11   A66     61 VTSHGDHYHYYNGKVPYDAIISEELLMKDPNYQLKDSDIVNEIKGGYVIKVNGKYYVYLK 120
BVH11   Rx1     61 VTSHGDHYHYYNGKVPYDAIISEELLMKDPNYQLKDSDIVNEIKGGYVIKVDGKYYVYLK 120
BVH11   JNR7/87 61 VTSHGDHYHYYNGKVPYDAIISEELLMKDPNYQLKDSDIVNEIKGGYVIKVNGKYYVYLK 120
BVH11   SP63    61 VTSHGDHYHYYNGKVPYDAIISEELLMKDPNYQLKDSDIVNEIKGGYVIKVDGKYYVYLK 120
BVH11   SP64    60 VTSHGDHYHYYNGKVPYDAIISEELLMKDPNYQLKDSDIVNEIKGGYVIKVNGKYYVYLK 119
                   ********************************************** **** ***

BVH11-2 SP64   121 DAAHADNIRTKEEIKRQKQEHSHNHNSRA---DNAVAAARAQGRYTTDDGYIFNASDIIE 177
BVH11-2 JNR7/87 121 DAAHADNIRTKEEIKRQKQEHSHNHGGGSN--DQAVVAARAQGRYTTDDGYIFNASDIIE 178
BVH11-2 P4241  121 DAAHADNIRTKEEIKRQKQEHSHNHGGGSN--DQAVVAARAQGRYTTDDGYIFNASDIIE 178
BVH11-2 A66    121 DAAHADNIRTKEEIKRQKQEHSHNHGGGSN--DQAVVAARAQGRYTTDDGYIFNASDIIE 178
BVH11-2 WU2    121 DAAHADNIRTKEEIKRQKQEHSHNHGGGSN--DQAVVAARAQGRYTTDDGYIFNASDIIE 178
BVH11-2 Rx1    121 DAAHADNIRTKEEIKRQKQERSHNHNSRA---DNAVAAARAQGRYTTDDGYIFNASDIIE 177
BVH11   P4241  121 DAAHADNIRTKEEIKRQKQEHSHNHGGGSN--DQAVVAARAQGRYTTDDGYIFNASDIIE 178
BVH11   WU2    121 DAAHADNIRTKEEIKRQKQEHSHNHGGGSN--DQAVVAARAQGRYTTDDGYIFNASDIIE 178
BVH11   A66    121 DAAHADNIRTKEEIKRQKQEHSHNHGGGSN--DQAVVAARAQGRYTTDDGYIFNASDIIE 178
BVH11   Rx1    121 DAAHADNIRTKEEIKRQKQERSHNHNSRA---DNAVAAARAQGRYTTDDGYIFNASDIIE 177
BVH11   JNR7/87 121 DAAHADNIRTKEEIKRQKQERSHNHNSRA---DNAVAAARAQGRYTTDDGYIFNASDIIE 177
BVH11   SP63   121 DAAHADNIRTKEEIKRQKQERSHNHNSRA---DNAVAAARAQGRYTTDDGYIFNASDIIE 177
BVH11   SP64   120 DAAHADNVRTKEEINRQKQEHSQHREGGTSANDGAVAFARSQGRYTTDDGYIFNASDIIE 179
                   *******.****** *****.*..*...    *.**.***.******************

BVH11-2 SP64   178 DTGDAYIVPHGDHYHYIPKNELSASELAAAEAYWNGKQGSRPSSSSSYNANPVQPRLSEN 237
BVH11-2 JNR7/87 179 DTGDAYIVPHGDHYHYIPKNELSASELAAAEAYWNGKQGSRPSSSSSYNANPAQPRLSEN 238
BVH11-2 P4241  179 DTGDAYIVPHGNHFHYIPKSDLSASELAAAQAYWNGKQGSRPSSSSSHNANPAQPRLSEN 238
BVH11-2 A66    179 DTGDAYIVPHGNHFHYIPKSDLSASELAAAQAYWNGKQGSRPSSSSSHNANPAQPRLSEN 238
BVH11-2 WU2    179 DTGDAYIVPRGNHFHYIPKSDLSASELAAAQAYWNGKQGSRPSSSSSHNANPAQPRLSEN 238
BVH11-2 Rx1    178 DTGDAYIVPHGDHYHYIPKSDLSASELAAAQAYWNGKQGSRPSSSSSHNANPAQPRLSEN 237
BVH11   P4241  179 DTGDAYIVPHGNHFHYIPKSDLSASELAAAQAYWNGKQGSRPSSSSSHNANPAQPRLSEN 238
BVH11   WU2    179 DTGDAYIVPHGNHFHYIPKSDLSASELAAAQAYWNGKQGSRPSSSSSHNANPAQPRLSEN 238
BVH11   A66    179 DTGDAYIVPHGNHFHYIPKSDLSASELAAAQAYWNGKQGSRPSSSSSHNANPAQPRLSEN 238
BVH11   Rx1    178 DTGDAYIVPHGDHYHYIPKSDLSASELAAAQAYWNGKQGSRPSSSSSHNANPAQPRLSEN 237
BVH11   JNR7/87 178 DTGDAYIVPHGDHYHYIPKNELSASELAAAEAYWNGKQGSRPSSSSSYNANPAQPRLSEN 237
BVH11   SP63   178 DTGDAYIVPHGNHFHYIPKSDLSASELAAAQAYWNGKQGSRPSSSSSHNANPAQPRLSEN 237
BVH11   SP64   180 DTGDAYIVPHGDHYHYIPKNELSASELAAAEAFLSGRENLSNLRTYRRQNSDNTPRTNWV 239
                   ********.*.*.*****.*********.*..*...   *.**  **.*..**
```

*FIG. 12A*

```
BVH11-2 SP64      238 HNLTVTPTYHQN------------QGENISSLLRELYAKPLSERHVESDGLIFDPAQITS 285
BVH11-2 JNR7/87   239 HNLTVTPTYHQN------------QGENISSLLRELYAKPLSERHVESDGLIFDPAQITS 286
BVH11-2 P4241     239 HNLTVTPTYHQN------------QGENISSLLRELYAKPLSERHVESDGLIFDPAQITS 286
BVH11-2 A66       239 HNLTVTPTYHQN------------QGENISSLLRELYAKPLSERHVESDGLIFDPAQITS 286
BVH11-2 WU2       239 HNLTVTPTYHQN------------QGENISSLLRELYAKPLSERRVESDGLIFDPAQITS 286
BVH11-2 Rx1       238 HNLTVTPTYHQN------------QGENISSLLRELYAKPLSERHVESDGLIFDPAQITS 285
BVH11   P4241     239 HNLTVTPTYHQN------------QGENISSLLRELYAKPLSERHVESDGLIFDPAQITS 286
BVH11   WU2       239 HNLTVTPTYHQN------------QGENISSLLRELYAKPLSERHVESDGLIFDPAQITS 286
BVH11   A66       239 HNLTVTPTYHQN------------QGENISSLLRELYAKPLSERHVESDGLIFDPAQITS 286
BVH11   Rx1       238 HNLTVTPTYHQN------------QGENISSLLRELYAKPLSERHVESDGLIFDPAQITS 285
BVH11   JNR7/87   238 HNLTVTPTYHQN------------QGENISSLLRELYAKPLSERHVESDGLIFDPAQITS 285
BVH11   SP63      238 HNLTVTPTYHQN------------QGENISSLLRELYAKPLSERHVESDGLIFDPAQITS 285
BVH11   SP64      240 PSVSNPGTTNTNTSNNSNTNSQASQSNDIDSLLKQLYKLPLSQRHVESDGLIFDPAQITS 299
                       ..   *  . *          *  * *** .**  *** .*.**************

BVH11-2 SP64      286 RTARGVAVPHGNHYHFIPYEQMSELEKRIARIIPLRYRSNHWVPDSRPEQPSPQSTPEPS 345
BVH11-2 JNR7/87   287 RTARGVAVPHGNHYHFIPYEQMSELEKRIARIIPLRYRSNHWVPDSRPEQPSPQSTPEPS 346
BVH11-2 P4241     287 RTARGVAVPHGNHYHFIPYEQMSELEERIARIIPLRYRSNHWVPDSRPEQPSPQ----PS 342
BVH11-2 A66       287 RTARGVAVPHGNHYHFIPYEQMSELEERIARIIPLRYRSNHWVPDSRPEQPSPQ----PS 342
BVH11-2 WU2       287 RTARGVAVPHGNHYHFIPYEQMSELEERIARIIPLRYRSNHWVPDSRPEQPSPQ----PS 342
BVH11-2 Rx1       286 RTANGVAVPHGDHYHFIPYSQLSPLEEKLARIIPLRYRSNHWVPDSRPEQPSPQSTPEPS 345
BVH11   P4241     287 RTARGVAVPHGNHYHFIPYEQMSELEERIARIIPLRYRSNHWVPDSRPEQPSPQ----PS 342
BVH11   WU2       287 RTARGVAVPHGNHYHFIPYEQMSELEERIARIIPLRYRSNHWVPDSRPEQPSPQ----PS 342
BVH11   A66       287 RTARGVAVPHGNHYHFIPYEQMSELEERIARIIPLRYRSNHWVPDSRPEQPSPQ----PS 342
BVH11   Rx1       286 RTANGVAVPHGDHYHFIPYSQLSPLEEKLARIIPLRYRSNHWVPDSRPEQPSPQPTPEPS 345
BVH11   JNR7/87   286 RTARGVAVPHGNHYHFIPYEQMSELEKRIARIIPLRYRSNHWVPDSRPEEPSPQPTPEPS 345
BVH11   SP63      286 RTARGVAVPHGNHYHFIPYSQMSELEERIARIIPLRYRSNHWVPDSRPEQPSPQSTPEPS 345
BVH11   SP64      300 RTARGVAVPHGNHYHFIPYEQMSELEKRIARIIPLRYRSNHWVPDSRPEEPSPQPTPEPS 359
                      *** ******* ****** *.* **  .*********************.****  **

BVH11-2 SP64      346 PSLQPAPNPQPAPSNPIDEKLVKEAVRKVGDGYVFEENGVSRYIPAKDLSAETAAGIDSK 405
BVH11-2 JNR7/87   347 PSPQPAPNPQPAPSNPIDEKLVKEAVRKVGDGYVFEENGVSRYIPAKDLSAETAAGIDSK 406
BVH11-2 P4241     343 PSPQPAPNPQPAPSNPIDEKLVKEAVRKVGDGYVFEENGVSRYIPAKDLSAETAAGIDSK 402
BVH11-2 A66       343 PSPQPAPNPQPAPSNPIDEKLVKEAVRKVGDGYVFEENGVSRYIPAKDLSAETAAGIDSK 402
BVH11-2 WU2       343 PSPQPAPNPQPAPSNPIDEKLVKEAVRKVGDGYVFEENGVSRYIPAKDLSAETAAGIDSK 402
BVH11-2 Rx1       346 PSPQPAPNPQPAPSNPIDEKLVKEAVRKVGDGYVFEENGVPRYIPAKDLSAETAAGIDSK 405
BVH11   P4241     343 PSPQPAPNPQPAPSNPIDEKLVKEAVRKVGDGYVFEENGVSRYIPAKDLSAETAAGIDSK 402
BVH11   WU2       343 PSPQPAPNPQPAPSNPIDEKLVKEAVRKVGDGYVFEENGVSRYIPAKDLSAETAAGIDSK 402
BVH11   A66       343 PSPQPAPNPQPAPSNPIDEKLVKEAVRKVGDGYVFEENGVSRYIPAKDLSAETAAGIDSK 402
BVH11   Rx1       346 PSPQPAPNPQPAPSNPIDEKLVKEAVRKVGDGYVFEENGVPRYIPAKDLSAETAAGIDSK 405
BVH11   JNR7/87   346 PSP------QPAPSNPIDEKLVKEAVRKVGDGYVFEENGVSRYIPAKDLSAETAAGIDSK 399
BVH11   SP63      346 PSPQSAPNPQPAPSNPIDEKLVKEVVRKVGDGYVFEKNGVSRYIPAKNLSAETAAGIDSK 405
BVH11   SP64      360 PSPQPAPNPQPAPSNPIDEKLVKEAVRKVGDGYVFEENGVSRYIPAKNLSAETAAGIDSK 419
                      **          ************* ********** *** ***** ************

BVH11-2 SP64      406 LAKQESLSHKLGAKKTDLPSSDREFYNKAYDLLARIHQDLLDNKGRQVDFEVLDNLLERL 465
BVH11-2 JNR7/87   407 LAKQESLSHKLGAKKTDLPSSDREFYNKAYDLLARIHQDLLDNKGRQVDFEALDNLLERL 466
BVH11-2 P4241     403 LAKQESLSHKLGTKKTDLPSSDREFYNKAYDLLARIHQDLLDNKGRQVDFEALDNLLERL 462
BVH11-2 A66       403 LAKQESLSHKLGTKKTDLPSSDREFYNKAYDLLARIHQDLLDNKGRQVDFEALDNLLERL 462
BVH11-2 WU2       403 LAKQESLSHKLGTKKTDLPSSDREFYNKAYDLLARIHQDLLDNKGRQVDFEALDNLLERL 462
BVH11-2 Rx1       406 LAKQESLSHKLGAKKTDLPSSDREFYNKAYDLLARIHQDLLDNKGRQVDFEALDNLLERL 465
BVH11   P4241     403 LAKQESLSHKLGTKKTDLPSSDREFYNKAYDLLARIHQDLLDNKGRQVDFEALDNLLERL 462
BVH11   WU2       403 LAKQESLSHKLGTKKTDLPSSDREFYNKAYDLLARIHQDLLDNKGRQVDFEALDNLLERL 462
BVH11   A66       403 LAKQESLSHKLGTKKTDLPSSDREFYNKAYDLLARIHQDLLDNKGRQVDFEALDNLLERL 462
BVH11   Rx1       406 LAKQESLSHKLGAKKTDLPSSDREFYNKAYDLLARIHQDLLDNKGRQVDFEALDNLLERL 465
BVH11   JNR7/87   400 LAKQESLSHKLGAKKTDLPSSDREFYNKAYDLLARIHQDLLDNKGRQVDFEALDNLLERL 459
BVH11   SP63      406 LAKQESLSHKLGAKKTDLPSSDREFYNKAYDLLARIHQDLLDNKGRQVDFEALDNLLERL 465
BVH11   SP64      420 LAKQESLSHKLGAKKTDLPSSDREFYNKAYDLLARIHQDLLDNKGRQVDFEALDNLLERL 479
                      *********** ************************************* ********
```

*FIG. 12B*

```
BVH11-2 SP64      466 KDVSSDKVKLVDDILAFLAPIRHPERLGKPNAQITYTDDEIQVAKLAGKYTTEDGYIFDP 525
BVH11-2 JNR7/87   467 KDVPSDKVKLVDDILAFLAPIRHPERLGKPNAQITYTDDEIQVAKLAGKYTTEDGYIFDP 526
BVH11-2 P4241     463 KDVSSDKVKLVEDILAFLAPIRHPERLGKPNSQITYTDDEIQVAKLAGKYTTEDGYIFDP 522
BVH11-2 A66       463 KDVSSDKVKLVEDILAFLAPIRHPERLGKPNSQITYTDDEIQVAKLAGKYTTEDGYIFDP 522
BVH11-2 WU2       463 KDVSSDKVKLVEDILAFLAPIRHPERLGKPNSQITYTDDEIQVAKLAGKYTTEDGYIFDP 522
BVH11-2 Rx1       466 KDVSSDKVKLVDDILAFLAPIRHPERLGKPNAQITYTDDEIQVAKLAGKYTTEDGYIFDP 525
BVH11   P4241     463 KDVSSDKVKLVEDILAFLAPIRHPERLGKPNSQITYTDDEIQVAKLAGKYTTEDGYIFDP 522
BVH11   WU2       463 KDVSSDKVKLVEDILAFLAPIRHPERLGKPNSQITYTDDEIQVAKLAGKYTTEDGYIFDP 522
BVH11   A66       463 KDVSSDKVKLVEDILAFLAPIRHPERLGKPNSQITYTDDEIQVAKLAGKYTTEDGYIFDP 522
BVH11   Rx1       466 KDVSSDKVKLVDDILAFLAPIRHPERLGKPNAQITYTDDEIQVAKLAGKYTTEDGYIFDP 525
BVH11   JNR7/87   460 KDVSSDKVKLVDDILAFLAPIRHPERLGKPNAQITYTDDEIQVAKLAGKYTTEDGYIFDP 519
BVH11   SP63      466 EDVPSDKVKLVDDILAFLAPIRHPERLGKPNAQITYTDDEIQVAKLAGKYTTEDGYIFDP 525
BVH11   SP64      480 KDVSSDKVKLVDDILAFLAPIRHPERLGKPNAQITYTDDEIQVAKLAGKYTTEDGYIFDP 539
                      ** ******.********************.*****************************

BVH11-2 SP64      526 RDITSDEGDAYVTPHMTHSHWIKKDSLSEAERAAAQAYAKEKGLTPPSTDHQDSGNTEAK 585
BVH11-2 JNR7/87   527 RDITSDEGDAYVTPHMTHSHWIKKDSLSEAERAAAQAYAKEKGLTPPSTDHQDSGNTEAK 586
BVH11-2 P4241     523 RDITSDEGDAYVTPHMTHSHWIKKDSLSEAERAAAQAYAKEKGLTPPSTDHRDSGNTEAK 582
BVH11-2 A66       523 RDITSDEGDAYVTPHMTHSHWIKKDSLSEAERAAAQAYAKEKGLTPPSTDHQDSGNTEAK 582
BVH11-2 WU2       523 RDITSDEGDAYVTPHMTHSHWIKKDSLSEAERAAAQAYAKEKGLTPPSTDHQDSGNTEAK 582
BVH11-2 Rx1       526 RDITSDEGDAYVTPHMTHSHWIKKDSLSEAERAAAQAYAKEKGLTPPSTDHQDSGNTEAK 585
BVH11   P4241     523 RDITSDEGDAYVTPHMTHSHWIKKDSLSEAERAAAQAYAKEKGLTPPSTDHQDSGNTEAK 582
BVH11   WU2       523 RDITSDEGDAYVTPHMTHSHWIKKDSLSEAERAAAQAYAKEKGLTPPSTDHQDSGNTEAK 582
BVH11   A66       523 RDITSDEGDAYVTPHMTHSHWIKKDSLSEAERAAAQAYAKEKGLTPPSTDHQDSGNTEAK 582
BVH11   Rx1       526 RDITSDEGDAYVTPHMTHSHWIKKDSLSEAERAAAQAYAKEKGLTPPSTDHQDSGNTEAK 585
BVH11   JNR7/87   520 RDITSDEGDAYVTPHMTHSHWIKKDSLSEAERAAAQAYAKEKGLTPPSTDHQDSGNTEAK 579
BVH11   SP63      526 RDITSDEGDAYVTPHMTHSHWIKKDSLSEAERAAAQAYAKEKGLTPPSTDHQDSGNTEAK 585
BVH11   SP64      540 RDITSDEGDAYVTPHMTHSHWIKKDSLSEAERAAAQAYAKEKGLTPPSTDHQDSGNTEAK 599
                      ***********************************************************.*******

BVH11-2 SP64      586 GAEAIYNRVKAAKKVPLDRMPYNLQYTVEVKNGSLIIPHYDHYHNIKFEWFDEGLYEAPK 645
BVH11-2 JNR7/87   587 GAEAIYNRVKAAKKVPLDRMPYNLQYTVEVKNGSLIIPHYDHYHNIKFEWFDEGLYEAPK 646
BVH11-2 P4241     583 GAEAIYNRVKAAKKVPLDRMPYNLQYTVEVKNGSLIIPHYDHYHNIKFEWFDEGLYEAPK 642
BVH11-2 A66       583 GAEAIYNRVKAAKKVPLDRMPYNLQYTVEVKNGSLIIPHYDHYHNIKFEWFDEGLYEAPK 642
BVH11-2 WU2       583 GAEAIYNRVKAAKKVPLDRMPYNLQYTVEVKNGSLIIPHYDHYHNIKFEWFDEGLYEAPK 642
BVH11-2 Rx1       586 GAEAIYNRVKAAKKVPLDRMPYNLQYTVEVKNGSLIIPHYDHYHNIKFEWFDEGLYEAPK 645
BVH11   P4241     583 GAEAIYNRVKAAKKVPLDRMPYNLQYTVEVKNGSLIIPHYDHYHNIKFEWFDEGLYEAPK 642
BVH11   WU2       583 GAEAIYNRVKAAKKVPLDRMPYNLQYTVEVKNGSLIIPHYDHYHNIKFEWFDEGLYEAPK 642
BVH11   A66       583 GAEAIYNRVKAAKKVPLDRMPYNLQYTVEVKNGSLIIPHYDHYHNIKFEWFDEGLYEAPK 642
BVH11   Rx1       586 GAEAIYNRVKAAKKVPLDRMPYNLQYTVEVKNGSLIIPHYDHYHNIKFEWFDEGLYEAPK 645
BVH11   JNR7/87   580 GAEAIYNRVKAAKKVPLDRMPYNLQYTVEVKNGSLIIPHYDHYHNIKFEWFDEGLYEAPK 639
BVH11   SP63      586 GAEAIYNRVKAAKKVPLDRMPYNLQYTVEVKNGSLIIPHYDHYHNIKFEWFDEGLYEAPK 645
BVH11   SP64      600 GAEAIYNRVKAAKKVPLDRMPYNLQYTVEVKNGSLIIPHYDHYHNIKFEWFDEGLYEAPK 659
                      ************************************************************

BVH11-2 SP64      646 GYSLEDLLATVKYYVEHPNERPHSDNGFGNASDHVRKNK---------------ADQDSK 690
BVH11-2 JNR7/87   647 GYTLEDLLATVKYYVEHPNERPHSDNGFGNASDHVRKNK---------------VDQDSK 691
BVH11-2 P4241     643 GYTLEDLLATVKYYVEHPNERPHSDNGFGNASDHVRKNK---------------ADQDSK 687
BVH11-2 A66       643 GYTLEDLLATVKYYVEHPNERPHSDNGFGNASDHVRKNK---------------ADQDSK 687
BVH11-2 WU2       643 GYTLEDLLATVKYYVEHPNERPHSDNGFGNASDHVRKNK---------------ADQDSK 687
BVH11-2 Rx1       646 GYSLEDLLATVKYYVEHPNERPHSDNGFGNASDHVQRNKNGQADTNQTEKPNEEKPQTEK 705
BVH11   P4241     643 GYTLEDLLATVKYYVEHPNERPHSDNGFGNASDHVRKNK---------------ADQDSK 687
BVH11   WU2       643 GYTLEDLLATVKYYVEHPNERPHSDNGFGNASDHVRKNK---------------ADQDSK 687
BVH11   A66       643 GYTLEDLLATVKYYVEHPNERPHSDNGFGNASDHVRKNK---------------ADQDSK 687
BVH11   Rx1       646 GYSLEDLLATVKYYVEHPNERPHSDNGFGNASDHVQRNK------------------NGQ 687
BVH11   JNR7/87   640 GYSLEDLLATVKYYVEHPNERPHSDNGFGNASDHVQRNK------------------NGQ 681
BVH11   SP63      646 GYTLEDLLATVKYYVEHPNERPHSDNGFGNASDHVRKNK------------------NGQ 687
BVH11   SP64      660 GYTLEDLLATVKYYVEHPNERPHSDNGFGNASDHVQRNK------------------NGQ 701
                      **.*******************************..**
```

*FIG. 12C*

```
BVH11-2 SP64      691 PDEDKEHDEVSEPTHPESDEKENHAGLNPSADNLYKPSTDTEETEEEAEDTTDEAEIPQV 750
BVH11-2 JNR7/87   692 PDEDKEHDEVSEPTHPESDEKENHAGLNPSADNLYKPSTDTEETEEEAEDTTDEAEIPQV 751
BVH11-2 P4241     688 PDEDKGHDEVSEPTHPESDEKENHAGLNPSADNLYKPSTDTEETEEEAEDTTDEAEIPQV 747
BVH11-2 A66       688 PDEDKGHDEVSEPTHPESDEKENHAGLNPSADNLYKPSTDTEETEEEAEDTTDEAEIPQV 747
BVH11-2 WU2       688 PDEDKGHDEVSEPTHPESDEKENHAGLNPSADNLYKPSTDTEETEEEAEDTTDEAEIPQV 747
BVH11-2 Rx1       706 PEEDKEHDEVSEPTHPESDEKENHVGLNPSADNLYKPSTDTEETEEEAEDTTDEAEIPQV 765
BVH11   P4241     688 PDEDKGHDEVSEPTHPESDEKENHAGLNPSADNLYKPSTDTEETEEEAEDTTDEAEIPQV 747
BVH11   WU2       688 PDEDKGHDEVSEPTHPESDEKENHAGLNPSADNLYKPSTDTEETEEEAEDTTDEAEIPQV 747
BVH11   A66       688 PDEDKGHDEVSEPTHPESDEKENHAGLNPSADNLYKPSTDTEETEEEAEDTTDEAEIPQV 747
BVH11   Rx1       688 ADTNQTEKPNEEKPQTEKPEEETPREEKPQSEKPESPKPTEEPEEESPEESPEESEEPQV 747
BVH11   JNR7/87   682 ADTNQTEKPNEEKPQTEKPEEETPREEKPQSEKPESPKPTEEPEEESPEESPEESEEPQV 741
BVH11   SP63      688 ADTNQTEKPSEEKPQTEKPEEETPREEKPQSEKPESP----KPTEEPEEESPEESEEPQV 743
BVH11   SP64      702 ADTNQTEKPSEEKPQTEKPEEETPREEKPQSEKPESP----KPTEEPEEESPEESEEPQV 757
                       .  .  * . * *,   *  ..  *       **  * . . .*.*  ***

BVH11-2 SP64      751 ENSVINAKIADAEALLEKVTDPSIRQNAMETLTGLKSSLLLGTKDNNTISAEVDSLLALL 810
BVH11-2 JNR7/87   752 ENSVINAKIADAEALLEKVTDPSIRQNAMETLTGLKSSLLLGTKDNNTISAEVDSLLALL 811
BVH11-2 P4241     748 EHSVINAKIADAEALLEKVTDPSIRQNAMETLTGLKSSLLLGTKDNNTISAEVDSLLALL 807
BVH11-2 A66       748 EHSVINAKIADAEALLEKVTDPSIRQNAMETLTGLKSSLLLGTKDNNTISAEVDSLLALL 807
BVH11-2 WU2       748 EHSVINAKIADAEALLEKVTDPSIRQNAMETLTGLKSSLLLGTKDNNTISAEVDSLLALL 807
BVH11-2 Rx1       766 EYSVINAKIAEAEALLEKVTDSSIRQNAVETLTGLKSSLLLGTKDNNTISAEVDSLLALL 825
BVH11   P4241     748 EHSVINAKIADAEALLEKVTDPSIRQNAMETLTGLKSSLLLGTKDNNTISAEVDSLLALL 807
BVH11   WU2       748 EHSVINAKIADAEALLEKVTDPSIRQNAMETLTGLKSSLLLGTKDNNTISAEVDSLLALL 807
BVH11   A66       748 EHSVINAKIADAEALLEKVTDPSIRQNAMETLTGLKSSLLLGTKDNNTISAEVDSLLALL 807
BVH11   Rx1       748 ETEKVKEKLREAEDLLGKIQNPIIKSNAKETLTGLKNNLLFGTQDNNTIMAEAEKLLALL 807
BVH11   JNR7/87   742 ETEKVKEKLREAEDLLGKIQNPIIKSNAKETLTGLKNNLLFGTQDNNTIMAEAEKLLALL 801
BVH11   SP63      744 ETEKVEEKLREAEDLLGKIQDPIIKSNAKETLTGLKNNLLFGTQDNNTIMAEAEKLLALL 803
BVH11   SP64      758 ETEKVEEKLREAEDLLGKIQDPIIKSNAKETLTGLKNNLLFGTQDNNTIMAEAEKLLALL 817
                       *  . *.** ** *. *. ** *******  ** **.*****  **  .  *****

BVH11-2 SP64      811 KESQPAPIQ 819
BVH11-2 JNR7/87   812 KESQPAPIQ 820
BVH11-2 P4241     808 KKSQPAPIQ 816
BVH11-2 A66       808 KKSQPAPIQ 816
BVH11-2 WU2       808 KKSQPAPIQ 816
BVH11-2 Rx1       826 KESQPAPIQ 834
BVH11   P4241     808 KESK      811
BVH11   WU2       808 KESK      811
BVH11   A66       808 KESK      811
BVH11   Rx1       808 KESK      811
BVH11   JNR7/87   802 KESK      805
BVH11   SP63      804 KESK      807
BVH11   SP64      818 KESK      821
                       * *.
```

| | BVH11-2 SP64 | BVH11 SP63 | BVH11 JNR.7/87 | BVH11-2 JNR.7/87 | BVH11 WU2 | BVH11-2 WU2 | BVH11 A66 | BVH11-2 A66 | BVH11 P4241 | BVH11-2 P4241 | BVH11 Rx-1 | BVH11-2 Rx-1 | |
|---|---|---|---|---|---|---|---|---|---|---|---|---|---|
| BVH11 SP64 | I 81% S 86% | I 88% S 90% | I 88% S 91% | I 82% S 87% | I 80% S 85% | I 80% S 85% | I 80% S 85% | I 80% S 85% | I 80% S 85% | I 80% S 85% | I 88% S 91% | I 81% S 85% | |
| BVH11-2 SP64 | | I 87% S 90% | I 87% S 90% | I 98% S 98% | I 95% S 96% | I 96% S 97% | I 95% S 96% | I 96% S 97% | I 95% S 96% | I 96% S 97% | I 87% S 90% | I 94% S 95% | |
| BVH11 SP63 | | | I 96% S 96% | I 88% S 91% | I 88% S 91% | I 88% S 91% | I 88% S 91% | I 88% S 91% | I 88% S 91% | I 87% S 90% | I 97% S 97% | I 89% S 91% | |
| BVH11 JNR.7/87 | | | | I 87% S 91% | I 87% S 91% | I 86% S 90% | I 87% S 91% | I 86% S 90% | I 87% S 91% | I 86% S 90% | I 96% S 96% | I 88% S 90% | |
| BVH11-2 JNR.7/87 | | | | | I 96% S 97% | I 97% S 98% | I 96% S 97% | I 97% S 98% | I 96% S 97% | I 97% S 98% | I 87% S 90% | I 94% S 95% | |
| BVH11 WU2 | | | | | | I 98% S 98% | I 92% S 94% | I 98% S 98% | I 99% S 99% | I 98% S 98% | I 87% S 91% | I 92% S 94% | |
| BVH11-2 WU2 | | | | | | | I 98% S 98% | I 99% S 99% | I 98% S 98% | I 99% S 99% | I 86% S 90% | I 93% S 95% | |
| BVH11 A66 | | | | | | | | I 99% S 99% | I 99% S 99% | I 99% S 99% | I 87% S 91% | I 92% S 94% | |
| BVH11-2 A66 | | | | | | | | | I 99% S 99% | I 99% S 99% | I 86% S 90% | I 93% S 95% | |
| BVH11 P4241 | | | | | | | | | | I 100% | I 87% S 91% | I 92% S 94% | |
| BVH11-2 P4241 | | | | | | | | | | | I 86% S 90% | I 93% S 95% | |
| BVH11 Rx-1 | | | | | | | | | | | | I 91% S 92% | |

| | | | | | | |
|---|---|---|---|---|---|---|
| AATTCCTTGT | CGGGTAAGTT | CCGACCCGCA | CGAAAGGCGT | AATGATTTGG | GCACTGTCTC | 60 |
| AACGAGAGAC | TCGGTGAAAT | TTTAGTACCT | GTGAAGATGC | AGGTTACCCG | CGACAGGACG | 120 |
| GAAAGACCCC | ATGGAGCTTT | ACTGCAGTTT | GATATTGAGT | GTCTGTACCA | CATGTACAGG | 180 |
| ATAGGTAGGA | GTCTAAGAGA | TCGGACGCC | AGTTTCGAAG | GAGACGCTGT | TGGGATACTA | 240 |
| CCCTTGTGTT | ATGGCCACTC | TAACCCAGAT | AGGTGATCCC | TATCGGAGAC | AGTGTCTGAC | 300 |
| GGGCAGTTTG | ACTGGGGCGG | TCGCCTCCTA | AAAGGTAACG | GAGGCGCCCA | AAGGTTCCCT | 360 |
| CAGAATGGTT | GGAAATCATT | CGCAGAGTGT | AAAGGTATAA | GGGAGCTTGA | CTGCGAGAGC | 420 |
| TACAACTCGA | GCAGGGACGA | AAGTCGGGCT | TAGTGATCCG | GTGGTTCCGT | ATGGAAGGGC | 480 |
| CATCGCTCAA | CGGATAAAAG | CTACCCTGGG | GATAACAGGC | TTATCTCCCC | CAAGAGTTCA | 540 |
| CATCGACGGG | GAGGTTTGGC | ACCTCGATGT | CGGCTCGTCG | CATCCTGGGG | CTGTAGTCGG | 600 |
| TCCCAAGGGT | TGGGCTGTTC | GCCCATTAAA | GCGGCACGCG | AGCTGGGTTC | AGAACGTCGT | 660 |
| GAGACAGTTC | GGTCCCTATC | CGTCGCGGGC | GTAGGAAATT | TGAGAGGATC | TGCTCCTAGT | 720 |
| ACGAGAGGAC | CAGAGTGGAC | TTACCGCTGG | TGTACCAGTT | GTCTTGCCAA | AGGCATCGCT | 780 |
| GGGTAGCTAT | GTAGGGAAGG | GATAAACGCT | GAAAGCATCT | AAGTGTGAAA | CCCACCTCAA | 840 |
| GATGAGATTT | CCCATGATTA | TATATCAGTA | AGAGCCCTGA | GAGATGATCA | GGTAGATAGG | 900 |
| TTAGAAGTGG | AAGTGTGGCG | ACACATGTAG | CGGACTAATA | CTAATAGCTC | GAGGACTTAT | 960 |
| CCAAAGTAAC | TGAGAATATG | AAAGCGAACG | GTTTTCTTAA | ATTGAATAGA | TATTCAATTT | 1020 |
| TGAGTAGGTA | TTACTCAGAG | TTAAGTGACG | ATAGCCTAGG | AGATACACCT | GTACCCATGC | 1080 |
| CGAACACAGA | AGTTAAGCCC | TAGAACGCCG | GAAGTAGTTG | GGGGTTGCCC | CCTGTGAGAT | 1140 |
| AGGGAAGTCG | CTTAGCTCTA | GGGAGTTTAG | CTCAGCTGGG | AGAGCATCTG | CCTTACAAGC | 1200 |
| AGAGGGTCAG | CGGTTCGATC | CCGTTAACTC | CCAAAGGTCC | CGTAGTGTAG | CGGTTATCAC | 1260 |
| GTCGCCCTGT | CACGGCGAAG | ATCGCGGGTT | CGATTCCCGT | CGGGACCGTT | TAAGGTAACG | 1320 |
| CAAGTTATTT | TAGACTCGTT | AGCTCAGTTG | GTAGAGCAAT | TGACTTTTAA | TCAATGGGTC | 1380 |
| ACTGGTTCGA | GCCCAGTACG | GGTCATATAT | GCGGGTTTGG | CGGAATTCTA | ATCTCTTTGA | 1440 |
| AATCATCTTC | TCTCACTTTC | CAAAACTCTA | TTACCTCTTA | TTATACCACA | TTTCAATCTT | 1500 |
| CAACTTCCCA | GTAATATAAG | CACCTCTGGC | GAAAGAAGTT | TCAATGTCCT | AAAGTAATAA | 1560 |
| GTGAATCCAA | TTCAGGAACT | CCAAGAACAA | AAGAAACATC | TGGTGTCACA | AGTATTGGAT | 1620 |
| GGCACAGAGT | CACGTGGTAG | TCTGACCCTA | GCAGAAATTT | TAAATAGTAA | ACTATTTACT | 1680 |
| GGTTAATTAA | ATGGTTAAAT | AACCGGTTTA | GAAAACTATT | TAATAAAGTA | AAAGAAGTTG | 1740 |
| AGAAAAAACT | TCATCATTTA | TTGAAATGAG | GGATTTATGA | AATTTAGTAA | AAAATATATA | 1800 |
| GCAGCTGGAT | CAGCTGTTAT | CGTATCCTTG | AGTCTATGTG | CCTATGCACT | AAACCAGCAT | 1860 |
| CGTTCGCAGG | AAAATAAGGA | CAATAATCGT | GTCTCTTATG | TGGATGGCAG | CCAGTCAAGT | 1920 |
| CAGAAAAGTG | AAAACTTGAC | ACCAGACCAG | GTTAGCCAGA | AAGAAGGAAT | TCAGGCTGAG | 1980 |
| CAAATTGTAA | TCAAAATTAC | AGATCAGGGC | TATGTAACGT | CACACGGTGA | CCACTATCAT | 2040 |
| TACTATAATG | GGAAAGTTCC | TTATGATGCC | CTCTTTAGTG | AAGAACTCTT | GATGAAGGAT | 2100 |
| CCAAACTATC | AACTTAAAGA | CGCTGATATT | GTCAATGAAG | TCAAGGGTGG | TTATATCATC | 2160 |
| AAGGTCGATG | GAAAATATTA | TGTCTACCTG | AAAGATGCAG | CTCATGCTGA | TAATGTTCGA | 2220 |
| ACTAAAGATG | AAATCAATCG | TCAAAAACAA | GAACATGTCA | AAGATAATGA | GAAGGTTAAC | 2280 |
| TCTAATGTTG | CTGTAGCAAG | GTCTCAGGGA | CGATATACGA | CAAATGATGG | TTATGTCTTT | 2340 |
| AATCCAGCTG | ATATTCGA | AGATACGGGT | AATGCTTATA | TCGTTCCTCA | TGGAGGTCAC | 2400 |
| TATCACTACA | TTCCCAAAAG | CGATTTATCT | GCTAGTGAAT | TAGCAGCAGC | TAAAGCACAT | 2460 |
| CTGGCTGGAA | AAAATATGCA | ACCGAGTCAG | TTAAGCTATT | CTTCAACAGC | TAGTGACAAT | 2520 |
| AACACGCAAT | CTGTAGCAAA | AGGATCAACT | AGCAAGCCAG | CAAATAAATC | TGAAAATCTC | 2580 |
| CAGAGTCTTT | TGAAGGAACT | CTATGATTCA | CCTAGCGCCC | AACGTTACAG | TGAATCAGAT | 2640 |
| GGCCTGGTCT | TTGACCCTGC | TAAGATTATC | AGTCGTACAC | CAAATGGAGT | TGCGATTCCG | 2700 |
| CATGGCGACC | ATTACCACTT | TATTCCTTAC | AGCAAGCTTT | CTGCTTTAGA | AGAAAAGATT | 2760 |
| GCCAGAATGG | TGCCTATCAG | TGGAACTGGT | TCTACAGTTT | CTACAAATGC | AAAACCTAAT | 2820 |
| GAAGTAGTGT | CTAGTCTAGG | CAGTCTTTCA | AGCAATCCTT | CTTCTTTAAC | GACAAGTAAG | 2880 |
| GAGCTCTCTT | CAGCATCTGA | TGGTTATATT | TTAATCCAA | AAGATATCGT | TGAAGAAACG | 2940 |
| GCTACAGCTT | ATATTGTAAG | ACATGGTGAT | CATTTCCATT | ACATTCCAAA | ATCAAATCAA | 3000 |
| ATTGGGCAAC | CGACTCTTCC | AAACAATAGT | CTAGCAACAC | CTTCTCCATC | TCTTCCAATC | 3060 |
| AATCCAGGAA | CTTCACATGA | GAAACATGAA | GAAGATGGAT | ACGGATTTGA | TGCTAATCGT | 3120 |
| ATTATCGCTG | AAGATGAATC | AGGTTTTGTC | ATGAGTCACG | GAGACCACAA | TCATTATTTC | 3180 |
| TTCAAGAAGG | ACTTGACAGA | AGAGCAAATT | AAGGCTGCGC | AAAAACATTT | AGAGGAAGTT | 3240 |
| AAAACTAGTC | ATAATGGATT | AGATTCTTTG | TCATCTCATG | AACAGGATTA | TCCAGGTAAT | 3300 |
| GCCAAAGAAA | TGAAAGATTT | AGATAAAAAA | ATCGAAGAAA | AAATTGCTGG | CATTATGAAA | 3360 |
| CAATATGGTG | TCAAACGTGA | AGTATTGTC | GTGAATAAAG | AAAAAAATGC | GATTATTTAT | 3420 |
| CCGCATGGAG | ATCACCATCA | TGCAGATCCG | ATTGATGAAC | ATAAACCGGT | TGGAATTGGT | 3480 |
| CATTCTCACA | GTAACTATGA | ACTGTTTAAA | CCCGAAGAAG | GAGTTGCTAA | AAAAGAAGGG | 3540 |

FIG. 14A

```
AATAAAGTTT ATACTGGAGA AGAATTAACG AATGTTGTTA ATTTGTTAAA AAATAGTACG    3600
TTTAATAATC AAAACTTTAC TCTAGCCAAT GGTCAAAAAC GCGTTTCTTT TAGTTTTCCG    3660
CCTGAATTGG AGAAAAAATT AGGTATCAAT ATGCTAGTAA AATTAATAAC ACCAGATGGA    3720
AAAGTATTGG AGAAAGTATC TGGTAAAGTA TTTGGAGAAG GAGTAGGGAA TATTGCAAAC    3780
TTTGAATTAG ATCAACCTTA TTTACCAGGA CAAACATTTA AGTATACTAT CGCTTCAAAA    3840
GATTATCCAG AAGTAAGTTA TGATGGTACA TTTACAGTTC CAACCTCTTT AGCTTACAAA    3900
ATGGCCAGTC AAACGATTTT CTATCCTTTC CATGCAGGGG ATACTTATTT AAGAGTGAAC    3960
CCTCAATTTG CAGTGCCTAA AGGAACTGAT GCTTTAGTCA GAGTGTTTGA TGAATTTCAT    4020
GGAAATGCTT ATTTAGAAAA TAACTATAAA GTTGGTGAAA TCAAATTACC GATTCCGAAA    4080
TTAAACCAAG GAACAACCAG AACGGCCGGA AATAAAATTC CTGTAACCTT CATGGCAAAT    4140
GCTTATTTGG ACAATCAATC GACTTATATT GTGGAAGTAC CTATCTTGGA AAAAGAAAAT    4200
CAAACTGATA AACCAAGTAT TCTACCACAA TTTAAAAGGA ATAAAGCACA AGAAAACTCA    4260
AAACTTGATG AAAAGGTAGA AGAACCAAAG ACTAGTGAGA AGGTAGAAAA AGAAAAACTT    4320
TCTGAAACTG GAATAGTAC TAGTAATTCA ACGTTAGAAG AAGTTCCTAC AGTGGATCCT    4380
GTACAAGAAA AAGTAGCAAA ATTTGCTGAA AGTTATGGGA TGAAGCTAGA AAATGTCTTG    4440
TTTAATATGG ACGGAACAAT TGAATTATAT TTACCATCAG GAGAAGTCAT TAAAAAGAAT    4500
ATGGCAGATT TTACAGGAGA AGCACCTCAA GGAAATGGTG AAAATAAACC ATCTGAAAAT    4560
GGAAAAGTAT CTACTGGAAC AGTTGAGAAC CAACCAACAG AAAATAAACC AGCAGATTCT    4620
TTACCAGAGG CACCAAACGA AAAACCTGTA AAACCAGAAA ACTCAACGGA TAATGGAATG    4680
TTGAATCCAG AAGGGAATGT GGGGAGTGAC CCTATGTTAG ATCCAGCATT AGAGGAAGCT    4740
CCAGCAGTAG ATCCTGTACA AGAAAAATTA GAAAATTTA CAGCTAGTTA CGGATTAGGC    4800
TTAGATAGTG TTATATTCAA TATGGATGGA ACGATTGAAT TAAGATTGCC AAGTGGAGAA    4860
GTGATAAAAA AGAATTTATC TGATTTCATA GCGTAAGGAA TAGCAGTAGA AAAAGTCTGA    4920
ATCAAAAATG AAGTTCTCTC AAAAGTTAGA AATAAAACTC TGACTTTGGG AGAATTTCAT    4980
TTTATTATTA ATATATAAAA TTTCTTGACA TACAACTTAA AAAGAGGTGG AATATTTACT    5040
AGTTAATT    (SEQ ID NO : 11)                                         5048
```

*FIG. 14B*

```
CAGAGATCTT AGTGAATCAA ATATACTTAA GAAAAGAGGA AAGAATGAAA ATCAATAAAA      60
AATATCTAGC TGGGTCAGTA GCTACACTTG TTTTAAGTGT CTGTGCTTAT GAACTAGGTT     120
TGCATCAAGC TCAAACTGTA AAAGAAAATA ATCGTGTTTC CTATATAGAT GGAAAACAAG     180
CGACGCAAAA AACGAGAAT  TTGACTCCTG ATGAGGTTAG CAAGCGTGAA GGAATCAACG     240
CCGAACAAAT CGTCATCAAG ATTACGGATC AAGGTTATGT GACCTCTCAT GGAGACCATT     300
ATCATTACTA TAATGGCAAG GTCCCTTATG ATGCCATCAT CAGTGAAGAG CTCCTCATGA     360
AAGATCCGAA TTATCAGTTG AAGGATTCAG ACATTGTCAA TGAAATCAAG GGTGGTTATG     420
TCATTAAGGT AAACGGTAAA TACTATGTTT ACCTTAAGGA TGCAGCTCAT GCGGATAATG     480
TCCGTACAAA AGAAGAAATC AATGGCAAA  AACAAGAACA TAGTCAGCAT CGTGAAGGAG     540
GGACTTCAGC AAACGATGGT GCGGTAGCCT TTGCACGTTC ACAGGGACGC TACACCACAG     600
ATGATGGTTA TATCTTCAAT GCATCTGATA TCATCGAAGA TACGGGCGAT GCCTATATCG     660
TTCCTCATGG AGATCATTAC CATTACATTC CTAAGAATGA GTTATCAGCT AGCGAGTTGG     720
CTGCTGCAGA AGCCTTCCTA TCTGGTCGGG AAAATCTGTC AAATTTAAGA ACCTATCGCC     780
GACAAAATAG CGATAACACT CCAAGAACAA ACTGGGTACC TTCTGTAAGC AATCCAGGAA     840
CTACAAATAC TAACACAAGC AACAACAGCA ACACTAACAG TCAAGCAAGT CAAAGTAATG     900
ACATTGATAG TCTCTTGAAA CAGCTCTACA AACTGCCTTT GAGTCAACGC CATGTAGAAT     960
CTGATGGCCT TATTTTCGAC CCAGCGCAAA TCACAAGTCG AACCGCCAGA GGTGTAGCTG    1020
TCCCTCATGG TAACCATTAC CACTTTATCC CTTATGAACA AATGTCTGAA TTGGAAAAAC    1080
GAATTGCTCG TATTATTCCC CTTCGTTATC GTTCAAACCA TTGGGTACCA GATTCAAGAC    1140
CAGAAGAACC AAGTCCACAA CCGACTCCAG AACCTAGTCC AAGTCCGCAA CCTGCACCAA    1200
ATCCTCAACC AGCTCCAAGC AATCCAATTG ATGAGAAATT GGTCAAAGAA GCTGTTCGAA    1260
AAGTAGGCGA TGGTTATGTC TTTGAGGAGA ATGGAGTTTC TCGTTATATC CCAGCCAAGA    1320
ATCTTTCAGC AGAAACAGCA GCAGGCATTG ATAGCAAACT GGCCAAGCAG GAAAGTTTAT    1380
CTCATAAGCT AGGAGCTAAG AAAACTGACC TCCCATCTAG TGATCGAGAA TTTTACAATA    1440
AGGCTTATGA CTTACTAGCA AGAATTCACC AAGATTACT  TGATAATAAA GGTCGACAAG    1500
TTGATTTTGA GGCTTTGGAT AACCTGTTGG AACGACTCAA GGATGTCTCA AGTGATAAAG    1560
TCAAGTTAGT GGATGATATT CTTGCCTTCT TAGCTCCGAT TCGTCATCCA GAACGTTTAG    1620
GAAAACCAAA TGCGCAAATT ACCTACACTG ATGATGAGAT TCAAGTAGCC AAGTTGGCAG    1680
GCAAGTACAC AACAGAAGAC GGTTATATCT TGATCCTCG  TGATATAACC AGTGATGAGG    1740
GGGATGCCTA TGTAACTCCA CATATGACCC ATAGCCACTG GATTAAAAAA GATAGTTTGT    1800
CTGAAGCTGA GAGAGCGGCA GCCCAGGCTT ATGCTAAAGA GAAAGGTTTG ACCCCTCCTT    1860
CGACAGACCA TCAGGATTCA GGAAATACTG AGGCAAAAGG AGCAGAAGCT ATCTACAACC    1920
GCGTGAAAGC AGCTAAGAAG GTGCCACTTG ATCGTATGCC TTACAATCTT CAATATACTG    1980
TAGAAGTCAA AAACGGTAGT TTAATCATAC CTCATTATGA CCATTACCAT AACATCAAAT    2040
TTGAGTGGTT TGACGAAGGC CTTTATGAGG CACCTAAGGG GTATACTCTT GAGGATCTTT    2100
TGGCGACTGT CAAGTACTAT GTCGAACATC CAAACGAACG TCCGCATTCA GATAATGGTT    2160
TTGGTAACGC TAGCGACCAT GTTCAAAGAA ACAAAAATGG TCAAGCTGAT ACCAATCAAA    2220
CGGAAAAACC AAGCGAGGAG AAACCTCAGA CAGAAAAACC TGAGGAAGAA ACCCCTCGAG    2280
AAGAGAAACC ACAAAGCGAG AAACCAGAGT CTCCAAAACC AACAGAGGAA CCAGAAGAAG    2340
AATCACCAGA GGAATCAGAA GAACCTCAGG TCGAGACTGA AAAGGTTGAA GAAAAACTGA    2400
GAGAGGCTGA AGATTTACTT GGAAAAATCC AGGATCCAAT TATCAAGTCC AATGCCAAAG    2460
AGACTCTCAC AGGATTAAAA AATAATTTAC TATTTGGCAC CCAGGACAAC AATACTATTA    2520
TGGCAGAAGC TGAAAAACTA TTGGCTTTAT TAAAGGAGAG TAAGTAAAGG TAGCAGCATT    2580
TTCTAACTCC TAAAAACAGG ATAGGAGAAC GGGAAAACGA AAAATGAGAG CAGAATGTGA    2640
GTTCTAG     (SED ID NO : 12)                                         2647
```

FIG. 15

```
GGGTCTTAAA ACTCTGAATC CTTTAGAGGC AGACCCACAA AATGACAAGA CCTATTTAGA      60
AAATCTGGAA GAAAATATGA GTGTTCTAGC AGAAGAATTA AAGTGAGGAA AGAATGAAAA     120
TCAATAAAAA ATATCTAGCA GGTTCAGTGG CAGTCCTTGC CCTAAGTGTT TGTTCCTATG     180
AACTTGGTCG TCACCAAGCT GGTCAGGTTA AGAAAGAGTC TAATCGAGTT TCTTATATAG     240
ATGGTGATCA GGCTGGTCAA AAGGCAGAAA ATTTGACACC AGATGAAGTC AGTAAGAGAG     300
AGGGGATCAA CGCCGAACAA ATTGTTATCA AGATTACGGA TCAAGGTTAT GTGACCTCTC     360
ATGGAGACCA TTATCATTAC TATAATGGCA AGGTTCCTTA TGATGCCATC ATCAGTGAAG     420
AACTTCTCAT GAAAGATCCG AATTATCAGT TGAAGGATTC AGACATTGTC AATGAAATCA     480
AGGGTGGCTA TGTGATTAAG GTAGACGGAA AATACTATGT TTACCTTAAA GATGCGGCCC     540
ATGCGGACAA TATTCGGACA AAAGAAGAGA TTAAACGTCA GAAGCAGGAA CACAGTCATA     600
ATCATAACTC AAGAGCAGAT AATGCTGTTG CTGCAGCCAG AGCCCAAGGA CGTTATACAA     660
CGGATGATGG GTATATCTTC AATGCATCTG ATATCATTGA GGACACGGGT GATGCTTATA     720
TCGTTCCTCA CGGCGACCAT TACCATTACA TTCCTAAGAA TGAGTTATCA GCTAGCGAGT     780
TAGCTGCTGC AGAAGCCTAT TGGAATGGGA AGCAGGGATC TCGTCCTTCT TCAAGTTCTA     840
GTTATAATGC AAATCCAGTT CAACCAAGAT TGTCAGAGAA CCACAATCTG ACTGTCACTC     900
CAACTTATCA TCAAAATCAA GGGGAAAACA TTTCAAGCCT TTTACGTGAA TTGTATGCTA     960
AACCCTTATC AGAACGCCAT GTAGAATCTG ATGGCCTTAT TTTCGACCCA GCGCAAATCA    1020
CAAGTCGAAC CGCCAGAGGT GTAGCTGTCC CTCATGGTAA CCATTACCAC TTTATCCCTT    1080
ATGAACAAAT GTCTGAATTG GAAAACGAA TTGCTCGTAT TATTCCCCTT CGTTATCGTT      1140
CAAACCATTG GGTACCAGAT TCAAGACCAG AACAACCAAG TCCACAATCG ACTCCGGAAC    1200
CTAGTCCAAG TCTGCAACCT GCACCAAATC CTCAACCAGC TCCAAGCAAT CCAATTGATG    1260
AGAAATTGGT CAAAGAAGCT GTTCGAAAAG TAGGCGATGG TTATGTCTTT GAGGAGAATG    1320
GAGTTTCTCG TTATATCCCA GCCAAGGATC TTTCAGCAGA AACAGCAGCA GGCATTGATA    1380
GCAAACTGGC CAAGCAGGAA AGTTTATCTC ATAAGCTAGG AGCTAAGAAA ACTGACCTCC    1440
CATCTAGTGA TCGAGAATTT TACAATAAGG CTTATGACTT ACTACCAAGA ATTCACCAAG    1500
ATTTACTTGA TAATAAAGGT CGACAAGTTG ATTTTGAGGT TTTGGATAAC CTGTTGGAAC    1560
GACTCAAGGA TGTCTCAAGT GATAAAGTCA AGTTAGTGGA TGATATTCTT GCCTTCTTAG    1620
CTCCGATTCG TCATCCAGAA CGTTTAGGAA AACCAAATGC GCAAATTACC TACACTGATG    1680
ATGAGATTCA AGTAGCCAAG TTGGCAGGCA AGTACACAAC AGAAGACGGT TATATCTTTG    1740
ATCCTCGTGA TATAACCAGT GATGAGGGGG ATGCCTATGT AACTCCACAT ATGACCCATA    1800
GCCACTGGAT TAAAAAAGAT AGTTTGTCTG AAGCTGAGAG AGCGGCAGCC AGGCTTATG     1860
CTAAAGAGAA AGGTTTGACC CCTCCTTCGA CAGACCACCA GGATTCAGGA AATACTGAGG    1920
CAAAAGGAGC AGAAGCTATC TACAACCGCG TGAAAGCAGC TAAGAAGGTG CCACTTGATC    1980
GTATGCCTTA CAATCTTCAA TATACTGTAG AAGTCAAAAA CGGTAGTTTA ATCATACCTC    2040
ATTATGACCA TTACCATAAC ATCAAATTTG AGTGGTTTGA CGAAGGCCTT TATGAGGCAC    2100
CTAAGGGGTA TAGTCTTGAG GATCTTTTGG CGACTGTCAA GTACTATGTC GAACATCCAA    2160
ACGAACGTCC GCATTCAGAT AATGGTTTTG GTAACGCTAG TGACCATGTT CGTAAAAATA    2220
AGGCAGACCA AGATAGTAAA CCTGATGAAG ATAAGGAACA TGATGAAGTA AGTGAGCCAA    2280
CTCACCCTGA ATCTGATGAA AAAGAGAATC ACGCTGGTTT AAATCCTTCA GCAGATAATC    2340
TTTATAAACC AAGCACTGAT ACGGAAGAGA CAGAGGAAGA AGCTGAAGAT ACCACAGATG    2400
AGGCTGAAAT TCCTCAAGTA GAGAATTCTG TTATTAACGC TAAGATAGCA GATGCGGAGG    2460
CCTTGCTAGA AAAAGTAACA GATCCTAGTA TTAGACAAAA TGCTATGGAG ACATTGACTG    2520
GTCTAAAAAG TAGTCTTCTT CTCGGAACGA AAGATAATAA CACTATTTCA GCAGAAGTAG    2580
ATAGTCTCTT GGCTTTGTTA AAAGAAAGTC AACCGGCTCC TATACAGTAG TAAAATGAA    2639
(SEQ ID NO : 13)
```

*FIG. 16*

```
MKINKKYLAG SVAVLALSVC SYELGRHQAG QVKKESNRVS YIDGDQAGQK      50
AENLTPDEVS KREGINAEQI VIKITDQGYV TSHGDHYHYY NGKVPYDAII     100
SEELLMKDPN YQLKDSDIVN EIKGGYVIKV DGKYYVYLKD AAHADNIRTK     150
EEIKRQKQEH SHNHNSRADN AVAAARAQGR YTTDDGYIFN ASDIIEDTGD     200
AYIVPHGDHY HYIPKNELSA SELAAAEAYW NGKQGSRPSS SSSYNANPVQ     250
PRLSENHNLT VTPTYHQNQG ENISSLLREL YAKPLSERHV ESDGLIFDPA     300
QITSRTARGV AVPHGNHYHF IPYEQMSELE KRIARIIPLR YRSNHWVPDS     350
RPEQPSPQST PEPSPSLQPA PNPQPAPSNP IDEKLVKEAV RKVGDGYVFE     400
ENGVSRYIPA KDLSAETAAG IDSKLAKQES LSHKLGAKKT DLPSSDREFY     450
NKAYDLLARI HQDLLDNKGR QVDFEVLDNL LERLKDVSSD KVKLVDDILA     500
FLAPIRHPER LGKPNAQITY TDDEIQVAKL AGKYTTEDGY IFDPRDITSD     550
EGDAYVTPHM THSHWIKKDS LSEAERAAAQ AYAKEKGLTP PSTDHQDSGN     600
TEAKGAEAIY NRVKAAKKVP LDRMPYNLQY TVEVKNGSLI IPHYDHYHNI     650
KFEWFDEGLY EAPKGYSLED LLATVKYYVE HPNERPHSDN GFGNASDHVR     700
KNKADQDSKP DEDKEHDEVS EPTHPESDEK ENHAGLNPSA DNLYKPSTDT     750
EETEEEAEDT TDEAEIPQVE NSVINAKIAD AEALLEKVTD PSIRQNAMET     800
LTGLKSSLLL GTKDNNTISA EVDSLLALLK ESQPAPIQ                 838
(SEQ ID NO : 14)
```

FIG. 17

```
TGTGCCTATG CACTAAACCA GCATCGTTCG CAGGAAAATA AGGACAATAA TCGTGTCTCT    60
TATGTGGATG GCAGCCAGTC AAGTCAGAAA AGTGAAAACT TGACACCAGA CCAGGTTAGC   120
CAGAAAGAAG GAATTCAGGC TGAGCAAATT GTAATCAAAA TTACAGATCA GGGCTATGTA   180
ACGTCACACG GTGATCACTA TCATTACTAT AATGGGAAAG TTCCTTATGA TGCCCTCTTT   240
AGTGAAGAAC TCTTGATGAA GGATCCAAAC TATCAACTTA AAGACGCTGA TATTGTCAAT   300
GAAGTCAAGG GTGGTTATAT CATCAAGGTC GATGGAAAAT ATTATGTCTA CCTGAAAGAT   360
GCAGCTCATG CTGATAATGT TCGAACTAAA GATGAAATCA ATCGTCAAAA ACAAGAACAT   420
GTCAAAGATA ATGAGAAGGT TAACTCTAAT GTTGCTGTAG CAAGGTCTCA GGGACGATAT   480
ACGACAAATG ATGGTTATGT CTTTAATCCA GCTGATATTA TCGAAGATAC GGGTAATGCT   540
TATATCGTTC CTCATGGAGG TCACTATCAC TACATTCCCA AAAGCGATTT ATCTGCTAGT   600
GAATTAGCAG CAGCTAAAGC ACATCTGGCT GGAAAAAATA TGCAACCGAG TCAGTTAAGC   660
TATTCTTCAA CACCTTCTCC ATCTCTTCCA ATCAATCCAG GAACTTCACA TGAGAAACAT   720
GAAGAAGATG GATACGGATT TGATGCTAAT CGTATTATCG CTGAAGATGA ATCAGGTTTT   780
GTCATGAGTC ACGGAGACCA CAATCATTAT TTCTTCAAGA AGGACTTGAC AGAAGAGCAA   840
ATTAAGGCTG CGCAAAAACA TTTAGAGGAA GTTAAAACTA GTCATAATGG ATTAGATTCT   900
TTGTCATCTC ATGAACAGGA TTATCCAAGT AATGCCAAAG AAATGAAAGA TTTAGATAAA   960
AAAATCGAAG AAAAAATTGC TGGCATTATG AAACAATATG GTGTCAAACG TGAAAGTATT  1020
GTCGTGAATA AAGAAAAAAA TGCGATTATT TATCCGCATG GAGATCACCA TCATGCAGAT  1080
CCGATTGATG AACATAAACC GGTTGGAATT GGTCATTCTC ACAGTAACTA TGAACTGTTT  1140
AAACCCGAAG AAGGAGTTGC TAAAAAAGAA GGGAATAAAG TTTATACTGG AGAAGAATTA  1200
ACGAATGTTG TTAATTTGTT AAAAAAATAGT ACGTTTAATA ATCAAAACTT TACTCTAGCC  1260
AATGGTCAAA AACGCGTTTC TTTTAGTTTT CCGCCTGAAT TGGAGAAAAA ATTAGGTATC  1320
AATATGCTAG TAAAATTAAT AACACCAGAT GGAAAAGTAT TGGAGAAAGT ATCTGGTAAA  1380
GTATTTGGAG AAGGAGTAGG GAATATTGCA AACTTTGAAT TAGATCAACC TTATTTACCA  1440
GGACAAACAT TTAAGTATAC TATCGCCTTCA AAAGATTATC CAGAAGTAAG TTATGATGGT  1500
ACATTTACAG TTCCAACCTC TTTAGCTTAC AAAATGGCCA GTCAAACGAT TTTCTATCCT  1560
TTCCATGCAG GGGATACTTA TTTAAGAGTG AACCCTCAAT TTGCAGTGCC TAAAGGAACT  1620
GATGCTTTAG TCAGAGTGTT TGATGAATTT CATGGAAATG CTTATTTAGA AAATAACTAT  1680
AAAGTTGGTG AAATCAAATT ACCGATTCCG AAATTAAACC AAGGAACAAC CAGAACGGCC  1740
GGAAATAAAA TTCCTGTAAC CTTCATGGCA AATGCTTATT TGGACAATCA ATCGACTTAT  1800
ATTGTGGAAG TACCTATCTT GGAAAAAGAA AATCAAACTG ATAAACCAAG TATTCTACCA  1860
CAATTTAAAA GGAATAAAGC ACAAGAAAAC TCAAAACTTG ATGAAAAGGT AGAAGAACCA  1920
AAGACTAGTG AGAAGGTAGA AAAAGAAAAA CTTTCTGAAA CTGGGAATAG TACTAGTAAT  1980
TCAACGTTAG AAGAAGTTCC TACAGTGGAT CCTGTACAAG AAAAAGTAGC AAAATTTGCT  2040
GAAAGTTTAG GGATGAAGCT AGAAAATGTC TTGTTTAATA TGGACGGAAC AATTGAATTA  2100
TATTTACCAT CGGGAGAAGT CATTAAAAAG AATATGGCAG ATTTTACAGG AGAAGCACCT  2160
CAAGGAAATG GTGAAAATAA ACCATCTGAA AATGGAAAAG TATCTACTGG AACAGTTGAG  2220
AACCAACCAA CAGAAAATAA ACCAGCAGAT TCTTTACCAG AGGCACCAAA CGAAAAACCT  2280
GTAAAACCAG AAAACTCAAC GGATAATGGA ATGTTGAATC CAGAAGGGAA TGTGGGGAGT  2340
GACCCTATGT TAGATTCAGC ATTAGAGGAA GCTCCAGCAG TAGATCCTGT ACAAGAAAAA  2400
TTAGAAAAAT TTACAGCTAG TTACGGATTA GGCTTAGATA GTGTTATATT CAATATGGAT  2460
GGAACGATTG AATTAAGATT GCCAAGTGGA GAAGTGATAA AAAAGAATTT ATTGATCTCA  2520
TAGCGTAA    (SEQ ID NO : 15)                                      2528
```

FIG. 18

| | | | | | |
|---|---|---|---|---|---|
|CAYALNQHRS|QENKDNNRVS|YVDGSQSSQK|SENLTPDQVS|QKEGIQAEQI|50|
|VIKITDQGYV|TSHGDHYHYY|NGKVPYDALF|SEELLMKDPN|YQLKDADIVN|100|
|EVKGGYIIKV|DGKYYVYLKD|AAHADNVRTK|DEINRQKQEH|VKDNEKVNSN|150|
|VAVARSQGRY|TTNDGYVFNP|ADIIEDTGNA|YIVPHGGHYH|YIPKSDLSAS|200|
|ELAAAKAHLA|GKNMQPSQLS|YSSTPSPSLP|INPGTSHEKH|EEDGYGFDAN|250|
|RIIAEDESGF|VMSHGDHNHY|FFKKDLTEEQ|IKAAQKHLEE|VKTSHNGLDS|300|
|LSSHEQDYPS|NAKEMKDLDK|KIEEKIAGIM|KQYGVKRESI|VVNKEKNAII|350|
|YPHGDHHHAD|PIDEHKPVGI|GHSHSNYELF|KPEEGVAKKE|GNKVYTGEEL|400|
|TNVVNLLKNS|TFNNQNFTLA|NGQKRVSFSF|PPELEKKLGI|NMLVKLITPD|450|
|GKVLEKVSGK|VFGEGVGNIA|NFELDQPYLP|GQTFKYTIAS|KDYPEVSYDG|500|
|TFTVPTSLAY|KMASQTIFYP|FHAGDTYLRV|NPQFAVPKGT|DALVRVFDEF|550|
|HGNAYLENNY|KVGEIKLPIP|KLNQGTTRTA|GNKIPVTFMA|NAYLDNQSTY|600|
|IVEVPILEKE|NQTDKPSILP|QFKRNKAQEN|SKLDEKVEEP|KTSEKVEKEK|650|
|LSETGNSTSN|STLEEVPTVD|PVQEKVAKFA|ESYGMKLENV|LFNMDGTIEL|700|
|YLPSGEVIKK|NMADFTGEAP|QGNGENKPSE|NGKVSTGTVE|NQPTENKPAD|750|
|SLPEAPNEKP|VKPENSTDNG|MLNPEGNVGS|DPMLDSALEE|APAVDPVQEK|800|
|LEKFTASYGL|GLDSVIFNMD|GTIELRLPSG|EVIKKNLLIS| |840|
|(SEQ ID NO : 16)| | | | | |

FIG. 19

| | | | | | |
|---|---|---|---|---|---|
|CAYALNQHRS|QENKDNNRVS|YVDGSQSSQK|SENLTPDQVS|QKEGIQAEQI|50|
|VIKITDQGYV|TSHGDHYHYY|NGKVPYDALF|SEELLMKDPN|YQLKDADIVN|100|
|EVKGGYIIKV|DGKYYVYLKD|AAHADNVRTK|DEINRQKQEH|VKDNEKVNSN|150|
|VAVARSQGRY|TTNDGYVFNP|ADIIEDTGNA|YIVPHGGHYH|YIPKSDLSAS|200|
|ELAAAKAHLA|GKNMQPSQLS|YSSTASDNNT|QSVAKGSTSK|PANKSENLQS|250|
|LLKELYDSPS|AQRYSESDGL|VFDPAKIISR|TPNGVAIPHG|DHYHFIPYSK|300|
|LSALEEKIAR|MVPISGTGST|VSTNAKPNEV|VSSLGSLSSN|PSSLTTSKEL|350|
|SSASDGYIFN|PKDIVEETAT|AYIVRHGDHF|HYIPKSNQIG|QPTLPNNSLA|400|
|TPSPSLPINP|GTSHEKHEED|GYGFDANRII|AEDESGFVMS|HGDHNHYFFK|450|
|KDLTEEQIKA|AQKHLEEVKT|SHNGLDSLSS|HEQDYPGNAK|EMKDLDKKIE|500|
|EKIAGIMKQY|GVKRESIVVN|KEKNAIIYPH|GDHHHADPID|EHKPVGIGHS|550|
|HSNYELFKPE|EGVAKKEGNK|VYTGEELTNV|VNLLKNSTFN|NQNFTLANGQ|600|
|KRVSFSFPPE|LEKKLGINML|VKLITPDGKV|LEKVSGKVFG|EGVGNIANFE|650|
|LDQPYLPGQT|FKYTIASKDY|PEVSYDGTFT|VPTSLAYKMA|SQTIFYPFHA|700|
|GDTYLRVNPQ|FAVPKGTDAL|VRVFDEFHGN|AYLENNYKVG|EIKLPIPKLN|750|
|QGTTRTAGNK|IPVTFMANAY|LDNQSTYIVE|VPILEKENQT|DKPSILPQFK|800|
|RNKAQENSKL|DEKVEEPKTS|EKVEKEKLSE|TGNSTSNSTL|EEVPTVDPVQ|850|
|EKVAKFAESY|GMKLENVLFN|MDGTIELYLP|SGEVIKKNMA|DFTGEAPQGN|900|
|GENKPSENGK|VSTGTVENQP|TENKPADSLP|EAPNEKPVKP|ENSTDNGMLN|950|
|PEGNVGSDPM|LDPALEEAPA|VDPVQEKLEK|FTASYGLGLD|SVIFNMDGTI|1000|
|ELRLPSGEVI|KKNLSDFIA|(SEQ ID NO : 55)| | |1019|

FIG. 20

```
CAYALNQHRS  QENKDNNRVS  YVDGSQSSQK  SENLTPDQVS  QKEGIQAEQI   50
VIKITDQGYV  TSHGDHYHYY  NGKVPYDALF  SEELLMKDPN  YQLKDADIVN  100
EVKGGYIIKV  DGKYYVYLKD  AAHADNVRTK  DEINRQKQEH  VKDNEKVNSN  150
VAVARSQGRY  TTNDGYVFNP  ADIIEDTGNA  YIVPHGGHYH  YIPKSDLSAS  200
ELAAAKAHLA  GKNMQPSQLS  YSSTASDNNT  QSVAKGSTSK  PANKSENLQS  250
LLKELYDSPS  AQRYSESDGL  VFDPAKIISR  TPNGVAIPHG  DHYHFIPYSK  300
LSALEEKIAR  MVPISGTGST  VSTNAKPNEV  VSSLGSLSSN  PSSLTTSKEL  350
SSASDGYIFN  PKDIVEETAT  AYIVRHGDHF  HYIPKSNQIG  QPTLPNNSLA  400
TPSPSLPINP  GTSHEKHEED  GYGFDANRII  AEDESGFVMS  HGDHNHYFFK  450
KDLTEEQIKA  AQKHLEEVKT  SHNGLDSLSS  HEQDYPGNA              489
(SEQ ID NO : 56)
```

FIG. 21

```
MKFSKKYIAA  GSAVIVSLSL  CAYALNQHRS  QENKDNNRVS  YVDGSQSSQK  SENLTPDQVS
QKEGIQAEQI  VIKITDQGYV  TSHGDHYHYY  NGKVPYDALF  SEELLMKDPN  YQLKDADIVN
EVKGGYIIKV  DGKYYVYLKD  AAHADNVRTK  DEINRQKQEH  VKDNEKVNSN  VAVARSQGRY
TTNDGYVFNP  ADIIEDTGNA  YIVPHGGHYH  YIPKSDLSAS  ELAAAKAHLA  GKNMQPSQLS
YSSTASDNNT  QSVAKGSTSK  PANKSENLQS  LLKELYDSPS  AQRYSESDGL  VFDPAKIISR
TPNGVAIPHG  DHYHFIPYSK  LSALEEKIAR  MVPISGTGST  VSTNAKPNEV  VSSLGSLSSN
PSSLTTSKEL  SSASDGYIFN  PKDIVEETAT  AYIVRHGDHF  HYIPKSNQIG  QPTLPNNSLA
TPSPSLPINP  GTSHEKHEED  GYGFDANRII  AEDESGFVMS  HGDHNHYFFK  KDLTEEQIKA
AQKHLEEVKT  SHNGLDSLSS  HEQDYPGNA   (SEQ ID NO : 57)
```

FIG. 22

```
DLTEEQIKAA  QKHLEEVKTS  HNGLDSLSSH  EQDYPGNAKE  MKDLDKKIEE    50
KIAGIMKQYG  VKRESIVVNK  EKNAIIYPHG  DHHHADPIDE  HKPVGIGHSH   100
SNYELFKPEE  GVAKKEGNKV  YTGEELTNVV  NLLKNSTFNN  QNFTLANGQK   150
RVSFSFPPEL  EKKLGINMLV  KLITPDGKVL  EKVSGKVFGE  GVGNIANFEL   200
DQPYLPGQTF  KYTIASKDYP  EVSYDGTFTV  PTSLAYKMAS  QTIFYPFHAG   250
DTYLRVNPQF  AVPKGTDALV  RVFDEFHGNA  YLENNYKVGE  IKLPIPKLNQ   300
GTTRTAGNKI  PVTFMANAYL  DNQSTYIVEV  PILEKENQTD  KPSILPQFKR   350
NKAQENSKLD  EKVEEPKTSE  KVEKEKLSET  GNSTSNSTLE  EVPTVDPVQE   400
KVAKFAESYG  MKLENVLFNM  DGTIELYLPS  GEVIKKNMAD  FTGEAPQGNG   450
ENKPSENGKV  STGTVENQPT  ENKPADSLPE  APNEKPVKPE  NSTDNGMLNP   500
EGNVGSDPML  DPALEEAPAV  DPVQEKLEKF  TASYGLGLDS  VIFNMDGTIE   550
LRLPSGEVIK  KNLSDFIAKL  RYRSNHWVPD  SRPEEPSPQP  TPEPSPSPQP   600
APNPQPAPSN  PIDEKLVKEA  VRKVGDGYVF  EENGVSRYIP  AKNLSAETAA   650
GIDSKLAKQE  SLSHKLGAKK  TDLPSSDREF  YNKAYDLLAR  IHQDLLDNKG   700
RQVDFEALDN  LLERLKDVSS  DKVKLVDDIL  AFLAPIRHPE  RLGKPNAQIT   750
YTDDEIQVAK  LAGKYTTEDG  YIFDPRDITS  DEGDAYVTPH  MTHSHWIKKD   800
SLSEAERAAA  QAYAKEKGLT  PPSTDHQDSG  NTEAKGAEAI  YNRVKAAKKV   850
PLDRMPYNLQ  YTVEVKNGSL  IIPHYDHYHN  IKFEWFDEGL  YEAPKGYTLE   900
DLLATVKYYV  EHPNERPHSD  NGFGNASDHV  QRNKNGQADT  NQTEKPSEEK   950
PQTEKPEEET  PREEKPQSEK  PESPKPTEEP  EEESPEESEE  PQVETEKVEE  1000
KLREAEDLLG  KIQDPIIKSN  AKETLTGLKN  NLLFGTQDNN  TIMAEAEKLL  1050
ALLKESK  (SEQ ID NO : 58)                                  1057
```

FIG. 23

```
CAYALNQHRS QENKDNNRVS YVDGSQSSQK SENLTPDQVS QKEGIQAEQI      50
VIKITDQGYV TSHGDHYHYY NGKVPYDALF SEELLMKDPN YQLKDADIVN     100
EVKGGYIIKV DGKYYVYLKD AAHADNVRTK DEINRQKQEH VKDNEKVNSN     150
VAVARSQGRY TTNDGYVFNP ADIIEDTGNA YIVPHGGHYH YIPKSDLSAS     200
ELAAA      (SEQ ID NO : 59)                                205
```

FIG. 24

```
CAYELGLHQA QTVKENNRVS YIDGKQATQK TENLTPDEVS KREGINAEQI      50
VIKITDQGYV TSHGDHYHYY NGKVPYDAII SEELLMKDPN YQLKDSDIVN     100
EIKGGYVIKV NGKYYVYLKD AAHADNVRTK EEINRQKQEH SQHREGGTSA     150
NDGAVAFARS QGRYTTDDGY IFNASDIIED TGDAYIVPHG DHYHYIPKNE     200
LSASELAAAE AFLSGRENLS NLRTYRRQNS DNTPRTNWVP SVSNPGTTNT     250
NTSNNSNTNS QASQSNDIDS LLKQLYKLPL SQRHVESDGL IFDPAQITSR     300
TARGVAVPHG NHYHFIPYEQ MSELEKRIAR IIPLRYRSNH WVPDSRPEEP     350
SPQPTPEPSP SPQPAPNPQP APSNPIDEKL VKEAVRKVGD GYVFEENGVS     400
RYIPAKNLSA ETAAGIDSKL AKQESLSHKL GAKKTDLPSS DREFYNKAYD     450
LLARIHQDLL DNKGRQVDFE ALDNLLERLK DVSSDKVKLV DDILAFLAPI     500
RHPERLGKPN AQITYTDDEI QVAKLAGKYT TEDGYIFDPR DITSDEGDAY     550
VTPHMTHSHW IKKDSLSEAE RAAAQAYAKE KGLTPPSTDH QDSGNTEAKG     600
AEAIYNRVKA AKKVPLDRMP YNLQYTVEVK NGSLIIPHYD HYHNIKFEWF     650
DEGLYEAPKG YTLEDLLATV KYYVEHPNER PHSDNGFGNA SDHVQRNKNG     700
QADTNQTEKP SEEKPQTEKP EEETPREEKP QSEKPESPKP TEEPEEESPE     750
ESEEPQVETE KVEEKLREAE DLLGKIQDPI IKSNAKETLT GLKNNLLFGT     800
QDNNTIMAEA EKLLALLKES K    ((SEQ ID NO : 60)                821
```

FIG. 25

```
CAYELGLHQA QTVKENNRVS YIDGKQATQK TENLTPDEVS KREGINAEQI      50
VIKITDQGYV TSHGDHYHYY NGKVPYDAII SEELLMKDPN YQLKDSDIVN     100
EIKGGYVIKV NGKYYVYLKD AAHADNVRTK EEINRQKQEH SQHREGGTSA     150
NDGAVAFARS QGRYTTDDGY IFNASDIIED TGDAYIVPHG DHYHYIPKNE     200
LSASELAAAE AFLSGRENLS NLRTYRRQNS DNTPRTNWVP SVSNPGTTNT     250
NTSNNSNTNS QASQSNDIDS LLKQLYKLPL SQRHVESDGL IFDPAQITSR     300
TARGVAVPHG NHYHFIPYEQ MSELEKRIAR IIPL                      334
(SEQ ID NO : 61)
```

FIG. 26

```
RYRSNHWVPD SRPEEPSPQP TPEPSPSPQP APNPQPAPSN PIDEKLVKEA      50
VRKVGDGYVF EENGVSRYIP AKNLSAETAA GIDSKLAKQE SLSHKLGAKK     100
TDLPSSDREF YNKAYDLLAR IHQDLLDNKG RQVDFEALDN LLERLKDVSS     150
DKVKLVDDIL AFLAPIRHPE RLGKPNAQIT YTDDEIQVAK LAGKYTTEDG     200
YIFDPRDITS DEGDAYVTPH MTHSHWIKKD SLSEAERAAA QAYAKEKGLT     250
PPSTDHQDSG NTEAKGAEAI YNRVKAAKKV PLDRMPYNLQ YTVEVKNGSL     300
IIPHYDHYHN IKFEWFDEGL YEAPKGYTLE DLLATVKYYV EHPNERPHSD     350
NGFGNASDHV QRNKNGQADT NQTEKPSEEK PQTEKPEEET PREEKPQSEK     400
PESPKPTEEP EEESPEESEE PQVETEKVEE KLREAEDLLG KIQDPIIKSN     450
AKETLTGLKN NLLFGTQDNN TIMAEAEKLL ALLKESK                   487
(SEQ ID NO : 62)
```

FIG. 27

```
AEAFLSGREN  LSNLRTYRRQ  NSDNTPRTNW  VPSVSNPGTT  NTNTSNNSNT     50
NSQASQSNDI  DSLLKQLYKL  PLSQRHVESD  GLIFDPAQIT  SRTARGVAVP    100
HGNHYHFIPY  EQMSELEKRI  ARIIPLRYRS  NHWVPDSRPE  EPSPQPTPEP    150
SPSPQPAPNP  QPAPSNPIDE  KLVKEAVRKV  GDGYVFEENG  VSRYIPAKNL    200
SAETAAGIDS  KLAKQESLSH  KLGAKKTDLP  SSDREFYNKA  YDLLARIHQD    250
LLDNKGRQVD  FEALDNLLER  LKDVSSDKVK  LVDDILAFLA  PIRHPERLGK    300
PNAQITYTDD  EIQVAKLAGK  YTTEDGYIFD  PRDITSDEGD  AYVTPHMTHS    350
HWIKKDSLSE  AERAAAQAYA  KEKGLTPPST  DHQDSGNTEA  KGAEAIYNRV    400
KAAKKVPLDR  MPYNLQYTVE  VKNGSLIIPH  YDHYHNIKFE  WFDEGLYEAP    450
KGYTLEDLLA  TVKYYVEHPN  ERPHSDNGFG  NASDHVQRNK  NGGQADTNQTE   500
KPSEEKPQTE  KPEEETPREE  KPQSEKPESP  KPTEEPEEES  PEESEEPQVE    550
TEKVEEKLRE  AEDLLGKIQD  PIIKSNAKET  LTGLKNNLLF  GTQDNNTIMA    600
EAEKLLALLK  ESK       (SEQ ID NO : 63)                        613
```

FIG. 28

```
DLTEEQIKAA  QKHLEEVKTS  HNGLDSLSSH  EQDYPGNAKE  MKDLDKKIEE     50
KIAGIMKQYG  VKRESIVVNK  EKNAIIYPHG  DHHHADPIDE  HKPVGIGHSH    100
SNYELFKPEE  GVAKKEGNKV  YTGEELTNVV  NLLKNSTFNN  QNFTLANGQK    150
RVSFSFPPEL  EKKLGINMLV  KLITPDGKVL  EKVSGKVFGE  GVGNIANFEL    200
DQPYLPGQTF  KYTIASKDYP  EVSYDGTFTV  PTSLAYKMAS  QTIFYPFHAG    250
DTYLRVNPQF  AVPKGTDALV  RVFDEFHGNA  YLENNYKVGE  IKLPIPKLNQ    300
GTTRTAGNKI  PVTFMANAYL  DNQSTYIVEV  PILEKENQTD  KPSILPQFKR    350
NKAQENSKLD  EKVEEPKTSE  KVEKEKLSET  GNSTSNSTLE  EVPTVDPVQE    400
KVAKFAESYG  MKLENVLFNM  DGTIELYLPS  GEVIKKNMAD  FTGEAPQGNG    450
ENKPSENGKV  STGTVENQPT  ENKPADSLPE  APNEKPVKPE  NSTDNGMLNP    500
EGNVGSDPML  DPALEEAPAV  DPVQEKLEKF  TASYGLGLDS  VIFNMDGTIE    550
LRLPSGEVIK  KNLSDFIA   (SEQ ID NO : 64)                       568
```

FIG. 29

```
DLTEEQIKAA  QKHLEEVKTS  HNGLDSLSSH  EQDYPGNAKE  MKDLDKKIEE     50
KIAGIMKQYG  VKRESIVVNK  EKNAIIYPHG  DHHHADPIDE  HKPVGIGHSH    100
SNYELFKPEE  GVAKKEGNKV  YTGEELTNVV  NLLKNSTFNN  QNFTLANGQK    150
RVSFSFPPEL  EKKLGINMLV  KLITPDGKVL  EKVSGKVFGE  GVGNIANFEL    200
DQPYLPGQTF  KYTIASKDYP  EVSYDGTFTV  PTSLAYKMAS  QTIFYPFHAG    250
DTYLRVNPQF  AVPKGTDALV  RVFDEFHGNA  YLENNYKVGE  IKLPIPKLNQ    300
GTTRTAGNKI  PVTFMANAYL  DNQSTYIVE  (SEQ ID NO : 65)           329
```

FIG. 30

```
EVPILEKENQ TDKPSILPQF KRNKAQENSK LDEKVEEPKT SEKVEKEKLS      50
ETGNSTSNST LEEVPTVDPV QEKVAKFAES YGMKLENVLF NMDGTIELYL     100
PSGEVIKKNM ADFTGEAPQG NGENKPSENG KVSTGTVENQ PTENKPADSL     150
PEAPNEKPVK PENSTDNGML NPEGNVGSDP MLDPALEEAP AVDPVQEKLE     200
KFTASYGLGL DSVIFNMDGT IELRLPSGEV IKKNLSDFIA                240
(SEQ ID NO : 66)
```

FIG. 31

```
DIDSLLKQLY KLPLSQRHVE SDGLIFDPAQ ITSRTARGVA VPHGNHYHFI      50
PYEQMSELEK RIARIIPLRY RSNHWVPDSR PEEPSPQPTP EPSPSPQPAP     100
NPQPAPSNPI DEKLVKEAVR KVGDGYVFEE NGVSRYIPAK NLSAETAAGI     150
DSKLAKQESL SHKLGAKKTD LPSSDREFYN KAYDLLARIH QDLLDNKGRQ     200
VDFEALDNLL ERLKDVSSDK VKLVDDILAF LAPIRHPERL GKPNAQITYT     250
DDEIQVAKLA GKYTTEDGYI FDPRDITSDE GDAYVTPHMT HSHWIKKDSL     300
SEAERAAAQA YAKEKGLTPP STDHQDSGNT EAKGAEAIYN RVKAAKKVPL     350
DRMPYNLQYT VEVKNGSLII PHYDHYHNIK FEWFDEGLYE APKGYTLEDL     400
LATVKYYVEH PNERPHSDNG FGNASDHVQR NKNGQADTNQ TEKPSEEKPQ     450
TEKPEEETPR EEKPQSEKPE SPKPTEEPEE ESPEESEEPQ VETEKVEEKL     500
REAEDLLGKI QDPIIKSNAK ETLTGLKNNL LFGTQDNNTI MAEAEKLLAL     550
LKESK   (SEQ ID NO : 67)                                  555
```

FIG. 32

```
DIDSLLKQLY KLPLSQRHVE SDGLIFDPAQ ITSRTARGVA VPHGNHYHFI      50
PYEQMSELEK RIARIIPLRY RSNHWVPDSR PEEPSPQPTP EPSPSPQPAP     100
NPQPAPSNPI DEKLVKEAVR KVGDGYVFEE NGVSRYIPAK NLSAETAAGI     150
DSKLAKQESL SHKLGAKKTD LPSSDREFYN KAYDLLARIH QDLLDNKGRQ     200
VDFEALDNLL ERLKDVSSDK VKLVDDILAF LAPIRHPERL GKPNAQITYT     250
DDEIQVAKLA GKYTTEDGYI FDPRDITSDE GDAYVTPHMT HSHWIKKDSL     300
SEAERAAAQA YAKEKGLTPP STDHQDSGNT EAKGAEAIYN RVKAAKKVPL     350
DRMPYNLQYT VEVKNGSLII PHYDHYHNIK FEWFDEGLYE APKGYTLEDL     400
LATVKYYVEH PNERPHSDNG FGNASDHV   (SEQ ID NO : 68)          428
```

FIG. 33

```
GLYEAPKGYT LEDLLATVKY YVEHPNERPH SDNGFGNASD HVQRNKNGQA      50
DTNQTEKPSE EKPQTEKPEE ETPREEKPQS EKPESPKPTE EPEEESPEES     100
EEPQVETEKV EEKLREAEDL L  (SEQ ID NO : 69)                 121
```

FIG. 34

```
ASDHVQRNKN GQADTNQTEK PSEEKPQTEK PEEETPREEK PQSEKPESPK      50
PTEEPEEESP EESEEPQVET EKVEEKLREA EDLLGKIQDP IIKSNAKETL     100
TGLKNNLLFG TQDNNTIMAE AEKLLALLKE SK                        132
(SEQ ID NO : 70)
```

FIG. 35

```
DIDSLLKQLY  KLPLSQRHVE  SDGLIFDPAQ  ITSRTARGVA  VPHGNHYHFI       50
PYEQMSELEK  RIARIIPLRY  RSNHWVPDSR  PEEPSPQPTP  EPSPSPQPAP      100
NPQPAPSNPI  DEKLVKEAVR  KVGDGYVFEE  NGVSRYIPAK  NLSAETAAGI      150
DSKLAKQESL  SHKLGAKKTD  LPSSDREFYN  KAYDLLARIH  QDLLDNKGRQ      200
VDFEALDNLL  ERLKDVSSDK  VKLVDD       (SEQ ID NO : 71)           226
```

FIG. 36

```
DILAFLAPIR  HPERLGKPNA  QITYTDDEIQ  VAKLAGKYTT  EDGYIFDPRD       50
ITSDEGDAYV  TPHMTHSHWI  KKDSLSEAER  AAAQAYAKEK  GLTPPSTDHQ      100
DSGNTEAKGA  EAIYNRVKAA  KKVPLDRMPY  NLQYTVEVKN  GSLIIPHYDH      150
YHNIKFEWFD  EGLYEAPKGY  TLEDLLATVK  YYVEHPNERP  HSDNGFGNAS      200
DHV    (SEQ ID NO : 72)                                         203
```

FIG. 37

```
CSYELGRHQA  GQVKKESNRV  SYIDGDQAGQ  KAENLTPDEV  SKREGINAEQ       50
IVIKITDQGY  VTSHGDHYHY  YNGKVPYDAI  ISEELLMKDP  NYQLKDSDIV      100
NEIKGGYVIK  VDGKYYVYLK  DAAHADNIRT  KEEIKRQKQE  HSHNHNSRAD      150
NAVAAARAQG  RYTTDDGYIF  NASDIIEDTG  DAYIVPHGDH  YHYIPKNELS      200
ASELAAAEAY  WNGKQGSRPS  SSSSYNANPV  QPRLSENHNL  TVTPTYHQNQ      250
GENISSLLRE  LYAKPLSERH  VESDGLIFDP  AQITSRTARG  VAVPHGNHYH      300
FIPYEQMSEL  EKRIARIIPL  RYRSNHWVPD  SRPEQPSPQS  TPEPSPSLQP      350
APNPQPAPSN  PIDEKLVKEA  VRKVGDGYVF  EENGVSRYIP  AKDLSAETAA      400
GIDSKLAKQE  SLSHKLGAKK  TDLPSSDREF  YNKAYDLLAR  IHQDLLDNKG      450
RQVDFEVLDN  LLERLKDVSS  DKVKLVDDIL  AFLAPIRHPE  RLGKPNAQIT      500
YTDDEIQVAK  LAGKYTTEDG  YIFDPRDITS  DEGDAYVTPH  MTHSHWIKKD      550
SLSEAERAAA  QAYAKEKGLT  PPSTDHQDSG  NTEAKGAEAI  YNRVKAAKKV      600
PLDRMPYNLQ  YTVEVKNGSL  IIPHYDHYHN  IKFEWFDEGL  YEAPKGYSLE      650
DLLATVKYYV  EHPNERPHSD  NGFGNASDHV  RKNKADQDSK  PDEDKEHDEV      700
SEPTHPESDE  KENHAGLNPS  ADNLYKPSTD  TEETEEEAED  TTDEAEIPQV      750
ENSVINAKIA  DAEALLEKVT  DPSIRQNAME  TLTGLKSSLL  LGTKDNNTIS      800
AEVDSLLALL  KESQPAPIQ    (SEQ ID NO : 73)                       819
```

FIG. 38

```
ENISSLLREL  YAKPLSERHV  ESDGLIFDPA  QITSRTARGV  AVPHGNHYHF       50
IPYEQMSELE  KRIARIIPLR  YRSNHWVPDS  RPEQPSPQST  PEPSPSLQPA      100
PNPQPAPSNP  IDEKLVKEAV  RKVGDGYVFE  ENGVSRYIPA  KDLSAETAAG      150
IDSKLAKQES  LSHKLGAKKT  DLPSSDREFY  NKAYDLLARI  HQDLLDNKGR      200
QVDFEVLDNL  LERLKDVSSD  KVKLVDDILA  FLAPIRHPER  LGKPNAQITY      250
TDDEIQVAKL  AGKYTTEDGY  IFDPRDITSD  EGDAYVTPHM  THSHWIKKDS      300
LSEAERAAAQ  AYAKEKGLTP  PSTDHQDSGN  TEAKGAEAIY  NRVKAAKKVP      350
LDRMPYNLQY  TVEVKNGSLI  IPHYDHYHNI  KFEWFDEGLY  EAPKGYSLED      400
LLATVKYYVE  HPNERPHSDN  GFGNASDHVR  KNKADQDSKP  DEDKEHDEVS      450
EPTHPESDEK  ENHAGLNPSA  DNLYKPSTDT  EETEEEAEDT  TDEAEIPQVE      500
NSVINAKIAD  AEALLEKVTD  PSIRQNAMET  LTGLKSSLLL  GTKDNNTISA      550
EVDSLLALLK  ESQPAPIQ    (SEQ ID NO : 74)                        568
```

FIG. 39

VRKNKADQDS KPDEDKEHDE VSEPTHPESD EKENHAGLNP SADNLYKPST 50
DTEETEEEAE DTTDEAEIPQ VENSVINAKI ADAEALLEKV TDPSIRQNAM 100
ETLTGLKSSL LLGTKDNNTI SAEVDSLLAL LKESQPAPIQ 140
(SEQ ID NO : 75)

*FIG. 40*

| | | | | | |
|---|---|---|---|---|---|
| GACTTGACAG | AAGAGCAAAT | TAAGGCTGCG | CAAAAACATT | TAGAGGAAGT | 50 |
| TAAAACTAGT | CATAATGGAT | TAGATTCTTT | GTCATCTCAT | GAACAGGATT | 100 |
| ATCCAGGTAA | TGCCAAAGAA | ATGAAAGATT | TAGATAAAAA | AATCGAAGAA | 150 |
| AAAATTGCTG | GCATTATGAA | ACAATATGGT | GTCAAACGTG | AAAGTATTGT | 200 |
| CGTGAATAAA | GAAAAAAATG | CGATTATTTA | TCCGCATGGA | GATCACCATC | 250 |
| ATGCAGATCC | GATTGATGAA | CATAAACCGG | TTGGAATTGG | TCATTCTCAC | 300 |
| AGTAACTATG | AACTGTTTAA | ACCCGAAGAA | GGAGTTGCTA | AAAAAGAAGG | 350 |
| GAATAAAGTT | TATACTGGAG | AAGAATTAAC | GAATGTTGTT | AATTTGTTAA | 400 |
| AAAATAGTAC | GTTAATAAT | CAAAACTTTA | CTCTAGCCAA | TGGTCAAAAA | 450 |
| CGCGTTTCTT | TTAGTTTTCC | GCCTGAATTG | GAGAAAAAAT | TAGGTATCAA | 500 |
| TATGCTAGTA | AAATTAATAA | CACCAGATGG | AAAAGTATTG | GAGAAAGTAT | 550 |
| CTGGTAAAGT | ATTTGGAGAA | GGAGTAGGGA | ATATTGCAAA | CTTTGAATTA | 600 |
| GATCAACCTT | ATTTACCAGG | ACAAACATTT | AAGTATACTA | TCGCTTCAAA | 650 |
| AGATTATCCA | GAAGTAAGTT | ATGATGGTAC | ATTTACAGTT | CCAACCTCTT | 700 |
| TAGCTTACAA | AATGGCCAGT | CAAACGATTT | TCTATCCTTT | CCATGCAGGG | 750 |
| GATACTTATT | TAAGAGTGAA | CCCTCAATTT | GCAGTGCCTA | AAGGAACTGA | 800 |
| TGCTTTAGTC | AGAGTGTTTG | ATGAATTTCA | TGGAAATGCT | TATTTAGAAA | 850 |
| ATAACTATAA | AGTTGGTGAA | ATCAAATTAC | CGATTCCGAA | ATTAAACCAA | 900 |
| GGAACAACCA | GAACGGCCGG | AAATAAAATT | CCTGTAACCT | TCATGGCAAA | 950 |
| TGCTTATTTG | GACAATCAAT | CGACTTATAT | TGTGGAAGTA | CCTATCTTGG | 1000 |
| AAAAAGAAAA | TCAAACTGAT | AAACCAAGTA | TTCTACCACA | ATTTAAAAGG | 1050 |
| AATAAAGCAC | AAGAAAACTC | AAAACTTGAT | GAAAAGGTAG | AAGAACCAAA | 1100 |
| GACTAGTGAG | AAGGTAGAAA | AAGAAAAACT | TTCTGAAACT | GGGAATAGTA | 1150 |
| CTAGTAATTC | AACGTTAGAA | GAAGTTCCTA | CAGTGGATCC | TGTACAAGAA | 1200 |
| AAAGTAGCAA | AATTTGCTGA | AAGTTATGGG | ATGAAGCTAG | AAAATGTCTT | 1250 |
| GTTTAATATG | GACGGAACAA | TTGAATTATA | TTTACCATCA | GGAGAAGTCA | 1300 |
| TTAAAAAGAA | TATGGCAGAT | TTTACAGGAG | AAGCACCTCA | AGGAAATGGT | 1350 |
| GAAAATAAAC | CATCTGAAAA | TGGAAAAGTA | TCTACTGGAA | CAGTTGAGAA | 1400 |
| CCAACCAACA | GAAAATAAAC | CAGCAGATTC | TTTACCAGAG | GCACCAAACG | 1450 |
| AAAAACCTGT | AAAACCAGAA | AACTCAACGG | ATAATGGAAT | GTTGAATCCA | 1500 |
| GAAGGGAATG | TGGGAGTGA | CCCTATGTTA | GATCCAGCAT | TAGAGGAAGC | 1550 |
| TCCAGCAGTA | GATCCTGTAC | AAGAAAAATT | AGAAAAATTT | ACAGCTAGTT | 1600 |
| ACGGATTAGG | CTTAGATAGT | GTTATATTCA | ATATGGATGG | AACGATTGAA | 1650 |
| TTAAGATTGC | CAAGTGGAGA | AGTGATAAAA | AAGAATTTAT | CTGATTTCAT | 1700 |
| AGCGAAGCTT | CGTTATCGTT | CAAACCATTG | GGTACCAGAT | TCAAGACCAG | 1750 |
| AAGAACCAAG | TCCACAACCG | ACTCCAGAAC | CTAGTCCAAG | TCCGCAACCT | 1800 |
| GCACCAAATC | CTCAACCAGC | TCCAAGCAAT | CCAATTGATG | AGAAATTGGT | 1850 |
| CAAAGAAGCT | GTTCGAAAAG | TAGGCGATGG | TTATGTCTTT | GAGGAGAATG | 1900 |
| GAGTTTCTCG | TTATATCCCA | GCCAAGAATC | TTTCAGCAGA | AACAGCAGCA | 1950 |
| GGCATTGATA | GCAAACTGGC | CAAGCAGGAA | AGTTTATCTC | ATAAGCTAGG | 2000 |
| AGCTAAGAAA | ACTGACCTCC | CATCTAGTGA | TCGAGAATTT | ACAATAAGG | 2050 |
| CTTATGACTT | ACTAGCAAGA | ATTCACCAAG | ATTTACTTGA | TAATAAAGGT | 2100 |
| CGACAAGTTG | ATTTTGAGGC | TTTGGATAAC | CTGTTGGAAC | GACTCAAGGA | 2150 |
| TGTCTCAAGT | GATAAAGTCA | AGTTAGTGGA | TGATATTCTT | GCCTTCTTAG | 2200 |
| CTCCGATTCG | TCATCCAGAA | CGTTTAGGAA | AACCAAATGC | GCAAATTACC | 2250 |
| TACACTGATG | ATGAGATTCA | AGTAGCCAAG | TTGGCAGGCA | AGTACACAAC | 2300 |
| AGAAGACGGT | TATATCTTTG | ATCCTCGTGA | TATAACCAGT | GATGAGGGGG | 2350 |
| ATGCCTATGT | AACTCCACAT | ATGACCCATA | GCCACTGGAT | TAAAAAGAT | 2400 |
| AGTTTGTCTG | AAGCTGAGAG | AGCGGCAGCC | CAGGCTTATG | CTAAAGAGAA | 2450 |
| AGGTTTGACC | CCTCCTTCGA | CAGACCATCA | GGATTCAGGA | AATACTGAGG | 2500 |
| CAAAAGGAGC | AGAAGCTATC | TACAACCGCG | TGAAAGCAGC | TAAGAAGGTG | 2550 |

*FIG. 41A*

```
CCACTTGATC GTATGCCTTA CAATCTTCAA TATACTGTAG AAGTCAAAAA    2600
CGGTAGTTTA ATCATACCTC ATTATGACCA TTACCATAAC ATCAAATTTG    2650
AGTGGTTTGA CGAAGGCCTT TATGAGGCAC CTAAGGGGTA TACTCTTGAG    2700
GATCTTTTGG CGACTGTCAA GTACTATGTC GAACATCCAA ACGAACGTCC    2750
GCATTCAGAT AATGGTTTTG GTAACGCTAG CGACCATGTT CAAAGAAACA    2800
AAAATGGTCA AGCTGATACC AATCAAACGG AAAAACCAAG CGAGGAGAAA    2850
CCTCAGACAG AAAAACCTGA GGAAGAAACC CCTCGAGAAG AGAAACCACA    2900
AAGCGAGAAA CCAGAGTCTC AAAAACCAAC AGAGGAACCA GAAGAAGAAT    2950
CACCAGAGGA ATCAGAAGAA CCTCAGGTCG AGACTGAAAA GGTTGAAGAA    3000
AAACTGAGAG AGGCTGAAGA TTTACTTGGA AAAATCCAGG ATCCAATTAT    3050
CAAGTCCAAT GCCAAGAGA CTCTCACAGG ATTAAAAAAT AATTTACTAT    3100
TTGGCACCCA GGACAACAAT ACTATTATGG CAGAAGCTGA AAAACTATTG    3150
GCTTTATTAA AGGAGAGTAA G    (SEQ ID NO : 76)              3171
```

*FIG. 41B*

```
EAYWNGKQGS RPSSSSSYNA NPVQPRLSEN HNLTVTPTYH QNQGENISSL     50
LRELYAKPLS ERHVESDGLI FDPAQITSRT ARGVAVPHGN HYHFIPYEQM    100
SELEKRIARI IPLRYRSNHW VPDSRPEQPS PQSTPEPSPS LQPAPNPQPA    150
PSNPIDEKLV KEAVRKVGDG YVFEENGVSR YIPAKDLSAE TAAGIDSKLA    200
KQESLSHKLG AKKTDLPSSD REFYNKAYDL LARIHQDLLD NKGRQVDFEV    250
LDNLLERLKD VSSDKVKLVD DILAFLAPIR HPERLGKPNA QITYTDDEIQ    300
VAKLAGKYTT EDGYIFDPRD ITSDEGDAYV TPHMTHSHWI KKDSLSEAER    350
AAAQAYAKEK GLTPPSTDHQ DSGNTEAKGA EAIYNRVKAA KKVPLDRMPY    400
NLQYTVEVKN GSLIIPHYDH YHNIKFEWFD EGLYEAPKGY SLEDLLATVK    450
YYVEHPNERP HSDNGFGNAS DHV    (SEQ ID NO : 77)             473
```

*FIG. 42*

```
CAYALNQHRS  QENKDNNRVS  YVDGSQSSQK  SENLTPDQVS  QKEGIQAEQI        50
VIKITDQGYV  TSHGDHYHYY  NGKVPYDALF  SEELLMKDPN  YQLKDADIVN       100
EVKGGYIIKV  DGKYYVYLKD  AAHADNVRTK  DEINRQKQEH  VKDNEKVNSN       150
VAVARSQGRY  TTNDGYVFNP  ADIIEDTGNA  YIVPHGGHYH  YIPKSDLSAS       200
ELAAAKAHLA  GKNMQPSQLS  YSSTASDNNT  QSVAKGSTSK  PANKSENLQS       250
LLKELYDSPS  AQRYSESDGL  VFDPAKIISR  TPNGVAIPHG  DHYHFIPYSK       300
LSALEEKIAR  MVPISGTGST  VSTNAKPNEV  VSSLGSLSSN  PSSLTTSKEL       350
SSASDGYIFN  PKDIVEETAT  AYIVRHGDHF  HYIPKSNQIG  QPTLPNNSLA       400
TPSPSLPINP  GTSHEKHEED  GYGFDANRII  AEDESGFVMS  HGDHNHYFFK       450
KDLTEEQIKA  AQKHLEEVKT  SHNGLDSLSS  HEQDYPGNAK  EMKDLDKKIE       500
EKIAGIMKQY  GVKRESIVVN  KEKNAIIYPH  GDHHHADPID  EHKPVGIGHS       550
HSNYELFKPE  EGVAKKEGNK  VYTGEELTNV  VNLLKNSTFN  NQNFTLANGQ       600
KRVSFSFPPE  LEKKLGINML  VKLITPDGKV  LEKVSGKVFG  EGVGNIANFE       650
LDQPYLPGQT  FKYTIASKDY  PEVSYDGTFT  VPTSLAYKMA  SQTIFYPFHA       700
GDTYLRVNPQ  FAVPKGTDAL  VRVFDEFHGN  AYLENNYKVG  EIKLPIPKLN       750
QGTTRTAGNK  IPVTFMANAY  LDNQSTYIVE     (SEQ ID NO : 78)         780
```

FIG. 43

```
CAYELGLHQA  QTVKENNRVS  YIDGKQATQK  TENLTPDEVS  KREGINAEQI        50
VIKITDQGYV  TSHGDHYHYY  NGKVPYDAII  SEELLMKDPN  YQLKDSDIVN       100
EIKGGYVIKV  NGKYYVYLKD  AAHADNVRTK  EEINRQKQEH  SQHREGGTSA       150
NDGAVAFARS  QGRYTTDDGY  IFNASDIIED  TGDAYIVPHG  DHYHIPKNE        200
LSASELAAAE  AFLSGRENLS  NLRTYRRQNS  DNTPRTNWVP  SVSNPGTTNT       250
NTSNNSNTNS  QASQSNDIDS  LLKQLYKLPL  SQRHVESDGL  IFDPAQITSR       300
TARGVAVPHG  NHYHFIPYEQ  MSELEKRIAR  IIPLRYRSNH  WVPDSRPEEP       350
SPQPTPEPSP  SPQPAPNPQP  APSNPIDEKL  VKEAVRKVGD  GYVFEENGVS       400
RYIPAKNLSA  ETAAGIDSKL  AKQESLSHKL  GAKKTDLPSS  DREFYNKAYD       450
LLARIHQDLL  DNKGRQVDFE  ALDNLLERLK  DVSSDKVKLV  DDILAFLAPI       500
RHPERLGKPN  AQITYTDDEI  QVAKLAGKYT  TEDGYIFDPR  DITSDEGDAY       550
VTPHMTHSHW  IKKDSLSEAE  RAAAQAYAKE  KGLTPPSTDH  QDSGNTEAKG       600
AEAIYNRVKA  AKKVPLDRMP  YNLQYTVEVK  NGSLIIPHYD  HYHNIKFEWF       650
DEGLYEAPKG  YTLEDLLATV  KYYVEHPNER  PHSDNGFGNA                   690
(SEQ ID NO : 79)
```

FIG. 44

```
GTGAAGAAAA CATATGGTTA TATCGGCTCA GTTGCTGCCA TTTTACTAGC TACTCATATT      60
GGAAGTTACC AACTTGGTAA GCATCATATG GGTCTAGCAA CAAAGGACAA TCAGATTGCC     120
TATATTGATG ACAGCAAAGG TAAGGCAAAA GCCCCTAAAA CAAACAAAAC GATGGATCAA     180
ATCAGTGCTG AAGAAGGCAT CTCTGCTGAA CAGATCGTAG TCAAAATTAC TGACCAAGGC     240
TATGTGACCT CACACGGTGA CCATTATCAT TTTTACAATG GGAAAGTTCC TTATGATGCG     300
ATTATTAGTG AAGAGTTGTT GATGACGGAT CCTAATTACC GTTTTAAACA ATCAGACGTT     360
ATCAATGAAA TCTTAGACGG TTACGTTATT AAAGTCAATG CAACTATTA TGTTTACCTC      420
AAGCCAGGTA GTAAGCGCAA AAACATTCGA ACCAAACAAC AAATTGCTGA GCAAGTAGCC     480
AAAGGAACTA AGAAGCTAA AGAAAAAGGT TTAGCTCAAG TGGCCCATCT CAGTAAAGAA      540
GAAGTTGCGG CAGTCAATGA AGCAAAAAGA CAAGGACGCT ATACTACAGA CGATGGCTAT     600
ATTTTTAGTC CGACAGATAT CATTGATGAT TTAGGAGATG CTTATTTAGT ACCTCATGGT     660
AATCACTATC ATTATATTCC TAAAAAGGAT TTGTCTCCAA GTGAGCTAGC TGCTGCACAA     720
GCCTACTGGA GTCAAAAACA AGGTCGAGGT GCTAGACCGT CTGATTACCG CCCGACACCA     780
GCCCCAGGTC GTAGGAAAGC CCCAATTCCT GATGTGACGC CTAACCCTGG ACAAGGTCAT     840
CAGCCAGATA ACGGTGGCTA TCATCCAGCG CCTCCTAGGC AAATGATGC GTCACAAAAC      900
AAACACCAAA GAGATGAGTT TAAAGGAAAA ACCTTTAAGG AACTTTTAGA TCAACTACAC     960
CGTCTTGATT TGAAATACCG TCATGTGGAA GAAGATGGGT TGATTTTTGA ACCGACTCAA    1020
GTGATCAAAT CAAACGCTTT TGGGTATGTG GTGCCTCATG GAGATCATTA TCATATTATC    1080
CCAAGAAGTC AGTTATCACC TCTTGAAATG GAATTAGCAG ATCGATACTT AGCTGGCCAA    1140
ACTGAGGACA ATGACTCAGG TTCAGAGCAT TCAAAACCAT CAGATAAAGA AGTGACACAT    1200
ACCTTTCTTG GTCATCGCAT CAAAGCTTAC GGAAAAGGCT TAGATGGTAA ACCATATGAT    1260
ACGAGTGATG CTTATGTTTT TAGTAAAGAA TCCATTCATT CAGTGGATAA ATCAGGAGTT    1320
ACAGCTAAAC ACGGAGATCA TTTCCACTAT ATAGGATTTG GAGAACTTGA ACAATATGAG    1380
TTGGATGAGG TCGCTAACTG GGTGAAAGCA AAAGGTCAAG CTGATGAGCT TGCTGCTGCT    1440
TTGGATCAGG AACAAGGCAA AGAAAAACCA CTCTTTGACA CTAAAAAAGT GAGTCGCAAA    1500
GTAACAAAAG ATGGTAAAGT GGGCTATATG ATGCCAAAAG ATGGTAAGGA CTATTTCTAT    1560
GCTCGTGATC AACTTGATTT GACTCAGATT GCCTTTGCCG AACAGAACT AATGCTTAAA    1620
GATAAGAAGC ATTACCGTTA TGACATTGTT GACACAGGTA TTGAGCCACG ACTTGCTGTA    1680
GATGTGTCAA GTCTGCCGAT GCATGCTGGT AATGCTACTT ACGATACTGG AAGTTCGTTT    1740
GTTATCCCAC ATATTGATCA TATCCATGTC GTTCCGTATT CATGGTTGAC GCGCGATCAG    1800
ATTGCAACAG TCAAGTATGT GATGCAACAC CCCGAAGTTC GTCCGGATGT ATGGTCTAAG    1860
CCAGGGCATG AAGAGTCAGG TTCGGTCATT CCAAATGTTA CGCCTCTTGA TAAACGTGCT    1920
GGTATGCCAA ACTGGCAAAT TATCCATTCT GCTGAAGAAG TTCAAAAAGC CCTAGCAGAA    1980
GGTCGTTTTG CAACACCAGA CGGCTATATT TTCGATCCAC GAGATGTTTT GGCCAAAGAA    2040
ACTTTTGTAT GGAAAGATGG CTCCTTTAGC ATCCCAAGAG CAGATGGCAG TTCATTGAGA    2100
ACCATTAATA AATCTGATCT ATCCCAAGCT GAGTGGCAAC AAGCTCAAGA GTTATTGGCA    2160
AAGAAAAATA CTGGTGATGC TACTGATACG GATAAACCCA AGAAAAGCA ACAGGCAGAT    2220
AAGAGCAATG AAAACCAACA GCCAAGTGAA GCCAGTAAAG AAGAAAAAGA ATCAGATGAC    2280
TTTATAGACA GTTTACCAGA CTATGGTCTA GATAGAGCAA CCCTAGAAGA TCATATCAAT    2340
CAATTAGCAC AAAAAGCTAA TATCGATCCT AAGTATCTCA TTTTCCAACC AGAAGGTGTC    2400
CAATTTTATA ATAAAAATGG TGAATTGGTA ACTTATGATA TCAAGACACT TCAACAAATA    2460
AACCCTTAA      (SEQ ID NO : 80)                                     2469
```

```
VKKTYGYIGS VAAILLATHI GSYQLGKHHM GLATKDNQIA YIDDSKGKAK        50
APKTNKTMDQ ISAEEGISAE QIVVKITDQG YVTSHGDHYH FYNGKVPYDA       100
IISEELLMTD PNYRFKQSDV INEILDGYVI KVNGNYYVYL KPGSKRKNIR       150
TKQQIAEQVA KGTKEAKEKG LAQVAHLSKE EVAAVNEAKR QGRYTTDDGY       200
IFSPTDIIDD LGDAYLVPHG NHYHYIPKKD LSPSELAAAQ AYWSQKQGRG       250
ARPSDYRPTP APGRRKAPIP DVTPNPGQGH QPDNGGYHPA PPRPNDASQN       300
KHQRDEFKGK TFKELLDQLH RLDLKYRHVE EDGLIFEPTQ VIKSNAFGYV       350
VPHGDHYHII PRSQLSPLEM ELADRYLAGQ TEDNDSGSEH SKPSDKEVTH       400
TFLGHRIKAY GKGLDGKPYD TSDAYVFSKE SIHSVDKSGV TAKHGDHFHY       450
IGFGELEQYE LDEVANWVKA KGQADELAAA LDQEQGKEKP LFDTKKVSRK       500
VTKDGKVGYM MPKDGKDYFY ARDQLDLTQI AFAEQELMLK DKKHYRYDIV       550
DTGIEPRLAV DVSSLPMHAG NATYDTGSSF VIPHIDHIHV VPYSWLTRDQ       600
IATVKYVMQH PEVRPDVWSK PGHEESGSVI PNVTPLDKRA GMPNWQIIHS       650
AEEVQKALAE GRFATPDGYI FDPRDVLAKE TFVWKDGSFS IPRADGSSLR       700
TINKSDLSQA EWQQAQELLA KKNTGDATDT DKPKEKQQAD KSNENQQPSE       750
ASKEEKESDD FIDSLPDYGL DRATLEDHIN QLAQKANIDP KYLIFQPEGV       800
QFYNKNGELV TYDIKTLQQI NPP   (SEQ ID NO : 81)                823
```

*FIG. 46*

```
GTGAAGAAAA CATATGGTTA TATCGGCTCA GTTGCTGCCA TTTTACTAGC TACTCATATT    60
GGAAGTTACC AACTTGGTAA GCATCATATG GGTCTAGCAA CAAAGGACAA TCAGATTGCC   120
TATATTGATG ATAGCAAAGG TAAGGCAAAA GCCCCTAAAA CAAACAAAAC GATGGATCAA   180
ATCAGTGCTG AAGAAGGCAT CTCTGCTGAA CAGATCGTAG TCAAAATTAC TGACCAAGGT   240
TATGTGACCT CACACGGTGA CCATTATCAT TTTTACAATG GGAAAGTTCC TTATGATGCG   300
ATTATTAGTG AAGAGTTGTT GATGACGGAT CCTAATTACC ATTTTAAACA ATCAGACGTT   360
ATCAATGAAA TCTTAGACGG TTACGTTATT AAAGTCAATG GCAACTATTA TGTTTACCTC   420
AAGCCAGGTA GTAAGCGCAA AAACATTCGA ACCAAACAAC AAATTGCTGA GCAAGTAGCC   480
AAAGGAACTA AGAAGCTAA AGAAAAAGGT TTAGCTCAAG TGGCCCATCT CAGTAAAGAA   540
GAAGTTGCGG CAGTCAATGA AGCAAAAAGA CAAGGACGCT ATACTACAGA CGATGGCTAT   600
ATTTTTAGTC CGACAGATAT CATTGATGAT TTAGGAGACG CTTATTTAGT ACCTCATGGT   660
AATCACTATC ATTATATTCC TAAAAAAGAT TTGTCTCCAA GTGAGCTAGC TGCTGCACAA   720
GCTTACTGGA GTCAAAAACA AGGTCGAGGT GCTAGACCGT CTGATTACCG CCCGACACCA   780
GCCCCAGGTC GTAGGAAAGC TCCAATTCCT GATGTGACGC CTAACCCTGG ACAAGGTCAT   840
CAGCCAGATA ACGGTGGCTA TCATCCAGCG CCTCCTAGGC CAAATGATGC GTCACAAAAC   900
AAACACCAAA GAGATGAGTT TAAAGGAAAA ACCTTTAAGG AACTTTTAGA TCAACTACAC   960
CGTCTTGATT TGAAATACCG TCATGTGGAA GAAGATGGGT TGATTTTTGA ACCGACTCAA  1020
GTGATCAAAT CAAACGCTTT TGGGTATGTG GTGCCTCATG GAGATCATTA TCATATTATC  1080
CCAAGAAGTC AGTTATCACC TCTTGAAATG GAATTAGCAG ATCGATACTT AGCCGGTCAA  1140
ACTGAGGACA ATGATTCAGG TTCAGATCAC TCAAAACCAT CAGATAAAGA AGTGACACAT  1200
ACCTTTCTTG GTCATCGCAT CAAAGCTTAC GGAAAAGGCT TAGATGGTAA ACCATATGAT  1260
ACGAGTGATG CTTATGTTTT TAGTAAAGAA TCCATTCATT CAGTGGATAA ATCAGGAGTT  1320
ACAGCTAAAC ACGGAGATCA TTTCCACTAT ATAGGATTTG GAGAACTTGA ACAATATGAG  1380
TTGATGAGG TCGCTAACTG GGTGAAAGCA AAAGGTCAAG CTGATGAGCT TGCTGCTGCT  1440
TTGGATCAGG AACAAGGCAA AGAAAAACCA CTCTTTGACA CTAAAAAAGT GAGTCGCAAA  1500
GTAACAAAAG ATGGTAAAGT GGGCTATATT ATGCCAAAAG ATGGCAAGGA CTATTTCTAT  1560
GCTCGTGATC AACTTGATTT GACTCAGATT GCCTTTGCCG AACAAGAACT AATGCTTAAA  1620
GATAAGAACC ATTACCGTTA TGACATTGTT GACACAGGTA TTGAGCCACG ACTTGCTGTA  1680
GATGTGTCAA GTCTGCCGAT GCATGCTGGT AATGCTACTT ACGATACTGG AAGTTCGTTT  1740
GTTATCCCTC ATATTGATCA TATCCATGTC GTTCCGTATT CATGGTTGAC GCGCGATCAG  1800
ATTGCAACAA TCAAGTATGT GATGCAACAC CCCGAAGTTC GTCCAGATGT ATGGTCTAAG  1860
CCAGGGCATG AAGAGTCAGG TTCGGTCATT CCAAATGTTA CGCCTCTTGA TAAACGTGCT  1920
GGTATGCCAA ATTGGCAAAT CATCCATTCT GCTGAAGAAG TTCAAAAAGC CCTAGCAGAA  1980
GGTCGTTTTG CAACACCAGA CGGCTATATT TTCGATCCAC GAGATGTTTT GGCCAAAGAA  2040
ACTTTTGTAT GGAAAGATGG CTCCTTTAGC ATCCCAAGAG CAGATGGCAG TTCATTGAGA  2100
ACCATTAATA AATCTGATCT ATCCCAAGCT GAGTGGCAAC AAGCTCAAGA GTTATTGGCA  2160
AAGAAAAACG CTGGTGATGC TACTGATACG GATAAACCCA AGAAAAGCA ACAGGCAGAT  2220
AAGAGCAATG AAAACCAACA GCCAAGTGAA GCCAGTAAAG AAGAAGAAAA AGAATCAGAT  2280
GACTTTATAG ACAGTTTACC AGACTATGGT CTAGATAGAG CAACCCTAGA AGATCATATC  2340
AATCAATTAG CACAAAAAGC TAATATCGAT CCTAAGTATC TCATTTTCCA ACCAGAAGGT  2400
GTCCAATTTT ATAATAAAAA TGGTGAATTA GTAACTTATG ATATCAAGAC GCTTCAACAA  2460
ATAAACCCTT AA    (SEQ ID NO : 82)                                 2472
```

*FIG. 47*

```
VKKTYGYIGS VAAILLATHI GSYQLGKHHM GLATKDNQIA YIDDSKGKAK      50
APKTNKTMDQ ISAEEGISAE QIVVKITDQG YVTSHGDHYH FYNGKVPYDA     100
IISEELLMTD PNYHFKQSDV INEILDGYVI KVNGNYYVYL KPGSKRKNIR     150
TKQQIAEQVA KGTKEAKEKG LAQVAHLSKE EVAAVNEAKR QGRYTTDDGY     200
IFSPTDIIDD LGDAYLVPHG NHYHYIPKKD LSPSELAAAQ AYWSQKQGRG     250
ARPSDYRPTP APGRRKAPIP DVTPNPGQGH QPDNGGYHPA PPRPNDASQN     300
KHQRDEFKGK TFKELLDQLH RLDLKYRHVE EDGLIFEPTQ VIKSNAFGYV     350
VPHGDHYHII PRSQLSPLEM ELADRYLAGQ TEDNDSGSDH SKPSDKEVTH     400
TFLGHRIKAY GKGLDGKPYD TSDAYVFSKE SIHSVDKSGV TAKHGDHFHY     450
IGFGELEQYE LDEVANWVKA KGQADELAAA LDQEQGKEKP LFDTKKVSRK     500
VTKDGKVGYI MPKDGKDYFY ARDQLDLTQI AFAEQELMLK DKNHYRYDIV     550
DTGIEPRLAV DVSSLPMHAG NATYDTGSSF VIPHIDHIHV VPYSWLTRDQ     600
IATIKYVMQH PEVRPDVWSK PGHEESGSVI PNVTPLDKRA GMPNWQIIHS     650
AEEVQKALAE GRFATPDGYI FDPRDVLAKE TFVWKDGSFS IPRADGSSLR     700
TINKSDLSQA EWQQAQELLA KKNAGDATDT DKPKEKQQAD KSNENQQPSE     750
ASKEEEKESD DFIDSLPDYG LDRATLEDHI NQLAQKANID PKYLIFQPEG     800
VQFYNKNGEL VTYDIKTLQQ INPP    (SEQ ID NO : 83)             824
```

STREPTOCOCCUS ANTIGENS

This application claims priority from U.S. patent application 60/113,800, filed Dec. 23, 1998, which is herein incorporated by reference.

FIELD OF THE INVENTION

The present invention is related to antigens, more particularly protein antigens of *streptococcus* pneumoniae-pathogen which are useful as vaccine components for therapy and/or prophylaxis.

BACKGROUND OF THE INVENTION

*S. pneumoniae* is an important agent of disease in man especially among infants, the elderly and immunocompromised persons. It is a bacterium frequently isolated from patients with invasive diseases such as bacteraemia/septicaemia, pneumonia, meningitis with high morbidity and mortality throughout the world. Even with appropriate antibiotic therapy, pneumococcal infections still result in many deaths. Although the advent of antimicrobial drugs has reduced the overall mortality from pneumococcal disease, the presence of resistant pneumococcal organisms has become a major problem in the world today. Effective pneumococcal vaccines could have a major impact on the morbidity and mortality associated with *S. pneumoniae* disease. Such vaccines would also potentially be useful to prevent otitis media in infants and young children.

Efforts to develop a pneumococcal vaccine have generally concentrated on generating immune responses to the pneumococcal capsular polysaccharide. More than 80 pneumococcal capsular serotypes have been identified on the basis of antigenic differences. The currently available pneumococcal vaccine, comprising 23 capsular polysaccharides that most frequently caused disease, has significant shortcomings related primarily to the poor immunogenicity of some capsular polysaccharides, the diversity of the serotypes and the differences in the distribution of serotypes over time, geographic areas and age groups. In particular, the failure of existing vaccines and capsular conjugate vaccines currently in development to protect young children against all serotypes spurres evaluation of other *S. pneumoniae* components. Although immunogenicity of capsular polysaccharides can be improved, serotype specificity will still represent a major limitation of polysaccharide-based vaccines. The use of a antigenically conserved immunogenic pneumococcal protein antigen, either by itself or in combination with additional components, offers the possibility of a protein-based pneumococcal vaccine.

PCT publication number WO98/18930 published May 7, 1998, entitled "*Streptococcus pneumoniae* antigens and vaccines" describes certain polypeptides which are claimed to be antigenic. However, no biological activity of these polypeptides is reported.

Therefore their remains an unmet need for *Streptococcus* antigens that may be used as vaccine components for the prophylaxis and/or therapy of *Streptococcus* infection.

SUMMARY OF THE INVENTION

According to one aspect, the present invention provides an isolated polynucleotide encoding a polypeptide having at least 70% identity to a second polypeptide comprising a sequence chosen from SEQ ID NOs: 2, 4, 6, 8, 10, 14, 16, 55 to 75, 77 to 79, 81, 83 or fragments, analogs or derivatives thereof.

In other aspects, there are provided vectors comprising polynucleotides of the invention operably linked to an expression control region, as well as host cells transfected with said vectors and methods of producing polypeptides comprising culturing said host cells under conditions suitable for expression.

In yet another aspect, there are provided novel polypeptides encoded by polynucleotides of the invention.

BRIEF DESCRIPTION OF THE DRAWINGS

FIG. 1 is the DNA sequence of BVH-3 gene; SEQ ID NO: 1.

FIG. 2 is the amino acid sequence of BVH-3 protein; SEQ ID NO: 2.

FIG. 3 is the DNA sequence of BVH-11 gene; SEQ ID NO: 3.

FIG. 4 is the amino acid sequence of BVH-11 protein; SEQ ID NO: 4.

FIG. 5 is the DNA sequence of BVH-28 gene; SEQ ID NO: 5.

FIG. 6 is the amino acid sequence of BVH-28 protein; SEQ ID NO: 6.

FIG. 7 is the DNA sequence of BVH-3A gene which corresponds to the 5' terminal end of BVH-3; SEQ ID NO: 7.

FIG. 8 is the amino acid sequence of BVH-3A protein; SEQ ID NO: 8.

FIG. 9 is the DNA sequence of BVH-3B gene which corresponds to the 3' terminal end of BVH-3; SEQ ID NO: 9.

FIG. 10 is the amino acid sequence of BVH-3B protein; SEQ ID NO: 10.

FIGS. 11A and 11B depict the comparison of the predicted amino acid sequences of the BVH-3 open reading frames from WU2, RX1, JNR.7/87, SP64, P4241 and A66 *S. pneumoniae* strains by using the program Clustal W from MacVector sequence analysis software (version 6.5). Underneath the alignment, there is a consensus line where * and . characters indicate identical and similar amino acid residues, respectively.

FIGS. 12A–12D depict the comparison of the predicted amino acid sequences of the BVH-11 open reading frames from WU2, Rx1, JNR.7/87, SP64, P4241, A66 and SP63 *S. pneumoniae* strains by using the program Clustal W from MacVector sequence analysis software (version 6.5). Underneath the alignment, there is a consensus line where * and . characters indicate identical and similar amino acid residues, respectively.

FIG. 13 depicts the comparison of the predicted amino acid sequences of the BVH-11 proteins from various *S. pneumoniae* strains. The degrees of identity (I) and similarity (S) were determined by using the program Clustal W from MacVector sequence analysis software (version 6.5).

FIGS. 14A and 14B present a DNA sequence containing the complete BVH-3 gene (open reading frame "ORF" at nucleotides 1777 to 4896); SEQ ID NO: 11.

FIG. 15 is a DNA sequence containing the complete BVH-11 gene (ORF at nucleotides 45 to 2567); SEQ ID NO: 12.

FIG. 16 is a DNA sequence containing the complete BVH-11-2 gene (ORF at nucleotides 114 to 2630); SEQ ID NO: 13.

FIG. 17 is the amino acid sequence of BVH-11-2 protein; SEQ ID NO: 14.

FIG. 18 is the DNA sequence of SP63 BVH-3 gene; SEQ ID NO:15.

FIG. 19 is the amino acid sequence of SP63 BVH-3 protein; SEQ ID NO: 16.

FIG. 20 is the amino acid sequence of BVH-3M protein; SEQ ID NO: 55.

FIG. 21 is the amino acid sequence of BVH-3AD protein; SEQ ID NO: 56.

FIG. 22 is the amino acid sequence of L-BVH-3-AD protein; SEQ ID NO: 57.

FIG. 23 is the amino acid sequence of NEW12 protein; SEQ ID NO: 58.

FIG. 24 is the amino acid sequence of BVH-3C protein; SEQ ID NO: 59.

FIG. 25 is the amino acid sequence of BVH-11M protein; SEQ ID NO: 60.

FIG. 26 is the amino acid sequence of BVH-11A protein; SEQ ID NO: 61.

FIG. 27 is the amino acid sequence of BVH-11B (also called New13) protein; SEQ ID NO: 62.

FIG. 28 is the amino acid sequence of BVH-11C protein; SEQ ID NO: 63.

FIG. 29 is the amino acid sequence of NEW1 protein; SEQ ID NO: 64.

FIG. 30 is the amino acid sequence of NEW2 protein; SEQ ID NO: 65.

FIG. 31 is the amino acid sequence of NEW3 protein; SEQ ID NO: 66.

FIG. 32 is the amino acid sequence of NEW4 protein; SEQ ID NO: 67.

FIG. 33 is the amino acid sequence of NEW5 protein; SEQ ID NO: 68.

FIG. 34 is the amino acid sequence of NEW6 protein; SEQ ID NO: 69.

FIG. 35 is the amino acid sequence of NEW7 protein; SEQ ID NO: 70.

FIG. 36 is the amino acid sequence of NEW8 protein; SEQ ID NO: 71.

FIG. 37 is the amino acid sequence of NEW9 protein; SEQ ID NO: 72.

FIG. 38 is the amino acid sequence of BVH-11-2M protein; SEQ ID NO: 73.

FIG. 39 is the amino acid sequence of NEW10 protein; SEQ ID NO: 74.

FIG. 40 is the amino acid sequence of NEW11 protein; SEQ ID NO: 75.

FIGS. 41A and 41B present the DNA sequence of NEW12 gene; SEQ ID NO: 76.

FIG. 42 is the amino acid sequence of NEW14 protein; SEQ ID NO: 77.

FIG. 43 is the amino acid sequence of NEW15 protein; SEQ ID NO: 78.

FIG. 44 is the amino acid sequence of NEW16 protein; SEQ ID NO: 79.

FIG. 45 is the DNA sequence of GBS BVH-71 gene; SEQ ID NO: 80.

FIG. 46 is the amino acid sequence of GBS BVH-71 protein; SEQ ID NO: 81.

FIG. 47 is the DNA sequence of GAS BVH-71 gene; SEQ ID NO:82.

FIG. 48 is the amino acid sequence of GAS BVH-71 protein; SEQ ID NO:83.

DETAILED DESCRIPTION OF THE INVENTION

According to one aspect, the present invention provides an isolated polynucleotide encoding a polypeptide having at least 70% identity to a second polypeptide comprising a sequence chosen from SEQ ID NOs: 2, 4, 6, 8, 10, 14, 16, 55 to 75, 77 to 79, 81, 83 or fragments, analogs or derivatives thereof.

According to one aspect, the present invention provides an isolated polynucleotide encoding a polypeptide having at least 95% identity to a second polypeptide comprising a sequence chosen from SEQ ID NOs: 2, 4, 6, 8, 10, 14, 16, 55 to 75, 77 to 79, 81, 83 or fragments, analogs or derivatives thereof.

According to one aspect, the present invention provides an isolated polynucleotide encoding a polypeptide having at least 70% identity to a second polypeptide comprising a sequence chosen from SEQ ID NOs: 2, 4, 8, 10, 14, 16, 55 to 75, 77 to 79, 81, 83 or fragments, analogs or derivatives thereof.

According to one aspect, the present invention provides an isolated polynucleotide encoding a polypeptide having at least 70% identity to a second polypeptide comprising a sequence chosen from SEQ ID NOs: 2, 4, 10, 14, 16, 55 to 75, 77 to 79, 81, 83 or fragments, analogs or derivatives thereof.

According to one aspect, the present invention provides an isolated polynucleotide encoding a polypeptide having at least 70% identity to a second polypeptide comprising a sequence chosen from SEQ ID NOs: 2, 4, 8, 10, 14, 16, 55 to 75, 77 to 79 or fragments, analogs or derivatives thereof.

According to one aspect, the present invention provides an isolated polynucleotide encoding a polypeptide having at least 70% identity to a second polypeptide comprising a sequence chosen from SEQ ID NOs: 2, 8, 10, 16, 55, 56, 57, 58, 59, 64, 65, 66, 78 or fragments, analogs or derivatives thereof.

According to one aspect, the present invention provides an isolated polynucleotide encoding a polypeptide having at least 70% identity to a second polypeptide comprising a sequence chosen from SEQ ID NOs: 2, 8, 10, 16, 55, 56, 57, 59, 64, 65, 66, 78 or fragments, analogs or derivatives thereof.

According to one aspect, the present invention provides an isolated polynucleotide encoding a polypeptide having at least 70% identity to a second polypeptide comprising a sequence chosen from SEQ ID NOs: 4, 14, 58, 60, 61, 62, 63, 67, 68, 69, 70, 71, 72, 73, 74, 75, 77, 79 or fragments, analogs or derivatives thereof.

According to one aspect, the present invention provides an isolated polynucleotide encoding a polypeptide having at least 70% identity to a second polypeptide comprising a sequence chosen from SEQ ID NOs: 4, 14, 60, 61, 62, 63, 67, 68, 69, 70, 71, 72, 73, 74, 75, 77, 79 or fragments, analogs or derivatives thereof.

According to one aspect, the present invention provides an isolated polynucleotide encoding a polypeptide having at least 70% identity to a second polypeptide comprising a sequence chosen from SEQ ID NOs: 2, 4, 10, 14, 16, 55 to 75, 77 to 79 or fragments, analogs or derivatives thereof.

According to one aspect, the present invention provides an isolated polynucleotide encoding a polypeptide having at least 70% identity to a second polypeptide comprising sequence chosen from SEQ ID NOs: 10, 55 to 75, 77, 78, 79 or fragments, analogs or derivatives thereof.

According to one aspect, the present invention provides an isolated polynucleotide encoding a polypeptide having at least 70% identity to a second polypeptide comprising sequence chosen from SEQ ID NOs: 55 to 75, 77, 78, 79 or fragments, analogs or derivatives thereof.

According to one aspect, the present invention provides an isolated polynucleotide encoding a polypeptide having at least 70% identity to a second polypeptide comprising a sequence chosen from SEQ ID NOs: 2, 4, 6, 8, 10 or fragments, analogs or derivatives thereof.

According to one aspect, the present invention provides an isolated polynucleotide encoding a polypeptide having at least 70% identity to a second polypeptide comprising a sequence chosen from SEQ ID NOs: 2, 4, 10, 14, 16 or fragments, analogs or derivatives thereof.

According to one aspect, the present invention provides an isolated polynucleotide encoding a polypeptide having at least 70% identity to a second polypeptide comprising a sequence chosen from SEQ ID NOs: 2, 4, 14, 16 or fragments, analogs or derivatives thereof.

According to one aspect, the present invention provides an isolated polynucleotide encoding a polypeptide having at least 70% identity to a second polypeptide comprising sequence SEQ ID NO: 2 or fragments, analogs or derivatives thereof.

According to one aspect, the present invention provides an isolated polynucleotide encoding a polypeptide having at least 70% identity to a second polypeptide comprising sequence SEQ ID NO: 4 or fragments, analogs or derivatives thereof.

According to one aspect, the present invention provides an isolated polynucleotide encoding a polypeptide having at least 70% identity to a second polypeptide comprising sequence SEQ ID NO: 10 or fragments, analogs or derivatives thereof.

According to one aspect, the present invention provides an isolated polynucleotide encoding a polypeptide having at least 70% identity to a second polypeptide comprising sequence SEQ ID NO: 14 or fragments, analogs or derivatives thereof.

According to one aspect, the present invention provides an isolated polynucleotide encoding a polypeptide having at least 70% identity to a second polypeptide comprising sequence SEQ ID NO: 16 or fragments, analogs or derivatives thereof.

According to one aspect, the present invention provides an isolated polynucleotide encoding a polypeptide having at least 70% identity to a second polypeptide comprising sequence SEQ ID NO: 58 or fragments, analogs or derivatives thereof.

According to one aspect, the present invention provides an isolated polynucleotide encoding a polypeptide having at least 70% identity to a second polypeptide comprising sequence SEQ ID NO: 60 or fragments, analogs or derivatives thereof.

According to one aspect, the present invention provides an isolated polynucleotide encoding a polypeptide having at least 70% identity to a second polypeptide comprising sequence SEQ ID NO: 62 or fragments, analogs or derivatives thereof.

According to one aspect, the present invention provides an isolated polynucleotide encoding a polypeptide having at least 70% identity to a second polypeptide comprising sequence SEQ ID NO: 64 or fragments, analogs or derivatives thereof.

According to one aspect, the present invention provides an isolated polynucleotide encoding a polypeptide having at least 70% identity to a second polypeptide comprising sequence SEQ ID NO: 67 or fragments, analogs or derivatives thereof.

According to one aspect, the present invention provides an isolated polynucleotide encoding a polypeptide having at least 70% identity to a second polypeptide comprising sequence SEQ ID NO: 68 or fragments, analogs or derivatives thereof.

According to one aspect, the present invention provides an isolated polynucleotide encoding a polypeptide having at least 70% identity to a second polypeptide comprising sequence SEQ ID NO: 69 or fragments, analogs or derivatives thereof.

According to one aspect, the present invention provides an isolated polynucleotide encoding a polypeptide having at least 70% identity to a second polypeptide comprising sequence SEQ ID NO: 72 or fragments, analogs or derivatives thereof.

According to one aspect, the present invention provides an isolated polynucleotide encoding a polypeptide having at least 70% identity to a second polypeptide comprising sequence SEQ ID NO: 74 or fragments, analogs or derivatives thereof.

According to one aspect, the present invention provides an isolated polynucleotide encoding a polypeptide having at least 70% identity to a second polypeptide comprising sequence SEQ ID NO: 77 or fragments, analogs or derivatives thereof.

According to one aspect, the present invention relates to polypeptides characterized by the amino acid sequence chosen from SEQ ID NOs: 2, 4, 6, 8, 10 or fragments, analogs or derivatives thereof.

According to one aspect, the present invention relates to polypeptides characterized by the amino acid sequence chosen from SEQ ID NOs: 2, 4, 6, 8, 10, 14, 16, 55 to 75, 77 to 79, 81, 83 or fragments, analogs or derivatives thereof.

According to one aspect, the present invention relates to polypeptides characterized by the amino acid sequence chosen from SEQ ID NOs: 2, 4, 8, 10, 14, 16, 55 to 75, 77 to 79, 81, 83 or fragments, analogs or derivatives thereof.

According to one aspect, the present invention relates to polypeptides characterized by the amino acid sequence chosen from SEQ ID NOs: 2, 4, 10, 14, 16, 55 to 75, 77 to 79, 81, 83 or fragments, analogs or derivatives thereof.

According to one aspect, the present invention relates to polypeptides characterized by the amino acid sequence chosen from SEQ ID NOs: 2, 4, 8, 10, 14, 16, 55 to 75, 77 to 79 or fragments, analogs or derivatives thereof.

According to one aspect, the present invention relates to polypeptides characterized by the amino acid sequence chosen from SEQ ID NOs: 2, 4, 10, 14, 16, 55 to 75, 77 to 79 or fragments, analogs or derivatives thereof.

According to one aspect, the present invention relates to polypeptides characterized by the amino acid sequence chosen from SEQ ID NOs: 2, 4, 10, 14, 16 or fragments, analogs or derivatives thereof.

According to one aspect, the present invention relates to polypeptides characterized by the amino acid sequence comprising sequence SEQ ID NO: 2 or fragments, analogs or derivatives thereof.

According to one aspect, the present invention relates to polypeptides characterized by the amino acid sequence comprising sequence SEQ ID NO: 4 or fragments, analogs or derivatives thereof.

According to one aspect, the present invention relates to polypeptides characterized by the amino acid sequence comprising sequence SEQ ID NO: 10 or fragments, analogs or derivatives thereof.

According to one aspect, the present invention relates to polypeptides characterized by the amino acid sequence comprising sequence SEQ ID NO: 14 or fragments, analogs or derivatives thereof.

According to one aspect, the present invention relates to polypeptides characterized by the amino acid sequence comprising sequence SEQ ID NO: 16 or fragments, analogs or derivatives thereof.

According to one aspect, the present invention relates to polypeptides characterized by the amino acid sequence chosen from SEQ ID NOs: 10, 55 to 75, 77, 78, 79 or fragments, analogs or derivatives thereof.

According to one aspect, the present invention relates to polypeptides characterized by the amino acid sequence chosen from SEQ ID NO: 10, 58, 60, 62, 64, 67, 68, 69, 72, 74, 77 or fragments, analogs or derivatives thereof.

According to one aspect, the present invention relates to polypeptides characterized by the amino acid sequence chosen from SEQ ID NO: 10, 58, 60, 62, 64, 67, 68, 69, 72, 74, 77 or fragments, analogs or derivatives thereof.

According to one aspect, the present invention relates to polypeptides characterized by the amino acid sequence chosen from SEQ ID NO: 10, 58, 60, 62, 64, 67, 68, 69, 72, 74, 77 or fragments, analogs or derivatives thereof.

According to one aspect, the present invention relates to polypeptides characterized by the amino acid sequence chosen from SEQ ID NO: 10, 62, 64, 67, 68, 74, 77 or fragments, analogs or derivatives thereof.

According to one aspect, the present invention relates to polypeptides characterized by the amino acid sequence comprising sequence SEQ ID NO: 58 or fragments, analogs or derivatives thereof.

According to one aspect, the present invention relates to polypeptides characterized by the amino acid sequence comprising sequence SEQ ID NO: 62 or fragments, analogs or derivatives thereof.

According to one aspect, the present invention relates to polypeptides characterized by the amino acid sequence comprising sequence SEQ ID NO: 64 or fragments, analogs or derivatives thereof.

According to one aspect, the present invention relates to polypeptides characterized by the amino acid sequence comprising sequence SEQ ID NO: 67 or fragments, analogs or derivatives thereof.

According to one aspect, the present invention relates to polypeptides characterized by the amino acid sequence comprising sequence SEQ ID NO: 68 or fragments, analogs or derivatives thereof.

According to one aspect, the present invention relates to polypeptides characterized by the amino acid sequence comprising sequence SEQ ID NO: 74 or fragments, analogs or derivatives thereof.

According to one aspect, the present invention relates to polypeptides characterized by the amino acid sequence comprising sequence SEQ ID NO: 77 or fragments, analogs or derivatives thereof.

In a further embodiment, the present invention also relates to chimeric polypeptides which comprise one or more polypeptides or fragments, analogs or derivatives thereof as described in the present application.

In a further embodiment, the present invention also relates to chimeric polypeptides which comprise one or more polypeptides or fragments, analogs or derivatives thereof as defined in the figures of the present application.

In a further embodiment, the present application also relates to chimeric polypeptides which comprise two or more polypeptides chosen from SEQ ID NOs: 2, 4, 6, 8, 10, 14, 16, 55 to 75, 77 to 79, 81, 83 or fragments, analogs or derivatives thereof; provided that the polypeptides or fragments, analogs or derivatives thereof are linked as to form a chimeric polypeptide.

In a further embodiment, the chimeric polypeptide will comprise two or more polypeptides chosen from SEQ ID NOs:10, 58, 60, 62, 64, 67, 68, 69, 72, 74, 77 or fragments, analogs or derivatives thereof; provided that the polypeptides or fragments, analogs or derivatives thereof are linked as to form a chimeric polypeptide.

In a further embodiment, the chimeric polypeptide will comprise two or more polypeptides chosen from SEQ ID NOs:10, 58, 60, 62, 64, 67, 68, 74, 77 or fragments, analogs or derivatives thereof; provided that the polypeptides or fragments, analogs or derivatives thereof are linked as to form a chimeric polypeptide.

In a further embodiment, the chimeric polypeptide will comprise two or more polypeptides chosen from SEQ ID NOs:10, 62, 64, 67, 68, 74, 77 or fragments, analogs or derivatives thereof; provided that the polypeptides or fragments, analogs or derivatives thereof are linked as to form a chimeric polypeptide.

In a further embodiment, the chimeric polypeptide will comprise between 2 and 5 polypeptides.

In a further embodiment, the chimeric polypeptide will comprise between 2 and 4 polypeptides.

In a further embodiment, the chimeric polypeptide will comprise between 2 and 3 polypeptides.

In a further embodiment, the chimeric polypeptide will comprise 2 polypeptides.

In a further embodiment, there is provided a chimeric polypeptide of formula (I):

$$A-(B)_m-(C)_n-D \qquad (I)$$

Wherein;

m is 0 or 1, n is 0 or 1,

A is chosen from SEQ ID NOs: 2, 4, 6, 8, 10, 14, 16, 55 to 75, 77 to 79, 81, 83 or fragments, analogs or derivatives thereof;

B is chosen from SEQ ID NOs: 2, 4, 6, 8, 10, 14, 16, 55 to 75, 77 to 79, 81, 83 or fragments, analogs or derivatives thereof;

C is chosen from SEQ ID NOs: 2, 4, 6, 8, 10, 14, 16, 55 to 75, 77 to 79, 81, 83 or fragments, analogs or derivatives thereof; and D is chosen from SEQ ID NOs: 2, 4, 6, 8, 10, 14, 16, 55 to 75, 77 to 79, 81, 83 or fragments, analogs or derivatives thereof.

In a further embodiment,

A is chosen from SEQ ID NOs:10, 58, 60, 62, 64, 67, 68, 69, 72, 74, 77 or fragments, analogs or derivatives thereof;

B is chosen from SEQ ID NOs:10, 58, 60, 62, 64, 67, 68, 69, 72, 74, 77, or fragments, analogs or derivatives thereof;

C is chosen from SEQ ID NOs:10, 58, 60, 62, 64, 67, 68, 69, 72, 74, 77 or fragments, analogs or derivatives thereof; and D is chosen from SEQ ID NOs:10, 58, 60, 62, 64, 67, 68, 69, 72, 74, 77 or fragments, analogs or derivatives thereof.

In a further embodiment,

A is chosen from SEQ ID NOs:10, 58, 60, 62, 64, 67, 68, 74, 77 or fragments, analogs or derivatives thereof;

B is chosen from SEQ ID NOs:10, 58, 60, 62, 64, 67, 68, 74, 77, or fragments, analogs or derivatives thereof;

C is chosen from SEQ ID NOs:10, 58, 60, 62, 64, 67, 68, 74, 77 or fragments, analogs or derivatives thereof; and D is chosen from SEQ ID NOs:10, 58, 60, 62, 64, 67, 68, 74, 77 or fragments, analogs or derivatives thereof.

In one embodiment, chimeric polypeptides of the present invention comprise those wherein the following embodiments are present, either independently or in combination.

In a further embodiment, A is SEQ ID NOs:10, 58, 62, 64, 67, 68, 74, 77 or fragments, analogs or derivatives thereof.

In a further embodiment, A is SEQ ID NO:10 or fragments, analogs or derivatives thereof.

In a further embodiment, A is SEQ ID NO:58 or fragments, analogs or derivatives thereof.

In a further embodiment, A is SEQ ID NO:62 or fragments, analogs or derivatives thereof.

In a further embodiment, A is SEQ ID NO:64 or fragments, analogs or derivatives thereof.

In a further embodiment, A is SEQ ID NO:67 or fragments, analogs or derivatives thereof.

In a further embodiment, A is SEQ ID NO:68 or fragments, analogs or derivatives thereof.

In a further embodiment, A is SEQ ID NO:74 or fragments, analogs or derivatives thereof.

In a further embodiment, A is SEQ ID NO:77 or fragments, analogs or derivatives thereof.

In a further embodiment, B is SEQ ID NOs:10, 58, 62, 64, 67, 68, 74, 77 or fragments, analogs or derivatives thereof.

In a further embodiment, B is SEQ ID NO:10 or fragments, analogs or derivatives thereof.

In a further embodiment, B is SEQ ID NO:58 or fragments, analogs or derivatives thereof.

In a further embodiment, B is SEQ ID NO:64 or fragments, analogs or derivatives thereof.

In a further embodiment, B is SEQ ID NO:64 or fragments, analogs or derivatives thereof.

In a further embodiment, B is SEQ ID NO:67 or fragments, analogs or derivatives thereof.

In a further embodiment, B is SEQ ID NO:68 or fragments, analogs or derivatives thereof.

In a further embodiment, B is SEQ ID NO:74 or fragments, analogs or derivatives thereof.

In a further embodiment, B is SEQ ID NO: 77 or fragments, analogs or derivatives thereof.

In a further embodiment, C is SEQ ID NOs:10, 58, 62, 64, 67, 68, 74, 77 or fragments, analogs or derivatives thereof.

In a further embodiment, C is SEQ ID NO:10 or fragments, analogs or derivatives thereof.

In a further embodiment, C is SEQ ID NO:58 or fragments, analogs or derivatives thereof.

In a further embodiment, C is SEQ ID NO: 62 or fragments, analogs or derivatives thereof.

In a further embodiment, C is SEQ ID NO:64 or fragments, analogs or derivatives thereof.

In a further embodiment, C is SEQ ID NO: 67 or fragments, analogs or derivatives thereof.

In a further embodiment, C is SEQ ID NO: 68 or fragments, analogs or derivatives thereof.

In a further embodiment, C is SEQ ID NO: 74 or fragments, analogs or derivatives thereof.

In a further embodiment, C is SEQ ID NO: 77 or fragments, analogs or derivatives thereof.

In a further embodiment, D is SEQ ID NO:10, 58, 62, 64, 67, 68, 74, 77 or fragments, analogs or derivatives thereof.

In a further embodiment, D is SEQ ID NO:10 or fragments, analogs or derivatives thereof.

In a further embodiment, D is SEQ ID NO:58 or fragments, analogs or derivatives thereof.

In a further embodiment, D is SEQ ID NO:62 or fragments, analogs or derivatives thereof.

In a further embodiment, D is SEQ ID NO:64 or fragments, analogs or derivatives thereof.

In a further embodiment, D is SEQ ID NO:67 or fragments, analogs or derivatives thereof.

In a further embodiment, D is SEQ ID NO:68 or fragments, analogs or derivatives thereof.

In a further embodiment, D is SEQ ID NO:74 or fragments, analogs or derivatives thereof.

In a further embodiment, D is SEQ ID NO:77 or fragments, analogs or derivatives thereof.

In a further embodiment, m is 0.

In a further embodiment, n is 0.

In a further embodiment, m and n are 0.

In a further embodiment, m and n are 0, A is SEQ ID NO:64 or fragments, analogs or derivatives thereof, B is SEQ ID NO:62 or fragments, analogs or derivatives thereof.

In a further embodiment, m and n are 0, A is SEQ ID NO:62 or fragments, analogs or derivatives thereof, B is SEQ ID NO:64 or fragments, analogs or derivatives thereof.

In accordance with the present invention, all nucleotides encoding polypeptides and chimeric polypeptides are within the scope of the present invention.

In a further embodiment, the polypeptides or chimeric polypeptides in accordance with the present invention are antigenic.

In a further embodiment, the polypeptides or chimeric polypeptides in accordance with the present invention can elicit an immune response in an individual.

In a further embodiment, the present invention also relates to polypeptides which are able to raise antibodies having binding specificity to the polypeptides or chimeric polypeptides of the present invention as defined above.

An antibody that "has binding specificity" is an antibody that recognizes and binds the selected polypeptide but which does not substantially recognize and bind other molecules in a sample, e.g., a biological sample, which naturally includes the selected peptide. Specific binding can be measured using an ELISA assay in which the selected polypeptide is used as an antigen.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control. In addition, the materials, methods, and examples are illustrative only and not intended to be limiting.

As used herein, "fragments", "derivatives" or "analogs" of the polypeptides of the invention include those polypeptides in which one or more of the amino acid residues are substituted with a conserved or non-conserved amino acid residue (preferably conserved) and which may be natural or unnatural. In one embodiment, derivatives and analogs of polypeptides of the invention will have about 70% identity with those sequences illustrated in the figures or fragments thereof. That is, 70% of the residues are the same. In a further embodiment, polypeptides will have greater than 75% homology. In a further embodiment, polypeptides will have greater than 80% homology. In a further embodiment, polypeptides will have greater than 85% homology. In a further embodiment, polypeptides will have greater than 90% homology. In a further embodiment, polypeptides will have greater than 95% homology. In a further embodiment, polypeptides will have greater than 99% homology. In a further embodiment, derivatives and analogs of polypeptides of the invention will have fewer than about 20 amino acid residue substitutions, modifications or deletions and more preferably less than 10. Preferred substitutions are those known in the art as conserved i.e. the substituted residues share physical or chemical properties such as hydrophobicity, size, charge or functional groups.

In accordance with the present invention, polypeptides of the invention include both polypeptides and chimeric polypeptides. Also included are polypeptides which have fused thereto other compounds which alter the polypeptides biological or pharmacological properties i.e. polyethylene glycol (PEG) to increase half-life; leader or secretory amino acid sequences for ease of purification; prepro- and pro-sequences; and (poly)saccharides.

Furthermore, in those situations where amino acid regions are found to be polymorphic, it may be desirable to vary one or more particular amino acids to more effectively mimic the different epitopes of the different *streptococcus* strains.

Moreover, the polypeptides of the present invention can be modified by terminal —$NH_2$ acylation (eg. by acetylation, or thioglycolic acid amidation, terminal carbosy amidation, e.g. with ammonia or methylamine) to provide stability, increased hydrophobicity for linking or binding to a support or other molecule.

Also contemplated are hetero and homo polypeptide multimers of the polypeptide fragments, analogues and derivatives. These polymeric forms include, for example, one or more polypeptides that have been cross-linked with cross-linkers such as avidin/biotin, gluteraldehyde or dimethylsuperimidate. Such polymeric forms also include polypeptides containing two or more tandem or inverted contiguous sequences, produced from multicistronic mRNAs generated by recombinant DNA technology. Preferably, a fragment, analog or derivative of a polypeptide of the invention will comprise at least one antigenic region i.e. at least one epitope.

In order to achieve the formation of antigenic polymers (i.e. synthetic multimers), polypeptides may be utilized having bishaloacetyl groups, nitroarylhalides, or the like, where the reagents being specific for thio groups. Therefore, the link between two mercapto groups of the different peptides may be a single bond or may be composed of a linking group of at least two, typically at least four, and not more than 16, but usually not more than about 14 carbon atoms.

In a particular embodiment, polypeptide fragments, analogs and derivatives of the invention do not contain a methionine (Met) starting residue. Preferably, polypeptides will not incorporate a leader or secretory sequence (signal sequence). The signal portion of a polypeptide of the invention may be determined according to established molecular biological techniques. In general, the polypeptide of interest may be isolated from a *streptococcus* culture and subsequently sequenced to determine the initial residue of the mature protein and therefore the sequence of the mature polypeptide.

According to another aspect, there are provided vaccine compositions comprising one or more *streptococcus* polypeptides of the invention in admixture with a pharmaceutically acceptable carrier diluent or adjuvant. Suitable adjuvants include oils i.e. Freund's complete or incomplete adjuvant; salts i.e. $AlK(SO_4)_2$, $AlNa(SO_4)_2$, $AlNH_4(SO_4)_2$, silica, kaolin, carbon polynucleotides i.e. poly IC and poly AU. Preferred adjuvants include QuilA and Alhydrogel.

Vaccines of the invention may be administered parenterally by injection, rapid infusion, nasopharyngeal absorption, dermoabsorption, or bucal or oral. Pharmaceutically acceptable carriers also include tetanus toxoid.

Vaccine compositions of the invention are used for the treatment or prophylaxis of *streptococcus* infection and/or diseases and symptoms mediated by *streptococcus* infection as described in P. R. Murray (Ed, in chief), E. J. Baron, M. A. Pfaller, F. C. Tenover and R. H. Yolken. Manual of Clinical Microbiology, ASM Press, Washington, D.C. sixth edition, 1995, 1482p which are herein incorporated by reference. In one embodiment, vaccine compositions of the present invention are used for the treatment or prophylaxis of meningitis, otitis media, bacteremia or pneumonia. In one embodiment, vaccine compositions of the invention are used for the treatment or prophylaxis of *streptococcus* infection and/or diseases and symptoms mediated by *streptococcus* infection, in particular *S. pneumoniae*, group A *streptococcus* (pyogenes), group B *streptococcus* (GBS or agalactiae), *dysgalactiae, uberis, nocardia* as well as *Staphylococcus aureus*. In a further embodiment, the *streptococcus* infection is *S. pneumoniae*.

In a particular embodiment, vaccines are administered to those individuals at risk of *streptococcus* infection such as infants, elderly and immunocompromised individuals.

As used in the present application, the term "individuals" include mammals. In a further embodiment, the mammal is human.

Vaccine compositions are preferably in unit dosage form of about 0.001 to 100 µg/kg (antigen/body weight) and more preferably 0.01 to 10 µg/kg and most preferably 0.1 to 1 µg/kg 1 to 3 times with an interval of about 1 to 6 week intervals between immunizations.

According to another aspect, there are provided polynucleotides encoding polypeptides characterized by the amino acid sequence chosen from SEQ ID NOs: 2, 4, 6, 8, 10, 14, 16, 55 to 75, 77 to 79, 81, 83 or fragments, analogs or derivatives thereof.

In one embodiment, polynucleotides are those illustrated in SEQ ID Nos: 1, 3, 5, 7, 9, 11, 12, 13, 15, 76, 80, 82 which may include the open reading frames (ORF), encoding polypeptides of the invention. It will be appreciated that the polynucleotide sequences illustrated in the figures may be altered with degenerate codons yet still encode the polypeptides of the invention. Accordingly the present invention further provides polynucleotides which hybridize to the polynucleotide sequences herein above described (or the complement sequences thereof) having 50% identity between sequences. In one embodiment, at least 70% identity between sequences. In one embodiment, at least 75% identity between sequences. In one embodiment, at least 80% identity between sequences. In one embodiment, at least 85% identity between sequences. In one embodiment, at least 90% identity between sequences. In a further embodiment, polynucleotides are hybridizable under stringent conditions i.e. having at least 95% identity. In a further embodiment, more than 97% identity.

In a further embodiment, polynucleotides are those illustrated in SEQ ID NOs: 1, 3, 7, 9, 11, 12, 13, 15, 76, 80, 82 encoding polypeptides of the invention.

In a further embodiment, polynucleotides are those illustrated in SEQ ID NOs: 1, 3, 9, 11, 12, 13, 15, 76, 80, 82 which may include the open reading frames (ORF), encoding polypeptides of the invention.

In a further embodiment, polynucleotides are those illustrated in SEQ ID NOs: 1, 3, 9, 11, 12, 13, 15, 76 which may include the open reading frames (ORF), encoding polypeptides of the invention.

In a further embodiment, polynucleotides are those illustrated in SEQ ID NOs: 1, 3, 7, 9, 11, 12, 13, 15, 76 which may include the open reading frames (ORF), encoding polypeptides of the invention.

In a further embodiment, polynucleotides are those illustrated in SEQ ID NOs: 1, 7, 9, 11, 15, 76 which may include the open reading frames (ORF), encoding polypeptides of the invention.

In a further embodiment, polynucleotides are those illustrated in SEQ ID NOs 1, 9, 11, 15, 76 which may include the open reading frames (ORF), encoding polypeptides of the invention.

In a further embodiment, polynucleotides are those illustrated in SEQ ID NOs: 1, 7, 9, 11 which may include the open reading frames (ORF), encoding polypeptides of the invention.

In a further embodiment, polynucleotides are those illustrated in SEQ ID NO: 1, encoding polypeptides of the invention.

In a further embodiment, polynucleotides are those illustrated in SEQ ID NO:7, encoding polypeptides of the invention.

In a further embodiment, polynucleotides are those illustrated in SEQ ID NO:9, encoding polypeptides of the invention.

In a further embodiment, polynucleotides are those illustrated in SEQ ID NO:11, encoding polypeptides of the invention.

In a further embodiment, polynucleotides are those illustrated in SEQ ID NO:15, encoding polypeptides of the invention.

In a further embodiment, polynucleotides are those illustrated in SEQ ID NOs: 3, 12, 13, 76, encoding polypeptides of the invention.

In a further embodiment, polynucleotides are those illustrated in SEQ ID NO:3, encoding polypeptides of the invention.

In a further embodiment, polynucleotides are those illustrated in SEQ ID NO:12, encoding polypeptides of the invention.

In a further embodiment, polynucleotides are those illustrated in SEQ ID NO:13, encoding polypeptides of the invention.

In a further embodiment, polynucleotides are those illustrated in SEQ ID NO:76, encoding polypeptides of the invention.

As will be readily appreciated by one skilled in the art, polynucleotides include both DNA and RNA.

The present invention also includes polynucleotides complementary to the polynucleotides described in the present application.

In a further aspect, polynucleotides encoding polypeptides of the invention, or fragments, analogs or derivatives thereof, may be used in a DNA immunization method. That is, they can be incorporated into a vector which is replicable and expressible upon injection thereby producing the antigenic polypeptide in vivo. For example polynucleotides may be incorporated into a plasmid vector under the control of the CMV promoter which is functional in eukaryotic cells. Preferably the vector is injected intramuscularly.

According to another aspect, there is provided a process for producing polypeptides of the invention by recombinant techniques by expressing a polynucleotide encoding said polypeptide in a host cell and recovering the expressed polypeptide product. Alternatively, the polypeptides can be produced according to established synthetic chemical techniques i.e. solution phase or solid phase synthesis of oligopeptides which are ligated to produce the full polypeptide (block ligation).

General methods for obtention and evaluation of polynucleotides and polypeptides are described in the following references: Sambrook et al, Molecular Cloning: A Laboratory Manual, 2nd ed, Cold Spring Harbor, N.Y., 1989; Current Protocols in Molecular Biology, Edited by Ausubel F. M. et al., John Wiley and Sons, Inc. New York; PCR Cloning Protocols, from Molecular Cloning to Genetic Engineering, Edited by White B. A., Humana Press, Totowa, N.J., 1997, 490 pages; Protein Purification, Principles and Practices, Scopes R. K., Springer-Verlag, New York, 3rd Edition, 1993, 380 pages; Current Protocols in Immunology, Edited by Coligan J. E. et al., John Wiley & Sons Inc., New York which are herein incorporated by reference.

For recombinant production, host cells are transfected with vectors which encode the polypeptide, and then cultured in a nutrient media modified as appropriate for activating promoters, selecting transformants or amplifying the genes. Suitable vectors are those that are viable and replicable in the chosen host and include chromosomal, non-chromosomal and synthetic DNA sequences e.g. bacterial plasmids, phage DNA, baculovirus, yeast plasmids, vectors derived from combinations of plasmids and phage DNA. The polypeptide sequence may be incorporated in the vector at the appropriate site using restriction enzymes such that it is operably linked to an expression control region comprising a promoter, ribosome binding site (consensus region or Shine-Dalgarno sequence), and optionally an operator (control element). One can select individual components of the expression control region that are appropriate for a given host and vector according to established molecular biology principles (Sambrook et al, Molecular Cloning: A Laboratory Manual, 2nd ed, Cold Spring Harbor, N.Y., 1989; Current Protocols in Molecular Biology, Edited by Ausubel F. M. et al., John Wiley and Sons, Inc. New York incorporated herein by reference). Suitable promoters include but are not limited to LTR or SV40 promoter, $E.$ $coli$ lac, tac or trp promoters and the phage lambda $P_L$ promoter. Vectors will preferably incorporate an origin of replication as well as selection markers i.e. ampicilin resistance gene. Suitable bacterial vectors include pET, pQE70, pQE60, pQE-9, pbs, pD10 phagescript, psiX174, pbluescript SK, pbsks, pNH8A, pNH16a, pNH18A, pNH46A, ptrc99a, pKK223-3, pKK233-3, pDR540, pRIT5 and eukaryotic vectors pBlue-BacIII, pWLNEO, pSV2CAT, pOG44, pXT1, pSG, pSVK3, pBPV, pMSG and pSVL. Host cells may be bacterial i.e. $E.$ $coli,$ $Bacillus$ $subtilis,$ $Streptomyces$; fungal i.e. $Aspergillus$ $niger,$ $Aspergillus$ $nidulins$; yeast i.e. $Saccharomyces$ or eukaryotic i.e. CHO, COS.

Upon expression of the polypeptide in culture, cells are typically harvested by centrifugation then disrupted by physical or chemical means (if the expressed polypeptide is not secreted into the media) and the resulting crude extract retained to isolate the polypeptide of interest. Purification of the polypeptide from culture media or lysate may be achieved by established techniques depending on the properties of the polypeptide i.e. using ammonium sulfate or ethanol precipitation, acid extraction, anion or cation exchange chromatography, phosphocellulose chromatography, hydrophobic interaction chromatography, hydroxylapatite chromatography and lectin chromatography. Final purification may be achieved using HPLC.

The polypeptide may be expressed with or without a leader or secretion sequence. In the former case the leader may be removed using post-translational processing (see U.S. Pat. No. 4,431,739; U.S. Pat. No. 4,425,437; and U.S. Pat. No. 4,338,397 incorporated herein by reference) or be chemically removed subsequent to purifying the expressed polypeptide.

According to a further aspect, the *streptococcus* polypeptides of the invention may be used in a diagnostic test for *streptococcus* infection, in particular *S. pneumoniae* infection. Several diagnostic methods are possible, for example detecting *streptococcus* organism in a biological sample, the following procedure may be followed:

a) obtaining a biological sample from a patient;
b) incubating an antibody or fragment thereof reactive with a *streptococcus* polypeptide of the invention with the biological sample to form a mixture; and
c) detecting specifically bound antibody or bound fragment in the mixture which indicates the presence of *streptococcus*.

Alternatively, a method for the detection of antibody specific to a *streptococcus* antigen in a biological sample containing or suspected of containing said antibody may be performed as follows:

a) obtaining a biological sample from a patient;
b) incubating one or more *streptococcus* polypeptides of the invention or fragments thereof with the biological sample to form a mixture; and
c) detecting specifically bound antigen or bound fragment in the mixture which indicates the presence of antibody specific to *streptococcus*.

One of skill in the art will recognize that this diagnostic test may take several forms, including an immunological test such as an enzyme-linked immunosorbent assay (ELISA), a radioimmunoassay or a latex agglutination assay, essentially to determine whether antibodies specific for the protein are present in an organism.

The DNA sequences encoding polypeptides of the invention may also be used to design DNA probes for use in detecting the presence of *streptococcus* in a biological sample suspected of containing such bacteria. The detection method of this invention comprises:

a) obtaining the biological sample from a patient;
b) incubating one or more DNA probes having a DNA sequence encoding a polypeptide of the invention or fragments thereof with the biological sample to form a mixture; and
c) detecting specifically bound DNA probe in the mixture which indicates the presence of *streptococcus* bacteria.

The DNA probes of this invention may also be used for detecting circulating *streptococcus*, i.e., *S. pneumoniae* nucleic acids in a sample, for example using a polymerase chain reaction, as a method of diagnosing *streptococcus* infections. The probe may be synthesized using conventional techniques and may be immobilized on a solid phase, or may be labeled with a detectable label. A preferred DNA probe for this application is an oligomer having a sequence complementary to at least 6 contiguous nucleotides of the *Streptococcus pneumoniae* of the invention.

Another diagnostic method for the detection of *streptococcus* in a patient comprises:

a) labelling an antibody reactive with a polypeptide of the invention or fragment thereof with a detectable label;
b) administering the labelled antibody or labelled fragment to the patient; and
c) detecting specifically bound labelled antibody or labelled fragment in the patient which indicates the presence of *streptococcus*.

A further aspect of the invention is the use of the *streptococcus* polypeptides of the invention as immunogens for the production of specific antibodies for the diagnosis and in particular the treatment of *streptococcus* infection. Suitable antibodies may be determined using appropriate screening methods, for example by measuring the ability of a particular antibody to passively protect against *streptococcus* infection in a test model. One example of an animal model is the mouse model described in the examples herein. The antibody may be a whole antibody or an antigen-binding fragment thereof and may belong to any immunoglobulin class. The antibody or fragment may be of animal origin, specifically of mammalian origin and more specifically of murine, rat or human origin. It may be a natural antibody or a fragment thereof, or if desired, a recombinant antibody or antibody fragment. The term recombinant antibody or antibody fragment means antibody or antibody fragment which was produced using molecular biology techniques. The antibody or antibody fragments may be polyclonal, or preferably monoclonal. It may be specific for a number of epitopes associated with the *streptococcus pneumoniae* polypeptides but is preferably specific for one.

Without limiting its scope, the present invention also relates to new antigens designated BVH-3, BVH-11, BVH-11-2, BVH-28 and BVH-71. The present invention also relates to truncated polypeptides comprising fragments of the new antigens designated BVH-3, BVH-11, BVH-11-2, BVH-28 and BVH-71. The present invention also relates to chimeric polypeptides comprising fragments of the new antigens designated BVH-3, BVH-11, BVH-11-2, BVH-28 and BVH-71. The following is a reference table summarizing the relation between the antigens of the present invention:

| Family | Nucleotide SEQ ID NO | Polypeptide SEQ ID NO |
|---|---|---|
| BVH-3 | | |
| BVH-3 | 1, 11 | 2 |
| BVH-3A | 7 | 8 |
| BVH-3B | 9 | 10 |
| BVH-3 SP63 | 15 | 16 |
| BVH-3M | | 55 |
| BVH-3AD | | 56 |
| L-BVH-3AD | | 57 |
| New12 | 76 | 58 |
| BVH-3C | | 59 |
| New1 | | 64 |
| New2 | | 65 |
| New3 | | 66 |
| New15 | | 78 |
| BVH-11 | | |
| BVH-11 | 3, 12 | 4 |
| BVH-11-2 | 13 | 14 |
| BVH-11M | | 60 |
| BVH-11A | | 61 |
| BVH-11B also referred to as NEW13 | | 62 |
| BVH-11C | | 63 |
| New4 | | 67 |
| New5 | | 68 |
| New6 | | 69 |
| New7 | | 70 |
| New8 | | 71 |
| New9 | | 72 |

-continued

| Family | Nucleotide SEQ ID NO | Polypeptide SEQ ID NO |
|---|---|---|
| BVH-11-2M | | 73 |
| New10 | | 74 |
| New11 | | 75 |
| New12 | 76 | 58 |
| New14 | | 77 |
| New16 | | 79 |
| BVH-28 | | |
| BVH-28 | 5 | 6 |
| BVH-71 | | |
| GBS | 80 | 81 |
| GAS | 82 | 83 |

EXAMPLE 1

This example illustrates the cloning of S. pneumoniae genes.

The coding region of S. pneumoniae gene BVH-3 (SEQ ID NO: 1) and the coding region of S. pneumoniae gene BVH-28 (SEQ ID NO: 5) were amplified by PCR (DNA Thermal Cycler GeneAmp PCR system 2400 Perkin Elmer, San Jose, Calif.) from genomic DNA of serogroup 6 S. pneumoniae strain SP64 using the oligos that contained base extensions for the addition of restriction sites BglII (AGATCT) and XbaI (TCTAGA). PCR products were purified from agarose gel using a QIAquick gel extraction kit from QIAgen (Chatsworth, Calif.), digested BglII-XbaI (Pharmacia Canada Inc, Baie d'Urfé, Canada), extracted with phenol:chloroform and precipitated with ethanol. The Superlinker vector pSL301 (Invitrogen, San Diego, Calif.) was digested with BglII and XbaI and purified from agarose gel using a QIAquick gel extraction kit from QIAgen (Chatsworth, Calif.). The BglII-XbaI genomic DNA fragments were ligated to the BglII-XbaI pSL301 vector. The ligated products were transformed into E. coli strain DH5a [f80 lacZ DM15 enda1 recA1 hsdR17 ($^r$K$^{-m}$K$^+$) supE44 thi-1l$^-$ gyrA96 relA1 D(lacZYA-argF)U169] (Gibco BRL, Gaithersburg, Md.) according to the method of Simanis (Hanahan, D. DNA Cloning, 1985, D. M. Glover (ed), pp. 109–135). Recombinant pSL301 plasmids (rpSL301) containing either BVH-3 or BVH-28 gene were purified using a QIAgen kit (Chatsworth, Calif.) and DNA inserts were confirmed by nucleotide sequence analysis (Taq Dye Deoxy Terminator Cycle Sequencing kit, ABI, Foster City, Calif.). Recombinant rpSL301 (rpSL301) were digested with the restriction enzymes BglII (AGATCT) and XhoI (CTCGAG). DNA fragments BglII-XhoI were purified using the QIAquick gel extraction kit from QIAgen (Chatsworth, Calif.). pET-32c (+) expression vector (Novagen, Madison, Wis.) containing the thioredoxin-His-Tag sequence was digested with BamHI (GGATCC) and XhoI and gel extracted using the QIAquick gel extraction kit from QIAgen (Chatsworth, Calif.). The BglII-XhoI DNA fragments were ligated to the BamHI-XhoI pET-32c(+) vector to create the coding sequence for thioredoxin-His·Tag-BVH-3 or thioredoxin-His·Tag-BVH-28 fusion protein. The ligated products were transformed into E. coli strain DH5a [f80 lacZ DM15 endA1 recA1 hsdR17 ($^r$K$^{-m}$K$^+$) supE44 thi-1l$^-$ gyrA96 relA1 D(lacZYA-argF) U169] (Gibco BRL, Gaithersburg, Md.) according to the method of Simanis (Hanahan, D. DNA Cloning, 1985, D. M. Glover (ed), pp. 109–135). Recombinant pET-32c(+) plasmids were purified using a QIAgen kit (Chatsworth, Calif.) and the nucleotide sequences at the fusion sites of thioredoxin-His·Tag and DNA insert were verified by DNA sequencing (Taq Dye Deoxy Terminator Cycle Sequencing kit, ABI, Foster City, Calif.).

EXAMPLE 2

This example illustrates the cloning of S. pneumoniae protein genes in CMV plasmid pCMV-GH.

The DNA coding region of a S. pneumoniae protein was inserted in phase downstream of a human growth hormone (hGH) gene which was under the transcriptional control of the cytomegalavirus (CMV) promotor in the plasmid vector PCMV-GH (Tang et al., Nature, 1992, 356:152). The CMV promotor is non functional plasmid in E. coli cells but active upon administration of the plasmid in eukaryotic cells. The vector also incorporated the ampicillin resistance gene.

The coding region of BVH-3 gene (SEQ ID NO: 1) and BVH-28 gene (SEQ ID NO: 5) were obtained from rpSL301 (see example 1) using restriction enzymes BglII (AGATCT) and XbaI (TCTAGA). The digested products were purified from agarose gel using the QIAquick gel extraction kit from QIAgen (Chatsworth, Calif.). The pCMV-GH vector (Laboratory of Dr. Stephen A. Johnston, Department of Biochemistry, The University of Texas, Dallas, Tex.) containing the human growth hormone to create fusion proteins was digested with BglII and XbaI and purified from agarose gel using the QIAquick gel extraction kit from QIAgen (Chatsworth, Calif.). The BglII-XbaI DNA fragments were ligated to the BglII-XbaI pCMV-GH vector to create the hGH-BVH-3 or hGH-BVH-28 fusion protein under the control of the CMV promoter. The ligated products were transformed into E. coli strain DH5a [f80 lacZ DM15 endA1 recA1 hsdR17 ($^r$K$^{-m}$K$^+$) supE44 thi-1l$^-$ gyrA96 relA1 D(lacZYA-argF)U169] (Gibco BRL, Gaithersburg, Md.) according to the method of Simanis (Hanahan, D. DNA Cloning, 1985, D. M. Glover (ed), pp. 109–135). The recombinant pCMV plasmids were purified using a QIAgen kit (QIAgen, Chatsworth, Calif.).

The coding region of BVH-11 gene (SEQ ID NO: 3) was amplified by PCR (DNA Thermal Cycler GeneAmp PCR system 2400 Perkin Elmer, San Jose, Calif.) from genomic DNA of serogroup 6 S. pneumoniae strain SP64 using the oligos that contained base extensions for the addition of restriction sites BglII (AGATCT) and HindIII (AAGCTT). The PCR product was purified from agarose gel using a QIAquick gel extraction kit from QIAgen (Chatsworth, Calif.), digested with restriction enzymes (Pharmacia Canada Inc, Baie d'Urfe, Canada), extracted with phenol: chloroform and precipitated with ethanol. The pCMV-GH vector (Laboratory of Dr. Stephen A. Johnston, Department of Biochemistry, The University of Texas, Dallas, Tex.) was digested with BglII and HindIII and purified from agarose gel using the QIAquick gel extraction kit from QIAgen (Chatsworth, Calif.). The BglII-HindIII DNA fragment was ligated to the BglII-HindIII pCMV-GH vector to create the hGH-BVH-11 fusion protein under the control of the CMV promoter. The ligated products were transformed into E. coli strain DH5a [f80 lacZ DM15 endA1 recA1 hsdR17 ($^r$K$^-$$_m$K$^+$) supE44 thi-1l$^-$ gyrA96 relA1 D(lacZYA-argF)U169] (Gibco BRL, Gaithersburg, Md.) according to the method of Simanis (Hanahan, D. DNA Cloning, 1985, D. M. Glover (ed), pp. 109–135). The recombinant pCMV plasmid was purified using a QIAgen kit (Chatsworth, Calif.) and the nucleotide sequence of the DNA insert was verified by DNA sequencing.

EXAMPLE 3

This example illustrates the use of DNA to elicit an immune response to *S. pneumoniae* antigens.

A group of 8 female BALB/c mice (Charles River, St-Constant, Quebec, Canada) were immunized by intramuscular injection of 50 µl three times at two- or three-week intervals with 100 µg of recombinant pCMV-GH encoding the BVH-3, BVH-11 or the BVH-28 gene in presence of 50 µg of granulocyte-macrophage colony-stimulating factor (GM-CSF)-expressing plasmid pCMV-GH-GM-CSF (Laboratory of Dr. Stephen A. Johnston, Department of Biochemistry, The University of Texas, Dallas, Tex.). As control, a group of mice were injected with 100 µg of pCMV-GH in presence of 50 µg of pCMV-GH-GM-CSF. Blood samples were collected from the orbital prior to each immunization and seven days following the third injection and serum antibody responses were determined by ELISA using thioredoxin-His·Tag-*S. pneumoniae* fusion protein as coating antigen. DNA immunization with recombinant plasmid pCMV-GH encoding the BVH-3, BVH-11 or the BVH-28 *S. pneumoniae* protein induced antibody reactive against the respective recombinant protein. The reciprocal antibody titers, defined as the highest serum dilution at which the absorbance values were 0.1 above the background values, were above $4 \times 10^3$.

EXAMPLE 4

This example illustrates the production and purification of recombinant *S. pneumoniae* proteins.

The recombinant pET plasmids containing the BVH-3, BVH-11 or the BVH-28 gene corresponding to the SEQ ID NO: 1, SEQ ID NO: 3 or the SEQ ID NO: 5 respectively were transformed by electroporation (Gene Pulser II apparatus, BIO-RAD Labs, Mississauga, Canada) into *E. coli* strain AD494 (DE3) (Dara⁻ leu7697 DlacX74 DphoA PvuII phoR DmalF3 F' [lac⁺(lacI$^q$) pro] trxB::Kan) (Novagen, Madison, Wis.). In this strain of *E. coli*, the T7 promotor controlling expression of the fusion protein is specifically recognized by the T7 RNA polymerase (present on the lDE3 prophage) whose gene is under the control of the lac promotor which is inducible by isopropyl-β-d-thio-galactopyranoside (IPTG). The transformant AD494(DE3)/rpET was grown at 37° C. with agitation at 250 rpm in LB broth (peptone log/L, yeast extract 5 g/L, NaCl 10 g/L) containing 100 µg of ampicillin (Sigma-Aldrich Canada Ltd., Oakville, Canada) per ml until the $A_{600}$ reached a value of 0.6. In order to induce the production of the thioredoxin-His·Tag-BVH-3, thioredoxin-His·Tag-BVH-11 or thioredoxin-His·Tag-BVH-28 fusion protein, the cells were incubated for 2 additional hours in the presence of IPTG at a final concentration of 1 mM. Induced cells from a 100 ml culture were pelleted by centrifugation and frozen at −70° C.

The purification of the fusion proteins from the soluble cytoplasmic fraction of IPTG-induced AD494(DE3)/rpET was done by affinity chromatography based on the properties of the His-Tag sequence (6 consecutive histidine residues) to bind to divalent cations ($Ni^{2+}$) immobilized on the His-Bind metal chelation resin. Briefly, the pelleted cells obtained from a 100 mL culture induced with IPTG were resuspended in phosphate-buffered (PBS):500 mM NaCl pH7.1, sonicated and spun at 20,000×g for 20 min to remove debris. The supernatant was filtered (0.22 µm pore size membrane) and deposited on a HiTrap® 1 mL chelating pre-packed ready-to-use column (Pharmacia Biotech, Baie d'Urfé, Canada). The thioredoxin-His·Tag-*S. pneumoniae* fusion protein was eluted with 1M imidazole-500 mM NaCl-PBS pH7.1. The removal of the salt and imidazole from the sample was done by dialysis against PBS at 4° C. The quantities of fusion protein obtained from the soluble fraction of *E. coli* was estimated by MicroBCA (Pierce, Rockford, Ill.).

EXAMPLE 5

This example illustrates the protection of mice against fatal pneumococcal infection by immunization.

Groups of 8 female BALB/c mice (Charles River) were immunized subcutaneously three times at three-week intervals with either 25 µg of affinity purified thioredoxin-His-Tag-BVH-3 fusion protein in presence of 15 µg of QuilA adjuvant (Cedarlane Laboratories Ltd, Hornby, Canada) or, as control, with QuilA adjuvant alone in PBS. Blood samples were collected from the orbital sinus on day 1, 22 and 43 prior to each immunization and seven days (day 50) following the third injection. One week later the mice were challenged with approximately $10^6$ CFU of the type 3 *S. pneumoniae* strain WU2. Samples of the *S. pneumoniae* challenge inoculum were plated on chocolate agar plates to determine the CFU and to verify the challenge dose. Deaths were recorded for a period of 14 days and on day 14 post-challenge, the surviving mice were sacrificied and blood samples tested for the presence of *S. pneumoniae* organisms. The survival data are shown in table 1.

Prechallenge sera were analyzed for the presence of antibodies reactive with *S. pneumoniae* by standard immunoassays. Elisa and immunoblot analyses indicated that immunization with recombinant *S. pneumoniae* protein produced in *E. coli* elicited antibodies reactive with both, recombinant and native pneumococcal protein.

TABLE 1

| Protection mediated by recombinant BVH-3 protein | | |
|---|---|---|
| Immunogen | No. of mice alive:<br>no. of mice dead<br>14 days post-challenge | Median day of death |
| BVH-3 | 8:0 | >14 |
| none | 0:8 | 1 |

All mice immunized with BVH-3 recombinant protein survived to infection while none of the control mice given adjuvant alone survived. There was a significant difference in survival between the two groups of mice (P<0.0001, log rank test for nonparametric analysis of survival curves; P=0.0002, Fisher's exact test). All hemocultures from surviving mice were negative at day 14 post-challenge.

EXAMPLE 6

This example describes the cloning of BVH-3 and BVH-11 genes from a variety of *S. pneumoniae* strains and the molecular conservation of these genes.

Molecular analysis of chromosomal DNA from various *S. pneumoniae* isolates with DNA probes spanning different regions of BVH-3 or BVH-11 revealed the presence of one BVH-3 gene copy and two BVH-11 gene copies. The two BVH-11 gene copies are not identical and the genes were arbitrarily designated BVH-11 (SEQ ID NO:12; ORF at nucleotides 45 to 2567) and BVH-11-2 (SEQ ID NO:13; ORF at nucleotides 114 to 2630).

The first amino acids of the BVH-3 and BVH-11 coding regions have the characteristics of leader sequences also known as signal peptides. The consensus signal peptidase cleavage site L-X-X-C of lipoprotein modification/processing sites was present in the sequences. Mature BVH-3, BVH-11 and BVH-11-2 proteins from *S. pneumoniae* SP64 have 1019, 821 and 819 amino acids, respectively. The regions of *S. pneumoniae* genes coding for mature BVH-3, termed BVH-3M, (nucleotides 1837–4896; SEQ. ID. NO: 11), BVH-11M (nucleotides 102–2567; SEQ. ID. NO: 12) and BVH-11-2M (nucleotides 171–2630; SEQ. ID. NO: 13), were amplified by PCR (DNA Thermal Cycler GeneAmp PCR system 2400 Perkin Elmer, San Jose, Calif.) from genomic DNA of 6 or 7 *S. pneumoniae* strains. Serogroup 6 *S. Pneumoniae* SP64 and serogroup 9 SP63 clinical isolates were provided by the laboratoire de la santé publique du Québec, Sainte-Anne-de-Bellevue; serotype 4 strain JNR.7/87 was provided by Andrew Camilli, Tufts University School of Medicine, Boston; Rx1 strain, a nonencapsulated derivative of the type 2 strain D39 and the type 3 strains A66 and WU2 were provided by David E. Briles from University of Alabama, Birmingham and the type 3 clinical isolate P4241 was provided by the centre de recherche en infectiologie du centre hospitalier de l'université Laval, Sainte-Foy. The sets of oligonucleotide primers OCRR479-OCRR480; HAMJ160-OCRR488 and HAMJ160-HAMJ186, that contained base extensions for the addition of restriction sites were used for the amplification of BVH-3, BVH-11 and BVH-11-2 gene, respectively, with the exception of BVH-11 gene from SP64 strain which was amplified using the set of primers consisting of HAMJ487 and OCRR488. Primer sequences are listed below (Table 2). PCR products were purified from agarose gel using a QIAquick gel extraction kit from QIAgen (Chatsworth, Calif.) and digested BglII-XbaI or BglII-HindIII (Pharmacia Canada Inc, Baie d'Urfé, Canada). Digestions were cleaned using a QIAquick PCR purification kit from QIAgen (Chatsworth, Calif.). The PCR products were ligated to the BglII-XbaI or BglII-HindIII pSL301 vector. The ligated products were transformed into *E. coli* strain DH5α [φ80 lacZ ΔM15 endA1 recA1 hsdR17 (⁻K⁻ᵐK⁺) supE44 thi-1λ⁻ gyrA96 relA1 Δ(lacZYA-argF)U169] (Gibco BRL, Gaithersburg, Md.) according to the method of Simanis (Hanahan, D. DNA Cloning, 1985, D. M. Glover (ed), pp. 109–135). Recombinant pSL301 plasmids (rpSL301) containing BVH-3, BVH-11 or BVH11-2 were purified using a QIAgen kit (Chatsworth, Calif.) and DNA inserts were sequenced (Taq Dye Deoxy Terminator Cycle Sequencing kit, ABI, Foster City, Calif.). The FIGS. 11 and 12 depict the consensus sequence established from the BVH-3, and BVH-11 deduced amino acid sequences, respectively. Comparison of BVH-3 protein sequences revealed 99 to 100% identity of sequences for all strains with the exception that BVH-3 from serogroup 9 SP63 strain (SEQ. ID. NO: 15 and SEQ. ID. NO: 16) misses a stretch of 177 amino acids corresponding to residues 244 to 420 on BVH-3 protein sequence of *S. pneumoniae* SP64. Analysis of sequences of additional serogroup 9 strains revealed BVH-3 molecule having the same deletion in 3 out of 4 strains thus suggesting that the 3 strains are members of a *S. pneumoniae* serogroup 9 clone.

Comparison of 13 BVH-11 nucleotide sequences obtained from 7 *S. pneumoniae* strains, revealed that the nucleotide sequences are very similar. Computer analysis (Macvector, Clustal W 1.4) using multiple alignment of the predicted BVH-11 protein sequences revealed that these sequences were 75% identical and 82% homologous on a length of 834 amino acids. Pairwise alignment revealed 80 to 100% identity (FIG. 13). The sequences showed great similarity in overall organization. Variability in the primary sequence of these proteins is almost restricted to the last 125 amino acids in the C-terminal portion of the proteins. This region constitutes a domain. Close examination of this domain revealed two groups of sequences. The first 9 sequences from the FIG. 13 belong to one group while the last 4 sequences belong to another group. A 39% identity value is obtained when the domain sequences of the 13 proteins are compared (MacVector, Clustal W 1.4). The identity value increased to more than 92% when sequences belonging to a same group are compared.

EXAMPLE 7

This example illustrates the homology of portions of BVH-3 and BVH-11 genes.

Molecular analysis with DNA probes derived from BVH-3 and BVH-11 genes indicated that BVH-3 and BVH-11 were related. In dot blot hybridization studies, DNA probe consisting of either, BVH-3 or BVH-11, gene sequence hybridized to both, BVH-3 and BVH-11 genes thus indicating that BVH-3 and BVH-11 genes shared homologous sequences. Comparison of sequences revealed that the ORFs and the proteins were 43 and 33% identical, respectively. Closer examination revealed that the region corresponding to amino acids 1 to 225 in BVH-3 and 1 to 228 in BVH-11 were 73 and 75% identical at the DNA and protein level, respectively. In contrast, the 3' regions corresponding to amino acids 226 to 1039 from BVH-3 and amino acids 229–840 from BVH-11 were only 34 and 22% identical at the DNA and protein level, respectively. Thus the 5' termini of BVH-3 and BVH-11 genes appear to contain highly conserved sequences while the remaining parts of the genes are highly divergent. These results suggest that BVH-3 and BVH-11 might share similar functions mediated by sequences present in the conserved region whereas BVH-3- and BVH-11-specific functions might be mediated by sequences in the divergent region.

EXAMPLE 8

This example describes the cloning of truncated BVH-3, BVH-11 and BVH-11-2 genes by polymerase chain reaction (PCR) and the expression of truncated BVH-3 and BVH-11 molecules.

Gene fragments were amplified by PCR using pairs of oligonucleotide engineered to amplify fragments spanning the BVH-3 (SEQ ID NO: 1 and SEQ ID NO: 11), BVH-11 (SEQ ID NO: 3 and SEQ ID NO: 12) or BVH-11-2 (SEQ ID NO: 13) gene from *S. pneumoniae* strain SP64. Each of the primers had a restriction endonuclease site at the 5' end, thereby allowing directional in-frame cloning of the amplified product into the digested plasmid vector (Tables 2 and 3). PCR-amplified products were digested with restriction endonucleases and ligated to either linearized plasmid pSL301 (see example 1), PCMV-GH (see example 2) or pET (Novagen, Madison, Wis.) expression vector digested likewise or digested with enzymes that produce compatible cohesive ends. Recombinant pSL301 and recombinant pCMV-GH plasmids were digested with restriction enzymes for the in-frame cloning in pET expression vector. Clones were first stabilized in *E. coli* DH5α before introduction into *E. coli* BL21(λDE3) or AD494 (λDE3) for expression of truncated BVH-3 or BVH-11 molecules. Each of the resultant plasmid constructs was confirmed by nucleotide sequence analysis. The recombinant proteins were expressed as N-terminal fusions with the thioredoxin and His-tag or as C-terminal fusions with an His-tag. The expressed recombinant proteins were purified from supernatant fractions obtained from centrifugation of sonicated IPTG-induced *E. coli* cultures using a His-Bind metal chelation resin (QIAgen, Chatsworth, Calif.). The gene products generated are listed in the table 3. The gene products corresponding to the N-terminal region including the signal sequence are designated as Lipidated-proteins or lipoproteins (L-proteins). The gene products corresponding to the N-terminal region lacking the signal sequence are identified as protein without signal sequence (w/o ss).

TABLE 2

List of PCR oligonucleotide primers

| Primer | SEQ. ID. | Sequence 5'–3' | Nucleotide position | Restriction sites |
|---|---|---|---|---|
| OCRR 479 | 17 | cagtagatctgtgcctatgcactaaac | SEQ ID 1:61–78 | BglII |
| OCRR 480 | 18 | gatctctagactactgctattccttacgctatg | SEQ ID 11: 4909–4887 | XbaI |
| OCRR 497 | 19 | atcactcgagcattacctggataatcctgt | SEQ ID 1: 1525–1506 | XhoI |
| OCRR 498 | 20 | ctgctaagcttatgaaagatttagat | SEQ ID 1: 1534–1548 | HindIII |
| OCRR 499 | 21 | gatactcgagctgctattccttac | SEQ ID 11: 4906–4893 | XhoI |
| HAMJ 172 | 22 | gaatctcgagttaagctgctgctaattc | SEQ ID 1: 675–661 | XhoI |
| HAMJ 247 | 23 | gacgctcgagcgctatgaaatcagataaattc | SEQ ID 1: 3117–3096 | XhoI |
| HAMJ 248 | 24 | gacgctcgagggcattacctggataatcctgttcatg | SEQ ID 1: 1527–1501 | XhoI |
| HAMJ 249 | 25 | cagtagatctcttcatcatttattgaaaagagg | SEQ ID 11: 1749–1771 | BglII |
| HAMJ 278 | 26 | ttatttcttccatatggacttgacagaagagcaaattaag | SEQ ID 1: 1414–1437 | NdeI |
| HAMJ 279 | 27 | cgccaagcttcgctatgaaatcagataaattc | SEQ ID 1: 3117–3096 | HindIII |
| HAMJ 280 | 28 | cgccaagcttttccacaatataagtcgattgatt | SEQ ID 1: 2400–2377 | HindIII |
| HAMJ 281 | 29 | ttatttcttccatatggaagtacctatcttggaaaaagaa | SEQ ID 1: 2398–2421 | NdeI |
| HAMJ 300 | 30 | ttatttcttccatatggtgcctatgcactaaaccagc | SEQ ID 1:61–82 | NdeI |
| HAMJ 313 | 31 | ataagaatgcggccgcttccacaatataagtcgattgatt | SEQ ID 1: 2400–2377 | NotI |
| OCRR 487 | 32 | cagtagatctgtgcttatgaactaggtttgc | SEQ ID 3:58–79 | BglII |
| OCRR 488 | 33 | gatcaagcttgctgctacctttacttactctc | SEQ ID 12: 2577–2556 | HindIII |
| HAMJ 171 | 34 | ctgagatatccgttatcgttcaaacc | SEQ ID 3: 1060–1075 | EcoRV |
| HAMJ 251 | 35 | ctgcaagcttttaaaggggaataatacg | SEQ ID 3: 1059–1045 | HindIII |
| HAMJ 264 | 36 | cagtagatctgcagaagcctt cctatctg | SEQ ID 3: 682–700 | BglII |
| HAMJ 282 | 37 | tcgccaagcttcgttatcgttcaaaccattggg | SEQ ID 3: 1060–1081 | HindIII |
| HAMJ 283 | 38 | ataagaatgcggccgccttactctcctttaataaagccaatagtt | SEQ ID 3: 2520–2492 | NdeI |
| HAMJ 284 | 39 | catgccatggacattgatagtctcttgaaacagc | SEQ ID 3: 856–880 | NcoI |
| HAMJ 285 | 40 | cgccaagcttcttactctcctttaataaagccaatag | SEQ ID 3: 2520–2494 | HindIII |
| HAMJ 286 | 41 | cgacaagcttaacatggtcgctagcgttacc | SEQ ID 3: 2139–2119 | HindIII |
| HAMJ 287 | 42 | cataccatgggccttt atgaggcacctaag | SEQ ID 3: 2014–2034 | NcoI |
| HAMJ 288 | 43 | cgacaagcttaagtaaatcttcagcctctctcag | SEQ ID 3: 2376–2353 | HindIII |
| HAMJ 289 | 44 | gataccatggctagcgaccatgttcaaagaa | SEQ ID 3: 2125–2146 | NcoI |
| HAMJ 290 | 45 | cgccaagcttatcatccactaacttgactttatcac | SEQ ID 3: 1533–1508 | HindIII |
| HAMJ 291 | 46 | cataccatggatattcttgccttcttagctccg | SEQ ID 3: 1531–1554 | NcoI |
| HAMJ 301 | 47 | catgccatggtgcttatgaactaggtttgc | SEQ ID 3:59–79 | NcoI |
| HAMJ 302 | 48 | cgccaagctttagcgttaccaaaaccattatc | SEQ ID 3: 2128–2107 | HindIII |
| HAMJ 160 | 49 | gtattagatctgttcctatgaacttggtcgtcacca | SEQ ID 13: 172–196 | BglII |
| HAMJ 186 | 50 | cgcctctagactactgtataggagccgg | SEQ ID 13: 2460–2443 | XbaI |
| HAMJ 292 | 51 | catgccatggaaaacatttcaagccttttacgtg | SEQ ID 11: 754–778 | NcoI |

TABLE 2-continued

List of PCR oligonucleotide primers

| Primer | SEQ. ID. | Sequence 5'–3' | Nucleotide position | Restriction sites |
|---|---|---|---|---|
| HAMJ 293 | 52 | cgacaagcttctgtataggagccggttgactttc | SEQ ID 11: 2457–2434 | HindIII |
| HAMJ 294 | 53 | catgccatggttcgtaaaaataaggcagaccaag | SEQ ID 11: 2038–2062 | NcoI |
| HAMJ 297 | 54 | catgccatggaagcctattggaatgggaag | SEQ ID 11: 622–642 | NcoI |

TABLE 3

Lists of truncated BVH-3 and BVH-11 gene products generated from *S.pneumoniae* SP64

| PCR-primer sets | Protein designation | Identification (encoded amino acids) | SEQ. ID. NO. | Cloning vector |
|---|---|---|---|---|
| OCRR479–OCRR480 | BVH-3M | BVH-3 w/o ss (21–1039) | 55 | pSL301 |
| OCRR479–OCRR497 | BVH-3AD | BVH-3 N'end w/o ss (21–509) | 56 | pSL301 |
| HAMJ248–HAMJ249 | L-BVH-3AD | BVH-3 N'end (1–509) | 57 | pET-21(+) |
| OCRR498–OCRR499 | BVH-3B | BVH-3 C'end (512–1039) | 10 | pSL301 |
| OCRR479–HAMJ172 | BVH-3C | BVH-3 N'end w/o ss (21–225) | 59 | pET-32c(+) |
| OCRR487–OCRR488 | BVH-11M | BVH-11 w/o ss (20–840) | 60 | pCMV-GH |
| HAMJ251–OCRR487 | BVH-11A | BVH-11 N'end w/o ss (20–353) | 61 | pET-32c(+) |
| HAMJ171–OCRR488 | BVH-11B | BVH-11 C'end (354–840) | 62 | pET-32a(+) |
| HAMJ264–OCRR488 | BVH-11C | BVH-11 C'end (228–840) | 63 | pET-32a(+) |
| HAMJ278–HAMJ279 | NEW1 | BVH-3 C'end (472–1039) | 64 | pET-21b(+) |
| HAMJ278–HAMJ280 | NEW2 | BVH-3 C'end (472–800) | 65 | pET-21b(+) |
| HAMJ281–HAMJ279 | NEW3 | BVH-3 C'end (800–1039) | 66 | pET-21b(+) |
| HAMJ284–HAMJ285 | NEW4 | BVH-11 C'end (286–840) | 67 | pET-21d(+) |
| HAMJ284–HAMJ286 | NEW5 | BVH-11 internal (286–713) | 68 | pET-21d(+) |
| HAMJ287–HAMJ288 | NEW6 | BVH-11 internal (672–792) | 69 | pET-21d(+) |
| HAMJ285–HAMJ289 | NEW7 | BVH-11 internal (709–840) | 70 | pET-21d(+) |
| HAMJ284–HAMJ290 | NEW8 | BVH-11 internal (286–511) | 71 | pET-21d(+) |
| HAMJ286–HAMJ291 | NEW9 | BVH-11 internal (511–713) | 72 | pET-21d(+) |
| HAMJ160–HAMJ186 | BVH-11-2M | BVH-11-2 w/o ss (20–838) | 73 | pSL301 |
| HAMJ292–HAMJ293 | NEW10 | BVH-11-2 C'end (271–838) | 74 | pET-21d(+) |
| HAMJ293–HAMJ294 | NEW11 | BVH-11-2 C'end (699–838) | 75 | pET-21d(+) |
| HAMJ282–HAMJ283 | BVH-11B | BVH-11 C'end (354–840) | 62 | pET-21b(+) |
| HAMJ286–HAMJ297 | NEW14 | BVH-11-2 internal (227–699) | 77 | pET-21d(+) |
| HAMJ300–HAMJ313 | NEW15 | BVH-3 N'end w/o ss (21–800) | 78 | pET-21b(+) |
| HAMJ301–HAMJ302 | NEW16 | BVH-11 N'end w/o ss (20–709) | 79 | pET-21d(+) |

EXAMPLE 9

This example describes the isolation of monoclonal antibodies (Mabs) and the use of Mabs to characterize BVH-3, BVH-11 and BVH-11-2 protein epitopes.

Female BALB/c mice (Charles River) were immunized subcutaneously with BVH-3, BVH-11 or BVH-11-2 gene products from *S. pneumoniae* strain SP64 in presence of 15 μg of QuilA adjuvant (Cedarlane Laboratories Ltd, Hornby, Canada). One set of mice (fusion experiment 1) were immunized on day 1 and 14 with 25 μg of affinity purified thioredoxin-His·Tag-BVH-3M fusion protein. A second group of mice (fusion experiment 2) were immunized three times at three-week intervals with 25 μg of affinity purified thioredoxin-His·Tag-BVH-11M. A third group of mice (fusion experiment 3) were immunized on day 1 and day 15 with 25 μg of affinity purified thioredoxin-His·Tag-BVH-11-2M fusion protein. A fourth group of mice (fusion experiment 4) were immunized on day 1 with 25 μg of affinity purified thioredoxin-His·BVH-11B fusion protein and boosted by intravenous injection on day 16 and on day 37 with recombinant BVH-11B in PBS. Three to four days before fusion, mice were injected intravenously with 25 μg of the respective antigen suspended in PBS alone. Hybridomas were produced by fusion of spleen cells with nonsecreting SP2/0 myeloma cells as previously described by J. Hamel et al. [J. Med. Microbiol., 23, pp163–170 (1987)]. Culture supernatants of hybridomas were initially screened by enzyme-linked-immunoassay according to the procedure described by Hamel et al. (Supra) using plates coated with preparations of purified recombinant proteins or suspensions of heat-killed *S. pneumoniae* cells. Positive hybridomas selected on the basis of ELISA reactivity with a variety of antigens were then cloned by limiting dilutions, expanded and frozen.

Hybridomas were tested by ELISA or Western immunoblotting against BVH-3 and BVH-11 gene products in order to characterize the epitopes recognized by the Mabs. BVH-3 and BVH-11 shared common epitopes with 6 Mabs (H3-1-F9, H3-1-D4, H3-1-H12, H11-1-E7, H11-1-H10 and H11-1.1-G11) showing reactivities with both proteins (Table 4). BVH-11 and BVH-11-2 molecules from *S. pneumoniae* SP64 shared common epitopes not present on BVH-3 with Mabs (3A1, 13C11, 10H10, 1D8, 10G9, 10A2, 3E8, 10D7, 2H7 and 6H7) reactive with both, BVH-11 and BVH-11-2, recombinant proteins (Table 5).

TABLE 4

Reactivity of BVH-3-immunoreactive Mabs with a
20 panel of BVH-3 and BVH-11 gene products a. Immunoreactivity with

| MAbs | BVH-3M 21–1039 | BVH-3A 21–509 | BVH-32 512–1039 | BVH-3C 21–225 | NEW2 472–800 | NEW3 800–1039 | BVH-11M 20–840 |
|---|---|---|---|---|---|---|---|
| H3-1-F9 | + | + | − | + | − | − | + |
| H3-1-D4 | + | + | − | + | − | − | + |
| H3-1-H12 | + | + | − | + | − | − | + |
| H3-2-G2 | + | + | − | − | − | − | − |
| H3-3-A1 | + | + | − | − | − | − | − |
| H3-4-D3 | + | − | + | − | − | + | − |
| H11-1-E7 | + | + | − | + | − | − | + |
| H11-1-H10 | + | + | − | + | − | − | + |
| H11-1.1-G11 | + | + | − | + | + | − | + |

TABLE 5

Reactivity of Mabs raised against BVH-11-2
protein from *S. pneumoniae* strain SP64 with a panel of BVH-
11 gene products b. Immunoreactivity with

| | c. BVH-11 products | | | | d. BVH-11-2 products | | | |
|---|---|---|---|---|---|---|---|---|
| Mabs[a] | BVH-11M 20–840 | NEW8 286–511 | NEW9 511–713 | BVH-11B 354–840 | BVH-11-2 20–838 | NEW10 271–838 | NEW11 699–838 | NEW14 227–699 |
| 3A1 | + | + | − | + | + | + | − | + |
| 13C1 | + | + | + | + | + | + | − | + |
| 10H10 | + | + | + | + | + | + | − | + |
| 1D8 | + | + | − | + | + | + | − | + |
| 10G9 | + | − | − | + | + | + | − | + |
| 10A2 | + | − | − | + | + | + | − | + |
| 3E8 | + | − | − | + | + | + | − | + |
| 10D7 | + | − | − | + | + | + | − | + |
| 2H7 | + | − | − | − | + | − | − | − |
| 6H7 | + | − | − | − | + | − | − | − |
| 3A4 | − | − | − | − | + | + | + | − |
| 14H6 | − | − | − | − | + | + | + | − |
| 7G2 | − | − | − | − | + | + | − | + |
| 13H10 | − | − | − | − | + | − | − | + |
| 7E8 | − | − | − | − | + | − | − | − |
| 7H6 | − | − | − | − | + | − | − | − |

[a]Mabs listed in this table were not reactive with recombinant BVH-3 molecule

The results obtained from the immunoreactivity studies of the Mabs (Table 4 and Table 5) are in agreement with the protein sequences derived from the respective gene sequences. Indeed the Mabs cross-reactive with BVH-3 and BVH-11 molecules recognized BVH-3C protein corresponding to the conserved region, and BVH-11 and BVH-11-2 specific Mabs were reactive with epitopes located on variable parts of these molecules. BVH-3 and BVH-11, and BVH-11 and BVH-11-2 can be distinguished by their reactivity with Mabs.

EXAMPLE 10

This example illustrates the simultaneous expression of BVH-3 and BVH-11 gene products by *S. pneumoniae*.

A standard Western blot technique was used to investigate whether BVH-3 and BVH-11 genes were expressed in *S. pneumoniae*. *S. pneumoniae* strain SP64 and SP63 were grown overnight at 37° C. in 5% $CO_2$ on chocolate agar plates, bacteria were suspended in PBS and heat-killed at 56° C. for 20 min. For the preparation of antigens, suspensions of *S. pneumoniae* were treated with sample buffer containing SDS and 2-mercaptoethanol for 5 min at 100° C. Pneumococcal protein antigens were resolved by SDS-PAGE electrophoresis according to the method of Laemmli [Nature, 227, pp. 680–685 (1970)]. After SDS-PAGE, the proteins were transferred electrophoretically from the gel to nitrocellulose paper by the method of Towbin [Proc. Natl. Acad. Sci. USA, 76, pp. 4350–4354 (1979)] and probed with mouse antiserum or monoclonal antibodies. The detection of antigens reactive with the antibodies was performed by indirect enzyme-immunoassay using conjugated-anti-mouse immunoglobulins and a colour substrate. When antiserum raised to recombinant BVH-3 was tested against *S. pneumoniae* SP64 antigens, two reactive bands having apparent molecular masses of 127 kDa and 99 kDa were detected. Bands having the same apparent molecular masses were also detected when Mabs H3-1-F9, H3-1-D4, H3-1-H12, H11-1-E7, H11-1-H10 and H11-1.1-G11 were used individually as immunological probes. In contrast, Mabs specific for the BVH-3 molecule detected the 127 kDa band only and Mabs specific for BVH-11 detected the 99 kDa band only thus confirming the identity of the 127 and 99 kDa bands as BVH-3 and BVH-11, respectively. These studies provide evidence that BVH-3 and BVH-11 proteins are simultaneously present on *S. pneumoniae*. Moreover, the results are consistent with our previous observations that BVH-3 and BVH-11 possess epitopes that are common to both proteins and epitopes that are exclusive to either protein.

In *S. pneumoniae* SP64, mature BVH-3, BVH-11 and BVH-11-2 are proteins of 1019, 821 and 819 amino acids with predicted molecular mass of 112.5 kDa, 92.4 kDa, and 91.7 kDa, respectively. Although there is a discrepancy between the molecular mass predicted from the sequence and the molecular mass calculated on SDS-PAGE, BVH-3 can be distinguished from BVH-11 by its higher molecular mass. Moreover, BVH-3 molecules from *S. pneumoniae* strain SP63 have an apparent molecular mass of 112 kDa in SDS-PAGE compared to 127 kDa for BVH-3 of SP64 strain. This data is consistent with the deletion of a stretch of 177 amino acid residues in BVH-3 of *S. pneumoniae* strain SP63.

EXAMPLE 11

This example describes the protection conferred in experimental infection of mice vaccinated with recombinant BVH-3 or BVH-11 gene products.

Groups of 7 or 8 female BALB/c mice (Charles River) were immunized subcutaneously three times at three-week intervals with either affinity purified thioredoxin-His·Tag-BVH-3M fusion protein, affinity purified thioredoxin-His·Tag-BVH-11M fusion protein or, as control, with QuilA adjuvant alone in PBS. Twelve to 14 days following the third immunization, the mice were challenged intravenously with *S. pneumoniae* WU2 strain or intranasally with P4241 strain. Samples of the *S. pneumoniae* challenge inoculum were plated on chocolate agar plates to determine the CFU and to verify the challenge dose. The challenge dose was approximately $10^6$ CFU. Deaths were recorded for a period of 14 days and on day 14 post-challenge, the surviving mice were sacrificed and blood samples tested for the presence of *S. pneumoniae* organisms. The survival data are shown in Tables 6 and 7.

TABLE 6

Protection mediated by recombinant BVH-3M and BVH-11M proteins in experimental infection with virulent *S.pneumoniae* WU2

| Experiment | Immunogen | Alive:dead[a] | Median days alive |
|---|---|---|---|
| 1 | BVH-3M | 8:0 | >14 |
|  | none | 0:8 | 1 |
| 2 | BVH-11M | 8:0 | >14 |
|  | none | 0:8 | 1 |

[a]The number of mice alive:the number of mice dead on day 14 post-challenge.

TABLE 7

Protection mediated by recombinant BVH-3M and BVH-11M proteins in experimental pneumonia with virulent *S.pneumoniae* P4241

| Experiment | Immunogen | Alive:dead[a] | Median day alive |
|---|---|---|---|
| 1 | BVH-3M | 6:1 | >14 |
|  | none | 1:7 | 4.5 |
| 2 | BVH-3M | 8:0 | >14 |

TABLE 7-continued

Protection mediated by recombinant BVH-3M and BVH-11M proteins in experimental pneumonia with virulent *S.pneumoniae* P4241

| Experiment | Immunogen | Alive:dead[a] | Median day alive |
|---|---|---|---|
|  | BVH-11M | 8:0 | >14 |
|  | none | 0:8 | 4 |

[a]The number of mice alive:the number of mice dead on day 14 post-challenge.

All mice immunized with recombinant BVH-3M or BVH-11M protein survived to infection with WU2 while none of the control mice given adjuvant alone survived. All except one mice immunized with recombinant BVH-3M or BVH-11M protein survived to infection with P4241 while only one control mice given adjuvant alone survived. All hemocultures from surviving mice were negative at day 14 post-challenge. These results clearly indicate that both, BVH-3M and BVH-11M, elicit protective anti-pneumococcal immune responses in mice. The fact that these proteins are highly conserved among *S. pneumoniae* isolates emphasize the potential of BVH-3 and BVH-11 as universal vaccine candidates. Indeed, the BVH-3 and BVH-11 proteins from serogroup 6 *S. pneumoniae* strain SP64 elicited protection against pneumococcal infections with strains of different capsular serotypes.

Ideally, a vaccine that could protect against pneumococcal disease, could protect against meningitis, otitis media, bacteremia and pneumonia. BVH-3 and BVH-11 were protective against lethal systemic- and pneumonia-infection models thus suggesting that, in humans, BVH-3- and BVH11-protein-based vaccines could reduce the incidence of a wide spectrum of disease caused by virtually all *S. pneumoniae* independently of the capsular serotype.

Data from Tables 6 and 7 clearly demonstrate that BVH-3 and BVH-11 were, both, protection-eliciting molecules of *S. pneumoniae*. It was not known, however, whether protection can be mediated by specific sequences that were not shared on BVH-3 and BVH-11 molecules. Groups of female BALB/c mice (Charles River) were immunized subcutaneously three times at three-week intervals with either affinity purified thioredoxin-His·Tag- BVH-3AD, -BVH-3B or -BVH-3C fusion protein in presence of 15 µg of QuilA adjuvant (Cedarlane Laboratories Ltd, Hornby, Canada). Control mice were immunized with QuilA adjuvant alone in PBS or affinity purified thioredoxin-His·Tag or thioredoxin-His·Tag-fusion protein (His-Thio) in presence of QuilA.

To determine the protective ability of a set of truncated proteins, termed NEW4, NEW5, NEW6, NEW7, NEW8, NEW9, NEW10, NEW11, NEW14 and BVH-11B, groups of female BALB/c mice (Charles River) were immunized subcutaneously two times at three-week intervals with 25 µg of either affinity purified His·Tag-fusion protein in presence of 15 µg of QuilA adjuvant. Ten to 14 days following the last immunization, the mice were challenged with virulent *S. pneumoniae*. Our results indicate that, BVH-3B, a truncated BVH-3 molecule consisting of amino acids 512–1039, elicited protection against the mouse-virulent strains WU2 and P4241. Similarly, BVH-11B, NEW4 and NEW5 molecules, three truncated BVH-11 molecules consisting of amino acids 354–840, amino acids 286–840 and amino acids 286–713, respectively, elicited protection against experiment intravenous challenge with WU2 and intranasal challenge with P4241. Moreover, vaccination with NEW10 and NEW14, consisting of amino acids 272–838 and amino acids 227–699 from BVH-11-2 molecule also resulted in protection against death with the pneumococcal strains. These results indicate that the region comprising 428 amino acids extending from amino acids 286–713 and amino acids 272–699 on *S. pneumoniae* SP64 BVH-11 and BVH-11-2 protein sequences, respectively, contains protective epitopes. This region is highly conserved with a global 91% identity and 94% homology among thirteen BVH-11 protein sequences.

TABLE 8

Evaluation of protection elicited by vaccination of mice with BVH-3 and BVH-11 gene products

| Experiment | Immunogen | Challenge with WU2 | | Challenge with P4241 | |
|---|---|---|---|---|---|
| | | Alive:dead[a] | Median day alive | Alive:dead | Median day alive |
| 1[b] | None | 0:8 | 1.5 | 1:7 | 4.5 |
| | NEW4 | 8:0 | >14 | 8:0 | >14 |
| | NEW5 | 8:0 | >14 | 8:0 | >14 |
| | NEW7 | 0:8 | 2 | 0:8 | 5 |
| | BVH-11M | 8:0 | >14 | 8:0 | >14 |
| 2[b] | None | 0:8 | 1 | 0:8 | 4 |
| | NEW5 | 8:0 | >14 | 8:0 | >14 |
| | NEW8 | 0:8 | 1.5 | 0:8 | 5.5 |
| | NEW9 | 3:5 | 3.5 | 2:6 | 7 |
| | BVH-11M | 8:0 | >14 | 8:0 | >14 |
| 3[b] | None | 0:8 | 1 | 0:8 | 4 |
| | NEW6 | 0:8 | 1 | 4:4 | 10.5[c] |
| | NEW10 | 8:0 | >14 | 8:0 | >14 |
| | NEW11 | 0:8 | 1.5 | 1:7 | 6 |
| | BVH-11M | 8:0 | >14 | 8:0 | >14 |
| 4[b] | None | 0:8 | 2 | 0:8 | 4 |
| | BVH-11B | 7:1 | >14 | 8:0 | >14 |
| | NEW14 | 8:0 | >14 | 8:0 | >14 |
| 5 | His-Thio | 0:8 | 2 | | |
| | BVH-3AD | 1:7 | 2.5 | | |
| | BVH-32 | 5:3 | >14 | | |
| 6 | His-Thio | 0:8 | 1 | | |
| | BVH-3C | 0:8 | 1 | | |

[a]The number of mice alive:the number of mice dead on day 14 post-challenge.
[b]The WU2 challenge dose was $10^5$ CFU.
[c]Mice living longer than 14 days were assigned a survival time of 14 days for the determination of median values.

EXAMPLE 12

This example described the cloning and expression of a chimeric gene encoding for a chimeric polypeptide corresponding to the carboxy-terminal region of BVH-3 in fusion at the C' end to the carboxy-terminal region of BVH-11 and the additive protection observed after vaccination with a chimeric polypeptide.

It is clear from the studies described above that BVH-3 and BVH-11 are serologically distinct molecules simultaneously present on *S. pneumoniae*. The results of immunological studies of mice indicate that both proteins are good vaccine candidates. These proteins have the potential to provide protection against all pneumococci, regardless of serotype. Even though the two proteins share epitopes and sequences, they have different characteristics and may serve different biological functions. Thus, immunization against the two proteins may provide a higher level of protection than that imparted by each individually. To examine this, several avenues where full-length or truncated BVH-3 and BVH-11 are administered in combination or in conjugation can be explored. Here we describe the genetic engineering of a BVH-3-BVH-11 fusion gene and protein, termed NEW12 (SEQ ID NO:76 and SEQ ID NO:58, respectively), and the potential use of NEW12 protein as a vaccine.

BVH-3 and BVH-11 gene fragments corresponding to the 3' end of the genes were amplified by PCR using pairs of oligonucleotides engineered to amplify fragments spanning nucleotides 1414 to 3117 (SEQ ID NO: 1) and nucleotides 1060 to 2520 (SEQ ID NO: 3) from *S. pneumoniae* strain SP64 BVH-3 and BVH-11 genes, respectively. The primers used, HAMJ278 and HAMJ279; HAMJ282 and HAMJ283 had a restriction endonuclease site at the 5' end, thereby allowing directional in-frame cloning of the amplified product into the digested pET21b(+) plasmid vector (Table 2). PCR-amplified products were digested with restriction endonucleases and ligated to linearized plasmid pET21b(+) vector digested likewise. The resultant plasmid constructs were confirmed by nucleotide sequence analysis. The recombinant pET21b(+) plasmid containing the NdeI-HindIII BVH-3 PCR product was linearized by digestion with the restriction enzymes HindIII and NotI for the in-frame cloning of the HindIII-NotI DNA fragment obtained from the recombinant pET21(+) vector containing the BVH-11 gene fragment. Clones were first stabilized in *E. coli* DH5α before introduction into *E. coli* BL21(λDE3) for expression of a chimeric pneumococcal protein molecule. The recombinant chimeric polypeptide, termed NEW 12, was expressed as C-terminal fusion with an His-tag. The expressed recombinant NEW 12 protein was purified from supernatant fractions obtained from centrifugation of sonicated IPTG-induced *E. coli* cultures using a His-Bind metal chelation resin (QIAgen, Chatsworth, Calif.).

According to the same procedure described above, it is possible to construct other chimeric polypeptides, as a result of a simultaneous expression of New 1 and New 4, New 1 and New 5, New 1 and New 10, or New 1 and New 14. The construction can be with New 1 upstream or downstream of New 4, New 5, New 10, BVH-11B or New 14. It is also possible to construct other chimeric polypeptides as a result of a simultaneous expression of more than two fragments of either genes of BVH-3, BVH-11 or BVH-11-2.

Groups of 8 female BALB/c mice (Charles River) were immunized subcutaneously two times at three-week intervals with 25 μg of either affinity purified His·Tag-fusion NEW1, BVH-11B or NEW12 protein in presence of 15 μg of QuilA adjuvant. Ten to 14 days following the last immunization, the mice were challenged with virulent *S. pneumoniae*. As demonstrated before, NEW1 and BVH-11B molecules comprising amino acids 472 to 1039 from BVH-3 protein and amino acids 354–840 from BVH-11 protein, respectively, correspond to portions of the proteins capable of eliciting a protective immune response. To determine if a chimeric polypeptide would significantly improve the protection compared with those seen for the individual counterparts, the challenge dose was adjusted in a manner that protection was not expected with NEW1 and BVH-11B molecules. Interestingly, the chimeric NEW12 protein, elicited protection against the mouse-virulent strains WU2 and P4241. Seven out of 8 mice immunized with NEW12 were still alive 10 days after the challenge while 28 out of 32 mice immunized with NEW1, BVH-11B, BVH-3M or adjuvant alone were dead by five days post-challenge. Thus, vaccination of mice with NEW12 provided the highest degree of protection against WU2 challenge.

These results indicate that immunization with a chimeric polypeptide and possibly a combination of BVH-3 and BVH-11 gene products can provide additional protection to that obtained by administration of BVH-3 or BVH-11 antigens alone.

TABLE 9

Evaluation of protection elicited by vaccination of mice with the chimeric NEW12 molecule

| Immunogen | Challenge with WU2 | | Challenge with P4241 | |
| --- | --- | --- | --- | --- |
| | Alive:dead[a] | Median day alive | Alive:dead | Median day alive |
| None | 0:8 | 1 | 0:8 | 5 |
| NEW1 | 2:6 | 2 | 1:7 | 8 |
| BVH-11B | 1:7 | 3.5 | 8:0 | >14 |
| NEW12 | 6:2 | >14 | 7:1 | >14 |
| BVH-3M | 1:7 | 3 | 8:1 | >14 |

EXAMPLE 13

This example illustrates the identification of additional BVH-3 and BVH-11 related sequences in *Streptococcus* species other than *S. pneumoniae*.

It was previously shown that BVH-3, BVH-11 and BVH-11-2 are a family of related proteins sharing common sequences. Homology searches were performed with the nucleotide sequence from the conserved region of these genes and compared with GenBank and EMBL sequences using FASTA. The most significant homology was observed with a 2.469-kb gene coding for a calculated 92-kDa protein (SEQ ID NO: 81) of unknown function in *S. agalactiae* also called group B *streptococcus* or GBS. The gene was designated BVH-71. A protein demonstrating 99.2% identity and 99.5% similarity with that of GBS was also identified in *S. pyogenes* also called group A *streptococcus* or GAS (SEQ ID NO: 83). The 5' region of the BVH-71 sequences (SEQ ID NO: 80 and SEQ ID NO: 82), spanning nucleotides 1 to 717, demonstrated 58 and 60% identity with the conserved regions of BVH-3 (nucleotides 1 to 675) and BVH-11 (nucleotides 1 to 684) genes respectively. The first 239 amino acids of the translated sequences of the GBS and GAS BVH-71 open reading frames are 51 and 54% identical to the first 225 and 228 amino acids of BVH-3 and BVH-11, respectively. In addition to structural similarities, streptococcal BVH-3, BVH-11 and BVH-71 proteins also share antigenic epitopes. A 97-kDa band was revealed on Western blots of GAS or GBS whole cells, using Mab H11-1.1-G11 reactive with the BVH-3 and BVH-11 conserved regions. Similarly, GAS and GBS recombinant BVH-71 proteins were detected in Western immunoblot analysis.

These results indicate that BVH-71, BVH-3 and BVH-11 proteins might share similar functions. Our results also suggest that BVH-71 proteins can be used as protein vaccine components of anti-*streptococcus*. In a further embodiment BVH-71 proteins can be used as protein vaccine components of anti-GAS or anti-GBS vaccines.

---

What is claimed is:

1. An isolated polypeptide having at least 95% identity to SEQ ID NO: 2, wherein said isolated polypeptide elicits a protective antistreptococcal immune response in an individual when administered to the individual.

2. An isolated polypeptide comprising the amino acid sequence consisting of SEQ ID NO:2.

3. An isolated polypeptide comprising the amino acid sequence consisting of amino acids 2 to 1039 of SEQ ID NO:2.

4. An isolated polypeptide comprising the amino acid sequence consisting of amino acids 21 to 1039 of SEQ ID NO:2.

5. A vaccine composition comprising a polypeptide having at least 95% identity to SEQ ID NO: 2, wherein said polypeptide elicits a protective antistreptococcal immune response in an individual when administered to the individual, and a pharmaceutically acceptable adjuvant.

6. A vaccine composition comprising a polypeptide having at least 95% sequence identity with a polypeptide comprising the amino acid sequence consisting of amino acids 2 to 1039 of SEQ ID NO:2, wherein said polypeptide elicits a protective antistreptococcal immune response in an individual when administered to the individual, and a pharmaceutically acceptable adjuvant.

7. A vaccine composition comprising a polypeptide having at least 95% sequence identity with a polypeptide comprising the amino acid sequence consisting of amino acids 21 to 1039 of SEQ ID NO:2, wherein said polypeptide elicits a protective antistreptococcal immune response in an individual when administered to the individual, and a pharmaceutically acceptable adjuvant.

8. The isolated polypeptide of claim 1, wherein the individual is a human, a mouse or a rat.

9. The vaccine composition of claim 5, wherein said adjuvant is selected from the group consisting of Freund's complete adjuvant, Freund's incomplete adjuvant, AlK (SO$_4$)$_2$, AlNa(SO$_4$)$_2$, AlNH$_4$(SO$_4$)$_2$, silica, kaolin, carbon polynucleotides, QuilA and Alhydrogel.

10. The isolated polypeptide of claim 1, said polypeptide having at least a 99% identity to SEQ ID NO:2.

11. The vaccine composition of claim 5, said polypeptide having at least a 99% identity to SEQ ID NO:2.

12. An isolated polypeptide comprising at least 95% sequence identity to amino acids 521 to 1039 of SEQ ID NO:2, wherein said polypeptide elicits a protective antistreptococcal immune response in an individual when administered to the individual.

13. An isolated polypeptide comprising at least 95% sequence identity to amino acids 800 to 1039 of SEQ ID NO:2, wherein said polypeptide elicits a protective antistreptococcal immune response in an individual when administered to the individual.

14. An isolated polypeptide comprising at least 95% sequence identity to amino acids 21 to 800 of SEQ ID NO:2, wherein said polypeptide elicits a protective antistreptococcal immune response in an individual when administered to the individual.

15. An isolated polypeptide comprising at least 95% sequence identity to amino acids 472 to 1039 of SEQ ID NO:2, wherein said polypeptide elicits a protective antistreptococcal immune response in an individual when administered to the individual.

16. A vaccine composition comprising a polypeptide having at least 95% sequence identity to amino acids 521 to 1039 of SEQ ID NO:2, and a pharmaceutically acceptable carrier, wherein said polypeptide elicits a protective antistreptococcal immune response in an individual when administered to the individual.

17. A vaccine composition comprising a polypeptide having at least 95% sequence identity to amino acids 800 to 1039 of SEQ ID NO:2, and a pharmaceutically acceptable carrier, wherein said polypeptide elicits a protective antistreptococcal immune response in an individual when administered to the individual.

18. A vaccine composition comprising a polypeptide having at least 95% sequence identity to amino acids 21 to 800 of SEQ ID NO:2, and a pharmaceutically acceptable carrier, wherein said polypeptide elicits a protective antistreptococcal immune response in an individual when administered to the individual.

19. A vaccine composition comprising a polypeptide having at least 95% sequence identity to amino acids 472 to 1039 of SEQ ID NO:2, and a pharmaceutically acceptable carrier, wherein said polypeptide elicits a protective antistreptococcal immune response in an individual when administered to the individual.

* * * * *

SEQUENCE LISTING

<160> NUMBER OF SEQ ID NOS: 102

<210> SEQ ID NO 1
<211> LENGTH: 3120
<212> TYPE: DNA
<213> ORGANISM: S. pneumoniae
<220> FEATURE:

<400> SEQUENCE: 1

```
atg aaa ttt agt aaa aaa tat ata gca gct gga tca gct gtt atc gta      48 tcc ttg agt cta tgt gcc tat gca cta aac cag cat cgt tcg cag gaa      96 aat aag gac aat aat cgt gtc tct tat gtg gat ggc agc cag tca agt     144 cag aaa agt gaa aac ttg aca cca gac cag gtt agc cag aaa gaa gga     192 att cag gct gag caa att gta atc aaa att aca gat cag ggc tat gta     240 acg tca cac ggt gac cac tat cat tac tat aat ggg aaa gtt cct tat     288 gat gcc ctc ttt agt gaa gaa ctc ttg atg aag gat cca aac tat caa     336 ctt aaa gac gct gat att gtc aat gaa gtc aag ggt ggt tat atc atc     384 aag gtc gat gga aaa tat tat gtc tac ctg aaa gat gca gct cat gct     432 gat aat gtt cga act aaa gat gaa atc aat cgt caa aaa caa gaa cat     480 gtc aaa gat aat gag aag gtt aac tct aat gtt gct gta gca agg tct     528 cag gga cga tat acg aca aat gat ggt tat gtc ttt aat cca gct gat     576 att atc gaa gat acg ggt aat gct tat atc gtt cct cat gga ggt cac     624 tat cac tac att ccc aaa agc gat tta tct gct agt gaa tta gca gca     672 gct aaa gca cat ctg gct gga aaa aat atg caa ccg agt cag tta agc     720 tat tct tca aca gct agt gac aat aac acg caa tct gta gca aaa gga     768
```

-continued

| | |
|---|---|
| tca act agc aag cca gca aat aaa tct gaa aat ctc cag agt ctt ttg | 816 |
| aag gaa ctc tat gat tca cct agc gcc caa cgt tac agt gaa tca gat | 864 |
| ggc ctg gtc ttt gac cct gct aag att atc agt cgt aca cca aat gga | 912 |
| gtt gcg att ccg cat ggc gac cat tac cac ttt att cct tac agc aag | 960 |
| ctt tct gct tta gaa gaa aag att gcc aga atg gtg cct atc agt gga | 1008 |
| act ggt tct aca gtt tct aca aat gca aaa cct aat gaa gta gtg tct | 1056 |
| agt cta ggc agt ctt tca agc aat cct tct tct tta acg aca agt aag | 1104 |
| gag ctc tct tca gca tct gat ggt tat att ttt aat cca aaa gat atc | 1152 |
| gtt gaa gaa acg gct aca gct tat att gta aga cat ggt gat cat ttc | 1200 |
| cat tac att cca aaa tca aat caa att ggg caa ccg act ctt cca aac | 1248 |
| aat agt cta gca aca cct tct cca tct ctt cca atc aat cca gga act | 1296 |
| tca cat gag aaa cat gaa gaa gat gga tac gga ttt gat gct aat cgt | 1344 |
| att atc gct gaa gat gaa tca ggt ttt gtc atg agt cac gga gac cac | 1392 |
| aat cat tat ttc ttc aag aag gac ttg aca gaa gag caa att aag gct | 1440 |
| gcg caa aaa cat tta gag gaa gtt aaa act agt cat aat gga tta gat | 1488 |
| tct ttg tca tct cat gaa cag gat tat cca ggt aat gcc aaa gaa atg | 1536 |
| aaa gat tta gat aaa aaa atc gaa gaa aaa att gct ggc att atg aaa | 1584 |
| caa tat ggt gtc aaa cgt gaa agt att gtc gtg aat aaa gaa aaa aat | 1632 |
| gcg att att tat ccg cat gga gat cac cat cat gca gat ccg att gat | 1680 |
| gaa cat aaa ccg gtt gga att ggt cat tct cac agt aac tat gaa ctg | 1728 |
| ttt aaa ccc gaa gaa gga gtt gct aaa aaa gaa ggg aat aaa gtt tat | 1776 |
| act gga gaa gaa tta acg aat gtt gtt aat ttg tta aaa aat agt acg | 1824 |
| ttt aat aat caa aac ttt act cta gcc aat ggt caa aaa cgc gtt tct | 1872 |
| ttt agt ttt ccg cct gaa ttg gag aaa aaa tta ggt atc aat atg cta | 1920 |
| gta aaa tta ata aca cca gat gga aaa gta ttg gag aaa gta tct ggt | 1968 |
| aaa gta ttt gga gaa gga gta ggg aat att gca aac ttt gaa tta gat | 2016 |
| caa cct tat tta cca gga caa aca ttt aag tat act atc gct tca aaa | 2064 |
| gat tat cca gaa gta agt tat gat ggt aca ttt aca gtt cca acc tct | 2112 |
| tta gct tac aaa atg gcc agt caa acg att ttc tat cct ttc cat gca | 2160 |
| ggg gat act tat tta aga gtg aac cct caa ttt gca gtg cct aaa gga | 2208 |
| act gat gct tta gtc aga gtg ttt gat gaa ttt cat gga aat gct tat | 2256 |
| tta gaa aat aac tat aaa gtt ggt gaa atc aaa tta ccg att ccg aaa | 2304 |
| tta aac caa gga aca acc aga acg gcc gga aat aaa att cct gta acc | 2352 |
| ttc atg gca aat gct tat ttg gac aat caa tcg act tat att gtg gaa | 2400 |
| gta cct atc ttg gaa aaa gaa aat caa act gat aaa cca agt att cta | 2448 |
| cca caa ttt aaa agg aat aaa gca caa gaa aac tca aaa ctt gat gaa | 2496 |
| aag gta gaa gaa cca aag act agt gag aag gta gaa aaa gaa aaa ctt | 2544 |
| tct gaa act ggg aat agt act agt aat tca acg tta gaa gaa gtt cct | 2592 |
| aca gtg gat cct gta caa gaa aaa gta gca aaa ttt gct gaa agt tat | 2640 |

-continued

```
ggg atg aag cta gaa aat gtc ttg ttt aat atg gac gga aca att gaa      2688 tta tat tta cca tca gga gaa gtc att aaa aag aat atg gca gat ttt      2736 aca gga gaa gca cct caa gga aat ggt gaa aat aaa cca tct gaa aat      2784 gga aaa gta tct act gga aca gtt gag aac caa cca aca gaa aat aaa      2832 cca gca gat tct tta cca gag gca cca aac gaa aaa cct gta aaa cca      2880 gaa aac tca acg gat aat gga atg ttg aat cca gaa ggg aat gtg ggg      2928 agt gac cct atg tta gat cca gca tta gag gaa gct cca gca gta gat      2976 cct gta caa gaa aaa tta gaa aaa ttt aca gct agt tac gga tta ggc      3024 tta gat agt gtt ata ttc aat atg gat gga acg att gaa tta aga ttg      3072 cca agt gga gaa gtg ata aaa aag aat tta tct gat ttc ata gcg         3117 taa                                                                  3120
```

<210> SEQ ID NO 2
<211> LENGTH: 1039
<212> TYPE: PRT
<213> ORGANISM: S. pneumoniae

<400> SEQUENCE: 2

```
Met Lys Phe Ser Lys Lys Tyr Ile Ala Ala Gly Ser Ala Val Ile Val
 1               5                  10                  15

Ser Leu Ser Leu Cys Ala Tyr Ala Leu Asn Gln His Arg Ser Gln Glu
            20                  25                  30

Asn Lys Asp Asn Asn Arg Val Ser Tyr Val Asp Gly Ser Gln Ser Ser
        35                  40                  45

Gln Lys Ser Glu Asn Leu Thr Pro Asp Gln Val Ser Gln Lys Glu Gly
    50                  55                  60

Ile Gln Ala Glu Gln Ile Val Ile Lys Ile Thr Asp Gln Gly Tyr Val
65                  70                  75                  80

Thr Ser His Gly Asp His Tyr His Tyr Tyr Asn Gly Lys Val Pro Tyr
                85                  90                  95

Asp Ala Leu Phe Ser Glu Glu Leu Leu Met Lys Asp Pro Asn Tyr Gln
            100                 105                 110

Leu Lys Asp Ala Asp Ile Val Asn Glu Val Lys Gly Gly Tyr Ile Ile
        115                 120                 125

Lys Val Asp Gly Lys Tyr Tyr Val Tyr Leu Lys Asp Ala Ala His Ala
    130                 135                 140

Asp Asn Val Arg Thr Lys Asp Glu Ile Asn Arg Gln Lys Gln Glu His
145                 150                 155                 160

Val Lys Asp Asn Glu Lys Val Asn Ser Asn Val Ala Val Ala Arg Ser
                165                 170                 175

Gln Gly Arg Tyr Thr Thr Asn Asp Gly Tyr Val Phe Asn Pro Ala Asp
            180                 185                 190

Ile Ile Glu Asp Thr Gly Asn Ala Tyr Ile Val Pro His Gly Gly His
        195                 200                 205

Tyr His Tyr Ile Pro Lys Ser Asp Leu Ser Ala Ser Glu Leu Ala Ala
    210                 215                 220

Ala Lys Ala His Leu Ala Gly Lys Asn Met Gln Pro Ser Gln Leu Ser
225                 230                 235                 240

Tyr Ser Ser Thr Ala Ser Asp Asn Asn Thr Gln Ser Val Ala Lys Gly
                245                 250                 255

Ser Thr Ser Lys Pro Ala Asn Lys Ser Glu Asn Leu Gln Ser Leu Leu
```

-continued

```
                260                 265                 270
Lys Glu Leu Tyr Asp Ser Pro Ser Ala Gln Arg Tyr Ser Glu Ser Asp
                275                 280                 285
Gly Leu Val Phe Asp Pro Ala Lys Ile Ile Ser Arg Thr Pro Asn Gly
                290                 295                 300
Val Ala Ile Pro His Gly Asp His Tyr His Phe Ile Pro Tyr Ser Lys
305                 310                 315                 320
Leu Ser Ala Leu Glu Glu Lys Ile Ala Arg Met Val Pro Ile Ser Gly
                325                 330                 335
Thr Gly Ser Thr Val Ser Thr Asn Ala Lys Pro Asn Glu Val Val Ser
                340                 345                 350
Ser Leu Gly Ser Leu Ser Ser Asn Pro Ser Ser Leu Thr Thr Ser Lys
                355                 360                 365
Glu Leu Ser Ser Ala Ser Asp Gly Tyr Ile Phe Asn Pro Lys Asp Ile
                370                 375                 380
Val Glu Glu Thr Ala Thr Ala Tyr Ile Val Arg His Gly Asp His Phe
385                 390                 395                 400
His Tyr Ile Pro Lys Ser Asn Gln Ile Gly Gln Pro Thr Leu Pro Asn
                405                 410                 415
Asn Ser Leu Ala Thr Pro Ser Pro Ser Leu Pro Ile Asn Pro Gly Thr
                420                 425                 430
Ser His Glu Lys His Glu Glu Asp Gly Tyr Gly Phe Asp Ala Asn Arg
                435                 440                 445
Ile Ile Ala Glu Asp Glu Ser Gly Phe Val Met Ser His Gly Asp His
450                 455                 460
Asn His Tyr Phe Phe Lys Lys Asp Leu Thr Glu Glu Gln Ile Lys Ala
465                 470                 475                 480
Ala Gln Lys His Leu Glu Glu Val Lys Thr Ser His Asn Gly Leu Asp
                485                 490                 495
Ser Leu Ser Ser His Glu Gln Asp Tyr Pro Gly Asn Ala Lys Glu Met
                500                 505                 510
Lys Asp Leu Asp Lys Lys Ile Glu Glu Lys Ile Ala Gly Ile Met Lys
                515                 520                 525
Gln Tyr Gly Val Lys Arg Glu Ser Ile Val Val Asn Lys Glu Lys Asn
                530                 535                 540
Ala Ile Ile Tyr Pro His Gly Asp His His Ala Asp Pro Ile Asp
545                 550                 555                 560
Glu His Lys Pro Val Gly Ile Gly His Ser His Ser Asn Tyr Glu Leu
                565                 570                 575
Phe Lys Pro Glu Glu Gly Val Ala Lys Lys Glu Gly Asn Lys Val Tyr
                580                 585                 590
Thr Gly Glu Glu Leu Thr Asn Val Val Asn Leu Leu Lys Asn Ser Thr
                595                 600                 605
Phe Asn Asn Gln Asn Phe Thr Leu Ala Asn Gly Gln Lys Arg Val Ser
                610                 615                 620
Phe Ser Phe Pro Pro Glu Leu Glu Lys Lys Leu Gly Ile Asn Met Leu
625                 630                 635                 640
Val Lys Leu Ile Thr Pro Asp Gly Lys Val Leu Glu Lys Val Ser Gly
                645                 650                 655
Lys Val Phe Gly Glu Gly Val Gly Asn Ile Ala Asn Phe Glu Leu Asp
                660                 665                 670
Gln Pro Tyr Leu Pro Gly Gln Thr Phe Lys Tyr Thr Ile Ala Ser Lys
                675                 680                 685
```

```
Asp Tyr Pro Glu Val Ser Tyr Asp Gly Thr Phe Thr Val Pro Thr Ser
    690             695                 700

Leu Ala Tyr Lys Met Ala Ser Gln Thr Ile Phe Tyr Pro Phe His Ala
705             710                 715                 720

Gly Asp Thr Tyr Leu Arg Val Asn Pro Gln Phe Ala Val Pro Lys Gly
            725                 730                 735

Thr Asp Ala Leu Val Arg Val Phe Asp Glu Phe His Gly Asn Ala Tyr
        740                 745                 750

Leu Glu Asn Asn Tyr Lys Val Gly Glu Ile Lys Leu Pro Ile Pro Lys
    755                 760                 765

Leu Asn Gln Gly Thr Thr Arg Thr Ala Gly Asn Lys Ile Pro Val Thr
770                 775                 780

Phe Met Ala Asn Ala Tyr Leu Asp Asn Gln Ser Thr Tyr Ile Val Glu
785                 790                 795                 800

Val Pro Ile Leu Glu Lys Glu Asn Gln Thr Asp Lys Pro Ser Ile Leu
                805                 810                 815

Pro Gln Phe Lys Arg Asn Lys Ala Gln Glu Asn Ser Lys Leu Asp Glu
            820                 825                 830

Lys Val Glu Glu Pro Lys Thr Ser Glu Lys Val Glu Lys Glu Lys Leu
    835                 840                 845

Ser Glu Thr Gly Asn Ser Thr Ser Asn Ser Thr Leu Glu Glu Val Pro
850                 855                 860

Thr Val Asp Pro Val Gln Glu Lys Val Ala Lys Phe Ala Glu Ser Tyr
865                 870                 875                 880

Gly Met Lys Leu Glu Asn Val Leu Phe Asn Met Asp Gly Thr Ile Glu
                885                 890                 895

Leu Tyr Leu Pro Ser Gly Glu Val Ile Lys Lys Asn Met Ala Asp Phe
            900                 905                 910

Thr Gly Glu Ala Pro Gln Gly Asn Gly Glu Asn Lys Pro Ser Glu Asn
        915                 920                 925

Gly Lys Val Ser Thr Gly Thr Val Glu Asn Gln Pro Thr Glu Asn Lys
    930                 935                 940

Pro Ala Asp Ser Leu Pro Glu Ala Pro Asn Glu Lys Pro Val Lys Pro
945                 950                 955                 960

Glu Asn Ser Thr Asp Asn Gly Met Leu Asn Pro Glu Gly Asn Val Gly
                965                 970                 975

Ser Asp Pro Met Leu Asp Pro Ala Leu Glu Glu Ala Pro Ala Val Asp
            980                 985                 990

Pro Val Gln Glu Lys Leu Glu Lys Phe Thr Ala Ser Tyr Gly Leu Gly
        995                 1000                1005

Leu Asp Ser Val Ile Phe Asn Met Asp Gly Thr Ile Glu Leu Arg Leu
    1010                1015                1020

Pro Ser Gly Glu Val Ile Lys Lys Asn Leu Ser Asp Phe Ile Ala
1025                1030                1035
```

<210> SEQ ID NO 3
<211> LENGTH: 2523
<212> TYPE: DNA
<213> ORGANISM: S. pneumoniae
<220> FEATURE:
<221> NAME/KEY: CDS
<222> LOCATION: (1)...(2520)
<223> OTHER INFORMATION: Coding region of BVH-11 gene

<400> SEQUENCE: 3

-continued

```
atg aaa atc aat aaa aaa tat cta gct ggg tca gta gct aca ctt gtt    48
Met Lys Ile Asn Lys Lys Tyr Leu Ala Gly Ser Val Ala Thr Leu Val
 1               5                  10                  15 tta agt gtc tgt gct tat gaa cta ggt ttg cat caa gct caa act gta    96
Leu Ser Val Cys Ala Tyr Glu Leu Gly Leu His Gln Ala Gln Thr Val
             20                  25                  30 aaa gaa aat aat cgt gtt tcc tat ata gat gga aaa caa gcg acg caa   144
Lys Glu Asn Asn Arg Val Ser Tyr Ile Asp Gly Lys Gln Ala Thr Gln
         35                  40                  45 aaa acg gag aat ttg act cct gat gag gtt agc aag cgt gaa gga atc   192
Lys Thr Glu Asn Leu Thr Pro Asp Glu Val Ser Lys Arg Glu Gly Ile
     50                  55                  60 aac gcc gaa caa atc gtc atc aag att acg gat caa ggt tat gtg acc   240
Asn Ala Glu Gln Ile Val Ile Lys Ile Thr Asp Gln Gly Tyr Val Thr
 65                  70                  75                  80 tct cat gga gac cat tat cat tac tat aat ggc aag gtc cct tat gat   288
Ser His Gly Asp His Tyr His Tyr Tyr Asn Gly Lys Val Pro Tyr Asp
                 85                  90                  95 gcc atc atc agt gaa gag ctc ctc atg aaa gat ccg aat tat cag ttg   336
Ala Ile Ile Ser Glu Glu Leu Leu Met Lys Asp Pro Asn Tyr Gln Leu
            100                 105                 110 aag gat tca gac att gtc aat gaa atc aag ggt ggt tat gtc att aag   384
Lys Asp Ser Asp Ile Val Asn Glu Ile Lys Gly Gly Tyr Val Ile Lys
        115                 120                 125 gta aac ggt aaa tac tat gtt tac ctt aag gat gca gct cat gcg gat   432
Val Asn Gly Lys Tyr Tyr Val Tyr Leu Lys Asp Ala Ala His Ala Asp
    130                 135                 140 aat gtc cgt aca aaa gaa gaa atc aat cgg caa aaa caa gaa cat agt   480
Asn Val Arg Thr Lys Glu Glu Ile Asn Arg Gln Lys Gln Glu His Ser
145                 150                 155                 160 cag cat cgt gaa gga ggg act tca gca aac gat ggt gcg gta gcc ttt   528
Gln His Arg Glu Gly Gly Thr Ser Ala Asn Asp Gly Ala Val Ala Phe
                165                 170                 175 gca cgt tca cag gga cgc tac acc aca gat gat ggt tat atc ttc aat   576
Ala Arg Ser Gln Gly Arg Tyr Thr Thr Asp Asp Gly Tyr Ile Phe Asn
            180                 185                 190 gca tct gat atc atc gaa gat acg ggc gat gcc tat atc gtt cct cat   624
Ala Ser Asp Ile Ile Glu Asp Thr Gly Asp Ala Tyr Ile Val Pro His
        195                 200                 205 gga gat cat tac cat tac att cct aag aat gag tta tca gct agc gag   672
Gly Asp His Tyr His Tyr Ile Pro Lys Asn Glu Leu Ser Ala Ser Glu
    210                 215                 220 ttg gct gct gca gaa gcc ttc cta tct ggt cgg gaa aat ctg tca aat   720
Leu Ala Ala Ala Glu Ala Phe Leu Ser Gly Arg Glu Asn Leu Ser Asn
225                 230                 235                 240 tta aga acc tat cgc cga caa aat agc gat aac act cca aga aca aac   768
Leu Arg Thr Tyr Arg Arg Gln Asn Ser Asp Asn Thr Pro Arg Thr Asn
                245                 250                 255 tgg gta cct tct gta agc aat cca gga act aca aat act aac aca agc   816
Trp Val Pro Ser Val Ser Asn Pro Gly Thr Thr Asn Thr Asn Thr Ser
            260                 265                 270 aac aac agc aac act aac agt caa gca agt caa agt aat gac att gat   864
Asn Asn Ser Asn Thr Asn Ser Gln Ala Ser Gln Ser Asn Asp Ile Asp
        275                 280                 285 agt ctc ttg aaa cag ctc tac aaa ctg cct ttg agt caa cgc cat gta   912
Ser Leu Leu Lys Gln Leu Tyr Lys Leu Pro Leu Ser Gln Arg His Val
    290                 295                 300 gaa tct gat ggc ctt att ttc gac cca gcg caa atc aca agt cga acc   960
Glu Ser Asp Gly Leu Ile Phe Asp Pro Ala Gln Ile Thr Ser Arg Thr
305                 310                 315                 320
```

-continued

```
gcc aga ggt gta gct gtc cct cat ggt aac cat tac cac ttt atc cct      1008
Ala Arg Gly Val Ala Val Pro His Gly Asn His Tyr His Phe Ile Pro
            325                 330                 335 tat gaa caa atg tct gaa ttg gaa aaa cga att gct cgt att att ccc      1056
Tyr Glu Gln Met Ser Glu Leu Glu Lys Arg Ile Ala Arg Ile Ile Pro
        340                 345                 350 ctt cgt tat cgt tca aac cat tgg gta cca gat tca aga cca gaa gaa      1104
Leu Arg Tyr Arg Ser Asn His Trp Val Pro Asp Ser Arg Pro Glu Glu
    355                 360                 365 cca agt cca caa ccg act cca gaa cct agt cca agt ccg caa cct gca      1152
Pro Ser Pro Gln Pro Thr Pro Glu Pro Ser Pro Ser Pro Gln Pro Ala
370                 375                 380 cca aat cct caa cca gct cca agc aat cca att gat gag aaa ttg gtc      1200
Pro Asn Pro Gln Pro Ala Pro Ser Asn Pro Ile Asp Glu Lys Leu Val
385                 390                 395                 400 aaa gaa gct gtt cga aaa gta ggc gat ggt tat gtc ttt gag gag aat      1248
Lys Glu Ala Val Arg Lys Val Gly Asp Gly Tyr Val Phe Glu Glu Asn
                405                 410                 415 gga gtt tct cgt tat atc cca gcc aag aat ctt tca gca gaa aca gca      1296
Gly Val Ser Arg Tyr Ile Pro Ala Lys Asn Leu Ser Ala Glu Thr Ala
            420                 425                 430 gca ggc att gat agc aaa ctg gcc aag cag gaa agt tta tct cat aag      1344
Ala Gly Ile Asp Ser Lys Leu Ala Lys Gln Glu Ser Leu Ser His Lys
        435                 440                 445 cta gga gct aag aaa act gac ctc cca tct agt gat cga gaa ttt tac      1392
Leu Gly Ala Lys Lys Thr Asp Leu Pro Ser Ser Asp Arg Glu Phe Tyr
    450                 455                 460 aat aag gct tat gac tta cta gca aga att cac caa gat tta ctt gat      1440
Asn Lys Ala Tyr Asp Leu Leu Ala Arg Ile His Gln Asp Leu Leu Asp
465                 470                 475                 480 aat aaa ggt cga caa gtt gat ttt gag gct ttg gat aac ctg ttg gaa      1488
Asn Lys Gly Arg Gln Val Asp Phe Glu Ala Leu Asp Asn Leu Leu Glu
                485                 490                 495 cga ctc aag gat gtc tca agt gat aaa gtc aag tta gtg gat gat att      1536
Arg Leu Lys Asp Val Ser Ser Asp Lys Val Lys Leu Val Asp Asp Ile
            500                 505                 510 ctt gcc ttc tta gct ccg att cgt cat cca gaa cgt tta gga aaa cca      1584
Leu Ala Phe Leu Ala Pro Ile Arg His Pro Glu Arg Leu Gly Lys Pro
        515                 520                 525 aat gcg caa att acc tac act gat gat gag att caa gta gcc aag ttg      1632
Asn Ala Gln Ile Thr Tyr Thr Asp Asp Glu Ile Gln Val Ala Lys Leu
    530                 535                 540 gca ggc aag tac aca aca gaa gac ggt tat atc ttt gat cct cgt gat      1680
Ala Gly Lys Tyr Thr Thr Glu Asp Gly Tyr Ile Phe Asp Pro Arg Asp
545                 550                 555                 560 ata acc agt gat gag ggg gat gcc tat gta act cca cat atg acc cat      1728
Ile Thr Ser Asp Glu Gly Asp Ala Tyr Val Thr Pro His Met Thr His
                565                 570                 575 agc cac tgg att aaa aaa gat agt ttg tct gaa gct gag aga gcg gca      1776
Ser His Trp Ile Lys Lys Asp Ser Leu Ser Glu Ala Glu Arg Ala Ala
            580                 585                 590 gcc cag gct tat gct aaa gag aaa ggt ttg acc cct cct tcg aca gac      1824
Ala Gln Ala Tyr Ala Lys Glu Lys Gly Leu Thr Pro Pro Ser Thr Asp
        595                 600                 605 cat cag gat tca gga aat act gag gca aaa gga gca gaa gct atc tac      1872
His Gln Asp Ser Gly Asn Thr Glu Ala Lys Gly Ala Glu Ala Ile Tyr
    610                 615                 620 aac cgc gtg aaa gca gct aag aag gtg cca ctt gat cgt atg cct tac      1920
Asn Arg Val Lys Ala Ala Lys Lys Val Pro Leu Asp Arg Met Pro Tyr
```

```
                                                                         1968
aat ctt caa tat act gta gaa gtc aaa aac ggt agt tta atc ata cct
Asn Leu Gln Tyr Thr Val Glu Val Lys Asn Gly Ser Leu Ile Ile Pro
                645                 650                 655 cat tat gac cat tac cat aac atc aaa ttt gag tgg ttt gac gaa ggc          2016
His Tyr Asp His Tyr His Asn Ile Lys Phe Glu Trp Phe Asp Glu Gly
            660                 665                 670 ctt tat gag gca cct aag ggg tat act ctt gag gat ctt ttg gcg act          2064
Leu Tyr Glu Ala Pro Lys Gly Tyr Thr Leu Glu Asp Leu Leu Ala Thr
        675                 680                 685 gtc aag tac tat gtc gaa cat cca aac gaa cgt ccg cat tca gat aat          2112
Val Lys Tyr Tyr Val Glu His Pro Asn Glu Arg Pro His Ser Asp Asn
    690                 695                 700 ggt ttt ggt aac gct agc gac cat gtt caa aga aac aaa aat ggt caa          2160
Gly Phe Gly Asn Ala Ser Asp His Val Gln Arg Asn Lys Asn Gly Gln
705                 710                 715                 720 gct gat acc aat caa acg gaa aaa cca agc gag gag aaa cct cag aca          2208
Ala Asp Thr Asn Gln Thr Glu Lys Pro Ser Glu Glu Lys Pro Gln Thr
                725                 730                 735 gaa aaa cct gag gaa gaa acc cct cga gaa gag aaa cca caa agc gag          2256
Glu Lys Pro Glu Glu Glu Thr Pro Arg Glu Glu Lys Pro Gln Ser Glu
            740                 745                 750 aaa cca gag tct cca aaa cca aca gag gaa cca gaa gaa gaa tca cca          2304
Lys Pro Glu Ser Pro Lys Pro Thr Glu Glu Pro Glu Glu Glu Ser Pro
        755                 760                 765 gag gaa tca gaa gaa cct cag gtc gag act gaa aag gtt gaa gaa aaa          2352
Glu Glu Ser Glu Glu Pro Gln Val Glu Thr Glu Lys Val Glu Glu Lys
    770                 775                 780 ctg aga gag gct gaa gat tta ctt gga aaa atc cag gat cca att atc          2400
Leu Arg Glu Ala Glu Asp Leu Leu Gly Lys Ile Gln Asp Pro Ile Ile
785                 790                 795                 800 aag tcc aat gcc aaa gag act ctc aca gga tta aaa aat aat tta cta          2448
Lys Ser Asn Ala Lys Glu Thr Leu Thr Gly Leu Lys Asn Asn Leu Leu
                805                 810                 815 ttt ggc acc cag gac aac aat act att atg gca gaa gct gaa aaa cta          2496
Phe Gly Thr Gln Asp Asn Asn Thr Ile Met Ala Glu Ala Glu Lys Leu
            820                 825                 830 ttg gct tta tta aag gag agt aag taa                                      2523
Leu Ala Leu Leu Lys Glu Ser Lys
        835                 840
```

<210> SEQ ID NO 4
<211> LENGTH: 840
<212> TYPE: PRT
<213> ORGANISM: S. pneumoniae

<400> SEQUENCE: 4

```
Met Lys Ile Asn Lys Lys Tyr Leu Ala Gly Ser Val Ala Thr Leu Val
1               5                   10                  15

Leu Ser Val Cys Ala Tyr Glu Leu Gly Leu His Gln Ala Gln Thr Val
                20                  25                  30

Lys Glu Asn Asn Arg Val Ser Tyr Ile Asp Gly Lys Gln Ala Thr Gln
            35                  40                  45

Lys Thr Glu Asn Leu Thr Pro Asp Glu Val Ser Lys Arg Glu Gly Ile
        50                  55                  60

Asn Ala Glu Gln Ile Val Ile Lys Ile Thr Asp Gln Gly Tyr Val Thr
65                  70                  75                  80

Ser His Gly Asp His Tyr His Tyr Tyr Asn Gly Lys Val Pro Tyr Asp
                85                  90                  95
```

-continued

```
Ala Ile Ile Ser Glu Glu Leu Leu Met Lys Asp Pro Asn Tyr Gln Leu
            100                 105                 110

Lys Asp Ser Asp Ile Val Asn Glu Ile Lys Gly Gly Tyr Val Ile Lys
            115                 120                 125

Val Asn Gly Lys Tyr Tyr Val Tyr Leu Lys Asp Ala Ala His Ala Asp
130             135                 140

Asn Val Arg Thr Lys Glu Glu Ile Asn Arg Gln Lys Gln Glu His Ser
145                 150                 155                 160

Gln His Arg Glu Gly Gly Thr Ser Ala Asn Asp Gly Ala Val Ala Phe
                165                 170                 175

Ala Arg Ser Gln Gly Arg Tyr Thr Thr Asp Asp Gly Tyr Ile Phe Asn
            180                 185                 190

Ala Ser Asp Ile Ile Glu Asp Thr Gly Asp Ala Tyr Ile Val Pro His
            195                 200                 205

Gly Asp His Tyr His Tyr Ile Pro Lys Asn Glu Leu Ser Ala Ser Glu
210                 215                 220

Leu Ala Ala Ala Glu Ala Phe Leu Ser Gly Arg Glu Asn Leu Ser Asn
225                 230                 235                 240

Leu Arg Thr Tyr Arg Arg Gln Asn Ser Asp Asn Thr Pro Arg Thr Asn
                245                 250                 255

Trp Val Pro Ser Val Ser Asn Pro Gly Thr Thr Asn Thr Asn Thr Ser
            260                 265                 270

Asn Asn Ser Asn Thr Asn Ser Gln Ala Ser Gln Ser Asn Asp Ile Asp
            275                 280                 285

Ser Leu Leu Lys Gln Leu Tyr Lys Leu Pro Leu Ser Gln Arg His Val
            290                 295                 300

Glu Ser Asp Gly Leu Ile Phe Asp Pro Ala Gln Ile Thr Ser Arg Thr
305                 310                 315                 320

Ala Arg Gly Val Ala Val Pro His Gly Asn His Tyr His Phe Ile Pro
                325                 330                 335

Tyr Glu Gln Met Ser Glu Leu Glu Lys Arg Ile Ala Arg Ile Ile Pro
            340                 345                 350

Leu Arg Tyr Arg Ser Asn His Trp Val Pro Asp Ser Arg Pro Glu Glu
            355                 360                 365

Pro Ser Pro Gln Pro Thr Pro Glu Pro Ser Pro Ser Pro Gln Pro Ala
            370                 375                 380

Pro Asn Pro Gln Pro Ala Pro Ser Asn Pro Ile Asp Glu Lys Leu Val
385                 390                 395                 400

Lys Glu Ala Val Arg Lys Val Gly Asp Gly Tyr Val Phe Glu Glu Asn
                405                 410                 415

Gly Val Ser Arg Tyr Ile Pro Ala Lys Asn Leu Ser Ala Glu Thr Ala
            420                 425                 430

Ala Gly Ile Asp Ser Lys Leu Ala Lys Gln Glu Ser Leu Ser His Lys
            435                 440                 445

Leu Gly Ala Lys Lys Thr Asp Leu Pro Ser Ser Asp Arg Glu Phe Tyr
450                 455                 460

Asn Lys Ala Tyr Asp Leu Leu Ala Arg Ile His Gln Asp Leu Leu Asp
465                 470                 475                 480

Asn Lys Gly Arg Gln Val Asp Phe Glu Ala Leu Asp Asn Leu Leu Glu
                485                 490                 495

Arg Leu Lys Asp Val Ser Ser Asp Lys Val Lys Leu Val Asp Asp Ile
            500                 505                 510
```

| Leu | Ala | Phe | Leu | Ala | Pro | Ile | Arg | His | Pro | Glu | Arg | Leu | Gly | Lys | Pro |
| 515 | | | | 520 | | | | 525 | | | | | | | |

Asn Ala Gln Ile Thr Tyr Thr Asp Asp Glu Ile Gln Val Ala Lys Leu
530             535             540

Ala Gly Lys Tyr Thr Thr Glu Asp Gly Tyr Ile Phe Asp Pro Arg Asp
545             550             555             560

Ile Thr Ser Asp Glu Gly Asp Ala Tyr Val Thr Pro His Met Thr His
                565             570             575

Ser His Trp Ile Lys Lys Asp Ser Leu Ser Glu Ala Glu Arg Ala Ala
            580             585             590

Ala Gln Ala Tyr Ala Lys Glu Lys Gly Leu Thr Pro Ser Thr Asp
            595             600             605

His Gln Asp Ser Gly Asn Thr Glu Ala Lys Gly Ala Glu Ala Ile Tyr
            610             615             620

Asn Arg Val Lys Ala Ala Lys Lys Val Pro Leu Asp Arg Met Pro Tyr
625             630             635             640

Asn Leu Gln Tyr Thr Val Glu Val Lys Asn Gly Ser Leu Ile Ile Pro
            645             650             655

His Tyr Asp His Tyr His Asn Ile Lys Phe Glu Trp Phe Asp Glu Gly
            660             665             670

Leu Tyr Glu Ala Pro Lys Gly Tyr Thr Leu Glu Asp Leu Leu Ala Thr
            675             680             685

Val Lys Tyr Tyr Val Glu His Pro Asn Glu Arg Pro His Ser Asp Asn
            690             695             700

Gly Phe Gly Asn Ala Ser Asp His Val Gln Arg Asn Lys Asn Gly Gln
705             710             715             720

Ala Asp Thr Asn Gln Thr Glu Lys Pro Ser Glu Glu Lys Pro Gln Thr
            725             730             735

Glu Lys Pro Glu Glu Glu Thr Pro Arg Glu Lys Pro Gln Ser Glu
            740             745             750

Lys Pro Glu Ser Pro Lys Pro Thr Glu Glu Pro Glu Glu Ser Pro
            755             760             765

Glu Glu Ser Glu Glu Pro Gln Val Glu Thr Glu Lys Val Glu Glu Lys
770             775             780

Leu Arg Glu Ala Glu Asp Leu Leu Gly Lys Ile Gln Asp Pro Ile Ile
785             790             795             800

Lys Ser Asn Ala Lys Glu Thr Leu Thr Gly Leu Lys Asn Asn Leu Leu
            805             810             815

Phe Gly Thr Gln Asp Asn Asn Thr Ile Met Ala Glu Ala Glu Lys Leu
            820             825             830

Leu Ala Leu Leu Lys Glu Ser Lys
            835             840

```
<210> SEQ ID NO 5
<211> LENGTH: 1581
<212> TYPE: DNA
<213> ORGANISM: S. pneumoniae
<220> FEATURE:
<221> NAME/KEY: CDS
<222> LOCATION: (1)...(1578)

<400> SEQUENCE: 5 atg gag aat ata gac atg ttt aaa tca aat cat gag cga aga atg cgt    48
Met Glu Asn Ile Asp Met Phe Lys Ser Asn His Glu Arg Arg Met Arg
 1               5                  10                  15 tat tcc att cgt aaa ttt agt gta gga gta gct agc gta gct gtt gcc    96
```

```
                Tyr Ser Ile Arg Lys Phe Ser Val Gly Val Ala Ser Val Ala Val Ala
                                20                  25                  30 agt ctt ttt atg gga agt gtt gta cat gcg aca gag aaa gag gga agt         144
Ser Leu Phe Met Gly Ser Val Val His Ala Thr Glu Lys Glu Gly Ser
        35                  40                  45 acc caa gca gcc act tct ttt aat agg gga aat gga agt cag gca gaa         192
Thr Gln Ala Ala Thr Ser Phe Asn Arg Gly Asn Gly Ser Gln Ala Glu
    50                  55                  60 caa cgt gga gaa ctc gat tta gaa cga gat aag gca atg aaa gcg gtc         240
Gln Arg Gly Glu Leu Asp Leu Glu Arg Asp Lys Ala Met Lys Ala Val
65                  70                  75                  80 agt gaa tat gta gga aaa atg gtg aga gat gcc tat gta aaa tca gat         288
Ser Glu Tyr Val Gly Lys Met Val Arg Asp Ala Tyr Val Lys Ser Asp
                85                  90                  95 aga aaa cga cat aaa aat act gta gct cta gtt aac cag ttg gga aac         336
Arg Lys Arg His Lys Asn Thr Val Ala Leu Val Asn Gln Leu Gly Asn
            100                 105                 110 att aag aac agg tat ttg aat gaa ata gtt cat tca acc tca aaa agc         384
Ile Lys Asn Arg Tyr Leu Asn Glu Ile Val His Ser Thr Ser Lys Ser
        115                 120                 125 caa cta cag gaa ctg atg atg aag agt caa tca gaa gta gat gaa gct         432
Gln Leu Gln Glu Leu Met Met Lys Ser Gln Ser Glu Val Asp Glu Ala
    130                 135                 140 gtg tct aaa ttt gaa aag gac tca ttt tct tcg tca agt tca gga tcc         480
Val Ser Lys Phe Glu Lys Asp Ser Phe Ser Ser Ser Ser Ser Gly Ser
145                 150                 155                 160 tcc act aaa cca gaa act ccg cag ccg gaa aat cca gag cat caa aaa         528
Ser Thr Lys Pro Glu Thr Pro Gln Pro Glu Asn Pro Glu His Gln Lys
                165                 170                 175 cca aca act cca tct ccg gat acc aaa cca agc cct caa cca gaa ggc         576
Pro Thr Thr Pro Ser Pro Asp Thr Lys Pro Ser Pro Gln Pro Glu Gly
            180                 185                 190 aag aaa cca agc gta cca gac att aat cag gaa aaa gaa aaa gct aag         624
Lys Lys Pro Ser Val Pro Asp Ile Asn Gln Glu Lys Glu Lys Ala Lys
        195                 200                 205 ctt gct gta gta acc tac atg agc aag att tta gat gat ata caa aaa         672
Leu Ala Val Val Thr Tyr Met Ser Lys Ile Leu Asp Asp Ile Gln Lys
    210                 215                 220 cat cat ctg cag aaa gaa aaa cat cgt cag att gtt gct ctt att aag         720
His His Leu Gln Lys Glu Lys His Arg Gln Ile Val Ala Leu Ile Lys
225                 230                 235                 240 gag ctt gat gag ctt aaa aag caa gct ctt tct gaa att gat aat gta         768
Glu Leu Asp Glu Leu Lys Lys Gln Ala Leu Ser Glu Ile Asp Asn Val
                245                 250                 255 aat acc aaa gta gaa att gaa aat aca gtc cac aag ata ttt gca gac         816
Asn Thr Lys Val Glu Ile Glu Asn Thr Val His Lys Ile Phe Ala Asp
            260                 265                 270 atg gat gca gtt gtg act aaa ttc aaa aaa ggc tta act cag gac aca         864
Met Asp Ala Val Val Thr Lys Phe Lys Lys Gly Leu Thr Gln Asp Thr
        275                 280                 285 cca aaa gaa cca ggt aac aaa aaa cca tct gct cca aaa cca ggt atg         912
Pro Lys Glu Pro Gly Asn Lys Lys Pro Ser Ala Pro Lys Pro Gly Met
    290                 295                 300 caa cca agt cct caa cca gag gtt aaa ccg cag ctg gaa aaa cca aaa         960
Gln Pro Ser Pro Gln Pro Glu Val Lys Pro Gln Leu Glu Lys Pro Lys
305                 310                 315                 320 cca gag gtt aaa ccg caa cca gaa aaa cca aaa cca gag gtt aaa ccg        1008
Pro Glu Val Lys Pro Gln Pro Glu Lys Pro Lys Pro Glu Val Lys Pro
                325                 330                 335
```

```
cag ccg gaa aaa cca aaa cca gag gtt aaa ccg cag ccg gaa aaa cca    1056
Gln Pro Glu Lys Pro Lys Pro Glu Val Lys Pro Gln Pro Glu Lys Pro
            340                 345                 350 aaa cca gag gtt aaa ccg cag ccg gaa aaa cca aaa cca gag gtt aaa    1104
Lys Pro Glu Val Lys Pro Gln Pro Glu Lys Pro Lys Pro Glu Val Lys
        355                 360                 365 ccg cag ccg gaa aaa cca aaa cca gag gtt aaa ccg cag ccg gaa aaa    1152
Pro Gln Pro Glu Lys Pro Lys Pro Glu Val Lys Pro Gln Pro Glu Lys
    370                 375                 380 cca aaa cca gag gtt aaa ccg cag ccg gaa aaa cca aaa cca gag gtt    1200
Pro Lys Pro Glu Val Lys Pro Gln Pro Glu Lys Pro Lys Pro Glu Val
385                 390                 395                 400 aaa ccg cag ccg gaa aaa cca aaa cca gag gtt aaa ccg cag ccg gaa    1248
Lys Pro Gln Pro Glu Lys Pro Lys Pro Glu Val Lys Pro Gln Pro Glu
                405                 410                 415 aaa cca aaa cca gag gtt aaa ccg cag ccg gaa aaa cca aaa cca gag    1296
Lys Pro Lys Pro Glu Val Lys Pro Gln Pro Glu Lys Pro Lys Pro Glu
            420                 425                 430 gtt aaa ccg caa cca gaa aaa cca aaa cca gag gtt aaa ccg caa cca    1344
Val Lys Pro Gln Pro Glu Lys Pro Lys Pro Glu Val Lys Pro Gln Pro
        435                 440                 445 gaa aaa cca aaa cca gat aat agc aag cca caa gca gat gat aag aag    1392
Glu Lys Pro Lys Pro Asp Asn Ser Lys Pro Gln Ala Asp Asp Lys Lys
    450                 455                 460 cca tca act aca aat aat tta agc aag gac aag caa cct tct aac caa    1440
Pro Ser Thr Thr Asn Asn Leu Ser Lys Asp Lys Gln Pro Ser Asn Gln
465                 470                 475                 480 gct tca aca aac gaa aaa gca aca aat aaa ccg aag aag tca ttg cca    1488
Ala Ser Thr Asn Glu Lys Ala Thr Asn Lys Pro Lys Lys Ser Leu Pro
                485                 490                 495 tca act gga tct att tca aat cta gca ctt gaa att gca ggt ctt ctt    1536
Ser Thr Gly Ser Ile Ser Asn Leu Ala Leu Glu Ile Ala Gly Leu Leu
            500                 505                 510 acc ttg gcg ggg gca acc att ctt gct aag aaa aga atg aaa            1578
Thr Leu Ala Gly Ala Thr Ile Leu Ala Lys Lys Arg Met Lys
        515                 520                 525 tag                                                                 1581

<210> SEQ ID NO 6
<211> LENGTH: 526
<212> TYPE: PRT
<213> ORGANISM: S. pneumoniae

<400> SEQUENCE: 6

Met Glu Asn Ile Asp Met Phe Lys Ser Asn His Glu Arg Arg Met Arg
 1               5                  10                  15

Tyr Ser Ile Arg Lys Phe Ser Val Gly Val Ala Ser Val Ala Val Ala
            20                  25                  30

Ser Leu Phe Met Gly Ser Val His Ala Thr Glu Lys Glu Gly Ser
        35                  40                  45

Thr Gln Ala Ala Thr Ser Phe Asn Arg Gly Asn Gly Ser Gln Ala Glu
    50                  55                  60

Gln Arg Gly Glu Leu Asp Leu Glu Arg Asp Lys Ala Met Lys Ala Val
65                  70                  75                  80

Ser Glu Tyr Val Gly Lys Met Val Arg Asp Ala Tyr Val Lys Ser Asp
                85                  90                  95

Arg Lys Arg His Lys Asn Thr Val Ala Leu Val Asn Gln Leu Gly Asn
            100                 105                 110
```

```
Ile Lys Asn Arg Tyr Leu Asn Glu Ile Val His Ser Thr Ser Lys Ser
        115                 120                 125

Gln Leu Gln Glu Leu Met Met Lys Ser Gln Ser Glu Val Asp Glu Ala
    130                 135                 140

Val Ser Lys Phe Glu Lys Asp Ser Phe Ser Ser Ser Ser Ser Gly Ser
145                 150                 155                 160

Ser Thr Lys Pro Glu Thr Pro Gln Pro Glu Asn Pro Glu His Gln Lys
                165                 170                 175

Pro Thr Thr Pro Ser Pro Asp Thr Lys Pro Ser Pro Gln Pro Glu Gly
            180                 185                 190

Lys Lys Pro Ser Val Pro Asp Ile Asn Gln Glu Lys Glu Lys Ala Lys
        195                 200                 205

Leu Ala Val Val Thr Tyr Met Ser Lys Ile Leu Asp Asp Ile Gln Lys
    210                 215                 220

His His Leu Gln Lys Glu Lys His Arg Gln Ile Val Ala Leu Ile Lys
225                 230                 235                 240

Glu Leu Asp Glu Leu Lys Lys Gln Ala Leu Ser Glu Ile Asp Asn Val
                245                 250                 255

Asn Thr Lys Val Glu Ile Glu Asn Thr Val His Lys Ile Phe Ala Asp
            260                 265                 270

Met Asp Ala Val Val Thr Lys Phe Lys Lys Gly Leu Thr Gln Asp Thr
        275                 280                 285

Pro Lys Glu Pro Gly Asn Lys Lys Pro Ser Ala Pro Lys Pro Gly Met
    290                 295                 300

Gln Pro Ser Pro Gln Pro Glu Val Lys Pro Gln Leu Glu Lys Pro Lys
305                 310                 315                 320

Pro Glu Val Lys Pro Gln Pro Glu Lys Pro Lys Pro Glu Val Lys Pro
                325                 330                 335

Gln Pro Glu Lys Pro Lys Pro Glu Val Lys Pro Gln Pro Glu Lys Pro
            340                 345                 350

Lys Pro Glu Val Lys Pro Gln Pro Glu Lys Pro Lys Pro Glu Val Lys
        355                 360                 365

Pro Gln Pro Glu Lys Pro Lys Pro Glu Val Lys Pro Gln Pro Glu Lys
    370                 375                 380

Pro Lys Pro Glu Val Lys Pro Gln Pro Glu Lys Pro Lys Pro Glu Val
385                 390                 395                 400

Lys Pro Gln Pro Glu Lys Pro Lys Pro Glu Val Lys Pro Gln Pro Glu
                405                 410                 415

Lys Pro Lys Pro Glu Val Lys Pro Gln Pro Glu Lys Pro Lys Pro Glu
            420                 425                 430

Val Lys Pro Gln Pro Glu Lys Pro Lys Pro Glu Val Lys Pro Gln Pro
        435                 440                 445

Glu Lys Pro Lys Pro Asp Asn Ser Lys Pro Gln Ala Asp Asp Lys Lys
    450                 455                 460

Pro Ser Thr Thr Asn Asn Leu Ser Lys Asp Lys Gln Pro Ser Asn Gln
465                 470                 475                 480

Ala Ser Thr Asn Glu Lys Ala Thr Asn Lys Pro Lys Lys Ser Leu Pro
                485                 490                 495

Ser Thr Gly Ser Ile Ser Asn Leu Ala Leu Glu Ile Ala Gly Leu Leu
            500                 505                 510

Thr Leu Ala Gly Ala Thr Ile Leu Ala Lys Lys Arg Met Lys
        515                 520                 525
```

```
<210> SEQ ID NO 7
<211> LENGTH: 1455
<212> TYPE: DNA
<213> ORGANISM: S. pneumoniae
<220> FEATURE:
<221> NAME/KEY: CDS
<222> LOCATION: (1)...(1452)

<400> SEQUENCE: 7
```

| | | | | | | | | | | | | | | | | |
|---|---|---|---|---|---|---|---|---|---|---|---|---|---|---|---|---|
| atg | aaa | ttt | agt | aaa | aaa | tat | ata | gca | gct | gga | tca | gct | gtt | atc | gta | 48 |
| Met | Lys | Phe | Ser | Lys | Lys | Tyr | Ile | Ala | Ala | Gly | Ser | Ala | Val | Ile | Val | |
| 1 | | | | 5 | | | | | 10 | | | | | 15 | | |
| tcc | ttg | agt | cta | tgt | gcc | tat | gca | cta | aac | cag | cat | cgt | tcg | cag | gaa | 96 |
| Ser | Leu | Ser | Leu | Cys | Ala | Tyr | Ala | Leu | Asn | Gln | His | Arg | Ser | Gln | Glu | |
| | | | 20 | | | | | 25 | | | | | 30 | | | |
| aat | aag | gac | aat | aat | cgt | gtc | tct | tat | gtg | gat | ggc | agc | cag | tca | agt | 144 |
| Asn | Lys | Asp | Asn | Asn | Arg | Val | Ser | Tyr | Val | Asp | Gly | Ser | Gln | Ser | Ser | |
| | | 35 | | | | | 40 | | | | | 45 | | | | |
| cag | aaa | agt | gaa | aac | ttg | aca | cca | gac | cag | gtt | agc | cag | aaa | gaa | gga | 192 |
| Gln | Lys | Ser | Glu | Asn | Leu | Thr | Pro | Asp | Gln | Val | Ser | Gln | Lys | Glu | Gly | |
| | 50 | | | | | 55 | | | | | 60 | | | | | |
| att | cag | gct | gag | caa | att | gta | atc | aaa | att | aca | gat | cag | ggc | tat | gta | 240 |
| Ile | Gln | Ala | Glu | Gln | Ile | Val | Ile | Lys | Ile | Thr | Asp | Gln | Gly | Tyr | Val | |
| 65 | | | | | 70 | | | | | 75 | | | | | 80 | |
| acg | tca | cac | ggt | gac | cac | tat | cat | tac | tat | aat | ggg | aaa | gtt | cct | tat | 288 |
| Thr | Ser | His | Gly | Asp | His | Tyr | His | Tyr | Tyr | Asn | Gly | Lys | Val | Pro | Tyr | |
| | | | | 85 | | | | | 90 | | | | | 95 | | |
| gat | gcc | ctc | ttt | agt | gaa | gaa | ctc | ttg | atg | aag | gat | cca | aac | tat | caa | 336 |
| Asp | Ala | Leu | Phe | Ser | Glu | Glu | Leu | Leu | Met | Lys | Asp | Pro | Asn | Tyr | Gln | |
| | | | | 100 | | | | | 105 | | | | | 110 | | |
| ctt | aaa | gac | gct | gat | att | gtc | aat | gaa | gtc | aag | ggt | ggt | tat | atc | atc | 384 |
| Leu | Lys | Asp | Ala | Asp | Ile | Val | Asn | Glu | Val | Lys | Gly | Gly | Tyr | Ile | Ile | |
| | | | 115 | | | | | 120 | | | | | 125 | | | |
| aag | gtc | gat | gga | aaa | tat | tat | gtc | tac | ctg | aaa | gat | gca | gct | cat | gct | 432 |
| Lys | Val | Asp | Gly | Lys | Tyr | Tyr | Val | Tyr | Leu | Lys | Asp | Ala | Ala | His | Ala | |
| | | 130 | | | | | 135 | | | | | 140 | | | | |
| gat | aat | gtt | cga | act | aaa | gat | gaa | atc | aat | cgt | caa | aaa | caa | gaa | cat | 480 |
| Asp | Asn | Val | Arg | Thr | Lys | Asp | Glu | Ile | Asn | Arg | Gln | Lys | Gln | Glu | His | |
| 145 | | | | | 150 | | | | | 155 | | | | | 160 | |
| gtc | aaa | gat | aat | gag | aag | gtt | aac | tct | aat | gtt | gct | gta | gca | agg | tct | 528 |
| Val | Lys | Asp | Asn | Glu | Lys | Val | Asn | Ser | Asn | Val | Ala | Val | Ala | Arg | Ser | |
| | | | | 165 | | | | | 170 | | | | | 175 | | |
| cag | gga | cga | tat | acg | aca | aat | gat | ggt | tat | gtc | ttt | aat | cca | gct | gat | 576 |
| Gln | Gly | Arg | Tyr | Thr | Thr | Asn | Asp | Gly | Tyr | Val | Phe | Asn | Pro | Ala | Asp | |
| | | | 180 | | | | | 185 | | | | | 190 | | | |
| att | atc | gaa | gat | acg | ggt | aat | gct | tat | atc | gtt | cct | cat | gga | ggt | cac | 624 |
| Ile | Ile | Glu | Asp | Thr | Gly | Asn | Ala | Tyr | Ile | Val | Pro | His | Gly | Gly | His | |
| | | 195 | | | | | 200 | | | | | 205 | | | | |
| tat | cac | tac | att | ccc | aaa | agc | gat | tta | tct | gct | agt | gaa | tta | gca | gca | 672 |
| Tyr | His | Tyr | Ile | Pro | Lys | Ser | Asp | Leu | Ser | Ala | Ser | Glu | Leu | Ala | Ala | |
| | 210 | | | | | 215 | | | | | 220 | | | | | |
| gct | aaa | gca | cat | ctg | gct | gga | aaa | aat | atg | caa | ccg | agt | cag | tta | agc | 720 |
| Ala | Lys | Ala | His | Leu | Ala | Gly | Lys | Asn | Met | Gln | Pro | Ser | Gln | Leu | Ser | |
| 225 | | | | | 230 | | | | | 235 | | | | | 240 | |
| tat | tct | tca | aca | gct | agt | gac | aat | aac | acg | caa | tct | gta | gca | aaa | gga | 768 |
| Tyr | Ser | Ser | Thr | Ala | Ser | Asp | Asn | Asn | Thr | Gln | Ser | Val | Ala | Lys | Gly | |
| | | | | 245 | | | | | 250 | | | | | 255 | | |
| tca | act | agc | aag | cca | gca | aat | aaa | tct | gaa | aat | ctc | cag | agt | ctt | ttg | 816 |
| Ser | Thr | Ser | Lys | Pro | Ala | Asn | Lys | Ser | Glu | Asn | Leu | Gln | Ser | Leu | Leu | |
| | | | 260 | | | | | 265 | | | | | 270 | | | |
| aag | gaa | ctc | tat | gat | tca | cct | agc | gcc | caa | cgt | tac | agt | gaa | tca | gat | 864 |

-continued

```
Lys Glu Leu Tyr Asp Ser Pro Ser Ala Gln Arg Tyr Ser Glu Ser Asp
        275                 280                 285 ggc ctg gtc ttt gac cct gct aag att atc agt cgt aca cca aat gga         912
Gly Leu Val Phe Asp Pro Ala Lys Ile Ile Ser Arg Thr Pro Asn Gly
290                 295                 300 gtt gcg att ccg cat ggc gac cat tac cac ttt att cct tac agc aag         960
Val Ala Ile Pro His Gly Asp His Tyr His Phe Ile Pro Tyr Ser Lys
305                 310                 315                 320 ctt tct gct tta gaa gaa aag att gcc aga atg gtg cct atc agt gga        1008
Leu Ser Ala Leu Glu Glu Lys Ile Ala Arg Met Val Pro Ile Ser Gly
        325                 330                 335 act ggt tct aca gtt tct aca aat gca aaa cct aat gaa gta gtg tct        1056
Thr Gly Ser Thr Val Ser Thr Asn Ala Lys Pro Asn Glu Val Val Ser
        340                 345                 350 agt cta ggc agt ctt tca agc aat cct tct tct tta acg aca agt aag        1104
Ser Leu Gly Ser Leu Ser Ser Asn Pro Ser Ser Leu Thr Thr Ser Lys
    355                 360                 365 gag ctc tct tca gca tct gat ggt tat att ttt aat cca aaa gat atc        1152
Glu Leu Ser Ser Ala Ser Asp Gly Tyr Ile Phe Asn Pro Lys Asp Ile
370                 375                 380 gtt gaa gaa acg gct aca gct tat att gta aga cat ggt gat cat ttc        1200
Val Glu Glu Thr Ala Thr Ala Tyr Ile Val Arg His Gly Asp His Phe
385                 390                 395                 400 cat tac att cca aaa tca aat caa att ggg caa ccg act ctt cca aac        1248
His Tyr Ile Pro Lys Ser Asn Gln Ile Gly Gln Pro Thr Leu Pro Asn
        405                 410                 415 aat agt cta gca aca cct tct cca tct ctt cca atc aat cca gga act        1296
Asn Ser Leu Ala Thr Pro Ser Pro Ser Leu Pro Ile Asn Pro Gly Thr
        420                 425                 430 tca cat gag aaa cat gaa gaa gat gga tac gga ttt gat gct aat cgt        1344
Ser His Glu Lys His Glu Glu Asp Gly Tyr Gly Phe Asp Ala Asn Arg
        435                 440                 445 att atc gct gaa gat gaa tca ggt ttt gtc atg agt cac gga gac cac        1392
Ile Ile Ala Glu Asp Glu Ser Gly Phe Val Met Ser His Gly Asp His
450                 455                 460 aat cat tat ttc ttc aag aag gac ttg aca gaa gag caa att aag gtg        1440
Asn His Tyr Phe Phe Lys Lys Asp Leu Thr Glu Glu Gln Ile Lys Val
465                 470                 475                 480 cgc aaa aac att tag                                                    1455
Arg Lys Asn Ile <210> SEQ ID NO 8
<211> LENGTH: 484
<212> TYPE: PRT
<213> ORGANISM: S. pneumoniae

<400> SEQUENCE: 8

Met Lys Phe Ser Lys Lys Tyr Ile Ala Ala Gly Ser Ala Val Ile Val
1               5                   10                  15

Ser Leu Ser Leu Cys Ala Tyr Ala Leu Asn Gln His Arg Ser Gln Glu
            20                  25                  30

Asn Lys Asp Asn Asn Arg Val Ser Tyr Val Asp Gly Ser Gln Ser Ser
        35                  40                  45

Gln Lys Ser Glu Asn Leu Thr Pro Asp Gln Val Ser Gln Lys Glu Gly
    50                  55                  60

Ile Gln Ala Glu Gln Ile Val Ile Lys Ile Thr Asp Gln Gly Tyr Val
65                  70                  75                  80

Thr Ser His Gly Asp His Tyr His Tyr Tyr Asn Gly Lys Val Pro Tyr
                85                  90                  95
```

```
Asp Ala Leu Phe Ser Glu Glu Leu Leu Met Lys Asp Pro Asn Tyr Gln
            100                 105                 110

Leu Lys Asp Ala Asp Ile Val Asn Glu Val Lys Gly Gly Tyr Ile Ile
        115                 120                 125

Lys Val Asp Gly Lys Tyr Tyr Val Tyr Leu Lys Asp Ala Ala His Ala
    130                 135                 140

Asp Asn Val Arg Thr Lys Asp Glu Ile Asn Arg Gln Lys Gln Glu His
145                 150                 155                 160

Val Lys Asp Asn Glu Lys Val Asn Ser Asn Val Ala Val Ala Arg Ser
                165                 170                 175

Gln Gly Arg Tyr Thr Thr Asn Asp Gly Tyr Val Phe Asn Pro Ala Asp
            180                 185                 190

Ile Ile Glu Asp Thr Gly Asn Ala Tyr Ile Val Pro His Gly Gly His
        195                 200                 205

Tyr His Tyr Ile Pro Lys Ser Asp Leu Ser Ala Ser Glu Leu Ala Ala
    210                 215                 220

Ala Lys Ala His Leu Ala Gly Lys Asn Met Gln Pro Ser Gln Leu Ser
225                 230                 235                 240

Tyr Ser Ser Thr Ala Ser Asp Asn Asn Thr Gln Ser Val Ala Lys Gly
                245                 250                 255

Ser Thr Ser Lys Pro Ala Asn Lys Ser Glu Asn Leu Gln Ser Leu Leu
            260                 265                 270

Lys Glu Leu Tyr Asp Ser Pro Ser Ala Gln Arg Tyr Ser Glu Ser Asp
        275                 280                 285

Gly Leu Val Phe Asp Pro Ala Lys Ile Ile Ser Arg Thr Pro Asn Gly
    290                 295                 300

Val Ala Ile Pro His Gly Asp His Tyr His Phe Ile Pro Tyr Ser Lys
305                 310                 315                 320

Leu Ser Ala Leu Glu Glu Lys Ile Ala Arg Met Val Pro Ile Ser Gly
                325                 330                 335

Thr Gly Ser Thr Val Ser Thr Asn Ala Lys Pro Asn Glu Val Val Ser
            340                 345                 350

Ser Leu Gly Ser Leu Ser Ser Asn Pro Ser Ser Leu Thr Thr Ser Lys
        355                 360                 365

Glu Leu Ser Ser Ala Ser Asp Gly Tyr Ile Phe Asn Pro Lys Asp Ile
    370                 375                 380

Val Glu Glu Thr Ala Thr Ala Tyr Ile Val Arg His Gly Asp His Phe
385                 390                 395                 400

His Tyr Ile Pro Lys Ser Asn Gln Ile Gly Gln Pro Thr Leu Pro Asn
                405                 410                 415

Asn Ser Leu Ala Thr Pro Ser Pro Ser Leu Pro Ile Asn Pro Gly Thr
            420                 425                 430

Ser His Glu Lys His Glu Glu Asp Gly Tyr Gly Phe Asp Ala Asn Arg
        435                 440                 445

Ile Ile Ala Glu Asp Glu Ser Gly Phe Val Met Ser His Gly Asp His
    450                 455                 460

Asn His Tyr Phe Phe Lys Lys Asp Leu Thr Glu Glu Gln Ile Lys Val
465                 470                 475                 480

Arg Lys Asn Ile

<210> SEQ ID NO 9
<211> LENGTH: 1587
<212> TYPE: DNA
```

<213> ORGANISM: S pneumoniae
<220> FEATURE:
<221> NAME/KEY: CDS
<222> LOCATION: (1)...(1584)

<400> SEQUENCE: 9

| | | | | | | | | | | | | | | | | |
|---|---|---|---|---|---|---|---|---|---|---|---|---|---|---|---|---|
| atg | aaa | gat | tta | gat | aaa | aaa | atc | gaa | gaa | aaa | att | gct | ggc | att | atg | 48 |
| Met | Lys | Asp | Leu | Asp | Lys | Lys | Ile | Glu | Glu | Lys | Ile | Ala | Gly | Ile | Met | |
| 1 | | | | 5 | | | | | 10 | | | | | 15 | | |

| aaa | caa | tat | ggt | gtc | aaa | cgt | gaa | agt | att | gtc | gtg | aat | aaa | gaa | aaa | 96 |
|---|---|---|---|---|---|---|---|---|---|---|---|---|---|---|---|---|
| Lys | Gln | Tyr | Gly | Val | Lys | Arg | Glu | Ser | Ile | Val | Val | Asn | Lys | Glu | Lys | |
| | | | 20 | | | | | 25 | | | | | 30 | | | |

| aat | gcg | att | att | tat | ccg | cat | gga | gat | cac | cat | cat | gca | gat | ccg | att | 144 |
|---|---|---|---|---|---|---|---|---|---|---|---|---|---|---|---|---|
| Asn | Ala | Ile | Ile | Tyr | Pro | His | Gly | Asp | His | His | His | Ala | Asp | Pro | Ile | |
| | | 35 | | | | | 40 | | | | | 45 | | | | |

| gat | gaa | cat | aaa | ccg | gtt | gga | att | ggt | cat | tct | cac | agt | aac | tat | gaa | 192 |
|---|---|---|---|---|---|---|---|---|---|---|---|---|---|---|---|---|
| Asp | Glu | His | Lys | Pro | Val | Gly | Ile | Gly | His | Ser | His | Ser | Asn | Tyr | Glu | |
| 50 | | | | | 55 | | | | | 60 | | | | | | |

| ctg | ttt | aaa | ccc | gaa | gaa | gga | gtt | gct | aaa | aaa | gaa | ggg | aat | aaa | gtt | 240 |
|---|---|---|---|---|---|---|---|---|---|---|---|---|---|---|---|---|
| Leu | Phe | Lys | Pro | Glu | Glu | Gly | Val | Ala | Lys | Lys | Glu | Gly | Asn | Lys | Val | |
| 65 | | | | | 70 | | | | | 75 | | | | | 80 | |

| tat | act | gga | gaa | gaa | tta | acg | aat | gtt | gtt | aat | ttg | tta | aaa | aat | agt | 288 |
|---|---|---|---|---|---|---|---|---|---|---|---|---|---|---|---|---|
| Tyr | Thr | Gly | Glu | Glu | Leu | Thr | Asn | Val | Val | Asn | Leu | Leu | Lys | Asn | Ser | |
| | | | | 85 | | | | | 90 | | | | | 95 | | |

| acg | ttt | aat | aat | caa | aac | ttt | act | cta | gcc | aat | ggt | caa | aaa | cgc | gtt | 336 |
|---|---|---|---|---|---|---|---|---|---|---|---|---|---|---|---|---|
| Thr | Phe | Asn | Asn | Gln | Asn | Phe | Thr | Leu | Ala | Asn | Gly | Gln | Lys | Arg | Val | |
| | | | 100 | | | | | 105 | | | | | 110 | | | |

| tct | ttt | agt | ttt | ccg | cct | gaa | ttg | gag | aaa | aaa | tta | ggt | atc | aat | atg | 384 |
|---|---|---|---|---|---|---|---|---|---|---|---|---|---|---|---|---|
| Ser | Phe | Ser | Phe | Pro | Pro | Glu | Leu | Glu | Lys | Lys | Leu | Gly | Ile | Asn | Met | |
| | | 115 | | | | | 120 | | | | | 125 | | | | |

| cta | gta | aaa | tta | ata | aca | cca | gat | gga | aaa | gta | ttg | gag | aaa | gta | tct | 432 |
|---|---|---|---|---|---|---|---|---|---|---|---|---|---|---|---|---|
| Leu | Val | Lys | Leu | Ile | Thr | Pro | Asp | Gly | Lys | Val | Leu | Glu | Lys | Val | Ser | |
| 130 | | | | | 135 | | | | | 140 | | | | | | |

| ggt | aaa | gta | ttt | gga | gaa | gga | gta | ggg | aat | att | gca | aac | ttt | gaa | tta | 480 |
|---|---|---|---|---|---|---|---|---|---|---|---|---|---|---|---|---|
| Gly | Lys | Val | Phe | Gly | Glu | Gly | Val | Gly | Asn | Ile | Ala | Asn | Phe | Glu | Leu | |
| 145 | | | | | 150 | | | | | 155 | | | | | 160 | |

| gat | caa | cct | tat | tta | cca | gga | caa | aca | ttt | aag | tat | act | atc | gct | tca | 528 |
|---|---|---|---|---|---|---|---|---|---|---|---|---|---|---|---|---|
| Asp | Gln | Pro | Tyr | Leu | Pro | Gly | Gln | Thr | Phe | Lys | Tyr | Thr | Ile | Ala | Ser | |
| | | | | 165 | | | | | 170 | | | | | 175 | | |

| aaa | gat | tat | cca | gaa | gta | agt | tat | gat | ggt | aca | ttt | aca | gtt | cca | acc | 576 |
|---|---|---|---|---|---|---|---|---|---|---|---|---|---|---|---|---|
| Lys | Asp | Tyr | Pro | Glu | Val | Ser | Tyr | Asp | Gly | Thr | Phe | Thr | Val | Pro | Thr | |
| | | | 180 | | | | | 185 | | | | | 190 | | | |

| tct | tta | gct | tac | aaa | atg | gcc | agt | caa | acg | att | ttc | tat | cct | ttc | cat | 624 |
|---|---|---|---|---|---|---|---|---|---|---|---|---|---|---|---|---|
| Ser | Leu | Ala | Tyr | Lys | Met | Ala | Ser | Gln | Thr | Ile | Phe | Tyr | Pro | Phe | His | |
| | | 195 | | | | | 200 | | | | | 205 | | | | |

| gca | ggg | gat | act | tat | tta | aga | gtg | aac | cct | caa | ttt | gca | gtg | cct | aaa | 672 |
|---|---|---|---|---|---|---|---|---|---|---|---|---|---|---|---|---|
| Ala | Gly | Asp | Thr | Tyr | Leu | Arg | Val | Asn | Pro | Gln | Phe | Ala | Val | Pro | Lys | |
| 210 | | | | | 215 | | | | | 220 | | | | | | |

| gga | act | gat | gct | tta | gtc | aga | gtg | ttt | gat | gaa | ttt | cat | gga | aat | gct | 720 |
|---|---|---|---|---|---|---|---|---|---|---|---|---|---|---|---|---|
| Gly | Thr | Asp | Ala | Leu | Val | Arg | Val | Phe | Asp | Glu | Phe | His | Gly | Asn | Ala | |
| 225 | | | | | 230 | | | | | 235 | | | | | 240 | |

| tat | tta | gaa | aat | aac | tat | aaa | gtt | ggt | gaa | atc | aaa | tta | ccg | att | ccg | 768 |
|---|---|---|---|---|---|---|---|---|---|---|---|---|---|---|---|---|
| Tyr | Leu | Glu | Asn | Asn | Tyr | Lys | Val | Gly | Glu | Ile | Lys | Leu | Pro | Ile | Pro | |
| | | | | 245 | | | | | 250 | | | | | 255 | | |

| aaa | tta | aac | caa | gga | aca | acc | aga | acg | gcc | gga | aat | aaa | att | cct | gta | 816 |
|---|---|---|---|---|---|---|---|---|---|---|---|---|---|---|---|---|
| Lys | Leu | Asn | Gln | Gly | Thr | Thr | Arg | Thr | Ala | Gly | Asn | Lys | Ile | Pro | Val | |
| | | | 260 | | | | | 265 | | | | | 270 | | | |

| acc | ttc | atg | gca | aat | gct | tat | ttg | gac | aat | caa | tcg | act | tat | att | gtg | 864 |
|---|---|---|---|---|---|---|---|---|---|---|---|---|---|---|---|---|
| Thr | Phe | Met | Ala | Asn | Ala | Tyr | Leu | Asp | Asn | Gln | Ser | Thr | Tyr | Ile | Val | |
| | | 275 | | | | | 280 | | | | | 285 | | | | |

| | | | | | | | | | | | | | | | |
|---|---|---|---|---|---|---|---|---|---|---|---|---|---|---|---|
| gaa | gta | cct | atc | ttg | gaa | aaa | gaa | aat | caa | act | gat | aaa | cca | agt | att | 912 |
| Glu | Val | Pro | Ile | Leu | Glu | Lys | Glu | Asn | Gln | Thr | Asp | Lys | Pro | Ser | Ile |
| | 290 | | | | 295 | | | | | 300 | | | | | | cta cca caa ttt aaa agg aat aaa gca caa gaa aac tca aaa ctt gat  960
Leu Pro Gln Phe Lys Arg Asn Lys Ala Gln Glu Asn Ser Lys Leu Asp
305             310                 315                 320 gaa aag gta gaa gaa cca aag act agt gag aag gta gaa aaa gaa aaa  1008
Glu Lys Val Glu Glu Pro Lys Thr Ser Glu Lys Val Glu Lys Glu Lys
                325                 330                 335 ctt tct gaa act ggg aat agt act agt aat tca acg tta gaa gaa gtt  1056
Leu Ser Glu Thr Gly Asn Ser Thr Ser Asn Ser Thr Leu Glu Glu Val
            340                 345                 350 cct aca gtg gat cct gta caa gaa aaa gta gca aaa ttt gct gaa agt  1104
Pro Thr Val Asp Pro Val Gln Glu Lys Val Ala Lys Phe Ala Glu Ser
        355                 360                 365 tat ggg atg aag cta gaa aat gtc ttg ttt aat atg gac gga aca att  1152
Tyr Gly Met Lys Leu Glu Asn Val Leu Phe Asn Met Asp Gly Thr Ile
370                 375                 380 gaa tta tat tta cca tca gga gaa gtc att aaa aag aat atg gca gat  1200
Glu Leu Tyr Leu Pro Ser Gly Glu Val Ile Lys Lys Asn Met Ala Asp
385                 390                 395                 400 ttt aca gga gaa gca cct caa gga aat ggt gaa aat aaa cca tct gaa  1248
Phe Thr Gly Glu Ala Pro Gln Gly Asn Gly Glu Asn Lys Pro Ser Glu
                405                 410                 415 aat gga aaa gta tct act gga aca gtt gag aac caa cca aca gaa aat  1296
Asn Gly Lys Val Ser Thr Gly Thr Val Glu Asn Gln Pro Thr Glu Asn
            420                 425                 430 aaa cca gca gat tct tta cca gag gca cca aac gaa aaa cct gta aaa  1344
Lys Pro Ala Asp Ser Leu Pro Glu Ala Pro Asn Glu Lys Pro Val Lys
        435                 440                 445 cca gaa aac tca acg gat aat gga atg ttg aat cca gaa ggg aat gtg  1392
Pro Glu Asn Ser Thr Asp Asn Gly Met Leu Asn Pro Glu Gly Asn Val
450                 455                 460 ggg agt gac cct atg tta gat cca gca tta gag gaa gct cca gca gta  1440
Gly Ser Asp Pro Met Leu Asp Pro Ala Leu Glu Glu Ala Pro Ala Val
465                 470                 475                 480 gat cct gta caa gaa aaa tta gaa aaa ttt aca gct agt tac gga tta  1488
Asp Pro Val Gln Glu Lys Leu Glu Lys Phe Thr Ala Ser Tyr Gly Leu
                485                 490                 495 ggc tta gat agt gtt ata ttc aat atg gat gga acg att gaa tta aga  1536
Gly Leu Asp Ser Val Ile Phe Asn Met Asp Gly Thr Ile Glu Leu Arg
            500                 505                 510 ttg cca agt gga gaa gtg ata aaa aag aat tta tct gat ttc ata gcg  1584
Leu Pro Ser Gly Glu Val Ile Lys Lys Asn Leu Ser Asp Phe Ile Ala
        515                 520                 525 taa  1587

<210> SEQ ID NO 10
<211> LENGTH: 528
<212> TYPE: PRT
<213> ORGANISM: S pneumoniae

<400> SEQUENCE: 10

Met Lys Asp Leu Asp Lys Lys Ile Glu Glu Lys Ile Ala Gly Ile Met
1               5                   10                  15

Lys Gln Tyr Gly Val Lys Arg Glu Ser Ile Val Val Asn Lys Glu Lys
            20                  25                  30

Asn Ala Ile Ile Tyr Pro His Gly Asp His His Ala Asp Pro Ile
        35                  40                  45

-continued

```
Asp Glu His Lys Pro Val Gly Ile Gly His Ser His Ser Asn Tyr Glu
 50                  55                  60
Leu Phe Lys Pro Glu Glu Gly Val Ala Lys Lys Glu Gly Asn Lys Val
 65                  70                  75                  80
Tyr Thr Gly Glu Glu Leu Thr Asn Val Val Asn Leu Leu Lys Asn Ser
                     85                  90                  95
Thr Phe Asn Asn Gln Asn Phe Thr Leu Ala Asn Gly Gln Lys Arg Val
                    100                 105                 110
Ser Phe Ser Phe Pro Pro Glu Leu Glu Lys Lys Leu Gly Ile Asn Met
                115                 120                 125
Leu Val Lys Leu Ile Thr Pro Asp Gly Lys Val Leu Glu Lys Val Ser
130                 135                 140
Gly Lys Val Phe Gly Glu Gly Val Gly Asn Ile Ala Asn Phe Glu Leu
145                 150                 155                 160
Asp Gln Pro Tyr Leu Pro Gly Gln Thr Phe Lys Tyr Thr Ile Ala Ser
                165                 170                 175
Lys Asp Tyr Pro Glu Val Ser Tyr Asp Gly Thr Phe Thr Val Pro Thr
                180                 185                 190
Ser Leu Ala Tyr Lys Met Ala Ser Gln Thr Ile Phe Tyr Pro Phe His
                195                 200                 205
Ala Gly Asp Thr Tyr Leu Arg Val Asn Pro Gln Phe Ala Val Pro Lys
210                 215                 220
Gly Thr Asp Ala Leu Val Arg Val Phe Asp Glu Phe His Gly Asn Ala
225                 230                 235                 240
Tyr Leu Glu Asn Asn Tyr Lys Val Gly Glu Ile Lys Leu Pro Ile Pro
                245                 250                 255
Lys Leu Asn Gln Gly Thr Thr Arg Thr Ala Gly Asn Lys Ile Pro Val
                260                 265                 270
Thr Phe Met Ala Asn Ala Tyr Leu Asp Asn Gln Ser Thr Tyr Ile Val
                275                 280                 285
Glu Val Pro Ile Leu Glu Lys Glu Asn Gln Thr Asp Lys Pro Ser Ile
290                 295                 300
Leu Pro Gln Phe Lys Arg Asn Lys Ala Gln Glu Asn Ser Lys Leu Asp
305                 310                 315                 320
Glu Lys Val Glu Glu Pro Lys Thr Ser Glu Lys Val Glu Lys Glu Lys
                325                 330                 335
Leu Ser Glu Thr Gly Asn Ser Thr Ser Asn Ser Thr Leu Glu Glu Val
                340                 345                 350
Pro Thr Val Asp Pro Val Gln Glu Lys Val Ala Lys Phe Ala Glu Ser
                355                 360                 365
Tyr Gly Met Lys Leu Glu Asn Val Leu Phe Asn Met Asp Gly Thr Ile
370                 375                 380
Glu Leu Tyr Leu Pro Ser Gly Glu Val Ile Lys Lys Asn Met Ala Asp
385                 390                 395                 400
Phe Thr Gly Glu Ala Pro Gln Gly Asn Gly Glu Asn Lys Pro Ser Glu
                405                 410                 415
Asn Gly Lys Val Ser Thr Gly Thr Val Glu Asn Gln Pro Thr Glu Asn
                420                 425                 430
Lys Pro Ala Asp Ser Leu Pro Glu Ala Pro Asn Glu Lys Pro Val Lys
                435                 440                 445
Pro Glu Asn Ser Thr Asp Asn Gly Met Leu Asn Pro Glu Gly Asn Val
450                 455                 460
Gly Ser Asp Pro Met Leu Asp Pro Ala Leu Glu Glu Ala Pro Ala Val
```

```
                465                 470                 475                 480
Asp Pro Val Gln Glu Lys Leu Glu Lys Phe Thr Ala Ser Tyr Gly Leu
                    485                 490                 495

Gly Leu Asp Ser Val Ile Phe Asn Met Asp Gly Thr Ile Glu Leu Arg
            500                 505                 510

Leu Pro Ser Gly Glu Val Ile Lys Lys Asn Leu Ser Asp Phe Ile Ala
        515                 520                 525

<210> SEQ ID NO 11
<211> LENGTH: 5048
<212> TYPE: DNA
<213> ORGANISM: S. pneumoniae

<400> SEQUENCE: 11
aattccttgt cgggtaagtt ccgacccgca cgaaaggcgt aatgatttgg gcactgtctc      60
aacgagagac tcggtgaaat tttagtacct gtgaagatgc aggttacccg cgacaggacg     120
gaaagacccc atggagcttt actgcagttt gatattgagt gtctgtacca catgtacagg     180
ataggtagga gtctaagaga tcggacgcc agtttcgaag gagacgctgt tgggatacta      240
cccttgtgtt atggccactc taacccagat aggtgatccc tatcggagac agtgtctgac     300
gggcagtttg actggggcgg tcgcctccta aaaggtaacg gaggcgccca aggttccct     360 cagaatggtt ggaaatcatt cgcagagtgt aaaggtataa gggagcttga ctgcgagagc     420
tacaactcga gcagggacga aagtcgggct tagtgatccg gtggttccgt atggaagggc    480
catcgctcaa cggataaaag ctaccctggg ataacaggc ttatctcccc caagagttca     540
catcgacggg gaggtttggc acctcgatgt cggctcgtcg catcctgggg ctgtagtcgg    600
tcccaagggt tgggctgttc gcccattaaa gcggcacgcg agctgggttc agaacgtcgt    660
gagacagttc ggtccctatc cgtcgcgggc gtaggaaatt tgagaggatc tgctcctagt    720
acgagaggac cagagtggac ttaccgctgg tgtaccagtt gtcttgccaa aggcatcgct    780
gggtagctat gtagggaagg gataaacgct gaaagcatct aagtgtgaaa cccacctcaa    840
gatgagattt cccatgatta tatatcagta agagccctga gagatgatca ggtagatagg    900
ttagaagtgg aagtgtggcg acacatgtag cggactaata ctaatagctc gaggacttat    960
ccaaagtaac tgagaatatg aaagcgaacg gttttcttaa attgaataga tattcaattt   1020
tgagtaggta ttactcagag ttaagtgacg atagcctagg agatacacct gtacccatgc   1080
cgaacacaga agttaagccc tagaacgccg gaagtagttg ggggttgccc cctgtgagat   1140
agggaagtcg cttagctcta gggagtttag ctcagctggg agagcatctg ccttacaagc   1200
agagggtcag cggttcgatc ccgttaactc ccaaaggtcc cgtagtgtag cggttatcac   1260
gtcgccctgt cacggcgaag atcgcgggtt cgattcccgt cgggaccgtt taaggtaacg   1320
caagttattt tagactcgtt agctcagttg gtagagcaat tgacttttaa tcaatgggtc   1380
actggttcga gcccagtacg ggtcatatat gcgggtttgg cggaattcta atctctttga   1440
aatcatcttc tctcactttc caaaactcta ttacctctta ttataccaca tttcaatctt   1500
caacttccca gtaatataag cacctctggc gaaagaagtt tcaatgtcct aaagtaataa   1560
gtgaatccaa ttcaggaact ccaagaacaa agaaacatc tggtgtcaca agtattggat    1620
ggcacagagt cacgtggtag tctgacccta gcagaaattt taaatagtaa actatttact   1680
ggttaattaa atggttaaat aaccggttta gaaaactatt taataaagta aaagaagttg    1740
agaaaaaact tcatcattta ttgaaatgag ggatttatga aatttagtaa aaaatatata    1800
```

-continued

```
gcagctggat cagctgttat cgtatccttg agtctatgtg cctatgcact aaaccagcat    1860
cgttcgcagg aaaataagga caataatcgt gtctcttatg tggatggcag ccagtcaagt    1920
cagaaaagtg aaaacttgac accagaccag gttagccaga agaaggaat tcaggctgag     1980
caaattgtaa tcaaaattac agatcagggc tatgtaacgt cacacggtga ccactatcat    2040
tactataatg ggaaagttcc ttatgatgcc ctctttagtg aagaactctt gatgaaggat    2100
ccaaactatc aacttaaaga cgctgatatt gtcaatgaag tcaagggtgg ttatatcatc    2160
aaggtcgatg gaaatatta tgtctacctg aaagatgcag ctcatgctga taatgttcga     2220
actaaagatg aaatcaatcg tcaaaaacaa gaacatgtca agataatga aaggttaac      2280
tctaatgttg ctgtagcaag gtctcaggga cgatatacga caaatgatgg ttatgtcttt    2340
aatccagctg atattatcga agatacgggt aatgcttata tcgttcctca tggaggtcac    2400
tatcactaca ttcccaaaag cgatttatct gctagtgaat tagcagcagc taaagcacat    2460
ctggctggaa aaaatatgca accgagtcag ttaagctatt cttcaacagc tagtgacaat    2520
aacacgcaat ctgtagcaaa aggatcaact agcaagccag caaataaatc tgaaaatctc    2580
cagagtcttt tgaaggaact ctatgattca cctagcgccc aacgttacag tgaatcagat    2640
ggcctggtct ttgaccctgc taagattatc agtcgtacac caaatggagt tgcgattccg    2700
catggcgacc attaccactt tattccttac agcaagcttt ctgctttaga agaaaagatt    2760
gccagaatgg tgcctatcag tggaactggt tctacagttt ctacaaatgc aaaacctaat    2820
gaagtagtgt ctagtctagg cagtcttttca agcaatcctt cttctttaac gacaagtaag    2880
gagctctctt cagcatctga tggttatatt tttaatccaa agatatcgt tgaagaaacg     2940
gctacagctt atattgtaag acatggtgat catttccatt acattccaaa atcaaatcaa    3000
attgggcaac cgactcttcc aaacaatagt ctagcaacac cttctccatc tcttccaatc    3060
aatccaggaa cttcacatga gaaacatgaa gaagatggat acggatttga tgctaatcgt    3120
attatcgctg aagatgaatc aggttttgtc atgagtcacg gagaccacaa tcattatttc    3180
ttcaagaagg acttgacaga gagcaaatt aaggctgcgc aaaaacattt agaggaagtt    3240
aaaactagtc ataatggatt agattctttg tcatctcatg aacaggatta tccaggtaat    3300
gccaaagaaa tgaaagattt agataaaaaa atcgaagaaa aaattgctgg cattatgaaa    3360
caatatggtg tcaaacgtga agtattgtc gtgaataaag aaaaaaatgc gattatttat    3420
ccgcatggag atcaccatca tgcagatccg attgatgaac ataaaccggt tggaattggt    3480
cattctcaca gtaactatga actgttaaa cccgaagaag gagttgctaa aaaagaaggg    3540
aataaagttt atactggaga gaattaacg aatgttgtta atttgttaaa aaatagtacg    3600
tttaataatc aaaactttac tctagccaat ggtcaaaaac gcgtttcttt tagttttccg    3660
cctgaattgg agaaaaaatt aggtatcaat atgctagtaa aattaataac accagatgga    3720
aaagtattgg agaagtatc tggtaaagta tttggagaag gagtagggaa tattgcaaac    3780
tttgaattag atcaacctta tttaccagga caaacattta gtatactat cgcttcaaaa    3840
gattatccag aagtaagtta tgatggtaca tttacagttc caacctcttt agcttacaaa    3900
atggccagtc aaacgatttt ctatccttc catgcagggg atacttattt aagagtgaac    3960
cctcaatttg cagtgcctaa aggaactgat gctttagtca gagtgtttga tgaatttcat    4020
ggaaatgctt atttagaaaa taactataaa gttggtgaaa tcaaattacc gattccgaaa    4080
ttaaaccaag gaacaaccag aacggccgga aataaaattc ctgtaacctt catggcaaat    4140
gcttatttgg acaatcaatc gacttatatt gtggaagtac ctatcttgga aaaagaaaat    4200
```

```
caaactgata aaccaagtat tctaccacaa tttaaaagga ataaagcaca agaaaactca    4260
aaacttgatg aaaaggtaga agaaccaaag actagtgaga aggtagaaaa agaaaaactt    4320
tctgaaactg ggaatagtac tagtaattca acgttagaag aagttcctac agtggatcct    4380
gtacaagaaa aagtagcaaa atttgctgaa agttatggga tgaagctaga aaatgtcttg    4440
tttaatatgg acgaacaat  tgaattatat ttaccatcag gagaagtcat taaaaagaat    4500
atggcagatt ttacaggaga agcacctcaa ggaaatggtg aaaataaacc atctgaaaat    4560
ggaaaagtat ctactggaac agttgagaac caaccaacag aaaataaacc agcagattct    4620
ttaccagagg caccaaacga aaaacctgta aaaccagaaa actcaacgga taatggaatg    4680
ttgaatccag aagggaatgt ggggagtgac cctatgttag atccagcatt agaggaagct    4740
ccagcagtag atcctgtaca agaaaaatta gaaaaattta cagctagtta cggattaggc    4800
ttagatagtg ttatattcaa tatgatgga  acgattgaat taagattgcc aagtggagaa    4860
gtgataaaaa agaatttatc tgatttcata gcgtaaggaa tagcagtaga aaaagtctga    4920
atcaaaaatg aagttctctc aaaagttaga aataaaactc tgactttggg agaatttcat    4980
tttattatta atatataaaa tttcttgaca tacaacttaa aaagaggtgg aatatttact    5040
agttaatt                                                             5048
```

<210> SEQ ID NO 12
<211> LENGTH: 2647
<212> TYPE: DNA
<213> ORGANISM: S. pneumoniae

<400> SEQUENCE: 12

```
cagagatctt agtgaatcaa atatacttaa gaaaagagga aagaatgaaa atcaataaaa      60
aatatctagc tgggtcagta gctacacttg ttttaagtgt ctgtgcttat gaactaggtt     120
tgcatcaagc tcaaactgta aaagaaaata atcgtgtttc ctatatagat ggaaaacaag     180
cgacgcaaaa aacggagaat ttgactcctg atgaggttag caagcgtgaa ggaatcaacg     240
ccgaacaaat cgtcatcaag attacggatc aaggttatgt gacctctcat ggagaccatt     300
atcattacta taatggcaag gtcccttatg atgccatcat cagtgaagag ctcctcatga     360
aagatccgaa ttatcagttg aaggattcag acattgtcaa tgaaatcaag ggtggttatg     420
tcattaaggt aaacggtaaa tactatgttt accttaagga tgcagctcat gcggataatg     480
tccgtacaaa agaagaaatc aatcggcaaa acaagaaaca tagtcagcat cgtgaaggag     540
ggacttcagc aaacgatggt gcggtagcct ttgcacgttc acagggacgc tacaccacag     600
atgatggtta tatcttcaat gcatctgata tcatcgaaga tacgggcgat gcctatatcg     660
ttcctcatgg agatcattac cattacattc ctaagaatga gttatcagct agcgagttgg     720
ctgctgcaga agccttccta tctggtcggg aaaatctgtc aaatttaaga acctatcgcc     780
gacaaaatag cgataacact ccaagaacaa actgggtacc ttctgtaagc aatccaggaa     840
ctacaaatac taacacaagc aacaacagca acactaacag tcaagcaagt caaagtaatg     900
acattgatag tctcttgaaa cagctctaca aactgccttt gagtcaacgc catgtagaat     960
ctgatggcct tattttcgac ccagcgcaaa tcacaagtcg aaccgccaga ggtgtagctg    1020
tccctcatgg taaccattac cactttatcc cttatgaaca aatgtctgaa ttggaaaaac    1080
gaattgctcg tattattccc cttcgttatc gttcaaacca ttgggtacca gattcaagac    1140
cagaagaacc aagtccacaa ccgactccag aacctagtcc aagtccgcaa cctgcaccaa    1200
```

-continued

```
atcctcaacc agctccaagc aatccaattg atgagaaatt ggtcaaagaa gctgttcgaa      1260
aagtaggcga tggttatgtc tttgaggaga atggagtttc tcgttatatc ccagccaaga      1320
atctttcagc agaaacagca gcaggcattg atagcaaact ggccaagcag gaaagtttat      1380
ctcataagct aggagctaag aaaactgacc tcccatctag tgatcgagaa ttttacaata      1440
aggcttatga cttactagca agaattcacc aagatttact tgataataaa ggtcgacaag      1500
ttgattttga ggctttggat aacctgttgg aacgactcaa ggatgtctca agtgataaag      1560
tcaagttagt ggatgatatt cttgccttct tagctccgat tcgtcatcca aacgtttag       1620 gaaaaccaaa tgcgcaaatt acctacactg atgatgagat tcaagtagcc aagttggcag      1680
gcaagtacac aacagaagac ggttatatct ttgatcctcg tgataaaacc agtgatgagg      1740
gggatgccta tgtaactcca catatgaccc atagccactg gattaaaaaa gatagtttgt      1800
ctgaagctga gagagcggca gcccaggctt atgctaaaga gaaaggtttg acccctcctt      1860
cgacagacca tcaggattca ggaaatactg aggcaaaagg agcagaagct atctacaacc      1920
gcgtgaaagc agctaagaag gtgccacttg atcgtatgcc ttacaatctt caatatactg      1980
tagaagtcaa aaacggtagt ttaatcatac ctcattatga ccattaccat aacatcaaat      2040
ttgagtggtt tgacgaaggc ctttatgagg cacctaaggg gtatactctt gaggatcttt      2100
tggcgactgt caagtactat gtcgaacatc aaacgaacg tccgcattca gataatggtt      2160
ttggtaacgc tagcgaccat gttcaaagaa acaaaaatgg tcaagctgat accaatcaaa      2220
cggaaaaacc aagcgaggag aaacctcaga cagaaaaacc tgaggaagaa accctcgag       2280 aagagaaacc acaaagcgag aaaccagagt ctccaaaacc aacagaggaa ccagaagaag      2340
aatcaccaga ggaatcagaa gaacctcagg tcgagactga aaaggttgaa gaaaaactga      2400
gagaggctga agatttactt ggaaaaatcc aggatccaat tatcaagtcc aatgccaaag      2460
agactctcac aggattaaaa aataatttac tatttggcac ccaggacaac aatactatta      2520
tggcagaagc tgaaaaacta ttggctttat taaaggagag taagtaaagg tagcagcatt      2580
ttctaactcc taaaaacagg ataggagaac gggaaaacga aaatgagag cagaatgtga       2640 gttctag                                                                2647
```

<210> SEQ ID NO 13
<211> LENGTH: 2639
<212> TYPE: DNA
<213> ORGANISM: S. pneumoniae
<220> FEATURE:
<221> NAME/KEY: CDS
<222> LOCATION: (114)...(2627)

<400> SEQUENCE: 13

```
gggtcttaaa actctgaatc ctttagaggc agacccacaa aatgacaaga cctatttaga       60
aaatctggaa gaaaatatga gtgttctagc agaagaatta aagtgaggaa aga atg        116
                                                                  Met
                                                                    1 aaa atc aat aaa aaa tat cta gca ggt tca gtg gca gtc ctt gcc cta        164
Lys Ile Asn Lys Lys Tyr Leu Ala Gly Ser Val Ala Val Leu Ala Leu
         5                  10                  15 agt gtt tgt tcc tat gaa ctt ggt cgt cac caa gct ggt cag gtt aag        212
Ser Val Cys Ser Tyr Glu Leu Gly Arg His Gln Ala Gly Gln Val Lys
     20                  25                  30 aaa gag tct aat cga gtt tct tat ata gat ggt gat cag gct ggt caa        260
Lys Glu Ser Asn Arg Val Ser Tyr Ile Asp Gly Asp Gln Ala Gly Gln
 35                  40                  45
```

-continued

| | |
|---|---|
| aag gca gaa aat ttg aca cca gat gaa gtc agt aag aga gag ggg atc<br>Lys Ala Glu Asn Leu Thr Pro Asp Glu Val Ser Lys Arg Glu Gly Ile<br>50              55                  60                  65 | 308 |
| aac gcc gaa caa att gtt atc aag att acg gat caa ggt tat gtg acc<br>Asn Ala Glu Gln Ile Val Ile Lys Ile Thr Asp Gln Gly Tyr Val Thr<br>        70                  75                  80 | 356 |
| tct cat gga gac cat tat cat tac tat aat ggc aag gtt cct tat gat<br>Ser His Gly Asp His Tyr His Tyr Tyr Asn Gly Lys Val Pro Tyr Asp<br>            85                  90                  95 | 404 |
| gcc atc atc agt gaa gaa ctt ctc atg aaa gat ccg aat tat cag ttg<br>Ala Ile Ile Ser Glu Glu Leu Leu Met Lys Asp Pro Asn Tyr Gln Leu<br>    100                 105                 110 | 452 |
| aag gat tca gac att gtc aat gaa atc aag ggt ggc tat gtg att aag<br>Lys Asp Ser Asp Ile Val Asn Glu Ile Lys Gly Gly Tyr Val Ile Lys<br>115                 120                 125 | 500 |
| gta gac gga aaa tac tat gtt tac ctt aaa gat gcg gcc cat gcg gac<br>Val Asp Gly Lys Tyr Tyr Val Tyr Leu Lys Asp Ala Ala His Ala Asp<br>130                 135                 140                 145 | 548 |
| aat att cgg aca aaa gaa gag att aaa cgt cag aag cag gaa cac agt<br>Asn Ile Arg Thr Lys Glu Glu Ile Lys Arg Gln Lys Gln Glu His Ser<br>            150                 155                 160 | 596 |
| cat aat cat aac tca aga gca gat aat gct gtt gct gca gcc aga gcc<br>His Asn His Asn Ser Arg Ala Asp Asn Ala Val Ala Ala Ala Arg Ala<br>        165                 170                 175 | 644 |
| caa gga cgt tat aca acg gat gat ggg tat atc ttc aat gca tct gat<br>Gln Gly Arg Tyr Thr Thr Asp Asp Gly Tyr Ile Phe Asn Ala Ser Asp<br>    180                 185                 190 | 692 |
| atc att gag gac acg ggt gat gct tat atc gtt cct cac ggc gac cat<br>Ile Ile Glu Asp Thr Gly Asp Ala Tyr Ile Val Pro His Gly Asp His<br>195                 200                 205 | 740 |
| tac cat tac att cct aag aat gag tta tca gct agc gag tta gct gct<br>Tyr His Tyr Ile Pro Lys Asn Glu Leu Ser Ala Ser Glu Leu Ala Ala<br>210                 215                 220                 225 | 788 |
| gca gaa gcc tat tgg aat ggg aag cag gga tct cgt cct tct tca agt<br>Ala Glu Ala Tyr Trp Asn Gly Lys Gln Gly Ser Arg Pro Ser Ser Ser<br>            230                 235                 240 | 836 |
| tct agt tat aat gca aat cca gtt caa cca aga ttg tca gag aac cac<br>Ser Ser Tyr Asn Ala Asn Pro Val Gln Pro Arg Leu Ser Glu Asn His<br>        245                 250                 255 | 884 |
| aat ctg act gtc act cca act tat cat caa aat caa ggg gaa aac att<br>Asn Leu Thr Val Thr Pro Thr Tyr His Gln Asn Gln Gly Glu Asn Ile<br>    260                 265                 270 | 932 |
| tca agc ctt tta cgt gaa ttg tat gct aaa ccc tta tca gaa cgc cat<br>Ser Ser Leu Leu Arg Glu Leu Tyr Ala Lys Pro Leu Ser Glu Arg His<br>275                 280                 285 | 980 |
| gta gaa tct gat ggc ctt att ttc gac cca gcg caa atc aca agt cga<br>Val Glu Ser Asp Gly Leu Ile Phe Asp Pro Ala Gln Ile Thr Ser Arg<br>290                 295                 300                 305 | 1028 |
| acc gcc aga ggt gta gct gtc cct cat ggt aac cat tac cac ttt atc<br>Thr Ala Arg Gly Val Ala Val Pro His Gly Asn His Tyr His Phe Ile<br>            310                 315                 320 | 1076 |
| cct tat gaa caa atg tct gaa ttg gaa aaa cga att gct cgt att att<br>Pro Tyr Glu Gln Met Ser Glu Leu Glu Lys Arg Ile Ala Arg Ile Ile<br>        325                 330                 335 | 1124 |
| ccc ctt cgt tat cgt tca aac cat tgg gta cca gat tca aga cca gaa<br>Pro Leu Arg Tyr Arg Ser Asn His Trp Val Pro Asp Ser Arg Pro Glu<br>    340                 345                 350 | 1172 |
| caa cca agt cca caa tcg act ccg gaa cct agt cca agt ctg caa cct<br>Gln Pro Ser Pro Gln Ser Thr Pro Glu Pro Ser Pro Ser Leu Gln Pro<br>355                 360                 365 | 1220 |

```
gca cca aat cct caa cca gct cca agc aat cca att gat gag aaa ttg    1268
Ala Pro Asn Pro Gln Pro Ala Pro Ser Asn Pro Ile Asp Glu Lys Leu
370             375                 380                 385 gtc aaa gaa gct gtt cga aaa gta ggc gat ggt tat gtc ttt gag gag    1316
Val Lys Glu Ala Val Arg Lys Val Gly Asp Gly Tyr Val Phe Glu Glu
                390                 395                 400 aat gga gtt tct cgt tat atc cca gcc aag gat ctt tca gca gaa aca    1364
Asn Gly Val Ser Arg Tyr Ile Pro Ala Lys Asp Leu Ser Ala Glu Thr
            405                 410                 415 gca gca ggc att gat agc aaa ctg gcc aag cag gaa agt tta tct cat    1412
Ala Ala Gly Ile Asp Ser Lys Leu Ala Lys Gln Glu Ser Leu Ser His
        420                 425                 430 aag cta gga gct aag aaa act gac ctc cca tct agt gat cga gaa ttt    1460
Lys Leu Gly Ala Lys Lys Thr Asp Leu Pro Ser Ser Asp Arg Glu Phe
    435                 440                 445 tac aat aag gct tat gac tta cta gca aga att cac caa gat tta ctt    1508
Tyr Asn Lys Ala Tyr Asp Leu Leu Ala Arg Ile His Gln Asp Leu Leu
450             455                 460                 465 gat aat aaa ggt cga caa gtt gat ttt gag gtt ttg gat aac ctg ttg    1556
Asp Asn Lys Gly Arg Gln Val Asp Phe Glu Val Leu Asp Asn Leu Leu
                470                 475                 480 gaa cga ctc aag gat gtc tca agt gat aaa gtc aag tta gtg gat gat    1604
Glu Arg Leu Lys Asp Val Ser Ser Asp Lys Val Lys Leu Val Asp Asp
            485                 490                 495 att ctt gcc ttc tta gct ccg att cgt cat cca gaa cgt tta gga aaa    1652
Ile Leu Ala Phe Leu Ala Pro Ile Arg His Pro Glu Arg Leu Gly Lys
        500                 505                 510 cca aat gcg caa att acc tac act gat gat gag att caa gta gcc aag    1700
Pro Asn Ala Gln Ile Thr Tyr Thr Asp Asp Glu Ile Gln Val Ala Lys
    515                 520                 525 ttg gca ggc aag tac aca aca gaa gac ggt tat atc ttt gat cct cgt    1748
Leu Ala Gly Lys Tyr Thr Thr Glu Asp Gly Tyr Ile Phe Asp Pro Arg
530             535                 540                 545 gat ata acc agt gat gag ggg gat gcc tat gta act cca cat atg acc    1796
Asp Ile Thr Ser Asp Glu Gly Asp Ala Tyr Val Thr Pro His Met Thr
                550                 555                 560 cat agc cac tgg att aaa aaa gat agt ttg tct gaa gct gag aga gcg    1844
His Ser His Trp Ile Lys Lys Asp Ser Leu Ser Glu Ala Glu Arg Ala
            565                 570                 575 gca gcc cag gct tat gct aaa gag aaa ggt ttg acc cct cct tcg aca    1892
Ala Ala Gln Ala Tyr Ala Lys Glu Lys Gly Leu Thr Pro Pro Ser Thr
        580                 585                 590 gac cac cag gat tca gga aat act gag gca aaa gga gca gaa gct atc    1940
Asp His Gln Asp Ser Gly Asn Thr Glu Ala Lys Gly Ala Glu Ala Ile
    595                 600                 605 tac aac cgc gtg aaa gca gct aag aag gtg cca ctt gat cgt atg cct    1988
Tyr Asn Arg Val Lys Ala Ala Lys Lys Val Pro Leu Asp Arg Met Pro
610             615                 620                 625 tac aat ctt caa tat act gta gaa gtc aaa aac ggt agt tta atc ata    2036
Tyr Asn Leu Gln Tyr Thr Val Glu Val Lys Asn Gly Ser Leu Ile Ile
                630                 635                 640 cct cat tat gac cat tac cat aac atc aaa ttt gag tgg ttt gac gaa    2084
Pro His Tyr Asp His Tyr His Asn Ile Lys Phe Glu Trp Phe Asp Glu
            645                 650                 655 ggc ctt tat gag gca cct aag ggg tat agt ctt gag gat ctt ttg gcg    2132
Gly Leu Tyr Glu Ala Pro Lys Gly Tyr Ser Leu Glu Asp Leu Leu Ala
        660                 665                 670 act gtc aag tac tat gtc gaa cat cca aac gaa cgt ccg cat tca gat    2180
Thr Val Lys Tyr Tyr Val Glu His Pro Asn Glu Arg Pro His Ser Asp
```

-continued

```
               675                 680                 685
aat ggt ttt ggt aac gct agt gac cat gtt cgt aaa aat aag gca gac      2228
Asn Gly Phe Gly Asn Ala Ser Asp His Val Arg Lys Asn Lys Ala Asp
690                 695                 700                 705 caa gat agt aaa cct gat gaa gat aag gaa cat gat gaa gta agt gag      2276
Gln Asp Ser Lys Pro Asp Glu Asp Lys Glu His Asp Glu Val Ser Glu
            710                 715                 720 cca act cac cct gaa tct gat gaa aaa gag aat cac gct ggt tta aat      2324
Pro Thr His Pro Glu Ser Asp Glu Lys Glu Asn His Ala Gly Leu Asn
                725                 730                 735 cct tca gca gat aat ctt tat aaa cca agc act gat acg gaa gag aca      2372
Pro Ser Ala Asp Asn Leu Tyr Lys Pro Ser Thr Asp Thr Glu Glu Thr
            740                 745                 750 gag gaa gaa gct gaa gat acc aca gat gag gct gaa att cct caa gta      2420
Glu Glu Glu Ala Glu Asp Thr Thr Asp Glu Ala Glu Ile Pro Gln Val
        755                 760                 765 gag aat tct gtt att aac gct aag ata gca gat gcg gag gcc ttg cta      2468
Glu Asn Ser Val Ile Asn Ala Lys Ile Ala Asp Ala Glu Ala Leu Leu
770                 775                 780                 785 gaa aaa gta aca gat cct agt att aga caa aat gct atg gag aca ttg      2516
Glu Lys Val Thr Asp Pro Ser Ile Arg Gln Asn Ala Met Glu Thr Leu
            790                 795                 800 act ggt cta aaa agt agt ctt ctt ctc gga acg aaa gat aat aac act      2564
Thr Gly Leu Lys Ser Ser Leu Leu Leu Gly Thr Lys Asp Asn Asn Thr
        805                 810                 815 att tca gca gaa gta gat agt ctc ttg gct ttg tta aaa gaa agt caa      2612
Ile Ser Ala Glu Val Asp Ser Leu Leu Ala Leu Leu Lys Glu Ser Gln
    820                 825                 830 ccg gct cct ata cag tagtaaaatg aa                                    2639
Pro Ala Pro Ile Gln
    835
```

<210> SEQ ID NO 14
<211> LENGTH: 838
<212> TYPE: PRT
<213> ORGANISM: S. pneumoniae

<400> SEQUENCE: 14

```
Met Lys Ile Asn Lys Lys Tyr Leu Ala Gly Ser Val Ala Val Leu Ala
1               5                   10                  15

Leu Ser Val Cys Ser Tyr Glu Leu Gly Arg His Gln Ala Gly Gln Val
            20                  25                  30

Lys Lys Glu Ser Asn Arg Val Ser Tyr Ile Asp Gly Asp Gln Ala Gly
        35                  40                  45

Gln Lys Ala Glu Asn Leu Thr Pro Asp Glu Val Ser Lys Arg Glu Gly
    50                  55                  60

Ile Asn Ala Glu Gln Ile Val Ile Lys Ile Thr Asp Gln Gly Tyr Val
65                  70                  75                  80

Thr Ser His Gly Asp His Tyr His Tyr Tyr Asn Gly Lys Val Pro Tyr
                85                  90                  95

Asp Ala Ile Ile Ser Glu Glu Leu Leu Met Lys Asp Pro Asn Tyr Gln
            100                 105                 110

Leu Lys Asp Ser Asp Ile Val Asn Glu Ile Lys Gly Gly Tyr Val Ile
        115                 120                 125

Lys Val Asp Gly Lys Tyr Tyr Val Tyr Leu Lys Asp Ala Ala His Ala
    130                 135                 140

Asp Asn Ile Arg Thr Lys Glu Glu Ile Lys Arg Gln Lys Gln Glu His
145                 150                 155                 160
```

```
Ser His Asn His Asn Ser Arg Ala Asp Asn Ala Val Ala Ala Ala Arg
            165                 170                 175

Ala Gln Gly Arg Tyr Thr Thr Asp Asp Gly Tyr Ile Phe Asn Ala Ser
        180                 185                 190

Asp Ile Ile Glu Asp Thr Gly Asp Ala Tyr Ile Val Pro His Gly Asp
    195                 200                 205

His Tyr His Tyr Ile Pro Lys Asn Glu Leu Ser Ala Ser Glu Leu Ala
210                 215                 220

Ala Ala Glu Ala Tyr Trp Asn Gly Lys Gln Gly Ser Arg Pro Ser Ser
225                 230                 235                 240

Ser Ser Ser Tyr Asn Ala Asn Pro Val Gln Pro Arg Leu Ser Glu Asn
            245                 250                 255

His Asn Leu Thr Val Thr Pro Thr Tyr His Gln Asn Gln Gly Glu Asn
        260                 265                 270

Ile Ser Ser Leu Leu Arg Glu Leu Tyr Ala Lys Pro Leu Ser Glu Arg
    275                 280                 285

His Val Glu Ser Asp Gly Leu Ile Phe Asp Pro Ala Gln Ile Thr Ser
290                 295                 300

Arg Thr Ala Arg Gly Val Ala Val Pro His Gly Asn His Tyr His Phe
305                 310                 315                 320

Ile Pro Tyr Glu Gln Met Ser Glu Leu Glu Lys Arg Ile Ala Arg Ile
            325                 330                 335

Ile Pro Leu Arg Tyr Arg Ser Asn His Trp Val Pro Asp Ser Arg Pro
        340                 345                 350

Glu Gln Pro Ser Pro Gln Ser Thr Pro Glu Pro Ser Pro Ser Leu Gln
    355                 360                 365

Pro Ala Pro Asn Pro Gln Pro Ala Pro Ser Asn Pro Ile Asp Glu Lys
    370                 375                 380

Leu Val Lys Glu Ala Val Arg Lys Val Gly Asp Gly Tyr Val Phe Glu
385                 390                 395                 400

Glu Asn Gly Val Ser Arg Tyr Ile Pro Ala Lys Asp Leu Ser Ala Glu
            405                 410                 415

Thr Ala Gly Ile Asp Ser Lys Leu Ala Lys Gln Glu Ser Leu Ser
        420                 425                 430

His Lys Leu Gly Ala Lys Lys Thr Asp Leu Pro Ser Ser Asp Arg Glu
    435                 440                 445

Phe Tyr Asn Lys Ala Tyr Asp Leu Leu Ala Arg Ile His Gln Asp Leu
    450                 455                 460

Leu Asp Asn Lys Gly Arg Gln Val Asp Phe Glu Val Leu Asp Asn Leu
465                 470                 475                 480

Leu Glu Arg Leu Lys Asp Val Ser Ser Asp Lys Val Lys Leu Val Asp
            485                 490                 495

Asp Ile Leu Ala Phe Leu Ala Pro Ile Arg His Pro Glu Arg Leu Gly
        500                 505                 510

Lys Pro Asn Ala Gln Ile Thr Tyr Thr Asp Asp Glu Ile Gln Val Ala
    515                 520                 525

Lys Leu Ala Gly Lys Tyr Thr Thr Glu Asp Gly Tyr Ile Phe Asp Pro
530                 535                 540

Arg Asp Ile Thr Ser Asp Glu Gly Asp Ala Tyr Val Thr Pro His Met
545                 550                 555                 560

Thr His Ser His Trp Ile Lys Lys Asp Ser Leu Ser Glu Ala Glu Arg
            565                 570                 575
```

```
Ala Ala Ala Gln Ala Tyr Ala Lys Glu Lys Gly Leu Thr Pro Pro Ser
            580                 585                 590

Thr Asp His Gln Asp Ser Gly Asn Thr Glu Ala Lys Gly Ala Glu Ala
        595                 600                 605

Ile Tyr Asn Arg Val Lys Ala Ala Lys Lys Val Pro Leu Asp Arg Met
    610                 615                 620

Pro Tyr Asn Leu Gln Tyr Thr Val Glu Val Lys Asn Gly Ser Leu Ile
625                 630                 635                 640

Ile Pro His Tyr Asp His Tyr His Asn Ile Lys Phe Glu Trp Phe Asp
            645                 650                 655

Glu Gly Leu Tyr Glu Ala Pro Lys Gly Tyr Ser Leu Glu Asp Leu Leu
            660                 665                 670

Ala Thr Val Lys Tyr Tyr Val Glu His Pro Asn Glu Arg Pro His Ser
            675                 680                 685

Asp Asn Gly Phe Gly Asn Ala Ser Asp His Val Arg Lys Asn Lys Ala
        690                 695                 700

Asp Gln Asp Ser Lys Pro Asp Glu Asp Lys Glu His Asp Glu Val Ser
705                 710                 715                 720

Glu Pro Thr His Pro Glu Ser Asp Glu Lys Glu Asn His Ala Gly Leu
            725                 730                 735

Asn Pro Ser Ala Asp Asn Leu Tyr Lys Pro Ser Thr Asp Thr Glu Glu
            740                 745                 750

Thr Glu Glu Glu Ala Glu Asp Thr Thr Asp Glu Ala Glu Ile Pro Gln
            755                 760                 765

Val Glu Asn Ser Val Ile Asn Ala Lys Ile Ala Asp Ala Glu Ala Leu
            770                 775                 780

Leu Glu Lys Val Thr Asp Pro Ser Ile Arg Gln Asn Ala Met Glu Thr
785                 790                 795                 800

Leu Thr Gly Leu Lys Ser Ser Leu Leu Gly Thr Lys Asp Asn Asn
            805                 810                 815

Thr Ile Ser Ala Glu Val Asp Ser Leu Leu Ala Leu Leu Lys Glu Ser
            820                 825                 830

Gln Pro Ala Pro Ile Gln
            835

<210> SEQ ID NO 15
<211> LENGTH: 2528
<212> TYPE: DNA
<213> ORGANISM: S. pneumoniae
<220> FEATURE:
<221> NAME/KEY: CDS
<222> LOCATION: (1)...(2520)

<400> SEQUENCE: 15 tgt gcc tat gca cta aac cag cat cgt tcg cag gaa aat aag gac aat      48
Cys Ala Tyr Ala Leu Asn Gln His Arg Ser Gln Glu Asn Lys Asp Asn
 1               5                   10                  15 aat cgt gtc tct tat gtg gat ggc agc cag tca agt cag aaa agt gaa      96
Asn Arg Val Ser Tyr Val Asp Gly Ser Gln Ser Ser Gln Lys Ser Glu
                20                  25                  30 aac ttg aca cca gac cag gtt agc cag aaa gaa gga att cag gct gag     144
Asn Leu Thr Pro Asp Gln Val Ser Gln Lys Glu Gly Ile Gln Ala Glu
            35                  40                  45 caa att gta atc aaa att aca gat cag ggc tat gta acg tca cac ggt     192
Gln Ile Val Ile Lys Ile Thr Asp Gln Gly Tyr Val Thr Ser His Gly
        50                  55                  60 gat cac tat cat tac tat aat ggg aaa gtt cct tat gat gcc ctc ttt     240
```

|   |   |   |   |   |   |   |   |   |   |   |   |   |   |   |   |     |
|---|---|---|---|---|---|---|---|---|---|---|---|---|---|---|---|----|
|   | Asp | His | Tyr | His | Tyr | Tyr | Asn | Gly | Lys | Val | Pro | Tyr | Asp | Ala | Leu | Phe |
|   | 65  |     |     |     | 70  |     |     |     |     | 75  |     |     |     |     | 80  |     |

| agt | gaa | gaa | ctc | ttg | atg | aag | gat | cca | aac | tat | caa | ctt | aaa | gac | gct | 288 |
|-----|-----|-----|-----|-----|-----|-----|-----|-----|-----|-----|-----|-----|-----|-----|-----|-----|
| Ser | Glu | Glu | Leu | Leu | Met | Lys | Asp | Pro | Asn | Tyr | Gln | Leu | Lys | Asp | Ala |     |
|     |     |     |     | 85  |     |     |     |     | 90  |     |     |     |     | 95  |     |     |

| gat | att | gtc | aat | gaa | gtc | aag | ggt | ggt | tat | atc | atc | aag | gtc | gat | gga | 336 |
|-----|-----|-----|-----|-----|-----|-----|-----|-----|-----|-----|-----|-----|-----|-----|-----|-----|
| Asp | Ile | Val | Asn | Glu | Val | Lys | Gly | Gly | Tyr | Ile | Ile | Lys | Val | Asp | Gly |     |
|     |     |     | 100 |     |     |     |     | 105 |     |     |     |     | 110 |     |     |     |

| aaa | tat | tat | gtc | tac | ctg | aaa | gat | gca | gct | cat | gct | gat | aat | gtt | cga | 384 |
|-----|-----|-----|-----|-----|-----|-----|-----|-----|-----|-----|-----|-----|-----|-----|-----|-----|
| Lys | Tyr | Tyr | Val | Tyr | Leu | Lys | Asp | Ala | Ala | His | Ala | Asp | Asn | Val | Arg |     |
|     |     | 115 |     |     |     |     | 120 |     |     |     |     | 125 |     |     |     |     |

| act | aaa | gat | gaa | atc | aat | cgt | caa | aaa | caa | gaa | cat | gtc | aaa | gat | aat | 432 |
|-----|-----|-----|-----|-----|-----|-----|-----|-----|-----|-----|-----|-----|-----|-----|-----|-----|
| Thr | Lys | Asp | Glu | Ile | Asn | Arg | Gln | Lys | Gln | Glu | His | Val | Lys | Asp | Asn |     |
|     | 130 |     |     |     |     | 135 |     |     |     |     | 140 |     |     |     |     |     |

| gag | aag | gtt | aac | tct | aat | gtt | gct | gta | gca | agg | tct | cag | gga | cga | tat | 480 |
|-----|-----|-----|-----|-----|-----|-----|-----|-----|-----|-----|-----|-----|-----|-----|-----|-----|
| Glu | Lys | Val | Asn | Ser | Asn | Val | Ala | Val | Ala | Arg | Ser | Gln | Gly | Arg | Tyr |     |
| 145 |     |     |     |     | 150 |     |     |     |     | 155 |     |     |     |     | 160 |     |

| acg | aca | aat | gat | ggt | tat | gtc | ttt | aat | cca | gct | gat | att | atc | gaa | gat | 528 |
|-----|-----|-----|-----|-----|-----|-----|-----|-----|-----|-----|-----|-----|-----|-----|-----|-----|
| Thr | Thr | Asn | Asp | Gly | Tyr | Val | Phe | Asn | Pro | Ala | Asp | Ile | Ile | Glu | Asp |     |
|     |     |     |     | 165 |     |     |     |     | 170 |     |     |     |     | 175 |     |     |

| acg | ggt | aat | gct | tat | atc | gtt | cct | cat | gga | ggt | cac | tat | cac | tac | att | 576 |
|-----|-----|-----|-----|-----|-----|-----|-----|-----|-----|-----|-----|-----|-----|-----|-----|-----|
| Thr | Gly | Asn | Ala | Tyr | Ile | Val | Pro | His | Gly | Gly | His | Tyr | His | Tyr | Ile |     |
|     |     |     | 180 |     |     |     |     | 185 |     |     |     |     | 190 |     |     |     |

| ccc | aaa | agc | gat | tta | tct | gct | agt | gaa | tta | gca | gca | gct | aaa | gca | cat | 624 |
|-----|-----|-----|-----|-----|-----|-----|-----|-----|-----|-----|-----|-----|-----|-----|-----|-----|
| Pro | Lys | Ser | Asp | Leu | Ser | Ala | Ser | Glu | Leu | Ala | Ala | Ala | Lys | Ala | His |     |
|     |     | 195 |     |     |     |     | 200 |     |     |     |     | 205 |     |     |     |     |

| ctg | gct | gga | aaa | aat | atg | caa | ccg | agt | cag | tta | agc | tat | tct | tca | aca | 672 |
|-----|-----|-----|-----|-----|-----|-----|-----|-----|-----|-----|-----|-----|-----|-----|-----|-----|
| Leu | Ala | Gly | Lys | Asn | Met | Gln | Pro | Ser | Gln | Leu | Ser | Tyr | Ser | Ser | Thr |     |
|     | 210 |     |     |     |     | 215 |     |     |     |     | 220 |     |     |     |     |     |

| cct | tct | cca | tct | ctt | cca | atc | aat | cca | gga | act | tca | cat | gag | aaa | cat | 720 |
|-----|-----|-----|-----|-----|-----|-----|-----|-----|-----|-----|-----|-----|-----|-----|-----|-----|
| Pro | Ser | Pro | Ser | Leu | Pro | Ile | Asn | Pro | Gly | Thr | Ser | His | Glu | Lys | His |     |
| 225 |     |     |     |     | 230 |     |     |     |     | 235 |     |     |     |     | 240 |     |

| gaa | gaa | gat | gga | tac | gga | ttt | gat | gct | aat | cgt | att | atc | gct | gaa | gat | 768 |
|-----|-----|-----|-----|-----|-----|-----|-----|-----|-----|-----|-----|-----|-----|-----|-----|-----|
| Glu | Glu | Asp | Gly | Tyr | Gly | Phe | Asp | Ala | Asn | Arg | Ile | Ile | Ala | Glu | Asp |     |
|     |     |     |     | 245 |     |     |     |     | 250 |     |     |     |     | 255 |     |     |

| gaa | tca | ggt | ttt | gtc | atg | agt | cac | gga | gac | cac | aat | cat | tat | ttc | ttc | 816 |
|-----|-----|-----|-----|-----|-----|-----|-----|-----|-----|-----|-----|-----|-----|-----|-----|-----|
| Glu | Ser | Gly | Phe | Val | Met | Ser | His | Gly | Asp | His | Asn | His | Tyr | Phe | Phe |     |
|     |     |     |     | 260 |     |     |     |     | 265 |     |     |     |     | 270 |     |     |

| aag | aag | gac | ttg | aca | gaa | gag | caa | att | aag | gct | gcg | caa | aaa | cat | tta | 864 |
|-----|-----|-----|-----|-----|-----|-----|-----|-----|-----|-----|-----|-----|-----|-----|-----|-----|
| Lys | Lys | Asp | Leu | Thr | Glu | Glu | Gln | Ile | Lys | Ala | Ala | Gln | Lys | His | Leu |     |
|     |     |     | 275 |     |     |     |     | 280 |     |     |     |     | 285 |     |     |     |

| gag | gaa | gtt | aaa | act | agt | cat | aat | gga | tta | gat | tct | ttg | tca | tct | cat | 912 |
|-----|-----|-----|-----|-----|-----|-----|-----|-----|-----|-----|-----|-----|-----|-----|-----|-----|
| Glu | Glu | Val | Lys | Thr | Ser | His | Asn | Gly | Leu | Asp | Ser | Leu | Ser | Ser | His |     |
|     | 290 |     |     |     |     | 295 |     |     |     |     | 300 |     |     |     |     |     |

| gaa | cag | gat | tat | cca | agt | aat | gcc | aaa | gaa | atg | aaa | gat | tta | gat | aaa | 960 |
|-----|-----|-----|-----|-----|-----|-----|-----|-----|-----|-----|-----|-----|-----|-----|-----|-----|
| Glu | Gln | Asp | Tyr | Pro | Ser | Asn | Ala | Lys | Glu | Met | Lys | Asp | Leu | Asp | Lys |     |
| 305 |     |     |     | 310 |     |     |     |     | 315 |     |     |     |     | 320 |     |     |

| aaa | atc | gaa | gaa | aaa | att | gct | ggc | att | atg | aaa | caa | tat | ggt | gtc | aaa | 1008 |
|-----|-----|-----|-----|-----|-----|-----|-----|-----|-----|-----|-----|-----|-----|-----|-----|------|
| Lys | Ile | Glu | Glu | Lys | Ile | Ala | Gly | Ile | Met | Lys | Gln | Tyr | Gly | Val | Lys |      |
|     |     |     |     | 325 |     |     |     |     | 330 |     |     |     |     | 335 |     |      |

| cgt | gaa | agt | att | gtc | gtg | aat | aaa | gaa | aaa | aat | gcg | att | att | tat | ccg | 1056 |
|-----|-----|-----|-----|-----|-----|-----|-----|-----|-----|-----|-----|-----|-----|-----|-----|------|
| Arg | Glu | Ser | Ile | Val | Val | Asn | Lys | Glu | Lys | Asn | Ala | Ile | Ile | Tyr | Pro |      |
|     |     |     | 340 |     |     |     |     | 345 |     |     |     |     | 350 |     |     |      |

| cat | gga | gat | cac | cat | cat | gca | gat | ccg | att | gat | gaa | cat | aaa | ccg | gtt | 1104 |
|-----|-----|-----|-----|-----|-----|-----|-----|-----|-----|-----|-----|-----|-----|-----|-----|------|
| His | Gly | Asp | His | His | His | Ala | Asp | Pro | Ile | Asp | Glu | His | Lys | Pro | Val |      |
|     |     |     |     | 355 |     |     |     |     | 360 |     |     |     |     | 365 |     |      |

| gga | att | ggt | cat | tct | cac | agt | aac | tat | gaa | ctg | ttt | aaa | ccc | gaa | gaa | 1152 |
|-----|-----|-----|-----|-----|-----|-----|-----|-----|-----|-----|-----|-----|-----|-----|-----|------|
| Gly | Ile | Gly | His | Ser | His | Ser | Asn | Tyr | Glu | Leu | Phe | Lys | Pro | Glu | Glu |      |
|     |     |     | 370 |     |     |     |     | 375 |     |     |     |     | 380 |     |     |      |

```
gga gtt gct aaa aaa gaa ggg aat aaa gtt tat act gga gaa gaa tta       1200
Gly Val Ala Lys Lys Glu Gly Asn Lys Val Tyr Thr Gly Glu Glu Leu
385                 390                 395                 400 acg aat gtt gtt aat ttg tta aaa aat agt acg ttt aat aat caa aac       1248
Thr Asn Val Val Asn Leu Leu Lys Asn Ser Thr Phe Asn Asn Gln Asn
                405                 410                 415 ttt act cta gcc aat ggt caa aaa cgc gtt tct ttt agt ttt ccg cct       1296
Phe Thr Leu Ala Asn Gly Gln Lys Arg Val Ser Phe Ser Phe Pro Pro
            420                 425                 430 gaa ttg gag aaa aaa tta ggt atc aat atg cta gta aaa tta ata aca       1344
Glu Leu Glu Lys Lys Leu Gly Ile Asn Met Leu Val Lys Leu Ile Thr
        435                 440                 445 cca gat gga aaa gta ttg gag aaa gta tct ggt aaa gta ttt gga gaa       1392
Pro Asp Gly Lys Val Leu Glu Lys Val Ser Gly Lys Val Phe Gly Glu
450                 455                 460 gga gta ggg aat att gca aac ttt gaa tta gat caa cct tat tta cca       1440
Gly Val Gly Asn Ile Ala Asn Phe Glu Leu Asp Gln Pro Tyr Leu Pro
465                 470                 475                 480 gga caa aca ttt aag tat act atc gct tca aaa gat tat cca gaa gta       1488
Gly Gln Thr Phe Lys Tyr Thr Ile Ala Ser Lys Asp Tyr Pro Glu Val
                485                 490                 495 agt tat gat ggt aca ttt aca gtt cca acc tct tta gct tac aaa atg       1536
Ser Tyr Asp Gly Thr Phe Thr Val Pro Thr Ser Leu Ala Tyr Lys Met
            500                 505                 510 gcc agt caa acg att ttc tat cct ttc cat gca ggg gat act tat tta       1584
Ala Ser Gln Thr Ile Phe Tyr Pro Phe His Ala Gly Asp Thr Tyr Leu
        515                 520                 525 aga gtg aac cct caa ttt gca gtg cct aaa gga act gat gct tta gtc       1632
Arg Val Asn Pro Gln Phe Ala Val Pro Lys Gly Thr Asp Ala Leu Val
530                 535                 540 aga gtg ttt gat gaa ttt cat gga aat gct tat tta gaa aat aac tat       1680
Arg Val Phe Asp Glu Phe His Gly Asn Ala Tyr Leu Glu Asn Asn Tyr
545                 550                 555                 560 aaa gtt ggt gaa atc aaa tta ccg att ccg aaa tta aac caa gga aca       1728
Lys Val Gly Glu Ile Lys Leu Pro Ile Pro Lys Leu Asn Gln Gly Thr
                565                 570                 575 acc aga acg gcc gga aat aaa att cct gta acc ttc atg gca aat gct       1776
Thr Arg Thr Ala Gly Asn Lys Ile Pro Val Thr Phe Met Ala Asn Ala
            580                 585                 590 tat ttg gac aat caa tcg act tat att gtg gaa gta cct atc ttg gaa       1824
Tyr Leu Asp Asn Gln Ser Thr Tyr Ile Val Glu Val Pro Ile Leu Glu
        595                 600                 605 aaa gaa aat caa act gat aaa cca agt att cta cca caa ttt aaa agg       1872
Lys Glu Asn Gln Thr Asp Lys Pro Ser Ile Leu Pro Gln Phe Lys Arg
610                 615                 620 aat aaa gca caa gaa aac tca aaa ctt gat gaa aag gta gaa gaa cca       1920
Asn Lys Ala Gln Glu Asn Ser Lys Leu Asp Glu Lys Val Glu Glu Pro
625                 630                 635                 640 aag act agt gag aag gta gaa aaa gaa aaa ctt tct gaa act ggg aat       1968
Lys Thr Ser Glu Lys Val Glu Lys Glu Lys Leu Ser Glu Thr Gly Asn
                645                 650                 655 agt act agt aat tca acg tta gaa gaa gtt cct aca gtg gat cct gta       2016
Ser Thr Ser Asn Ser Thr Leu Glu Glu Val Pro Thr Val Asp Pro Val
            660                 665                 670 caa gaa aaa gta gca aaa ttt gct gaa agt tat ggg atg aag cta gaa       2064
Gln Glu Lys Val Ala Lys Phe Ala Glu Ser Tyr Gly Met Lys Leu Glu
        675                 680                 685 aat gtc ttg ttt aat atg gac gga aca att gaa tta tat tta cca tcg       2112
Asn Val Leu Phe Asn Met Asp Gly Thr Ile Glu Leu Tyr Leu Pro Ser
690                 695                 700
```

-continued

```
gga gaa gtc att aaa aag aat atg gca gat ttt aca gga gaa gca cct    2160
Gly Glu Val Ile Lys Lys Asn Met Ala Asp Phe Thr Gly Glu Ala Pro
705                 710                 715                 720 caa gga aat ggt gaa aat aaa cca tct gaa aat gga aaa gta tct act    2208
Gln Gly Asn Gly Glu Asn Lys Pro Ser Glu Asn Gly Lys Val Ser Thr
                725                 730                 735 gga aca gtt gag aac caa cca aca gaa aat aaa cca gca gat tct tta    2256
Gly Thr Val Glu Asn Gln Pro Thr Glu Asn Lys Pro Ala Asp Ser Leu
            740                 745                 750 cca gag gca cca aac gaa aaa cct gta aaa cca gaa aac tca acg gat    2304
Pro Glu Ala Pro Asn Glu Lys Pro Val Lys Pro Glu Asn Ser Thr Asp
        755                 760                 765 aat gga atg ttg aat cca gaa ggg aat gtg ggg agt gac cct atg tta    2352
Asn Gly Met Leu Asn Pro Glu Gly Asn Val Gly Ser Asp Pro Met Leu
770                 775                 780 gat tca gca tta gag gaa gct cca gca gta gat cct gta caa gaa aaa    2400
Asp Ser Ala Leu Glu Glu Ala Pro Ala Val Asp Pro Val Gln Glu Lys
785                 790                 795                 800 tta gaa aaa ttt aca gct agt tac gga tta ggc tta gat agt gtt ata    2448
Leu Glu Lys Phe Thr Ala Ser Tyr Gly Leu Gly Leu Asp Ser Val Ile
                805                 810                 815 ttc aat atg gat gga acg att gaa tta aga ttg cca agt gga gaa gtg    2496
Phe Asn Met Asp Gly Thr Ile Glu Leu Arg Leu Pro Ser Gly Glu Val
            820                 825                 830 ata aaa aag aat tta ttg atc tca tagcgtaa                           2528
Ile Lys Lys Asn Leu Leu Ile Ser
        835                 840
```

<210> SEQ ID NO 16
<211> LENGTH: 840
<212> TYPE: PRT
<213> ORGANISM: S. pneumoniae

<400> SEQUENCE: 16

```
Cys Ala Tyr Ala Leu Asn Gln His Arg Ser Gln Glu Asn Lys Asp Asn
1               5                   10                  15

Asn Arg Val Ser Tyr Val Asp Gly Ser Gln Ser Gln Lys Ser Glu
            20                  25                  30

Asn Leu Thr Pro Asp Gln Val Ser Gln Lys Glu Gly Ile Gln Ala Glu
        35                  40                  45

Gln Ile Val Ile Lys Ile Thr Asp Gln Gly Tyr Val Thr Ser His Gly
    50                  55                  60

Asp His Tyr His Tyr Tyr Asn Gly Lys Val Pro Tyr Asp Ala Leu Phe
65                  70                  75                  80

Ser Glu Glu Leu Leu Met Lys Asp Pro Asn Tyr Gln Leu Lys Asp Ala
                85                  90                  95

Asp Ile Val Asn Glu Val Lys Gly Gly Tyr Ile Ile Lys Val Asp Gly
            100                 105                 110

Lys Tyr Tyr Val Tyr Leu Lys Asp Ala Ala His Ala Asp Asn Val Arg
        115                 120                 125

Thr Lys Asp Glu Ile Asn Arg Gln Lys Gln Glu His Val Lys Asp Asn
    130                 135                 140

Glu Lys Val Asn Ser Asn Val Ala Val Ala Arg Ser Gln Gly Arg Tyr
145                 150                 155                 160

Thr Thr Asn Asp Gly Tyr Val Phe Asn Pro Ala Asp Ile Ile Glu Asp
                165                 170                 175

Thr Gly Asn Ala Tyr Ile Val Pro His Gly Gly His Tyr His Tyr Ile
```

-continued

```
                180                 185                 190
Pro Lys Ser Asp Leu Ser Ala Ser Glu Leu Ala Ala Lys Ala His
        195                 200                 205
Leu Ala Gly Lys Asn Met Gln Pro Ser Gln Leu Ser Tyr Ser Ser Thr
    210                 215                 220
Pro Ser Pro Ser Leu Pro Ile Asn Pro Gly Thr Ser His Glu Lys His
225                 230                 235                 240
Glu Glu Asp Gly Tyr Gly Phe Asp Ala Asn Arg Ile Ile Ala Glu Asp
                245                 250                 255
Glu Ser Gly Phe Val Met Ser His Gly Asp His Asn His Tyr Phe Phe
            260                 265                 270
Lys Lys Asp Leu Thr Glu Glu Gln Ile Lys Ala Ala Gln Lys His Leu
        275                 280                 285
Glu Glu Val Lys Thr Ser His Asn Gly Leu Asp Ser Leu Ser Ser His
    290                 295                 300
Glu Gln Asp Tyr Pro Ser Asn Ala Lys Glu Met Lys Asp Leu Asp Lys
305                 310                 315                 320
Lys Ile Glu Glu Lys Ile Ala Gly Ile Met Lys Gln Tyr Gly Val Lys
                325                 330                 335
Arg Glu Ser Ile Val Val Asn Lys Glu Lys Asn Ala Ile Ile Tyr Pro
            340                 345                 350
His Gly Asp His His His Ala Asp Pro Ile Asp Glu His Lys Pro Val
        355                 360                 365
Gly Ile Gly His Ser His Ser Asn Tyr Glu Leu Phe Lys Pro Glu Glu
    370                 375                 380
Gly Val Ala Lys Lys Glu Gly Asn Lys Val Tyr Thr Gly Glu Glu Leu
385                 390                 395                 400
Thr Asn Val Val Asn Leu Leu Lys Asn Ser Thr Phe Asn Asn Gln Asn
                405                 410                 415
Phe Thr Leu Ala Asn Gly Gln Lys Arg Val Ser Phe Ser Phe Pro Pro
            420                 425                 430
Glu Leu Glu Lys Lys Leu Gly Ile Asn Met Leu Val Lys Leu Ile Thr
        435                 440                 445
Pro Asp Gly Lys Val Leu Glu Lys Val Ser Gly Lys Val Phe Gly Glu
    450                 455                 460
Gly Val Gly Asn Ile Ala Asn Phe Glu Leu Asp Gln Pro Tyr Leu Pro
465                 470                 475                 480
Gly Gln Thr Phe Lys Tyr Thr Ile Ala Ser Lys Asp Tyr Pro Glu Val
                485                 490                 495
Ser Tyr Asp Gly Thr Phe Thr Val Pro Thr Ser Leu Ala Tyr Lys Met
            500                 505                 510
Ala Ser Gln Thr Ile Phe Tyr Pro Phe His Ala Gly Asp Thr Tyr Leu
        515                 520                 525
Arg Val Asn Pro Gln Phe Ala Val Pro Lys Gly Thr Asp Ala Leu Val
    530                 535                 540
Arg Val Phe Asp Glu Phe His Gly Asn Ala Tyr Leu Glu Asn Asn Tyr
545                 550                 555                 560
Lys Val Gly Glu Ile Lys Leu Pro Ile Pro Lys Leu Asn Gln Gly Thr
                565                 570                 575
Thr Arg Thr Ala Gly Asn Lys Ile Pro Val Thr Phe Met Ala Asn Ala
            580                 585                 590
Tyr Leu Asp Asn Gln Ser Thr Tyr Ile Val Glu Val Pro Ile Leu Glu
        595                 600                 605
```

-continued

```
Lys Glu Asn Gln Thr Asp Lys Pro Ser Ile Leu Pro Gln Phe Lys Arg
            610                 615                 620
Asn Lys Ala Gln Glu Asn Ser Lys Leu Asp Glu Lys Val Glu Glu Pro
625                 630                 635                 640
Lys Thr Ser Glu Lys Val Glu Lys Lys Leu Ser Glu Thr Gly Asn
            645                 650                 655
Ser Thr Ser Asn Ser Thr Leu Glu Glu Val Pro Thr Val Asp Pro Val
            660                 665                 670
Gln Glu Lys Val Ala Lys Phe Ala Glu Ser Tyr Gly Met Lys Leu Glu
            675                 680                 685
Asn Val Leu Phe Asn Met Asp Gly Thr Ile Glu Leu Tyr Leu Pro Ser
            690                 695                 700
Gly Glu Val Ile Lys Lys Asn Met Ala Asp Phe Thr Gly Glu Ala Pro
705                 710                 715                 720
Gln Gly Asn Gly Glu Asn Lys Pro Ser Glu Asn Gly Lys Val Ser Thr
            725                 730                 735
Gly Thr Val Glu Asn Gln Pro Thr Glu Asn Lys Pro Ala Asp Ser Leu
            740                 745                 750
Pro Glu Ala Pro Asn Glu Lys Pro Val Lys Pro Glu Asn Ser Thr Asp
            755                 760                 765
Asn Gly Met Leu Asn Pro Glu Gly Asn Val Gly Ser Asp Pro Met Leu
770                 775                 780
Asp Ser Ala Leu Glu Glu Ala Pro Ala Val Asp Pro Val Gln Glu Lys
785                 790                 795                 800
Leu Glu Lys Phe Thr Ala Ser Tyr Gly Leu Gly Leu Asp Ser Val Ile
            805                 810                 815
Phe Asn Met Asp Gly Thr Ile Glu Leu Arg Leu Pro Ser Gly Glu Val
            820                 825                 830
Ile Lys Lys Asn Leu Leu Ile Ser
            835                 840

<210> SEQ ID NO 17
<211> LENGTH: 27
<212> TYPE: DNA
<213> ORGANISM: Articial Sequence
<220> FEATURE:
<223> OTHER INFORMATION: PCR oligonucleotide primer

<400> SEQUENCE: 17
cagtagatct gtgcctatgc actaaac                                          27

<210> SEQ ID NO 18
<211> LENGTH: 33
<212> TYPE: DNA
<213> ORGANISM: Articial Sequence
<220> FEATURE:
<223> OTHER INFORMATION: PCR oligonucleotide primer

<400> SEQUENCE: 18
gatctctaga ctactgctat tccttacgct atg                                   33

<210> SEQ ID NO 19
<211> LENGTH: 30
<212> TYPE: DNA
<213> ORGANISM: Articial Sequence
<220> FEATURE:
<223> OTHER INFORMATION: PCR oligonucleotide primer

<400> SEQUENCE: 19
```
atcactcgag cattacctgg ataatcctgt                                  30

<210> SEQ ID NO 20
<211> LENGTH: 26
<212> TYPE: DNA
<213> ORGANISM: Articial Sequence
<220> FEATURE:
<223> OTHER INFORMATION: PCR oligonucleotide primer

<400> SEQUENCE: 20
ctgctaagct tatgaaagat ttagat                                      26

<210> SEQ ID NO 21
<211> LENGTH: 24
<212> TYPE: DNA
<213> ORGANISM: Articial Sequence
<220> FEATURE:
<223> OTHER INFORMATION: PCR oligonucleotide primer

<400> SEQUENCE: 21
gatactcgag ctgctattcc ttac                                        24

<210> SEQ ID NO 22
<211> LENGTH: 28
<212> TYPE: DNA
<213> ORGANISM: Articial Sequence
<220> FEATURE:
<223> OTHER INFORMATION: PCR oligonucleotide primer

<400> SEQUENCE: 22
gaatctcgag ttaagctgct gctaattc                                    28

<210> SEQ ID NO 23
<211> LENGTH: 32
<212> TYPE: DNA
<213> ORGANISM: Articial Sequence
<220> FEATURE:
<223> OTHER INFORMATION: PCR oligonucleotide primer

<400> SEQUENCE: 23
gacgctcgag cgctatgaaa tcagataaat tc                               32

<210> SEQ ID NO 24
<211> LENGTH: 37
<212> TYPE: DNA
<213> ORGANISM: Articial Sequence
<220> FEATURE:
<223> OTHER INFORMATION: PCR oligonucleotide primer

<400> SEQUENCE: 24
gacgctcgag ggcattacct ggataatcct gttcatg                          37

<210> SEQ ID NO 25
<211> LENGTH: 33
<212> TYPE: DNA
<213> ORGANISM: Articial Sequence
<220> FEATURE:
<223> OTHER INFORMATION: PCR oligonucleotide primer

<400> SEQUENCE: 25
cagtagatct cttcatcatt tattgaaaag agg                              33

<210> SEQ ID NO 26
<211> LENGTH: 40
<212> TYPE: DNA

-continued

<213> ORGANISM: Articial Sequence
<220> FEATURE:
<223> OTHER INFORMATION: PCR oligonucleotide primer

<400> SEQUENCE: 26
ttatttcttc catatggact tgacagaaga gcaaattaag                40

<210> SEQ ID NO 27
<211> LENGTH: 32
<212> TYPE: DNA
<213> ORGANISM: Articial Sequence
<220> FEATURE:
<223> OTHER INFORMATION: PCR oligonucleotide primer

<400> SEQUENCE: 27
cgccaagctt cgctatgaaa tcagataaat tc                        32

<210> SEQ ID NO 28
<211> LENGTH: 34
<212> TYPE: DNA
<213> ORGANISM: Articial Sequence
<220> FEATURE:
<223> OTHER INFORMATION: PCR oligonucleotide primer

<400> SEQUENCE: 28
cgccaagctt ttccacaata taagtcgatt gatt                      34

<210> SEQ ID NO 29
<211> LENGTH: 40
<212> TYPE: DNA
<213> ORGANISM: Articial Sequence
<220> FEATURE:
<223> OTHER INFORMATION: PCR oligonucleotide primer

<400> SEQUENCE: 29
ttatttcttc catatggaag tacctatctt ggaaaaagaa                40

<210> SEQ ID NO 30
<211> LENGTH: 37
<212> TYPE: DNA
<213> ORGANISM: Articial Sequence
<220> FEATURE:
<223> OTHER INFORMATION: PCR oligonucleotide primer

<400> SEQUENCE: 30
ttatttcttc catatggtgc ctatgcacta aaccagc                   37

<210> SEQ ID NO 31
<211> LENGTH: 40
<212> TYPE: DNA
<213> ORGANISM: Articial Sequence
<220> FEATURE:
<223> OTHER INFORMATION: PCR oligonucleotide primer

<400> SEQUENCE: 31
ataagaatgc ggccgcttcc acaatataag tcgattgatt                40

<210> SEQ ID NO 32
<211> LENGTH: 31
<212> TYPE: DNA
<213> ORGANISM: Articial Sequence
<220> FEATURE:
<223> OTHER INFORMATION: PCR oligonucleotide primer

<400> SEQUENCE: 32
cagtagatct gtgcttatga actaggtttg c                         31

```
<210> SEQ ID NO 33
<211> LENGTH: 32
<212> TYPE: DNA
<213> ORGANISM: Articial Sequence
<220> FEATURE:
<223> OTHER INFORMATION: PCR oligonucleotide primer

<400> SEQUENCE: 33
gatcaagctt gctgctacct ttacttactc tc                                32

<210> SEQ ID NO 34
<211> LENGTH: 26
<212> TYPE: DNA
<213> ORGANISM: Articial Sequence
<220> FEATURE:
<223> OTHER INFORMATION: PCR oligonucleotide primer

<400> SEQUENCE: 34
ctgagatatc cgttatcgtt caaacc                                       26

<210> SEQ ID NO 35
<211> LENGTH: 28
<212> TYPE: DNA
<213> ORGANISM: Articial Sequence
<220> FEATURE:
<223> OTHER INFORMATION: PCR oligonucleotide primer

<400> SEQUENCE: 35
ctgcaagctt ttaaagggga ataatacg                                     28

<210> SEQ ID NO 36
<211> LENGTH: 29
<212> TYPE: DNA
<213> ORGANISM: Articial Sequence
<220> FEATURE:
<223> OTHER INFORMATION: PCR oligonucleotide primer

<400> SEQUENCE: 36
cagtagatct gcagaagcct tcctatctg                                    29

<210> SEQ ID NO 37
<211> LENGTH: 33
<212> TYPE: DNA
<213> ORGANISM: Articial Sequence
<220> FEATURE:
<223> OTHER INFORMATION: PCR oligonucleotide primer

<400> SEQUENCE: 37
tcgccaagct tcgttatcgt tcaaaccatt ggg                               33

<210> SEQ ID NO 38
<211> LENGTH: 45
<212> TYPE: DNA
<213> ORGANISM: Articial Sequence
<220> FEATURE:
<223> OTHER INFORMATION: PCR oligonucleotide primer

<400> SEQUENCE: 38
ataagaatgc ggccgcctta ctctccttta ataaagccaa tagtt                  45

<210> SEQ ID NO 39
<211> LENGTH: 34
<212> TYPE: DNA
<213> ORGANISM: Articial Sequence
<220> FEATURE:
```

```
-continued
```

<223> OTHER INFORMATION: PCR oligonucleotide primer

<400> SEQUENCE: 39
catgccatgg acattgatag tctcttgaaa cagc          34

<210> SEQ ID NO 40
<211> LENGTH: 37
<212> TYPE: DNA
<213> ORGANISM: Articial Sequence
<220> FEATURE:
<223> OTHER INFORMATION: PCR oligonucleotide primer

<400> SEQUENCE: 40
cgccaagctt cttactctcc tttaataaag ccaatag       37

<210> SEQ ID NO 41
<211> LENGTH: 31
<212> TYPE: DNA
<213> ORGANISM: Articial Sequence
<220> FEATURE:
<223> OTHER INFORMATION: PCR oligonucleotide primer

<400> SEQUENCE: 41
cgacaagctt aacatggtcg ctagcgttac c             31

<210> SEQ ID NO 42
<211> LENGTH: 30
<212> TYPE: DNA
<213> ORGANISM: Articial Sequence
<220> FEATURE:
<223> OTHER INFORMATION: PCR oligonucleotide primer

<400> SEQUENCE: 42
cataccatgg gcctttatga ggcacctaag              30

<210> SEQ ID NO 43
<211> LENGTH: 34
<212> TYPE: DNA
<213> ORGANISM: Articial Sequence
<220> FEATURE:
<223> OTHER INFORMATION: PCR oligonucleotide primer

<400> SEQUENCE: 43
cgacaagctt aagtaaatct tcagcctctc tcag          34

<210> SEQ ID NO 44
<211> LENGTH: 31
<212> TYPE: DNA
<213> ORGANISM: Articial Sequence
<220> FEATURE:
<223> OTHER INFORMATION: PCR oligonucleotide primer

<400> SEQUENCE: 44
gataccatgg ctagcgacca tgttcaaaga a             31

<210> SEQ ID NO 45
<211> LENGTH: 36
<212> TYPE: DNA
<213> ORGANISM: Articial Sequence
<220> FEATURE:
<223> OTHER INFORMATION: PCR oligonucleotide primer

<400> SEQUENCE: 45
cgccaagctt atcatccact aacttgactt tatcac        36

```
<210> SEQ ID NO 46
<211> LENGTH: 33
<212> TYPE: DNA
<213> ORGANISM: Articial Sequence
<220> FEATURE:
<223> OTHER INFORMATION: PCR oligonucleotide primer

<400> SEQUENCE: 46
cataccatgg atattcttgc cttcttagct ccg                              33

<210> SEQ ID NO 47
<211> LENGTH: 30
<212> TYPE: DNA
<213> ORGANISM: Articial Sequence
<220> FEATURE:
<223> OTHER INFORMATION: PCR oligonucleotide primer

<400> SEQUENCE: 47
catgccatgg tgcttatgaa ctaggtttgc                                  30

<210> SEQ ID NO 48
<211> LENGTH: 32
<212> TYPE: DNA
<213> ORGANISM: Articial Sequence
<220> FEATURE:
<223> OTHER INFORMATION: PCR oligonucleotide primer

<400> SEQUENCE: 48
cgccaagctt tagcgttacc aaaaccatta tc                               32

<210> SEQ ID NO 49
<211> LENGTH: 36
<212> TYPE: DNA
<213> ORGANISM: Articial Sequence
<220> FEATURE:
<223> OTHER INFORMATION: PCR oligonucleotide primer

<400> SEQUENCE: 49
gtattagatc tgttcctatg aacttggtcg tcacca                           36

<210> SEQ ID NO 50
<211> LENGTH: 28
<212> TYPE: DNA
<213> ORGANISM: Articial Sequence
<220> FEATURE:
<223> OTHER INFORMATION: PCR oligonucleotide primer

<400> SEQUENCE: 50
cgcctctaga ctactgtata ggagccgg                                    28

<210> SEQ ID NO 51
<211> LENGTH: 34
<212> TYPE: DNA
<213> ORGANISM: Articial Sequence
<220> FEATURE:
<223> OTHER INFORMATION: PCR oligonucleotide primer

<400> SEQUENCE: 51
catgccatgg aaaacatttc aagccttta cgtg                              34

<210> SEQ ID NO 52
<211> LENGTH: 34
<212> TYPE: DNA
<213> ORGANISM: Articial Sequence
<220> FEATURE:
<223> OTHER INFORMATION: PCR oligonucleotide primer
```

-continued

```
<400> SEQUENCE: 52
cgacaagctt ctgtatagga gccggttgac tttc                               34

<210> SEQ ID NO 53
<211> LENGTH: 34
<212> TYPE: DNA
<213> ORGANISM: Articial Sequence
<220> FEATURE:
<223> OTHER INFORMATION: PCR oligonucleotide primer

<400> SEQUENCE: 53
catgccatgg ttcgtaaaaa taaggcagac caag                               34

<210> SEQ ID NO 54
<211> LENGTH: 30
<212> TYPE: DNA
<213> ORGANISM: Articial Sequence
<220> FEATURE:
<223> OTHER INFORMATION: PCR oligonucleotide primer

<400> SEQUENCE: 54
catgccatgg aagcctattg gaatgggaag                                    30

<210> SEQ ID NO 55
<211> LENGTH: 1019
<212> TYPE: PRT
<213> ORGANISM: S. pneumoniae

<400> SEQUENCE: 55
```

Cys Ala Tyr Ala Leu Asn Gln His Arg Ser Gln Glu Asn Lys Asp Asn
 1               5                  10                  15

Asn Arg Val Ser Tyr Val Asp Gly Ser Gln Ser Ser Gln Lys Ser Glu
             20                  25                  30

Asn Leu Thr Pro Asp Gln Val Ser Gln Lys Glu Gly Ile Gln Ala Glu
         35                  40                  45

Gln Ile Val Ile Lys Ile Thr Asp Gln Gly Tyr Val Thr Ser His Gly
     50                  55                  60

Asp His Tyr His Tyr Tyr Asn Gly Lys Val Pro Tyr Asp Ala Leu Phe
 65                  70                  75                  80

Ser Glu Glu Leu Leu Met Lys Asp Pro Asn Tyr Gln Leu Lys Asp Ala
                 85                  90                  95

Asp Ile Val Asn Glu Val Lys Gly Gly Tyr Ile Ile Lys Val Asp Gly
            100                 105                 110

Lys Tyr Tyr Val Tyr Leu Lys Asp Ala Ala His Ala Asp Asn Val Arg
        115                 120                 125

Thr Lys Asp Glu Ile Asn Arg Gln Lys Gln Glu His Val Lys Asp Asn
    130                 135                 140

Glu Lys Val Asn Ser Asn Val Ala Val Ala Arg Ser Gln Gly Arg Tyr
145                 150                 155                 160

Thr Thr Asn Asp Gly Tyr Val Phe Asn Pro Ala Asp Ile Ile Glu Asp
                165                 170                 175

Thr Gly Asn Ala Tyr Ile Val Pro His Gly Gly His Tyr His Tyr Ile
            180                 185                 190

Pro Lys Ser Asp Leu Ser Ala Ser Glu Leu Ala Ala Lys Ala His
        195                 200                 205

Leu Ala Gly Lys Asn Met Gln Pro Ser Gln Leu Ser Tyr Ser Ser Thr
    210                 215                 220

Ala Ser Asp Asn Asn Thr Gln Ser Val Ala Lys Gly Ser Thr Ser Lys

```
              225                 230                 235                 240
Pro Ala Asn Lys Ser Glu Asn Leu Gln Ser Leu Leu Lys Glu Leu Tyr
                245                 250                 255
Asp Ser Pro Ser Ala Gln Arg Tyr Ser Glu Ser Asp Gly Leu Val Phe
            260                 265                 270
Asp Pro Ala Lys Ile Ile Ser Arg Thr Pro Asn Gly Val Ala Ile Pro
        275                 280                 285
His Gly Asp His Tyr His Phe Ile Pro Tyr Ser Lys Leu Ser Ala Leu
    290                 295                 300
Glu Glu Lys Ile Ala Arg Met Val Pro Ile Ser Gly Thr Gly Ser Thr
305                 310                 315                 320
Val Ser Thr Asn Ala Lys Pro Asn Glu Val Val Ser Ser Leu Gly Ser
                325                 330                 335
Leu Ser Ser Asn Pro Ser Ser Leu Thr Thr Ser Lys Glu Leu Ser Ser
            340                 345                 350
Ala Ser Asp Gly Tyr Ile Phe Asn Pro Lys Asp Ile Val Glu Glu Thr
        355                 360                 365
Ala Thr Ala Tyr Ile Val Arg His Gly Asp His Phe His Tyr Ile Pro
    370                 375                 380
Lys Ser Asn Gln Ile Gly Gln Pro Thr Leu Pro Asn Asn Ser Leu Ala
385                 390                 395                 400
Thr Pro Ser Pro Ser Leu Pro Ile Asn Pro Gly Thr Ser His Glu Lys
                405                 410                 415
His Glu Glu Asp Gly Tyr Gly Phe Asp Ala Asn Arg Ile Ile Ala Glu
            420                 425                 430
Asp Glu Ser Gly Phe Val Met Ser His Gly Asp His Asn His Tyr Phe
        435                 440                 445
Phe Lys Lys Asp Leu Thr Glu Glu Gln Ile Lys Ala Ala Gln Lys His
    450                 455                 460
Leu Glu Glu Val Lys Thr Ser His Asn Gly Leu Asp Ser Leu Ser Ser
465                 470                 475                 480
His Glu Gln Asp Tyr Pro Gly Asn Ala Lys Glu Met Lys Asp Leu Asp
                485                 490                 495
Lys Lys Ile Glu Glu Lys Ile Ala Gly Ile Met Lys Gln Tyr Gly Val
            500                 505                 510
Lys Arg Glu Ser Ile Val Val Asn Lys Glu Lys Asn Ala Ile Ile Tyr
        515                 520                 525
Pro His Gly Asp His His Ala Asp Pro Ile Asp Glu His Lys Pro
    530                 535                 540
Val Gly Ile Gly His Ser His Ser Asn Tyr Glu Leu Phe Lys Pro Glu
545                 550                 555                 560
Glu Gly Val Ala Lys Lys Glu Gly Asn Lys Val Tyr Thr Gly Glu Glu
                565                 570                 575
Leu Thr Asn Val Val Asn Leu Leu Lys Asn Ser Thr Phe Asn Asn Gln
            580                 585                 590
Asn Phe Thr Leu Ala Asn Gly Gln Lys Arg Val Ser Phe Ser Phe Pro
        595                 600                 605
Pro Glu Leu Glu Lys Lys Leu Gly Ile Asn Met Leu Val Lys Leu Ile
    610                 615                 620
Thr Pro Asp Gly Lys Val Leu Glu Lys Val Ser Gly Lys Val Phe Gly
625                 630                 635                 640
Glu Gly Val Gly Asn Ile Ala Asn Phe Glu Leu Asp Gln Pro Tyr Leu
                645                 650                 655
```

```
Pro Gly Gln Thr Phe Lys Tyr Thr Ile Ala Ser Lys Asp Tyr Pro Glu
            660                 665                 670

Val Ser Tyr Asp Gly Thr Phe Thr Val Pro Thr Ser Leu Ala Tyr Lys
        675                 680                 685

Met Ala Ser Gln Thr Ile Phe Tyr Pro Phe His Ala Gly Asp Thr Tyr
    690                 695                 700

Leu Arg Val Asn Pro Gln Phe Ala Val Pro Lys Gly Thr Asp Ala Leu
705                 710                 715                 720

Val Arg Val Phe Asp Glu Phe His Gly Asn Ala Tyr Leu Glu Asn Asn
                725                 730                 735

Tyr Lys Val Gly Glu Ile Lys Leu Pro Ile Pro Lys Leu Asn Gln Gly
            740                 745                 750

Thr Thr Arg Thr Ala Gly Asn Lys Ile Pro Val Thr Phe Met Ala Asn
        755                 760                 765

Ala Tyr Leu Asp Asn Gln Ser Thr Tyr Ile Val Glu Val Pro Ile Leu
    770                 775                 780

Glu Lys Glu Asn Gln Thr Asp Lys Pro Ser Ile Leu Pro Gln Phe Lys
785                 790                 795                 800

Arg Asn Lys Ala Gln Glu Asn Ser Lys Leu Asp Glu Lys Val Glu Glu
                805                 810                 815

Pro Lys Thr Ser Glu Lys Val Glu Lys Glu Lys Leu Ser Glu Thr Gly
            820                 825                 830

Asn Ser Thr Ser Asn Ser Thr Leu Glu Glu Val Pro Thr Val Asp Pro
        835                 840                 845

Val Gln Glu Lys Val Ala Lys Phe Ala Glu Ser Tyr Gly Met Lys Leu
    850                 855                 860

Glu Asn Val Leu Phe Asn Met Asp Gly Thr Ile Glu Leu Tyr Leu Pro
865                 870                 875                 880

Ser Gly Glu Val Ile Lys Lys Asn Met Ala Asp Phe Thr Gly Glu Ala
                885                 890                 895

Pro Gln Gly Asn Gly Glu Asn Lys Pro Ser Glu Asn Gly Lys Val Ser
            900                 905                 910

Thr Gly Thr Val Glu Asn Gln Pro Thr Glu Asn Lys Pro Ala Asp Ser
        915                 920                 925

Leu Pro Glu Ala Pro Asn Glu Lys Pro Val Lys Pro Glu Asn Ser Thr
    930                 935                 940

Asp Asn Gly Met Leu Asn Pro Glu Gly Asn Val Gly Ser Asp Pro Met
945                 950                 955                 960

Leu Asp Pro Ala Leu Glu Glu Ala Pro Ala Val Asp Pro Val Gln Glu
                965                 970                 975

Lys Leu Glu Lys Phe Thr Ala Ser Tyr Gly Leu Gly Leu Asp Ser Val
            980                 985                 990

Ile Phe Asn Met Asp Gly Thr Ile Glu Leu Arg Leu Pro Ser Gly Glu
        995                 1000                1005

Val Ile Lys Lys Asn Leu Ser Asp Phe Ile Ala
    1010                1015

<210> SEQ ID NO 56
<211> LENGTH: 489
<212> TYPE: PRT
<213> ORGANISM: S. pneumoniae

<400> SEQUENCE: 56

Cys Ala Tyr Ala Leu Asn Gln His Arg Ser Gln Glu Asn Lys Asp Asn
```

```
              1               5                  10                 15
Asn Arg Val Ser Tyr Val Asp Gly Ser Gln Ser Gln Lys Ser Glu
                20                  25                  30

Asn Leu Thr Pro Asp Gln Val Ser Gln Lys Glu Gly Ile Gln Ala Glu
                35                  40                  45

Gln Ile Val Ile Lys Ile Thr Asp Gln Gly Tyr Val Thr Ser His Gly
                50                  55                  60

Asp His Tyr His Tyr Tyr Asn Gly Lys Val Pro Tyr Asp Ala Leu Phe
 65                  70                  75                  80

Ser Glu Glu Leu Leu Met Lys Asp Pro Asn Tyr Gln Leu Lys Asp Ala
                85                  90                  95

Asp Ile Val Asn Glu Val Lys Gly Gly Tyr Ile Ile Lys Val Asp Gly
                100                 105                 110

Lys Tyr Tyr Val Tyr Leu Lys Asp Ala Ala His Ala Asp Asn Val Arg
                115                 120                 125

Thr Lys Asp Glu Ile Asn Arg Gln Lys Gln His Val Lys Asp Asn
                130                 135                 140

Glu Lys Val Asn Ser Asn Val Ala Val Ala Arg Ser Gln Gly Arg Tyr
145                 150                 155                 160

Thr Thr Asn Asp Gly Tyr Val Phe Asn Pro Ala Asp Ile Ile Glu Asp
                165                 170                 175

Thr Gly Asn Ala Tyr Ile Val Pro His Gly Gly His Tyr His Tyr Ile
                180                 185                 190

Pro Lys Ser Asp Leu Ser Ala Ser Glu Leu Ala Ala Lys Ala His
                195                 200                 205

Leu Ala Gly Lys Asn Met Gln Pro Ser Gln Leu Ser Tyr Ser Ser Thr
                210                 215                 220

Ala Ser Asp Asn Asn Thr Gln Ser Val Ala Lys Gly Ser Thr Ser Lys
225                 230                 235                 240

Pro Ala Asn Lys Ser Glu Asn Leu Gln Ser Leu Leu Lys Glu Leu Tyr
                245                 250                 255

Asp Ser Pro Ser Ala Gln Arg Tyr Ser Glu Ser Asp Gly Leu Val Phe
                260                 265                 270

Asp Pro Ala Lys Ile Ile Ser Arg Thr Pro Asn Gly Val Ala Ile Pro
                275                 280                 285

His Gly Asp His Tyr His Phe Ile Pro Tyr Ser Lys Leu Ser Ala Leu
                290                 295                 300

Glu Glu Lys Ile Ala Arg Met Val Pro Ile Ser Gly Thr Gly Ser Thr
305                 310                 315                 320

Val Ser Thr Asn Ala Lys Pro Asn Glu Val Val Ser Ser Leu Gly Ser
                325                 330                 335

Leu Ser Ser Asn Pro Ser Ser Leu Thr Thr Ser Lys Glu Leu Ser Ser
                340                 345                 350

Ala Ser Asp Gly Tyr Ile Phe Asn Pro Lys Asp Ile Val Glu Glu Thr
                355                 360                 365

Ala Thr Ala Tyr Ile Val Arg His Gly Asp His Phe His Tyr Ile Pro
                370                 375                 380

Lys Ser Asn Gln Ile Gly Gln Pro Thr Leu Pro Asn Asn Ser Leu Ala
385                 390                 395                 400

Thr Pro Ser Pro Ser Leu Pro Ile Asn Pro Gly Thr Ser His Glu Lys
                405                 410                 415

His Glu Glu Asp Gly Tyr Gly Phe Asp Ala Asn Arg Ile Ile Ala Glu
                420                 425                 430
```

-continued

```
Asp Glu Ser Gly Phe Val Met Ser His Gly Asp His Asn His Tyr Phe
            435                 440                 445

Phe Lys Lys Asp Leu Thr Glu Glu Gln Ile Lys Ala Ala Gln Lys His
            450                 455                 460

Leu Glu Glu Val Lys Thr Ser His Asn Gly Leu Asp Ser Leu Ser Ser
465                 470                 475                 480

His Glu Gln Asp Tyr Pro Gly Asn Ala
                485

<210> SEQ ID NO 57
<211> LENGTH: 509
<212> TYPE: PRT
<213> ORGANISM: S. pneumoniae

<400> SEQUENCE: 57

Met Lys Phe Ser Lys Lys Tyr Ile Ala Ala Gly Ser Ala Val Ile Val
1               5                   10                  15

Ser Leu Ser Leu Cys Ala Tyr Ala Leu Asn Gln His Arg Ser Gln Glu
                20                  25                  30

Asn Lys Asp Asn Asn Arg Val Ser Tyr Val Asp Gly Ser Gln Ser Ser
            35                  40                  45

Gln Lys Ser Glu Asn Leu Thr Pro Asp Gln Val Ser Gln Lys Glu Gly
50                  55                  60

Ile Gln Ala Glu Gln Ile Val Ile Lys Ile Thr Asp Gln Gly Tyr Val
65                  70                  75                  80

Thr Ser His Gly Asp His Tyr His Tyr Tyr Asn Gly Lys Val Pro Tyr
                85                  90                  95

Asp Ala Leu Phe Ser Glu Glu Leu Leu Met Lys Asp Pro Asn Tyr Gln
                100                 105                 110

Leu Lys Asp Ala Asp Ile Val Asn Glu Val Lys Gly Gly Tyr Ile Ile
            115                 120                 125

Lys Val Asp Gly Lys Tyr Tyr Val Tyr Leu Lys Asp Ala Ala His Ala
130                 135                 140

Asp Asn Val Arg Thr Lys Asp Glu Ile Asn Arg Gln Lys Gln Glu His
145                 150                 155                 160

Val Lys Asp Asn Glu Lys Val Asn Ser Asn Val Ala Val Ala Arg Ser
                165                 170                 175

Gln Gly Arg Tyr Thr Thr Asn Asp Gly Tyr Val Phe Asn Pro Ala Asp
            180                 185                 190

Ile Ile Glu Asp Thr Gly Asn Ala Tyr Ile Val Pro His Gly Gly His
            195                 200                 205

Tyr His Tyr Ile Pro Lys Ser Asp Leu Ser Ala Ser Glu Leu Ala Ala
    210                 215                 220

Ala Lys Ala His Leu Ala Gly Lys Asn Met Gln Pro Ser Gln Leu Ser
225                 230                 235                 240

Tyr Ser Ser Thr Ala Ser Asp Asn Asn Thr Gln Ser Val Ala Lys Gly
                245                 250                 255

Ser Thr Ser Lys Pro Ala Asn Lys Ser Glu Asn Leu Gln Ser Leu Leu
            260                 265                 270

Lys Glu Leu Tyr Asp Ser Pro Ser Ala Gln Arg Tyr Ser Glu Ser Asp
            275                 280                 285

Gly Leu Val Phe Asp Pro Ala Lys Ile Ile Ser Arg Thr Pro Asn Gly
    290                 295                 300

Val Ala Ile Pro His Gly Asp His Tyr His Phe Ile Pro Tyr Ser Lys
```

```
                305                 310                 315                 320
Leu Ser Ala Leu Glu Glu Lys Ile Ala Arg Met Val Pro Ile Ser Gly
                325                 330                 335

Thr Gly Ser Thr Val Ser Thr Asn Ala Lys Pro Asn Glu Val Val Ser
                340                 345                 350

Ser Leu Gly Ser Leu Ser Ser Asn Pro Ser Ser Leu Thr Thr Ser Lys
                355                 360                 365

Glu Leu Ser Ser Ala Ser Asp Gly Tyr Ile Phe Asn Pro Lys Asp Ile
                370                 375                 380

Val Glu Glu Thr Ala Thr Ala Tyr Ile Val Arg His Gly Asp His Phe
385                 390                 395                 400

His Tyr Ile Pro Lys Ser Asn Gln Ile Gly Gln Pro Thr Leu Pro Asn
                405                 410                 415

Asn Ser Leu Ala Thr Pro Ser Pro Ser Leu Pro Ile Asn Pro Gly Thr
                420                 425                 430

Ser His Glu Lys His Glu Asp Gly Tyr Gly Phe Asp Ala Asn Arg
                435                 440                 445

Ile Ile Ala Glu Asp Glu Ser Gly Phe Val Met Ser His Gly Asp His
450                 455                 460

Asn His Tyr Phe Phe Lys Lys Asp Leu Thr Glu Glu Gln Ile Lys Ala
465                 470                 475                 480

Ala Gln Lys His Leu Glu Val Lys Thr Ser His Asn Gly Leu Asp
                485                 490                 495

Ser Leu Ser Ser His Gln Asp Tyr Pro Gly Asn Ala
                500                 505
```

<210> SEQ ID NO 58
<211> LENGTH: 1057
<212> TYPE: PRT
<213> ORGANISM: S. pneumoniae

<400> SEQUENCE: 58

```
Asp Leu Thr Glu Glu Gln Ile Lys Ala Ala Gln Lys His Leu Glu Glu
1               5                   10                  15

Val Lys Thr Ser His Asn Gly Leu Asp Ser Leu Ser Ser His Glu Gln
                20                  25                  30

Asp Tyr Pro Gly Asn Ala Lys Glu Met Lys Asp Leu Asp Lys Lys Ile
                35                  40                  45

Glu Glu Lys Ile Ala Gly Ile Met Lys Gln Tyr Gly Val Lys Arg Glu
                50                  55                  60

Ser Ile Val Val Asn Lys Glu Lys Asn Ala Ile Ile Tyr Pro His Gly
65                  70                  75                  80

Asp His His His Ala Asp Pro Ile Asp Glu His Lys Pro Val Gly Ile
                85                  90                  95

Gly His Ser His Ser Asn Tyr Glu Leu Phe Lys Pro Glu Glu Gly Val
                100                 105                 110

Ala Lys Lys Glu Gly Asn Lys Val Tyr Thr Gly Glu Glu Leu Thr Asn
                115                 120                 125

Val Val Asn Leu Leu Lys Asn Ser Thr Phe Asn Asn Gln Asn Phe Thr
                130                 135                 140

Leu Ala Asn Gly Gln Lys Arg Val Ser Phe Ser Phe Pro Pro Glu Leu
145                 150                 155                 160

Glu Lys Lys Leu Gly Ile Asn Met Leu Val Lys Leu Ile Thr Pro Asp
                165                 170                 175
```

```
Gly Lys Val Leu Glu Lys Val Ser Gly Lys Val Phe Gly Glu Gly Val
            180                 185                 190

Gly Asn Ile Ala Asn Phe Glu Leu Asp Gln Pro Tyr Leu Pro Gly Gln
            195                 200                 205

Thr Phe Lys Tyr Thr Ile Ala Ser Lys Asp Tyr Pro Glu Val Ser Tyr
    210                 215                 220

Asp Gly Thr Phe Thr Val Pro Thr Ser Leu Ala Tyr Lys Met Ala Ser
225                 230                 235                 240

Gln Thr Ile Phe Tyr Pro Phe His Ala Gly Asp Thr Tyr Leu Arg Val
                245                 250                 255

Asn Pro Gln Phe Ala Val Pro Lys Gly Thr Asp Ala Leu Val Arg Val
            260                 265                 270

Phe Asp Glu Phe His Gly Asn Ala Tyr Leu Glu Asn Tyr Lys Val
            275                 280                 285

Gly Glu Ile Lys Leu Pro Ile Pro Lys Leu Asn Gln Gly Thr Thr Arg
    290                 295                 300

Thr Ala Gly Asn Lys Ile Pro Val Thr Phe Met Ala Asn Ala Tyr Leu
305                 310                 315                 320

Asp Asn Gln Ser Thr Tyr Ile Val Glu Val Pro Ile Leu Glu Lys Glu
                325                 330                 335

Asn Gln Thr Asp Lys Pro Ser Ile Leu Pro Gln Phe Lys Arg Asn Lys
            340                 345                 350

Ala Gln Glu Asn Ser Lys Leu Asp Glu Lys Val Glu Glu Pro Lys Thr
            355                 360                 365

Ser Glu Lys Val Glu Lys Glu Lys Leu Ser Glu Thr Gly Asn Ser Thr
    370                 375                 380

Ser Asn Ser Thr Leu Glu Glu Val Pro Thr Val Asp Pro Val Gln Glu
385                 390                 395                 400

Lys Val Ala Lys Phe Ala Glu Ser Tyr Gly Met Lys Leu Glu Asn Val
                405                 410                 415

Leu Phe Asn Met Asp Gly Thr Ile Glu Leu Tyr Leu Pro Ser Gly Glu
            420                 425                 430

Val Ile Lys Lys Asn Met Ala Asp Phe Thr Gly Glu Ala Pro Gln Gly
            435                 440                 445

Asn Gly Glu Asn Lys Pro Ser Glu Asn Gly Lys Val Ser Thr Gly Thr
    450                 455                 460

Val Glu Asn Gln Pro Thr Glu Asn Lys Pro Ala Asp Ser Leu Pro Glu
465                 470                 475                 480

Ala Pro Asn Glu Lys Pro Val Lys Pro Glu Asn Ser Thr Asp Asn Gly
                485                 490                 495

Met Leu Asn Pro Glu Gly Asn Val Gly Ser Asp Pro Met Leu Asp Pro
            500                 505                 510

Ala Leu Glu Glu Ala Pro Ala Val Asp Pro Val Gln Glu Lys Leu Glu
            515                 520                 525

Lys Phe Thr Ala Ser Tyr Gly Leu Gly Leu Asp Ser Val Ile Phe Asn
    530                 535                 540

Met Asp Gly Thr Ile Glu Leu Arg Leu Pro Ser Gly Glu Val Ile Lys
545                 550                 555                 560

Lys Asn Leu Ser Asp Phe Ile Ala Lys Leu Arg Tyr Arg Ser Asn His
                565                 570                 575

Trp Val Pro Asp Ser Arg Pro Glu Glu Pro Ser Pro Gln Pro Thr Pro
            580                 585                 590

Glu Pro Ser Pro Ser Pro Gln Pro Ala Pro Asn Pro Gln Pro Ala Pro
```

-continued

```
                595                 600                 605
Ser Asn Pro Ile Asp Glu Lys Leu Val Lys Glu Ala Val Arg Lys Val
610                 615                 620
Gly Asp Gly Tyr Val Phe Glu Glu Asn Gly Val Ser Arg Tyr Ile Pro
625                 630                 635                 640
Ala Lys Asn Leu Ser Ala Glu Thr Ala Ala Gly Ile Asp Ser Lys Leu
                645                 650                 655
Ala Lys Gln Glu Ser Leu Ser His Lys Leu Gly Ala Lys Lys Thr Asp
                660                 665                 670
Leu Pro Ser Ser Asp Arg Glu Phe Tyr Asn Lys Ala Tyr Asp Leu Leu
                675                 680                 685
Ala Arg Ile His Gln Asp Leu Leu Asp Asn Lys Gly Arg Gln Val Asp
690                 695                 700
Phe Glu Ala Leu Asp Asn Leu Leu Glu Arg Leu Lys Asp Val Ser Ser
705                 710                 715                 720
Asp Lys Val Lys Leu Val Asp Asp Ile Leu Ala Phe Leu Ala Pro Ile
                725                 730                 735
Arg His Pro Glu Arg Leu Gly Lys Pro Asn Ala Gln Ile Thr Tyr Thr
                740                 745                 750
Asp Asp Glu Ile Gln Val Ala Lys Leu Ala Gly Lys Tyr Thr Thr Glu
                755                 760                 765
Asp Gly Tyr Ile Phe Asp Pro Arg Asp Ile Thr Ser Asp Glu Gly Asp
                770                 775                 780
Ala Tyr Val Thr Pro His Met Thr His Ser His Trp Ile Lys Lys Asp
785                 790                 795                 800
Ser Leu Ser Glu Ala Glu Arg Ala Ala Ala Gln Ala Tyr Ala Lys Glu
                805                 810                 815
Lys Gly Leu Thr Pro Pro Ser Thr Asp His Gln Asp Ser Gly Asn Thr
                820                 825                 830
Glu Ala Lys Gly Ala Glu Ala Ile Tyr Asn Arg Val Lys Ala Ala Lys
                835                 840                 845
Lys Val Pro Leu Asp Arg Met Pro Tyr Asn Leu Gln Tyr Thr Val Glu
850                 855                 860
Val Lys Asn Gly Ser Leu Ile Ile Pro His Tyr Asp His Tyr His Asn
865                 870                 875                 880
Ile Lys Phe Glu Trp Phe Asp Glu Gly Leu Tyr Glu Ala Pro Lys Gly
                885                 890                 895
Tyr Thr Leu Glu Asp Leu Leu Ala Thr Val Lys Tyr Tyr Val Glu His
                900                 905                 910
Pro Asn Glu Arg Pro His Ser Asp Asn Gly Phe Gly Asn Ala Ser Asp
                915                 920                 925
His Val Gln Arg Asn Lys Asn Gly Gln Ala Asp Thr Asn Gln Thr Glu
                930                 935                 940
Lys Pro Ser Glu Glu Lys Pro Gln Thr Glu Lys Pro Glu Glu Glu Thr
945                 950                 955                 960
Pro Arg Glu Glu Lys Pro Gln Ser Glu Lys Pro Glu Ser Pro Lys Pro
                965                 970                 975
Thr Glu Glu Pro Glu Glu Ser Pro Glu Glu Ser Glu Glu Pro Gln
                980                 985                 990
Val Glu Thr Glu Lys Val Glu Glu Lys Leu Arg Glu Ala Glu Asp Leu
                995                 1000                1005
Leu Gly Lys Ile Gln Asp Pro Ile Ile Lys Ser Asn Ala Lys Glu Thr
                1010                1015                1020
```

-continued

```
Leu Thr Gly Leu Lys Asn Asn Leu Leu Phe Gly Thr Gln Asp Asn Asn
1025                1030                1035                1040

Thr Ile Met Ala Glu Ala Glu Lys Leu Leu Ala Leu Leu Lys Glu Ser
                1045                1050                1055

Lys

<210> SEQ ID NO 59
<211> LENGTH: 205
<212> TYPE: PRT
<213> ORGANISM: S. pneumoniae

<400> SEQUENCE: 59

Cys Ala Tyr Ala Leu Asn Gln His Arg Ser Gln Glu Asn Lys Asp Asn
 1                5                  10                  15

Asn Arg Val Ser Tyr Val Asp Gly Ser Gln Ser Ser Gln Lys Ser Glu
                20                  25                  30

Asn Leu Thr Pro Asp Gln Val Ser Gln Lys Gly Ile Gln Ala Glu
            35                  40                  45

Gln Ile Val Ile Lys Ile Thr Asp Gln Gly Tyr Val Thr Ser His Gly
    50                  55                  60

Asp His Tyr His Tyr Tyr Asn Gly Lys Val Pro Tyr Asp Ala Leu Phe
65                  70                  75                  80

Ser Glu Glu Leu Leu Met Lys Asp Pro Asn Tyr Gln Leu Lys Asp Ala
                85                  90                  95

Asp Ile Val Asn Glu Val Lys Gly Tyr Ile Ile Lys Val Asp Gly
            100                 105                 110

Lys Tyr Tyr Val Tyr Leu Lys Asp Ala Ala His Ala Asp Asn Val Arg
        115                 120                 125

Thr Lys Asp Glu Ile Asn Arg Gln Lys Gln Glu His Val Lys Asp Asn
    130                 135                 140

Glu Lys Val Asn Ser Asn Val Ala Val Ala Arg Ser Gln Gly Arg Tyr
145                 150                 155                 160

Thr Thr Asn Asp Gly Tyr Val Phe Asn Pro Ala Asp Ile Ile Glu Asp
                165                 170                 175

Thr Gly Asn Ala Tyr Ile Val Pro His Gly His Tyr His Tyr Ile
            180                 185                 190

Pro Lys Ser Asp Leu Ser Ala Ser Glu Leu Ala Ala Ala
        195                 200                 205

<210> SEQ ID NO 60
<211> LENGTH: 821
<212> TYPE: PRT
<213> ORGANISM: S. pneumoniae

<400> SEQUENCE: 60

Cys Ala Tyr Glu Leu Gly Leu His Gln Ala Gln Thr Val Lys Glu Asn
 1                5                  10                  15

Asn Arg Val Ser Tyr Ile Asp Gly Lys Gln Ala Thr Gln Lys Thr Glu
                20                  25                  30

Asn Leu Thr Pro Asp Glu Val Ser Lys Arg Glu Gly Ile Asn Ala Glu
            35                  40                  45

Gln Ile Val Ile Lys Ile Thr Asp Gln Gly Tyr Val Thr Ser His Gly
    50                  55                  60

Asp His Tyr His Tyr Tyr Asn Gly Lys Val Pro Tyr Asp Ala Ile Ile
65                  70                  75                  80
```

-continued

```
Ser Glu Glu Leu Leu Met Lys Asp Pro Asn Tyr Gln Leu Lys Asp Ser
            85                  90                  95

Asp Ile Val Asn Glu Ile Lys Gly Gly Tyr Val Ile Lys Val Asn Gly
            100                 105                 110

Lys Tyr Tyr Val Tyr Leu Lys Asp Ala Ala His Ala Asp Asn Val Arg
            115                 120                 125

Thr Lys Glu Glu Ile Asn Arg Gln Lys Gln Glu His Ser Gln His Arg
            130                 135                 140

Glu Gly Gly Thr Ser Ala Asn Asp Gly Ala Val Ala Phe Ala Arg Ser
145                 150                 155                 160

Gln Gly Arg Tyr Thr Thr Asp Asp Gly Tyr Ile Phe Asn Ala Ser Asp
            165                 170                 175

Ile Ile Glu Asp Thr Gly Asp Ala Tyr Ile Val Pro His Gly Asp His
            180                 185                 190

Tyr His Tyr Ile Pro Lys Asn Glu Leu Ser Ala Ser Glu Leu Ala Ala
            195                 200                 205

Ala Glu Ala Phe Leu Ser Gly Arg Glu Asn Leu Ser Asn Leu Arg Thr
            210                 215                 220

Tyr Arg Arg Gln Asn Ser Asp Asn Thr Pro Arg Thr Asn Trp Val Pro
225                 230                 235                 240

Ser Val Ser Asn Pro Gly Thr Thr Asn Thr Asn Thr Ser Asn Asn Ser
            245                 250                 255

Asn Thr Asn Ser Gln Ala Ser Gln Ser Asn Asp Ile Asp Ser Leu Leu
            260                 265                 270

Lys Gln Leu Tyr Lys Leu Pro Leu Ser Gln Arg His Val Glu Ser Asp
            275                 280                 285

Gly Leu Ile Phe Asp Pro Ala Gln Ile Thr Ser Arg Thr Ala Arg Gly
            290                 295                 300

Val Ala Val Pro His Gly Asn His Tyr His Phe Ile Pro Tyr Glu Gln
305                 310                 315                 320

Met Ser Glu Leu Glu Lys Arg Ile Ala Arg Ile Ile Pro Leu Arg Tyr
            325                 330                 335

Arg Ser Asn His Trp Val Pro Asp Ser Arg Pro Glu Pro Ser Pro
            340                 345                 350

Gln Pro Thr Pro Glu Pro Ser Pro Ser Pro Gln Pro Ala Pro Asn Pro
            355                 360                 365

Gln Pro Ala Pro Ser Asn Pro Ile Asp Glu Lys Leu Val Lys Glu Ala
            370                 375                 380

Val Arg Lys Val Gly Asp Gly Tyr Val Phe Glu Asn Gly Val Ser
385                 390                 395                 400

Arg Tyr Ile Pro Ala Lys Asn Leu Ser Ala Glu Thr Ala Ala Gly Ile
            405                 410                 415

Asp Ser Lys Leu Ala Lys Gln Glu Ser Leu Ser His Lys Leu Gly Ala
            420                 425                 430

Lys Lys Thr Asp Leu Pro Ser Ser Asp Arg Glu Phe Tyr Asn Lys Ala
            435                 440                 445

Tyr Asp Leu Leu Ala Arg Ile His Gln Asp Leu Leu Asp Asn Lys Gly
            450                 455                 460

Arg Gln Val Asp Phe Glu Ala Leu Asp Asn Leu Leu Glu Arg Leu Lys
465                 470                 475                 480

Asp Val Ser Ser Asp Lys Val Lys Leu Val Asp Asp Ile Leu Ala Phe
            485                 490                 495

Leu Ala Pro Ile Arg His Pro Glu Arg Leu Gly Lys Pro Asn Ala Gln
```

```
                    500                 505                 510
Ile Thr Tyr Thr Asp Asp Glu Ile Gln Val Ala Lys Leu Ala Gly Lys
        515                 520                 525

Tyr Thr Thr Glu Asp Gly Tyr Ile Phe Asp Pro Arg Asp Ile Thr Ser
        530                 535                 540

Asp Glu Gly Asp Ala Tyr Val Thr Pro His Met Thr His Ser His Trp
545                 550                 555                 560

Ile Lys Lys Asp Ser Leu Ser Glu Ala Glu Arg Ala Ala Ala Gln Ala
                565                 570                 575

Tyr Ala Lys Glu Lys Gly Leu Thr Pro Pro Ser Thr Asp His Gln Asp
                580                 585                 590

Ser Gly Asn Thr Glu Ala Lys Gly Ala Glu Ala Ile Tyr Asn Arg Val
                595                 600                 605

Lys Ala Ala Lys Lys Val Pro Leu Asp Arg Met Pro Tyr Asn Leu Gln
        610                 615                 620

Tyr Thr Val Glu Val Lys Asn Gly Ser Leu Ile Ile Pro His Tyr Asp
625                 630                 635                 640

His Tyr His Asn Ile Lys Phe Glu Trp Phe Asp Glu Gly Leu Tyr Glu
                645                 650                 655

Ala Pro Lys Gly Tyr Thr Leu Glu Asp Leu Leu Ala Thr Val Lys Tyr
                660                 665                 670

Tyr Val Glu His Pro Asn Glu Arg Pro His Ser Asp Asn Gly Phe Gly
                675                 680                 685

Asn Ala Ser Asp His Val Gln Arg Asn Lys Asn Gly Gln Ala Asp Thr
        690                 695                 700

Asn Gln Thr Glu Lys Pro Ser Glu Glu Lys Pro Gln Thr Glu Lys Pro
705                 710                 715                 720

Glu Glu Glu Thr Pro Arg Glu Glu Lys Pro Gln Ser Glu Lys Pro Glu
                725                 730                 735

Ser Pro Lys Pro Thr Glu Glu Pro Glu Glu Ser Pro Glu Glu Ser
                740                 745                 750

Glu Glu Pro Gln Val Glu Thr Glu Lys Val Glu Glu Lys Leu Arg Glu
        755                 760                 765

Ala Glu Asp Leu Leu Gly Lys Ile Gln Asp Pro Ile Ile Lys Ser Asn
770                 775                 780

Ala Lys Glu Thr Leu Thr Gly Leu Lys Asn Asn Leu Leu Phe Gly Thr
785                 790                 795                 800

Gln Asp Asn Asn Thr Ile Met Ala Glu Ala Lys Leu Leu Ala Leu
                805                 810                 815

Leu Lys Glu Ser Lys
                820

<210> SEQ ID NO 61
<211> LENGTH: 334
<212> TYPE: PRT
<213> ORGANISM: S. pneumoniae

<400> SEQUENCE: 61

Cys Ala Tyr Glu Leu Gly Leu His Gln Ala Gln Thr Val Lys Glu Asn
1               5                   10                  15

Asn Arg Val Ser Tyr Ile Asp Gly Lys Gln Ala Thr Gln Lys Thr Glu
                20                  25                  30

Asn Leu Thr Pro Asp Glu Val Ser Lys Arg Glu Gly Ile Asn Ala Glu
        35                  40                  45
```

-continued

```
Gln Ile Val Ile Lys Ile Thr Asp Gln Gly Tyr Val Thr Ser His Gly
     50                  55                  60

Asp His Tyr His Tyr Tyr Asn Gly Lys Val Pro Tyr Asp Ala Ile Ile
 65                  70                  75                  80

Ser Glu Glu Leu Leu Met Lys Asp Pro Asn Tyr Gln Leu Lys Asp Ser
                 85                  90                  95

Asp Ile Val Asn Glu Ile Lys Gly Gly Tyr Val Ile Lys Val Asn Gly
             100                 105                 110

Lys Tyr Tyr Val Tyr Leu Lys Asp Ala Ala His Ala Asp Asn Val Arg
         115                 120                 125

Thr Lys Glu Glu Ile Asn Arg Gln Lys Gln Glu His Ser Gln His Arg
 130                 135                 140

Glu Gly Gly Thr Ser Ala Asn Asp Gly Ala Val Ala Phe Ala Arg Ser
145                 150                 155                 160

Gln Gly Arg Tyr Thr Thr Asp Asp Gly Tyr Ile Phe Asn Ala Ser Asp
                165                 170                 175

Ile Ile Glu Asp Thr Gly Asp Ala Tyr Ile Val Pro His Gly Asp His
             180                 185                 190

Tyr His Tyr Ile Pro Lys Asn Glu Leu Ser Ala Ser Glu Leu Ala Ala
         195                 200                 205

Ala Glu Ala Phe Leu Ser Gly Arg Glu Asn Leu Ser Asn Leu Arg Thr
 210                 215                 220

Tyr Arg Arg Gln Asn Ser Asp Asn Thr Pro Arg Thr Asn Trp Val Pro
225                 230                 235                 240

Ser Val Ser Asn Pro Gly Thr Thr Asn Thr Asn Thr Ser Asn Asn Ser
                245                 250                 255

Asn Thr Asn Ser Gln Ala Ser Gln Ser Asn Asp Ile Asp Ser Leu Leu
             260                 265                 270

Lys Gln Leu Tyr Lys Leu Pro Leu Ser Gln Arg His Val Glu Ser Asp
         275                 280                 285

Gly Leu Ile Phe Asp Pro Ala Gln Ile Thr Ser Arg Thr Ala Arg Gly
 290                 295                 300

Val Ala Val Pro His Gly Asn His Tyr His Phe Ile Pro Tyr Glu Gln
305                 310                 315                 320

Met Ser Glu Leu Glu Lys Arg Ile Ala Arg Ile Ile Pro Leu
                325                 330
```

<210> SEQ ID NO 62
<211> LENGTH: 487
<212> TYPE: PRT
<213> ORGANISM: S. pneumoniae

<400> SEQUENCE: 62

```
Arg Tyr Arg Ser Asn His Trp Val Pro Asp Ser Arg Pro Glu Glu Pro
  1               5                  10                  15

Ser Pro Gln Pro Thr Pro Glu Pro Ser Pro Ser Pro Gln Pro Ala Pro
                 20                  25                  30

Asn Pro Gln Pro Ala Pro Ser Asn Pro Ile Asp Glu Lys Leu Val Lys
             35                  40                  45

Glu Ala Val Arg Lys Val Gly Asp Gly Tyr Val Phe Glu Glu Asn Gly
         50                  55                  60

Val Ser Arg Tyr Ile Pro Ala Lys Asn Leu Ser Ala Glu Thr Ala Ala
 65                  70                  75                  80

Gly Ile Asp Ser Lys Leu Ala Lys Gln Glu Ser Leu Ser His Lys Leu
                 85                  90                  95
```

Gly Ala Lys Lys Thr Asp Leu Pro Ser Ser Asp Arg Glu Phe Tyr Asn
            100                 105                 110

Lys Ala Tyr Asp Leu Leu Ala Arg Ile His Gln Asp Leu Leu Asp Asn
            115                 120                 125

Lys Gly Arg Gln Val Asp Phe Glu Ala Leu Asp Asn Leu Leu Glu Arg
            130                 135                 140

Leu Lys Asp Val Ser Ser Asp Lys Val Lys Leu Val Asp Asp Ile Leu
145                 150                 155                 160

Ala Phe Leu Ala Pro Ile Arg His Pro Glu Arg Leu Gly Lys Pro Asn
                165                 170                 175

Ala Gln Ile Thr Tyr Thr Asp Asp Glu Ile Gln Val Ala Lys Leu Ala
            180                 185                 190

Gly Lys Tyr Thr Thr Glu Asp Gly Tyr Ile Phe Asp Pro Arg Asp Ile
            195                 200                 205

Thr Ser Asp Glu Gly Asp Ala Tyr Val Thr Pro His Met Thr His Ser
210                 215                 220

His Trp Ile Lys Lys Asp Ser Leu Ser Glu Ala Glu Arg Ala Ala Ala
225                 230                 235                 240

Gln Ala Tyr Ala Lys Glu Lys Gly Leu Thr Pro Pro Ser Thr Asp His
                245                 250                 255

Gln Asp Ser Gly Asn Thr Glu Ala Lys Gly Ala Glu Ala Ile Tyr Asn
            260                 265                 270

Arg Val Lys Ala Ala Lys Lys Val Pro Leu Asp Arg Met Pro Tyr Asn
            275                 280                 285

Leu Gln Tyr Thr Val Glu Val Lys Asn Gly Ser Leu Ile Ile Pro His
            290                 295                 300

Tyr Asp His Tyr His Asn Ile Lys Phe Glu Trp Phe Asp Glu Gly Leu
305                 310                 315                 320

Tyr Glu Ala Pro Lys Gly Tyr Thr Leu Glu Asp Leu Leu Ala Thr Val
                325                 330                 335

Lys Tyr Tyr Val Glu His Pro Asn Glu Arg Pro His Ser Asp Asn Gly
            340                 345                 350

Phe Gly Asn Ala Ser Asp His Val Gln Arg Asn Lys Asn Gly Gln Ala
            355                 360                 365

Asp Thr Asn Gln Thr Glu Lys Pro Ser Glu Lys Pro Gln Thr Glu
            370                 375                 380

Lys Pro Glu Glu Glu Thr Pro Arg Glu Glu Lys Pro Gln Ser Glu Lys
385                 390                 395                 400

Pro Glu Ser Pro Lys Pro Thr Glu Glu Pro Glu Glu Ser Pro Glu
                405                 410                 415

Glu Ser Glu Glu Pro Gln Val Glu Thr Glu Lys Val Glu Glu Lys Leu
            420                 425                 430

Arg Glu Ala Glu Asp Leu Leu Gly Lys Ile Gln Asp Pro Ile Ile Lys
            435                 440                 445

Ser Asn Ala Lys Glu Thr Leu Thr Gly Leu Lys Asn Asn Leu Leu Phe
450                 455                 460

Gly Thr Gln Asp Asn Asn Thr Ile Met Ala Glu Ala Glu Lys Leu Leu
465                 470                 475                 480

Ala Leu Leu Lys Glu Ser Lys
                485

<210> SEQ ID NO 63
<211> LENGTH: 613

```
<212> TYPE: PRT
<213> ORGANISM: S. pneumoniae

<400> SEQUENCE: 63

Ala Glu Ala Phe Leu Ser Gly Arg Glu Asn Leu Ser Asn Leu Arg Thr
 1               5                  10                  15

Tyr Arg Arg Gln Asn Ser Asp Asn Thr Pro Arg Thr Asn Trp Val Pro
                20                  25                  30

Ser Val Ser Asn Pro Gly Thr Thr Asn Thr Asn Thr Ser Asn Asn Ser
            35                  40                  45

Asn Thr Asn Ser Gln Ala Ser Gln Ser Asn Asp Ile Asp Ser Leu Leu
 50                  55                  60

Lys Gln Leu Tyr Lys Leu Pro Leu Ser Gln Arg His Val Glu Ser Asp
65                  70                  75                  80

Gly Leu Ile Phe Asp Pro Ala Gln Ile Thr Ser Arg Thr Ala Arg Gly
                85                  90                  95

Val Ala Val Pro His Gly Asn His Tyr His Phe Ile Pro Tyr Glu Gln
                100                 105                 110

Met Ser Glu Leu Glu Lys Arg Ile Ala Arg Ile Ile Pro Leu Arg Tyr
            115                 120                 125

Arg Ser Asn His Trp Val Pro Asp Ser Arg Pro Glu Glu Pro Ser Pro
130                 135                 140

Gln Pro Thr Pro Glu Pro Ser Pro Ser Pro Gln Pro Ala Pro Asn Pro
145                 150                 155                 160

Gln Pro Ala Pro Ser Asn Pro Ile Asp Glu Lys Leu Val Lys Glu Ala
                165                 170                 175

Val Arg Lys Val Gly Asp Gly Tyr Val Phe Glu Glu Asn Gly Val Ser
            180                 185                 190

Arg Tyr Ile Pro Ala Lys Asn Leu Ser Ala Glu Thr Ala Ala Gly Ile
                195                 200                 205

Asp Ser Lys Leu Ala Lys Gln Glu Ser Leu Ser His Lys Leu Gly Ala
            210                 215                 220

Lys Lys Thr Asp Leu Pro Ser Ser Asp Arg Glu Phe Tyr Asn Lys Ala
225                 230                 235                 240

Tyr Asp Leu Leu Ala Arg Ile His Gln Asp Leu Leu Asp Asn Lys Gly
                245                 250                 255

Arg Gln Val Asp Phe Glu Ala Leu Asp Asn Leu Leu Glu Arg Leu Lys
            260                 265                 270

Asp Val Ser Ser Asp Lys Val Lys Leu Val Asp Ile Leu Ala Phe
            275                 280                 285

Leu Ala Pro Ile Arg His Pro Glu Arg Leu Gly Lys Pro Asn Ala Gln
290                 295                 300

Ile Thr Tyr Thr Asp Glu Ile Gln Val Ala Lys Leu Ala Gly Lys
305                 310                 315                 320

Tyr Thr Thr Glu Asp Gly Tyr Ile Phe Asp Pro Arg Asp Ile Thr Ser
                325                 330                 335

Asp Glu Gly Asp Ala Tyr Val Thr Pro His Met Thr His Ser His Trp
            340                 345                 350

Ile Lys Lys Asp Ser Leu Ser Glu Ala Glu Arg Ala Ala Ala Gln Ala
            355                 360                 365

Tyr Ala Lys Glu Lys Gly Leu Thr Pro Pro Ser Thr Asp His Gln Asp
            370                 375                 380

Ser Gly Asn Thr Glu Ala Lys Gly Ala Glu Ala Ile Tyr Asn Arg Val
385                 390                 395                 400
```

```
Lys Ala Ala Lys Lys Val Pro Leu Asp Arg Met Pro Tyr Asn Leu Gln
            405                 410                 415

Tyr Thr Val Glu Val Lys Asn Gly Ser Leu Ile Ile Pro His Tyr Asp
        420                 425                 430

His Tyr His Asn Ile Lys Phe Glu Trp Phe Asp Glu Gly Leu Tyr Glu
        435                 440                 445

Ala Pro Lys Gly Tyr Thr Leu Glu Asp Leu Leu Ala Thr Val Lys Tyr
    450                 455                 460

Tyr Val Glu His Pro Asn Glu Arg Pro His Ser Asp Asn Gly Phe Gly
465                 470                 475                 480

Asn Ala Ser Asp His Val Gln Arg Asn Lys Asn Gly Gln Ala Asp Thr
                485                 490                 495

Asn Gln Thr Glu Lys Pro Ser Glu Glu Lys Pro Gln Thr Glu Lys Pro
            500                 505                 510

Glu Glu Glu Thr Pro Arg Glu Glu Lys Pro Gln Ser Glu Lys Pro Glu
        515                 520                 525

Ser Pro Lys Pro Thr Glu Glu Pro Glu Glu Glu Ser Pro Glu Glu Ser
    530                 535                 540

Glu Glu Pro Gln Val Glu Thr Glu Lys Val Glu Glu Lys Leu Arg Glu
545                 550                 555                 560

Ala Glu Asp Leu Leu Gly Lys Ile Gln Asp Pro Ile Ile Lys Ser Asn
                565                 570                 575

Ala Lys Glu Thr Leu Thr Gly Leu Lys Asn Asn Leu Leu Phe Gly Thr
            580                 585                 590

Gln Asp Asn Asn Thr Ile Met Ala Glu Ala Glu Lys Leu Leu Ala Leu
        595                 600                 605

Leu Lys Glu Ser Lys
        610

<210> SEQ ID NO 64
<211> LENGTH: 568
<212> TYPE: PRT
<213> ORGANISM: S. pneumoniae

<400> SEQUENCE: 64

Asp Leu Thr Glu Glu Gln Ile Lys Ala Ala Gln Lys His Leu Glu Glu
1               5                   10                  15

Val Lys Thr Ser His Asn Gly Leu Asp Ser Leu Ser Ser His Glu Gln
            20                  25                  30

Asp Tyr Pro Gly Asn Ala Lys Glu Met Lys Asp Leu Asp Lys Lys Ile
        35                  40                  45

Glu Glu Lys Ile Ala Gly Ile Met Lys Gln Tyr Gly Val Lys Arg Glu
    50                  55                  60

Ser Ile Val Val Asn Lys Glu Lys Asn Ala Ile Ile Tyr Pro His Gly
65                  70                  75                  80

Asp His His Ala Asp Pro Ile Asp Glu His Lys Pro Val Gly Ile
                85                  90                  95

Gly His Ser His Ser Asn Tyr Glu Leu Phe Lys Pro Glu Glu Gly Val
            100                 105                 110

Ala Lys Lys Glu Gly Asn Lys Val Tyr Thr Gly Glu Glu Leu Thr Asn
        115                 120                 125

Val Val Asn Leu Leu Lys Asn Ser Thr Phe Asn Asn Gln Asn Phe Thr
    130                 135                 140

Leu Ala Asn Gly Gln Lys Arg Val Ser Phe Ser Phe Pro Pro Glu Leu
```

```
            145                 150                 155                 160
    Glu Lys Lys Leu Gly Ile Asn Met Leu Val Lys Leu Ile Thr Pro Asp
                    165                 170                 175
    Gly Lys Val Leu Glu Lys Val Ser Gly Lys Val Phe Gly Glu Gly Val
                    180                 185                 190
    Gly Asn Ile Ala Asn Phe Glu Leu Asp Gln Pro Tyr Leu Pro Gly Gln
                    195                 200                 205
    Thr Phe Lys Tyr Thr Ile Ala Ser Lys Asp Tyr Pro Glu Val Ser Tyr
                210                 215                 220
    Asp Gly Thr Phe Thr Val Pro Thr Ser Leu Ala Tyr Lys Met Ala Ser
    225                 230                 235                 240
    Gln Thr Ile Phe Tyr Pro Phe His Ala Gly Asp Thr Tyr Leu Arg Val
                    245                 250                 255
    Asn Pro Gln Phe Ala Val Pro Lys Gly Thr Asp Ala Leu Val Arg Val
                    260                 265                 270
    Phe Asp Glu Phe His Gly Asn Ala Tyr Leu Glu Asn Tyr Lys Val
                    275                 280                 285
    Gly Glu Ile Lys Leu Pro Ile Pro Lys Leu Asn Gln Gly Thr Thr Arg
                290                 295                 300
    Thr Ala Gly Asn Lys Ile Pro Val Thr Phe Met Ala Asn Ala Tyr Leu
    305                 310                 315                 320
    Asp Asn Gln Ser Thr Tyr Ile Val Glu Val Pro Ile Leu Glu Lys Glu
                    325                 330                 335
    Asn Gln Thr Asp Lys Pro Ser Ile Leu Pro Gln Phe Lys Arg Asn Lys
                    340                 345                 350
    Ala Gln Glu Asn Ser Lys Leu Asp Glu Lys Val Glu Glu Pro Lys Thr
                    355                 360                 365
    Ser Glu Lys Val Glu Lys Glu Lys Leu Ser Glu Thr Gly Asn Ser Thr
                370                 375                 380
    Ser Asn Ser Thr Leu Glu Glu Val Pro Thr Val Asp Pro Val Gln Glu
    385                 390                 395                 400
    Lys Val Ala Lys Phe Ala Glu Ser Tyr Gly Met Lys Leu Glu Asn Val
                    405                 410                 415
    Leu Phe Asn Met Asp Gly Thr Ile Glu Leu Tyr Leu Pro Ser Gly Glu
                    420                 425                 430
    Val Ile Lys Lys Asn Met Ala Asp Phe Thr Gly Glu Ala Pro Gln Gly
                435                 440                 445
    Asn Gly Glu Asn Lys Pro Ser Glu Asn Gly Lys Val Ser Thr Gly Thr
                450                 455                 460
    Val Glu Asn Gln Pro Thr Glu Asn Lys Pro Ala Asp Ser Leu Pro Glu
    465                 470                 475                 480
    Ala Pro Asn Glu Lys Pro Val Lys Pro Glu Asn Ser Thr Asp Asn Gly
                    485                 490                 495
    Met Leu Asn Pro Glu Gly Asn Val Gly Ser Asp Pro Met Leu Asp Pro
                    500                 505                 510
    Ala Leu Glu Glu Ala Pro Ala Val Asp Pro Val Gln Glu Lys Leu Glu
                    515                 520                 525
    Lys Phe Thr Ala Ser Tyr Gly Leu Gly Leu Asp Ser Val Ile Phe Asn
                530                 535                 540
    Met Asp Gly Thr Ile Glu Leu Arg Leu Pro Ser Gly Glu Val Ile Lys
    545                 550                 555                 560
    Lys Asn Leu Ser Asp Phe Ile Ala
                    565
```

-continued

<210> SEQ ID NO 65
<211> LENGTH: 329
<212> TYPE: PRT
<213> ORGANISM: S. pneumoniae

<400> SEQUENCE: 65

Asp Leu Thr Glu Glu Gln Ile Lys Ala Ala Gln Lys His Leu Glu Glu
1               5                   10                  15

Val Lys Thr Ser His Asn Gly Leu Asp Ser Leu Ser Ser His Glu Gln
            20                  25                  30

Asp Tyr Pro Gly Asn Ala Lys Glu Met Lys Asp Leu Asp Lys Lys Ile
        35                  40                  45

Glu Glu Lys Ile Ala Gly Ile Met Lys Gln Tyr Gly Val Lys Arg Glu
    50                  55                  60

Ser Ile Val Val Asn Lys Glu Lys Asn Ala Ile Ile Tyr Pro His Gly
65                  70                  75                  80

Asp His His Ala Asp Pro Ile Asp Glu His Lys Pro Val Gly Ile
                85                  90                  95

Gly His Ser His Ser Asn Tyr Glu Leu Phe Lys Pro Glu Glu Gly Val
            100                 105                 110

Ala Lys Lys Glu Gly Asn Lys Val Tyr Thr Gly Glu Glu Leu Thr Asn
        115                 120                 125

Val Val Asn Leu Leu Lys Asn Ser Thr Phe Asn Asn Gln Asn Phe Thr
130                 135                 140

Leu Ala Asn Gly Gln Lys Arg Val Ser Phe Ser Phe Pro Pro Glu Leu
145                 150                 155                 160

Glu Lys Lys Leu Gly Ile Asn Met Leu Val Lys Leu Ile Thr Pro Asp
                165                 170                 175

Gly Lys Val Leu Glu Lys Val Ser Gly Lys Val Phe Gly Glu Gly Val
            180                 185                 190

Gly Asn Ile Ala Asn Phe Glu Leu Asp Gln Pro Tyr Leu Pro Gly Gln
        195                 200                 205

Thr Phe Lys Tyr Thr Ile Ala Ser Lys Asp Tyr Pro Glu Val Ser Tyr
    210                 215                 220

Asp Gly Thr Phe Thr Val Pro Thr Ser Leu Ala Tyr Lys Met Ala Ser
225                 230                 235                 240

Gln Thr Ile Phe Tyr Pro Phe His Ala Gly Asp Thr Tyr Leu Arg Val
                245                 250                 255

Asn Pro Gln Phe Ala Val Pro Lys Gly Thr Asp Ala Leu Val Arg Val
            260                 265                 270

Phe Asp Glu Phe His Gly Asn Ala Tyr Leu Glu Asn Asn Tyr Lys Val
        275                 280                 285

Gly Glu Ile Lys Leu Pro Ile Pro Lys Leu Asn Gln Gly Thr Thr Arg
    290                 295                 300

Thr Ala Gly Asn Lys Ile Pro Val Thr Phe Met Ala Asn Ala Tyr Leu
305                 310                 315                 320

Asp Asn Gln Ser Thr Tyr Ile Val Glu
                325

<210> SEQ ID NO 66
<211> LENGTH: 240
<212> TYPE: PRT
<213> ORGANISM: S. pneumoniae

<400> SEQUENCE: 66

```
Glu Val Pro Ile Leu Glu Lys Glu Asn Gln Thr Asp Lys Pro Ser Ile
1               5                   10                  15

Leu Pro Gln Phe Lys Arg Asn Lys Ala Gln Glu Asn Ser Lys Leu Asp
            20                  25                  30

Glu Lys Val Glu Glu Pro Lys Thr Ser Glu Lys Val Glu Lys Glu Lys
                35                  40                  45

Leu Ser Glu Thr Gly Asn Ser Thr Ser Asn Ser Thr Leu Glu Glu Val
    50                  55                  60

Pro Thr Val Asp Pro Val Gln Glu Lys Val Ala Lys Phe Ala Glu Ser
65                  70                  75                  80

Tyr Gly Met Lys Leu Glu Asn Val Leu Phe Asn Met Asp Gly Thr Ile
                85                  90                  95

Glu Leu Tyr Leu Pro Ser Gly Glu Val Ile Lys Lys Asn Met Ala Asp
                100                 105                 110

Phe Thr Gly Glu Ala Pro Gln Gly Asn Gly Glu Asn Lys Pro Ser Glu
            115                 120                 125

Asn Gly Lys Val Ser Thr Gly Thr Val Glu Asn Gln Pro Thr Glu Asn
130                 135                 140

Lys Pro Ala Asp Ser Leu Pro Glu Ala Pro Asn Glu Lys Pro Val Lys
145                 150                 155                 160

Pro Glu Asn Ser Thr Asp Asn Gly Met Leu Asn Pro Glu Gly Asn Val
                165                 170                 175

Gly Ser Asp Pro Met Leu Asp Pro Ala Leu Glu Glu Ala Pro Ala Val
            180                 185                 190

Asp Pro Val Gln Glu Lys Leu Glu Lys Phe Thr Ala Ser Tyr Gly Leu
            195                 200                 205

Gly Leu Asp Ser Val Ile Phe Asn Met Asp Gly Thr Ile Glu Leu Arg
    210                 215                 220

Leu Pro Ser Gly Glu Val Ile Lys Lys Asn Leu Ser Asp Phe Ile Ala
225                 230                 235                 240

<210> SEQ ID NO 67
<211> LENGTH: 555
<212> TYPE: PRT
<213> ORGANISM: S. pneumoniae

<400> SEQUENCE: 67

Asp Ile Asp Ser Leu Leu Lys Gln Leu Tyr Lys Leu Pro Leu Ser Gln
1               5                   10                  15

Arg His Val Glu Ser Asp Gly Leu Ile Phe Asp Pro Ala Gln Ile Thr
            20                  25                  30

Ser Arg Thr Ala Arg Gly Val Ala Val Pro His Gly Asn His Tyr His
        35                  40                  45

Phe Ile Pro Tyr Glu Gln Met Ser Glu Leu Lys Arg Ile Ala Arg
50                  55                  60

Ile Ile Pro Leu Arg Tyr Arg Ser Asn His Trp Val Pro Asp Ser Arg
65              70                  75                  80

Pro Glu Glu Pro Ser Pro Gln Pro Thr Pro Glu Pro Ser Pro Ser Pro
                85                  90                  95

Gln Pro Ala Pro Asn Pro Gln Pro Ala Pro Ser Asn Pro Ile Asp Glu
            100                 105                 110

Lys Leu Val Lys Glu Ala Val Arg Lys Val Gly Asp Gly Tyr Val Phe
        115                 120                 125

Glu Glu Asn Gly Val Ser Arg Tyr Ile Pro Ala Lys Asn Leu Ser Ala
```

```
            130                 135                 140
Glu Thr Ala Ala Gly Ile Asp Ser Lys Leu Ala Lys Gln Glu Ser Leu
145                 150                 155                 160

Ser His Lys Leu Gly Ala Lys Lys Thr Asp Leu Pro Ser Ser Asp Arg
                165                 170                 175

Glu Phe Tyr Asn Lys Ala Tyr Asp Leu Leu Ala Arg Ile His Gln Asp
                180                 185                 190

Leu Leu Asp Asn Lys Gly Arg Gln Val Asp Phe Glu Ala Leu Asp Asn
                195                 200                 205

Leu Leu Glu Arg Leu Lys Asp Val Ser Ser Asp Lys Val Lys Leu Val
            210                 215                 220

Asp Asp Ile Leu Ala Phe Leu Ala Pro Ile Arg His Pro Glu Arg Leu
225                 230                 235                 240

Gly Lys Pro Asn Ala Gln Ile Thr Tyr Thr Asp Glu Ile Gln Val
                245                 250                 255

Ala Lys Leu Ala Gly Lys Tyr Thr Thr Glu Asp Gly Tyr Ile Phe Asp
                260                 265                 270

Pro Arg Asp Ile Thr Ser Asp Glu Gly Asp Ala Tyr Val Thr Pro His
            275                 280                 285

Met Thr His Ser His Trp Ile Lys Lys Asp Ser Leu Ser Glu Ala Glu
            290                 295                 300

Arg Ala Ala Ala Gln Ala Tyr Ala Lys Glu Lys Gly Leu Thr Pro Pro
305                 310                 315                 320

Ser Thr Asp His Gln Asp Ser Gly Asn Thr Glu Ala Lys Gly Ala Glu
                325                 330                 335

Ala Ile Tyr Asn Arg Val Lys Ala Ala Lys Lys Val Pro Leu Asp Arg
                340                 345                 350

Met Pro Tyr Asn Leu Gln Tyr Thr Val Glu Val Lys Asn Gly Ser Leu
                355                 360                 365

Ile Ile Pro His Tyr Asp His Tyr His Asn Ile Lys Phe Glu Trp Phe
            370                 375                 380

Asp Glu Gly Leu Tyr Glu Ala Pro Lys Gly Tyr Thr Leu Glu Asp Leu
385                 390                 395                 400

Leu Ala Thr Val Lys Tyr Tyr Val Glu His Pro Asn Glu Arg Pro His
                405                 410                 415

Ser Asp Asn Gly Phe Gly Asn Ala Ser Asp His Val Gln Arg Asn Lys
                420                 425                 430

Asn Gly Gln Ala Asp Thr Asn Gln Thr Glu Lys Pro Ser Glu Glu Lys
            435                 440                 445

Pro Gln Thr Glu Lys Pro Glu Glu Glu Thr Pro Arg Glu Glu Lys Pro
450                 455                 460

Gln Ser Glu Lys Pro Glu Ser Pro Lys Pro Thr Glu Glu Pro Glu Glu
465                 470                 475                 480

Glu Ser Pro Glu Glu Ser Glu Pro Gln Val Glu Thr Glu Lys Val
                485                 490                 495

Glu Glu Lys Leu Arg Glu Ala Glu Asp Leu Leu Gly Lys Ile Gln Asp
            500                 505                 510

Pro Ile Ile Lys Ser Asn Ala Lys Glu Thr Leu Thr Gly Leu Lys Asn
            515                 520                 525

Asn Leu Leu Phe Gly Thr Gln Asp Asn Asn Thr Ile Met Ala Glu Ala
            530                 535                 540

Glu Lys Leu Leu Ala Leu Leu Lys Glu Ser Lys
545                 550                 555
```

<210> SEQ ID NO 68
<211> LENGTH: 428
<212> TYPE: PRT
<213> ORGANISM: S. pneumoniae

<400> SEQUENCE: 68

| | | | | | | | | | | | | | | |
|---|---|---|---|---|---|---|---|---|---|---|---|---|---|---|
| Asp | Ile | Asp | Ser | Leu | Leu | Lys | Gln | Leu | Tyr | Lys | Leu | Pro | Leu | Ser | Gln |
| 1 | | | | 5 | | | | | 10 | | | | | 15 | |

| Arg | His | Val | Glu | Ser | Asp | Gly | Leu | Ile | Phe | Asp | Pro | Ala | Gln | Ile | Thr |
|---|---|---|---|---|---|---|---|---|---|---|---|---|---|---|---|
| | | | 20 | | | | | 25 | | | | | 30 | | |

| Ser | Arg | Thr | Ala | Arg | Gly | Val | Ala | Val | Pro | His | Gly | Asn | His | Tyr | His |
|---|---|---|---|---|---|---|---|---|---|---|---|---|---|---|---|
| | | 35 | | | | | 40 | | | | | 45 | | | |

| Phe | Ile | Pro | Tyr | Glu | Gln | Met | Ser | Glu | Leu | Glu | Lys | Arg | Ile | Ala | Arg |
|---|---|---|---|---|---|---|---|---|---|---|---|---|---|---|---|
| | 50 | | | | | 55 | | | | | 60 | | | | |

| Ile | Ile | Pro | Leu | Arg | Tyr | Arg | Ser | Asn | His | Trp | Val | Pro | Asp | Ser | Arg |
|---|---|---|---|---|---|---|---|---|---|---|---|---|---|---|---|
| 65 | | | | | 70 | | | | | 75 | | | | | 80 |

| Pro | Glu | Glu | Pro | Ser | Pro | Gln | Pro | Thr | Pro | Glu | Pro | Ser | Pro | Ser | Pro |
|---|---|---|---|---|---|---|---|---|---|---|---|---|---|---|---|
| | | | | 85 | | | | | 90 | | | | | 95 | |

| Gln | Pro | Ala | Pro | Asn | Pro | Gln | Pro | Ala | Pro | Ser | Asn | Pro | Ile | Asp | Glu |
|---|---|---|---|---|---|---|---|---|---|---|---|---|---|---|---|
| | | | 100 | | | | | 105 | | | | | 110 | | |

| Lys | Leu | Val | Lys | Glu | Ala | Val | Arg | Lys | Val | Gly | Asp | Gly | Tyr | Val | Phe |
|---|---|---|---|---|---|---|---|---|---|---|---|---|---|---|---|
| | | 115 | | | | | 120 | | | | | 125 | | | |

| Glu | Glu | Asn | Gly | Val | Ser | Arg | Tyr | Ile | Pro | Ala | Lys | Asn | Leu | Ser | Ala |
|---|---|---|---|---|---|---|---|---|---|---|---|---|---|---|---|
| | 130 | | | | | 135 | | | | | 140 | | | | |

| Glu | Thr | Ala | Ala | Gly | Ile | Asp | Ser | Lys | Leu | Ala | Lys | Gln | Glu | Ser | Leu |
|---|---|---|---|---|---|---|---|---|---|---|---|---|---|---|---|
| 145 | | | | | 150 | | | | | 155 | | | | | 160 |

| Ser | His | Lys | Leu | Gly | Ala | Lys | Lys | Thr | Asp | Leu | Pro | Ser | Ser | Asp | Arg |
|---|---|---|---|---|---|---|---|---|---|---|---|---|---|---|---|
| | | | | 165 | | | | | 170 | | | | | 175 | |

| Glu | Phe | Tyr | Asn | Lys | Ala | Tyr | Asp | Leu | Leu | Ala | Arg | Ile | His | Gln | Asp |
|---|---|---|---|---|---|---|---|---|---|---|---|---|---|---|---|
| | | | 180 | | | | | 185 | | | | | 190 | | |

| Leu | Leu | Asp | Asn | Lys | Gly | Arg | Gln | Val | Asp | Phe | Glu | Ala | Leu | Asp | Asn |
|---|---|---|---|---|---|---|---|---|---|---|---|---|---|---|---|
| | | 195 | | | | | 200 | | | | | 205 | | | |

| Leu | Leu | Glu | Arg | Leu | Lys | Asp | Val | Ser | Ser | Asp | Lys | Val | Lys | Leu | Val |
|---|---|---|---|---|---|---|---|---|---|---|---|---|---|---|---|
| | 210 | | | | | 215 | | | | | 220 | | | | |

| Asp | Asp | Ile | Leu | Ala | Phe | Leu | Ala | Pro | Ile | Arg | His | Pro | Glu | Arg | Leu |
|---|---|---|---|---|---|---|---|---|---|---|---|---|---|---|---|
| 225 | | | | | 230 | | | | | 235 | | | | | 240 |

| Gly | Lys | Pro | Asn | Ala | Gln | Ile | Thr | Tyr | Thr | Asp | Asp | Glu | Ile | Gln | Val |
|---|---|---|---|---|---|---|---|---|---|---|---|---|---|---|---|
| | | | | 245 | | | | | 250 | | | | | 255 | |

| Ala | Lys | Leu | Ala | Gly | Lys | Tyr | Thr | Thr | Glu | Asp | Gly | Tyr | Ile | Phe | Asp |
|---|---|---|---|---|---|---|---|---|---|---|---|---|---|---|---|
| | | | 260 | | | | | 265 | | | | | 270 | | |

| Pro | Arg | Asp | Ile | Thr | Ser | Asp | Glu | Gly | Asp | Ala | Tyr | Val | Thr | Pro | His |
|---|---|---|---|---|---|---|---|---|---|---|---|---|---|---|---|
| | | 275 | | | | | 280 | | | | | 285 | | | |

| Met | Thr | His | Ser | His | Trp | Ile | Lys | Lys | Asp | Ser | Leu | Ser | Glu | Ala | Glu |
|---|---|---|---|---|---|---|---|---|---|---|---|---|---|---|---|
| | 290 | | | | | 295 | | | | | 300 | | | | |

| Arg | Ala | Ala | Gln | Ala | Tyr | Ala | Lys | Glu | Lys | Gly | Leu | Thr | Pro | Pro |
|---|---|---|---|---|---|---|---|---|---|---|---|---|---|---|
| 305 | | | | | 310 | | | | | 315 | | | | | 320 |

| Ser | Thr | Asp | His | Gln | Asp | Ser | Gly | Asn | Thr | Glu | Ala | Lys | Gly | Ala | Glu |
|---|---|---|---|---|---|---|---|---|---|---|---|---|---|---|---|
| | | | | 325 | | | | | 330 | | | | | 335 | |

| Ala | Ile | Tyr | Asn | Arg | Val | Lys | Ala | Ala | Lys | Lys | Val | Pro | Leu | Asp | Arg |
|---|---|---|---|---|---|---|---|---|---|---|---|---|---|---|---|
| | | | 340 | | | | | 345 | | | | | 350 | | |

| Met | Pro | Tyr | Asn | Leu | Gln | Tyr | Thr | Val | Glu | Val | Lys | Asn | Gly | Ser | Leu |
|---|---|---|---|---|---|---|---|---|---|---|---|---|---|---|---|
| | | 355 | | | | | 360 | | | | | 365 | | | |

| Ile | Ile | Pro | His | Tyr | Asp | His | Tyr | His | Asn | Ile | Lys | Phe | Glu | Trp | Phe |

```
                  370             375             380
Asp Glu Gly Leu Tyr Glu Ala Pro Lys Gly Tyr Thr Leu Glu Asp Leu
385                 390                 395                 400

Leu Ala Thr Val Lys Tyr Tyr Val Glu His Pro Asn Glu Arg Pro His
                405                 410                 415

Ser Asp Asn Gly Phe Gly Asn Ala Ser Asp His Val
                420                 425

<210> SEQ ID NO 69
<211> LENGTH: 121
<212> TYPE: PRT
<213> ORGANISM: S. pneumoniae

<400> SEQUENCE: 69

Gly Leu Tyr Glu Ala Pro Lys Gly Tyr Thr Leu Glu Asp Leu Leu Ala
 1               5                  10                  15

Thr Val Lys Tyr Tyr Val Glu His Pro Asn Glu Arg Pro His Ser Asp
                20                  25                  30

Asn Gly Phe Gly Asn Ala Ser Asp His Val Gln Arg Asn Lys Asn Gly
            35                  40                  45

Gln Ala Asp Thr Asn Gln Thr Glu Lys Pro Ser Glu Glu Lys Pro Gln
50                  55                  60

Thr Glu Lys Pro Glu Glu Thr Pro Arg Glu Glu Lys Pro Gln Ser
65                  70                  75                  80

Glu Lys Pro Glu Ser Pro Lys Pro Thr Glu Glu Pro Glu Glu Glu Ser
                85                  90                  95

Pro Glu Glu Ser Glu Glu Pro Gln Val Glu Thr Glu Lys Val Glu Glu
            100                 105                 110

Lys Leu Arg Glu Ala Glu Asp Leu Leu
        115                 120

<210> SEQ ID NO 70
<211> LENGTH: 132
<212> TYPE: PRT
<213> ORGANISM: S. pneumoniae

<400> SEQUENCE: 70

Ala Ser Asp His Val Gln Arg Asn Lys Asn Gly Gln Ala Asp Thr Asn
 1               5                  10                  15

Gln Thr Glu Lys Pro Ser Glu Glu Lys Pro Gln Thr Glu Lys Pro Glu
                20                  25                  30

Glu Glu Thr Pro Arg Glu Glu Lys Pro Gln Ser Glu Lys Pro Glu Ser
            35                  40                  45

Pro Lys Pro Thr Glu Glu Pro Glu Glu Glu Ser Pro Glu Glu Ser Glu
        50                  55                  60

Glu Pro Gln Val Glu Thr Glu Lys Val Glu Glu Lys Leu Arg Glu Ala
65                  70                  75                  80

Glu Asp Leu Leu Gly Lys Ile Gln Asp Pro Ile Ile Lys Ser Asn Ala
                85                  90                  95

Lys Glu Thr Leu Thr Gly Leu Lys Asn Asn Leu Leu Phe Gly Thr Gln
            100                 105                 110

Asp Asn Asn Thr Ile Met Ala Glu Ala Glu Lys Leu Leu Ala Leu Leu
        115                 120                 125

Lys Glu Ser Lys
    130
```

```
<210> SEQ ID NO 71
<211> LENGTH: 226
<212> TYPE: PRT
<213> ORGANISM: S. pneumoniae

<400> SEQUENCE: 71

Asp Ile Asp Ser Leu Lys Gln Leu Tyr Lys Leu Pro Leu Ser Gln
 1               5                  10                  15

Arg His Val Glu Ser Asp Gly Leu Ile Phe Asp Pro Ala Gln Ile Thr
             20                  25                  30

Ser Arg Thr Ala Arg Gly Val Ala Val Pro His Gly Asn His Tyr His
         35                  40                  45

Phe Ile Pro Tyr Glu Gln Met Ser Glu Leu Glu Lys Arg Ile Ala Arg
     50                  55                  60

Ile Ile Pro Leu Arg Tyr Arg Ser Asn His Trp Val Pro Asp Ser Arg
 65                  70                  75                  80

Pro Glu Glu Pro Ser Pro Gln Pro Thr Pro Glu Pro Ser Pro Ser Pro
                 85                  90                  95

Gln Pro Ala Pro Asn Pro Gln Pro Ala Pro Ser Asn Pro Ile Asp Glu
            100                 105                 110

Lys Leu Val Lys Glu Ala Val Arg Lys Val Gly Asp Gly Tyr Val Phe
        115                 120                 125

Glu Glu Asn Gly Val Ser Arg Tyr Ile Pro Ala Lys Asn Leu Ser Ala
    130                 135                 140

Glu Thr Ala Ala Gly Ile Asp Ser Lys Leu Ala Lys Gln Glu Ser Leu
145                 150                 155                 160

Ser His Lys Leu Gly Ala Lys Lys Thr Asp Leu Pro Ser Ser Asp Arg
                165                 170                 175

Glu Phe Tyr Asn Lys Ala Tyr Asp Leu Leu Ala Arg Ile His Gln Asp
            180                 185                 190

Leu Leu Asp Asn Lys Gly Arg Gln Val Asp Phe Glu Ala Leu Asp Asn
        195                 200                 205

Leu Leu Glu Arg Leu Lys Asp Val Ser Ser Asp Lys Val Lys Leu Val
    210                 215                 220

Asp Asp
225

<210> SEQ ID NO 72
<211> LENGTH: 203
<212> TYPE: PRT
<213> ORGANISM: S. pneumoniae

<400> SEQUENCE: 72

Asp Ile Leu Ala Phe Leu Ala Pro Ile Arg His Pro Glu Arg Leu Gly
 1               5                  10                  15

Lys Pro Asn Ala Gln Ile Thr Tyr Thr Asp Asp Glu Ile Gln Val Ala
             20                  25                  30

Lys Leu Ala Gly Lys Tyr Thr Thr Glu Asp Gly Tyr Ile Phe Asp Pro
         35                  40                  45

Arg Asp Ile Thr Ser Asp Glu Gly Asp Ala Tyr Val Thr Pro His Met
     50                  55                  60

Thr His Ser His Trp Ile Lys Lys Asp Ser Leu Ser Glu Ala Glu Arg
 65                  70                  75                  80

Ala Ala Ala Gln Ala Tyr Ala Lys Glu Lys Gly Leu Thr Pro Pro Ser
                 85                  90                  95

Thr Asp His Gln Asp Ser Gly Asn Thr Glu Ala Lys Gly Ala Glu Ala
```

```
            100                 105                 110
Ile Tyr Asn Arg Val Lys Ala Ala Lys Val Pro Leu Asp Arg Met
            115                 120                 125

Pro Tyr Asn Leu Gln Tyr Thr Val Glu Val Lys Asn Gly Ser Leu Ile
            130                 135                 140

Ile Pro His Tyr Asp His Tyr His Asn Ile Lys Phe Glu Trp Phe Asp
145                 150                 155                 160

Glu Gly Leu Tyr Glu Ala Pro Lys Gly Tyr Thr Leu Glu Asp Leu Leu
            165                 170                 175

Ala Thr Val Lys Tyr Tyr Val Glu His Pro Asn Glu Arg Pro His Ser
            180                 185                 190

Asp Asn Gly Phe Gly Asn Ala Ser Asp His Val
            195                 200

<210> SEQ ID NO 73
<211> LENGTH: 819
<212> TYPE: PRT
<213> ORGANISM: S. pneumoniae

<400> SEQUENCE: 73

Cys Ser Tyr Glu Leu Gly Arg His Gln Ala Gly Gln Val Lys Lys Glu
1               5                   10                  15

Ser Asn Arg Val Ser Tyr Ile Asp Gly Asp Gln Ala Gly Gln Lys Ala
            20                  25                  30

Glu Asn Leu Thr Pro Asp Glu Val Ser Lys Arg Glu Gly Ile Asn Ala
            35                  40                  45

Glu Gln Ile Val Ile Lys Ile Thr Asp Gln Gly Tyr Val Thr Ser His
            50                  55                  60

Gly Asp His Tyr His Tyr Tyr Asn Gly Lys Val Pro Tyr Asp Ala Ile
65                  70                  75                  80

Ile Ser Glu Glu Leu Leu Met Lys Asp Pro Asn Tyr Gln Leu Lys Asp
                85                  90                  95

Ser Asp Ile Val Asn Glu Ile Lys Gly Gly Tyr Val Ile Lys Val Asp
            100                 105                 110

Gly Lys Tyr Tyr Val Tyr Leu Lys Asp Ala Ala His Ala Asp Asn Ile
            115                 120                 125

Arg Thr Lys Glu Glu Ile Lys Arg Gln Lys Gln Glu His Ser His Asn
            130                 135                 140

His Asn Ser Arg Ala Asp Asn Ala Val Ala Ala Arg Ala Gln Gly
145                 150                 155                 160

Arg Tyr Thr Thr Asp Asp Gly Tyr Ile Phe Asn Ala Ser Asp Ile Ile
            165                 170                 175

Glu Asp Thr Gly Asp Ala Tyr Ile Val Pro His Gly Asp His Tyr His
            180                 185                 190

Tyr Ile Pro Lys Asn Glu Leu Ser Ala Ser Glu Leu Ala Ala Ala Glu
            195                 200                 205

Ala Tyr Trp Asn Gly Lys Gln Gly Ser Arg Pro Ser Ser Ser Ser Ser
            210                 215                 220

Tyr Asn Ala Asn Pro Val Gln Pro Arg Leu Ser Glu Asn His Asn Leu
225                 230                 235                 240

Thr Val Thr Pro Thr Tyr His Gln Asn Gln Gly Glu Asn Ile Ser Ser
            245                 250                 255

Leu Leu Arg Glu Leu Tyr Ala Lys Pro Leu Ser Glu Arg His Val Glu
            260                 265                 270
```

```
Ser Asp Gly Leu Ile Phe Asp Pro Ala Gln Ile Thr Ser Arg Thr Ala
            275                 280                 285

Arg Gly Val Ala Val Pro His Gly Asn His Tyr His Phe Ile Pro Tyr
            290                 295                 300

Glu Gln Met Ser Glu Leu Glu Lys Arg Ile Ala Arg Ile Ile Pro Leu
305                 310                 315                 320

Arg Tyr Arg Ser Asn His Trp Val Pro Asp Ser Arg Pro Glu Gln Pro
            325                 330                 335

Ser Pro Gln Ser Thr Pro Glu Pro Ser Pro Ser Leu Gln Pro Ala Pro
            340                 345                 350

Asn Pro Gln Pro Ala Pro Ser Asn Pro Ile Asp Glu Lys Leu Val Lys
            355                 360                 365

Glu Ala Val Arg Lys Val Gly Asp Gly Tyr Val Phe Glu Glu Asn Gly
370                 375                 380

Val Ser Arg Tyr Ile Pro Ala Lys Asp Leu Ser Ala Glu Thr Ala Ala
385                 390                 395                 400

Gly Ile Asp Ser Lys Leu Ala Lys Gln Glu Ser Leu Ser His Lys Leu
            405                 410                 415

Gly Ala Lys Lys Thr Asp Leu Pro Ser Ser Asp Arg Glu Phe Tyr Asn
            420                 425                 430

Lys Ala Tyr Asp Leu Leu Ala Arg Ile His Gln Asp Leu Leu Asp Asn
            435                 440                 445

Lys Gly Arg Gln Val Asp Phe Glu Val Leu Asp Asn Leu Leu Glu Arg
            450                 455                 460

Leu Lys Asp Val Ser Ser Asp Lys Val Lys Leu Val Asp Asp Ile Leu
465                 470                 475                 480

Ala Phe Leu Ala Pro Ile Arg His Pro Glu Arg Leu Gly Lys Pro Asn
            485                 490                 495

Ala Gln Ile Thr Tyr Thr Asp Glu Ile Gln Val Ala Lys Leu Ala
            500                 505                 510

Gly Lys Tyr Thr Thr Glu Asp Gly Tyr Ile Phe Asp Pro Arg Asp Ile
            515                 520                 525

Thr Ser Asp Glu Gly Asp Ala Tyr Val Thr Pro His Met Thr His Ser
            530                 535                 540

His Trp Ile Lys Lys Asp Ser Leu Ser Glu Ala Glu Arg Ala Ala Ala
545                 550                 555                 560

Gln Ala Tyr Ala Lys Glu Lys Gly Leu Thr Pro Ser Thr Asp His
            565                 570                 575

Gln Asp Ser Gly Asn Thr Glu Ala Lys Gly Ala Glu Ala Ile Tyr Asn
            580                 585                 590

Arg Val Lys Ala Ala Lys Lys Val Pro Leu Asp Arg Met Pro Tyr Asn
            595                 600                 605

Leu Gln Tyr Thr Val Glu Val Lys Asn Gly Ser Leu Ile Ile Pro His
            610                 615                 620

Tyr Asp His Tyr His Asn Ile Lys Phe Glu Trp Phe Asp Glu Gly Leu
625                 630                 635                 640

Tyr Glu Ala Pro Lys Gly Tyr Ser Leu Glu Asp Leu Leu Ala Thr Val
            645                 650                 655

Lys Tyr Tyr Val Glu His Pro Asn Glu Arg Pro His Ser Asp Asn Gly
            660                 665                 670

Phe Gly Asn Ala Ser Asp His Val Arg Lys Asn Lys Ala Asp Gln Asp
            675                 680                 685

Ser Lys Pro Asp Glu Asp Lys Glu His Asp Glu Val Ser Glu Pro Thr
```

```
                    690             695                 700
His Pro Glu Ser Asp Glu Lys Glu Asn His Ala Gly Leu Asn Pro Ser
705                     710                 715                 720

Ala Asp Asn Leu Tyr Lys Pro Ser Thr Asp Thr Glu Thr Glu Glu
                725                 730                 735

Glu Ala Glu Asp Thr Thr Asp Glu Ala Glu Ile Pro Gln Val Glu Asn
                740                 745                 750

Ser Val Ile Asn Ala Lys Ile Ala Asp Ala Glu Ala Leu Leu Glu Lys
                755                 760                 765

Val Thr Asp Pro Ser Ile Arg Gln Asn Ala Met Glu Thr Leu Thr Gly
770                     775                 780

Leu Lys Ser Ser Leu Leu Leu Gly Thr Lys Asp Asn Asn Thr Ile Ser
785                 790                 795                 800

Ala Glu Val Asp Ser Leu Leu Ala Leu Leu Lys Glu Ser Gln Pro Ala
                805                 810                 815

Pro Ile Gln

<210> SEQ ID NO 74
<211> LENGTH: 568
<212> TYPE: PRT
<213> ORGANISM: S. pneumoniae

<400> SEQUENCE: 74

Glu Asn Ile Ser Ser Leu Leu Arg Glu Leu Tyr Ala Lys Pro Leu Ser
1               5                   10                  15

Glu Arg His Val Glu Ser Asp Gly Leu Ile Phe Asp Pro Ala Gln Ile
                20                  25                  30

Thr Ser Arg Thr Ala Arg Gly Val Ala Val Pro His Gly Asn His Tyr
                35                  40                  45

His Phe Ile Pro Tyr Glu Gln Met Ser Glu Leu Glu Lys Arg Ile Ala
        50                  55                  60

Arg Ile Ile Pro Leu Arg Tyr Arg Ser Asn His Trp Val Pro Asp Ser
65                  70                  75                  80

Arg Pro Glu Gln Pro Ser Pro Gln Ser Thr Pro Glu Pro Ser Pro Ser
                85                  90                  95

Leu Gln Pro Ala Pro Asn Pro Gln Pro Ala Pro Ser Asn Pro Ile Asp
                100                 105                 110

Glu Lys Leu Val Lys Glu Ala Val Arg Lys Val Gly Asp Gly Tyr Val
                115                 120                 125

Phe Glu Glu Asn Gly Val Ser Arg Tyr Ile Pro Ala Lys Asp Leu Ser
        130                 135                 140

Ala Glu Thr Ala Ala Gly Ile Asp Ser Lys Leu Ala Lys Gln Glu Ser
145                 150                 155                 160

Leu Ser His Lys Leu Gly Ala Lys Lys Thr Asp Leu Pro Ser Ser Asp
                165                 170                 175

Arg Glu Phe Tyr Asn Lys Ala Tyr Asp Leu Leu Ala Arg Ile His Gln
                180                 185                 190

Asp Leu Leu Asp Asn Lys Gly Arg Gln Val Asp Phe Glu Val Leu Asp
                195                 200                 205

Asn Leu Leu Glu Arg Leu Lys Asp Val Ser Ser Asp Lys Val Lys Leu
                210                 215                 220

Val Asp Asp Ile Leu Ala Phe Leu Ala Pro Ile Arg His Pro Glu Arg
225                 230                 235                 240

Leu Gly Lys Pro Asn Ala Gln Ile Thr Tyr Thr Asp Asp Glu Ile Gln
```

```
                    245                 250                 255
Val Ala Lys Leu Ala Gly Lys Tyr Thr Thr Glu Asp Gly Tyr Ile Phe
            260                 265                 270

Asp Pro Arg Asp Ile Thr Ser Asp Glu Gly Asp Ala Tyr Val Thr Pro
        275                 280                 285

His Met Thr His Ser His Trp Ile Lys Lys Asp Ser Leu Ser Glu Ala
    290                 295                 300

Glu Arg Ala Ala Ala Gln Ala Tyr Ala Lys Glu Lys Gly Leu Thr Pro
305                 310                 315                 320

Pro Ser Thr Asp His Gln Asp Ser Gly Asn Thr Glu Ala Lys Gly Ala
                325                 330                 335

Glu Ala Ile Tyr Asn Arg Val Lys Ala Ala Lys Lys Val Pro Leu Asp
            340                 345                 350

Arg Met Pro Tyr Asn Leu Gln Tyr Thr Val Glu Val Lys Asn Gly Ser
        355                 360                 365

Leu Ile Ile Pro His Tyr Asp His Tyr His Asn Ile Lys Phe Glu Trp
    370                 375                 380

Phe Asp Glu Gly Leu Tyr Glu Ala Pro Lys Gly Tyr Ser Leu Glu Asp
385                 390                 395                 400

Leu Leu Ala Thr Val Lys Tyr Tyr Val Glu His Pro Asn Glu Arg Pro
                405                 410                 415

His Ser Asp Asn Gly Phe Gly Asn Ala Ser Asp His Val Arg Lys Asn
            420                 425                 430

Lys Ala Asp Gln Asp Ser Lys Pro Asp Glu Asp Lys Glu His Asp Glu
        435                 440                 445

Val Ser Glu Pro Thr His Pro Glu Ser Asp Glu Lys Glu Asn His Ala
    450                 455                 460

Gly Leu Asn Pro Ser Ala Asp Asn Leu Tyr Lys Pro Ser Thr Asp Thr
465                 470                 475                 480

Glu Glu Thr Glu Glu Glu Ala Glu Asp Thr Thr Asp Glu Ala Glu Ile
                485                 490                 495

Pro Gln Val Glu Asn Ser Val Ile Asn Ala Lys Ile Ala Asp Ala Glu
            500                 505                 510

Ala Leu Leu Glu Lys Val Thr Asp Pro Ser Ile Arg Gln Asn Ala Met
        515                 520                 525

Glu Thr Leu Thr Gly Leu Lys Ser Ser Leu Leu Gly Thr Lys Asp
    530                 535                 540

Asn Asn Thr Ile Ser Ala Glu Val Asp Ser Leu Leu Ala Leu Leu Lys
545                 550                 555                 560

Glu Ser Gln Pro Ala Pro Ile Gln
                565

<210> SEQ ID NO 75
<211> LENGTH: 140
<212> TYPE: PRT
<213> ORGANISM: S. pneumoniae

<400> SEQUENCE: 75

Val Arg Lys Asn Lys Ala Asp Gln Asp Ser Lys Pro Asp Glu Asp Lys
1               5                   10                  15

Glu His Asp Glu Val Ser Glu Pro Thr His Pro Glu Ser Asp Glu Lys
            20                  25                  30

Glu Asn His Ala Gly Leu Asn Pro Ser Ala Asp Asn Leu Tyr Lys Pro
        35                  40                  45
```

```
Ser Thr Asp Thr Glu Glu Thr Glu Glu Ala Glu Asp Thr Thr Asp
    50                  55                  60
Glu Ala Glu Ile Pro Gln Val Glu Asn Ser Val Ile Asn Ala Lys Ile
65                  70                  75                  80
Ala Asp Ala Glu Ala Leu Leu Glu Lys Val Thr Asp Pro Ser Ile Arg
                85                  90                  95
Gln Asn Ala Met Glu Thr Leu Thr Gly Leu Lys Ser Ser Leu Leu Leu
                100                 105                 110
Gly Thr Lys Asp Asn Asn Thr Ile Ser Ala Glu Val Asp Ser Leu Leu
            115                 120                 125
Ala Leu Leu Lys Glu Ser Gln Pro Ala Pro Ile Gln
        130                 135                 140

<210> SEQ ID NO 76
<211> LENGTH: 3171
<212> TYPE: DNA
<213> ORGANISM: S. pneumoniae

<400> SEQUENCE: 76
```

| | | | | | |
|---|---|---|---|---|---|
| gacttgacag | aagagcaaat | taaggctgcg | caaaaacatt | tagaggaagt | taaaactagt | 60 |
| cataatggat | tagattcttt | gtcatctcat | gaacaggatt | atccaggtaa | tgccaaagaa | 120 |
| atgaaagatt | tagataaaaa | aatcgaagaa | aaaattgctg | gcattatgaa | acaatatggt | 180 |
| gtcaaacgtg | aaagtattgt | cgtgaataaa | gaaaaaaatg | cgattatttta | tccgcatgga | 240 |
| gatcaccatc | atgcagatcc | gattgatgaa | cataaaccgg | ttggaattgg | tcattctcac | 300 |
| agtaactatg | aactgtttaa | acccgaagaa | ggagttgcta | aaaaagaagg | gaataaagtt | 360 |
| tatactggag | aagaattaac | gaatgttgtt | aatttgttaa | aaaatagtac | gtttaataat | 420 |
| caaaacttta | ctctagccaa | tggtcaaaaa | cgcgtttctt | ttagttttcc | gcctgaattg | 480 |
| gagaaaaaat | taggtatcaa | tatgctagta | aaattaataa | caccagatgg | aaaagtattg | 540 |
| gagaaagtat | ctggtaaagt | atttggagaa | ggagtaggga | atattgcaaa | ctttgaatta | 600 |
| gatcaacctt | atttaccagg | acaaacattt | aagtatacta | tcgcttcaaa | agattatcca | 660 |
| gaagtaagtt | atgatggtac | atttacagtt | ccaacctctt | tagcttacaa | aatggccagt | 720 |
| caaacgattt | tctatccttt | ccatgcaggg | gatacttatt | taagagtgaa | ccctcaattt | 780 |
| gcagtgccta | aggaactga | tgctttagtc | agagtgtttg | atgaatttca | tggaaatgct | 840 |
| tatttagaaa | ataactataa | agttggtgaa | atcaaattac | cgattccgaa | attaaaccaa | 900 |
| ggaacaacca | gaacggccgg | aaataaaatt | cctgtaacct | tcatggcaaa | tgcttatttg | 960 |
| gacaatcaat | cgacttatat | tgtggaagta | cctatcttgg | aaaaagaaaa | tcaaactgat | 1020 |
| aaaccaagta | ttctaccaca | atttaaaagg | aataaagcac | aagaaaactc | aaaacttgat | 1080 |
| gaaaaggtag | aagaaccaaa | gactagtgag | aaggtagaaa | aagaaaaact | ttctgaaact | 1140 |
| gggaatagta | ctagtaattc | aacgttagaa | gaagttccta | cagtggatcc | tgtacaagaa | 1200 |
| aaagtagcaa | aatttgctga | agttatggg | atgaagctag | aaaatgtctt | gtttaatatg | 1260 |
| gacggaacaa | ttgaattata | tttaccatca | ggagaagtca | ttaaaaagaa | tatggcagat | 1320 |
| tttacaggag | aagcacctca | aggaaatggt | gaaaataaac | catctgaaaa | tggaaaagta | 1380 |
| tctactggaa | cagttgagaa | ccaaccaaca | gaaaataaac | cagcagattc | tttaccagag | 1440 |
| gcaccaaacg | aaaaacctgt | aaaaccagaa | aactcaacgg | ataatggaat | gttgaatcca | 1500 |
| gaagggaatg | tggggagtga | ccctatgtta | gatccagcat | tagaggaagc | tccagcagta | 1560 |
| gatcctgtac | aagaaaaatt | agaaaaattt | acagctagtt | acggattagg | cttagatagt | 1620 |

-continued

```
gttatattca atatggatgg aacgattgaa ttaagattgc caagtggaga agtgataaaa    1680
aagaatttat ctgatttcat agcgaagctt cgttatcgtt caaaccattg ggtaccagat   1740
tcaagaccag aagaaccaag tccacaaccg actccagaac ctagtccaag tccgcaacct   1800
gcaccaaatc ctcaaccagc tccaagcaat ccaattgatg agaaattggt caaagaagct   1860
gttcgaaaag taggcgatgg ttatgtcttt gaggagaatg gagtttctcg ttatatccca   1920
gccaagaatc tttcagcaga aacagcagca ggcattgata gcaaactggc caagcaggaa   1980
agtttatctc ataagctagg agctaagaaa actgacctcc catctagtga tcgagaattt   2040
tacaataagg cttatgactt actagcaaga attcaccaag atttacttga taataaaggt   2100
cgacaagttg attttgaggc tttggataac ctgttggaac gactcaagga tgtctcaagt   2160
gataaagtca agttagtgga tgatattctt gccttcttag ctccgattcg tcatccagaa   2220
cgtttaggaa aaccaaatgc gcaaattacc tacactgatg atgagattca agtagccaag   2280
ttggcaggca agtacacaac agaagacggt tatatctttg atcctcgtga tataaccagt   2340
gatgaggggg atgcctatgt aactccacat atgaccccata gccactggat taaaaaagat   2400
agtttgtctg aagctgagag agcggcagcc caggcttatg ctaaagagaa aggtttgacc   2460
cctccttcga cagaccatca ggattcagga aatactgagg caaaggagc agaagctatc    2520 tacaaccgcg tgaaagcagc taagaaggtg ccacttgatc gtatgcctta caatcttcaa   2580
tatactgtag aagtcaaaaa cggtagttta atcatacctc attatgacca ttaccataac   2640
atcaaatttg agtggtttga cgaaggcctt tatgaggcac taagggta tactcttgag     2700 gatcttttgg cgactgtcaa gtactatgtc gaacatccaa acgaacgtcc gcattcagat   2760
aatggttttg gtaacgctag cgaccatgtt caaagaaaca aaaatggtca agctgatacc   2820
aatcaaacgg aaaaaccaag cgaggagaaa cctcagacag aaaaacctga ggaagaaacc   2880
cctcgagaag agaaaccaca aagcgagaaa ccagagtctc caaaaccaac agaggaacca   2940
gaagaagaat caccagagga atcagaagaa cctcaggtcg agactgaaaa ggttgaagaa   3000
aaactgagag aggctgaaga tttacttgga aaaatccagg atccaattat caagtccaat   3060
gccaaagaga ctctcacagg attaaaaaat aatttactat ttggcaccca ggacaacaat   3120
actattatgg cagaagctga aaaactattg gctttattaa aggagagtaa g            3171
```

<210> SEQ ID NO 77
<211> LENGTH: 473
<212> TYPE: PRT
<213> ORGANISM: S. pneumoniae

<400> SEQUENCE: 77

```
Glu Ala Tyr Trp Asn Gly Lys Gln Gly Ser Arg Pro Ser Ser Ser Ser
 1               5                  10                  15

Ser Tyr Asn Ala Asn Pro Val Gln Pro Arg Leu Ser Glu Asn His Asn
            20                  25                  30

Leu Thr Val Thr Pro Thr Tyr His Gln Asn Gln Gly Glu Asn Ile Ser
        35                  40                  45

Ser Leu Leu Arg Glu Leu Tyr Ala Lys Pro Leu Ser Glu Arg His Val
    50                  55                  60

Glu Ser Asp Gly Leu Ile Phe Asp Pro Ala Gln Ile Thr Ser Arg Thr
65                  70                  75                  80

Ala Arg Gly Val Ala Val Pro His Gly Asn His Tyr His Phe Ile Pro
                85                  90                  95
```

```
Tyr Glu Gln Met Ser Glu Leu Glu Lys Arg Ile Ala Arg Ile Ile Pro
                100                 105                 110

Leu Arg Tyr Arg Ser Asn His Trp Val Pro Asp Ser Arg Pro Glu Gln
            115                 120                 125

Pro Ser Pro Gln Ser Thr Pro Glu Pro Ser Pro Ser Leu Gln Pro Ala
        130                 135                 140

Pro Asn Pro Gln Pro Ala Pro Ser Asn Pro Ile Asp Glu Lys Leu Val
145                 150                 155                 160

Lys Glu Ala Val Arg Lys Val Gly Asp Gly Tyr Val Phe Glu Glu Asn
                165                 170                 175

Gly Val Ser Arg Tyr Ile Pro Ala Lys Asp Leu Ser Ala Glu Thr Ala
            180                 185                 190

Ala Gly Ile Asp Ser Lys Leu Ala Lys Gln Glu Ser Leu Ser His Lys
        195                 200                 205

Leu Gly Ala Lys Lys Thr Asp Leu Pro Ser Ser Asp Arg Glu Phe Tyr
    210                 215                 220

Asn Lys Ala Tyr Asp Leu Leu Ala Arg Ile His Gln Asp Leu Leu Asp
225                 230                 235                 240

Asn Lys Gly Arg Gln Val Asp Phe Glu Val Leu Asp Asn Leu Leu Glu
                245                 250                 255

Arg Leu Lys Asp Val Ser Ser Asp Lys Val Lys Leu Val Asp Asp Ile
            260                 265                 270

Leu Ala Phe Leu Ala Pro Ile Arg His Pro Glu Arg Leu Gly Lys Pro
        275                 280                 285

Asn Ala Gln Ile Thr Tyr Thr Asp Glu Ile Gln Val Ala Lys Leu
290                 295                 300

Ala Gly Lys Tyr Thr Thr Glu Asp Gly Tyr Ile Phe Asp Pro Arg Asp
305                 310                 315                 320

Ile Thr Ser Asp Glu Gly Asp Ala Tyr Val Thr Pro His Met Thr His
                325                 330                 335

Ser His Trp Ile Lys Lys Asp Ser Leu Ser Glu Ala Glu Arg Ala Ala
            340                 345                 350

Ala Gln Ala Tyr Ala Lys Glu Lys Gly Leu Thr Pro Pro Ser Thr Asp
        355                 360                 365

His Gln Asp Ser Gly Asn Thr Glu Ala Lys Gly Ala Glu Ala Ile Tyr
    370                 375                 380

Asn Arg Val Lys Ala Ala Lys Lys Val Pro Leu Asp Arg Met Pro Tyr
385                 390                 395                 400

Asn Leu Gln Tyr Thr Val Glu Val Lys Asn Gly Ser Leu Ile Ile Pro
                405                 410                 415

His Tyr Asp His Tyr His Asn Ile Lys Phe Glu Trp Phe Asp Glu Gly
            420                 425                 430

Leu Tyr Glu Ala Pro Lys Gly Tyr Ser Leu Glu Asp Leu Leu Ala Thr
        435                 440                 445

Val Lys Tyr Tyr Val Glu His Pro Asn Glu Arg Pro His Ser Asp Asn
    450                 455                 460

Gly Phe Gly Asn Ala Ser Asp His Val
465                 470

<210> SEQ ID NO 78
<211> LENGTH: 780
<212> TYPE: PRT
<213> ORGANISM: S. pneumoniae

<400> SEQUENCE: 78
```

-continued

```
Cys Ala Tyr Ala Leu Asn Gln His Arg Ser Gln Glu Asn Lys Asp Asn
 1               5                  10                  15

Asn Arg Val Ser Tyr Val Asp Gly Ser Gln Ser Ser Gln Lys Ser Glu
                20                  25                  30

Asn Leu Thr Pro Asp Gln Val Ser Gln Lys Glu Gly Ile Gln Ala Glu
            35                  40                  45

Gln Ile Val Ile Lys Ile Thr Asp Gln Gly Tyr Val Thr Ser His Gly
 50                  55                  60

Asp His Tyr His Tyr Tyr Asn Gly Lys Val Pro Tyr Asp Ala Leu Phe
65                   70                  75                  80

Ser Glu Glu Leu Leu Met Lys Asp Pro Asn Tyr Gln Leu Lys Asp Ala
                85                  90                  95

Asp Ile Val Asn Glu Val Lys Gly Gly Tyr Ile Ile Lys Val Asp Gly
               100                 105                 110

Lys Tyr Tyr Val Tyr Leu Lys Asp Ala Ala His Ala Asp Asn Val Arg
           115                 120                 125

Thr Lys Asp Glu Ile Asn Arg Gln Lys Gln Glu His Val Lys Asp Asn
130                 135                 140

Glu Lys Val Asn Ser Asn Val Ala Val Ala Arg Ser Gln Gly Arg Tyr
145                 150                 155                 160

Thr Thr Asn Asp Gly Tyr Val Phe Asn Pro Ala Asp Ile Ile Glu Asp
                165                 170                 175

Thr Gly Asn Ala Tyr Ile Val Pro His Gly His Tyr His Tyr Ile
            180                 185                 190

Pro Lys Ser Asp Leu Ser Ala Ser Glu Leu Ala Ala Lys Ala His
            195                 200                 205

Leu Ala Gly Lys Asn Met Gln Pro Ser Gln Leu Ser Tyr Ser Ser Thr
    210                 215                 220

Ala Ser Asp Asn Asn Thr Gln Ser Val Ala Lys Gly Ser Thr Ser Lys
225                 230                 235                 240

Pro Ala Asn Lys Ser Glu Asn Leu Gln Ser Leu Leu Lys Glu Leu Tyr
                245                 250                 255

Asp Ser Pro Ser Ala Gln Arg Tyr Ser Glu Ser Asp Gly Leu Val Phe
            260                 265                 270

Asp Pro Ala Lys Ile Ile Ser Arg Thr Pro Asn Gly Val Ala Ile Pro
            275                 280                 285

His Gly Asp His Tyr His Phe Ile Pro Tyr Ser Lys Leu Ser Ala Leu
    290                 295                 300

Glu Glu Lys Ile Ala Arg Met Val Pro Ile Ser Gly Thr Gly Ser Thr
305                 310                 315                 320

Val Ser Thr Asn Ala Lys Pro Asn Glu Val Val Ser Ser Leu Gly Ser
                325                 330                 335

Leu Ser Ser Asn Pro Ser Ser Leu Thr Thr Ser Lys Glu Leu Ser Ser
            340                 345                 350

Ala Ser Asp Gly Tyr Ile Phe Asn Pro Lys Asp Ile Val Glu Glu Thr
            355                 360                 365

Ala Thr Ala Tyr Ile Val Arg His Gly Asp His Phe His Tyr Ile Pro
370                 375                 380

Lys Ser Asn Gln Ile Gly Gln Pro Thr Leu Pro Asn Asn Ser Leu Ala
385                 390                 395                 400

Thr Pro Ser Pro Ser Leu Pro Ile Asn Pro Gly Thr Ser His Glu Lys
                405                 410                 415
```

| | | | | | | | | | | | |
|---|---|---|---|---|---|---|---|---|---|---|---|
|His|Glu|Glu|Asp|Gly|Tyr|Gly|Phe|Asp|Ala|Asn|Arg|Ile|Ile|Ala|Glu|
| | |420| | | |425| | | |430| |

Asp Glu Ser Gly Phe Val Met Ser His Gly Asp His Asn His Tyr Phe
        435                 440                 445

Phe Lys Lys Asp Leu Thr Glu Glu Gln Ile Lys Ala Ala Gln Lys His
    450                 455                 460

Leu Glu Glu Val Lys Thr Ser His Asn Gly Leu Asp Ser Leu Ser Ser
465                 470                 475                 480

His Glu Gln Asp Tyr Pro Gly Asn Ala Lys Glu Met Lys Asp Leu Asp
                485                 490                 495

Lys Lys Ile Glu Lys Ile Ala Gly Ile Met Lys Gln Tyr Gly Val
            500                 505                 510

Lys Arg Glu Ser Ile Val Val Asn Lys Glu Lys Asn Ala Ile Ile Tyr
        515                 520                 525

Pro His Gly Asp His His Ala Asp Pro Ile Asp Glu His Lys Pro
    530                 535                 540

Val Gly Ile Gly His Ser His Ser Asn Tyr Glu Leu Phe Lys Pro Glu
545                 550                 555                 560

Glu Gly Val Ala Lys Lys Glu Gly Asn Lys Val Tyr Thr Gly Glu Glu
                565                 570                 575

Leu Thr Asn Val Val Asn Leu Leu Lys Asn Ser Thr Phe Asn Asn Gln
            580                 585                 590

Asn Phe Thr Leu Ala Asn Gly Gln Lys Arg Val Ser Phe Ser Phe Pro
        595                 600                 605

Pro Glu Leu Glu Lys Lys Leu Gly Ile Asn Met Leu Val Lys Leu Ile
    610                 615                 620

Thr Pro Asp Gly Lys Val Leu Glu Lys Val Ser Gly Lys Val Phe Gly
625                 630                 635                 640

Glu Gly Val Gly Asn Ile Ala Asn Phe Glu Leu Asp Gln Pro Tyr Leu
                645                 650                 655

Pro Gly Gln Thr Phe Lys Tyr Thr Ile Ala Ser Lys Asp Tyr Pro Glu
            660                 665                 670

Val Ser Tyr Asp Gly Thr Phe Thr Val Pro Thr Ser Leu Ala Tyr Lys
        675                 680                 685

Met Ala Ser Gln Thr Ile Phe Tyr Pro Phe His Ala Gly Asp Thr Tyr
    690                 695                 700

Leu Arg Val Asn Pro Gln Phe Ala Val Pro Lys Gly Thr Asp Ala Leu
705                 710                 715                 720

Val Arg Val Phe Asp Glu Phe His Gly Asn Ala Tyr Leu Glu Asn Asn
                725                 730                 735

Tyr Lys Val Gly Glu Ile Lys Leu Pro Ile Pro Lys Leu Asn Gln Gly
            740                 745                 750

Thr Thr Arg Thr Ala Gly Asn Lys Ile Pro Val Thr Phe Met Ala Asn
        755                 760                 765

Ala Tyr Leu Asp Asn Gln Ser Thr Tyr Ile Val Glu
    770                 775                 780

<210> SEQ ID NO 79
<211> LENGTH: 690
<212> TYPE: PRT
<213> ORGANISM: S. pneumoniae

<400> SEQUENCE: 79

Cys Ala Tyr Glu Leu Gly Leu His Gln Ala Gln Thr Val Lys Glu Asn
1               5                   10                  15

```
Asn Arg Val Ser Tyr Ile Asp Gly Lys Gln Ala Thr Gln Lys Thr Glu
            20                  25                  30

Asn Leu Thr Pro Asp Glu Val Ser Lys Arg Glu Gly Ile Asn Ala Glu
        35                  40                  45

Gln Ile Val Ile Lys Ile Thr Asp Gln Gly Tyr Val Thr Ser His Gly
    50                  55                  60

Asp His Tyr His Tyr Tyr Asn Gly Lys Val Pro Tyr Asp Ala Ile Ile
65                  70                  75                  80

Ser Glu Glu Leu Leu Met Lys Asp Pro Asn Tyr Gln Leu Lys Asp Ser
                85                  90                  95

Asp Ile Val Asn Glu Ile Lys Gly Gly Tyr Val Ile Lys Val Asn Gly
            100                 105                 110

Lys Tyr Tyr Val Tyr Leu Lys Asp Ala Ala His Ala Asp Asn Val Arg
        115                 120                 125

Thr Lys Glu Glu Ile Asn Arg Gln Lys Gln Glu His Ser Gln His Arg
    130                 135                 140

Glu Gly Gly Thr Ser Ala Asn Asp Gly Ala Val Ala Phe Ala Arg Ser
145                 150                 155                 160

Gln Gly Arg Tyr Thr Thr Asp Asp Gly Tyr Ile Phe Asn Ala Ser Asp
                165                 170                 175

Ile Ile Glu Asp Thr Gly Asp Ala Tyr Ile Val Pro His Gly Asp His
            180                 185                 190

Tyr His Tyr Ile Pro Lys Asn Glu Leu Ser Ala Ser Glu Leu Ala Ala
        195                 200                 205

Ala Glu Ala Phe Leu Ser Gly Arg Glu Asn Leu Ser Asn Leu Arg Thr
    210                 215                 220

Tyr Arg Arg Gln Asn Ser Asp Asn Thr Pro Arg Thr Asn Trp Val Pro
225                 230                 235                 240

Ser Val Ser Asn Pro Gly Thr Thr Asn Thr Asn Thr Ser Asn Asn Ser
                245                 250                 255

Asn Thr Asn Ser Gln Ala Ser Gln Ser Asn Asp Ile Asp Ser Leu Leu
            260                 265                 270

Lys Gln Leu Tyr Lys Leu Pro Leu Ser Gln Arg His Val Glu Ser Asp
        275                 280                 285

Gly Leu Ile Phe Asp Pro Ala Gln Ile Thr Ser Arg Thr Ala Arg Gly
    290                 295                 300

Val Ala Val Pro His Gly Asn His Tyr His Phe Ile Pro Tyr Glu Gln
305                 310                 315                 320

Met Ser Glu Leu Glu Lys Arg Ile Ala Arg Ile Ile Pro Leu Arg Tyr
                325                 330                 335

Arg Ser Asn His Trp Val Pro Asp Ser Arg Pro Glu Glu Pro Ser Pro
            340                 345                 350

Gln Pro Thr Pro Glu Pro Ser Pro Ser Pro Gln Pro Ala Pro Asn Pro
        355                 360                 365

Gln Pro Ala Pro Ser Asn Pro Ile Asp Glu Lys Leu Val Lys Glu Ala
    370                 375                 380

Val Arg Lys Val Gly Asp Gly Tyr Val Phe Glu Glu Asn Gly Val Ser
385                 390                 395                 400

Arg Tyr Ile Pro Ala Lys Asn Leu Ser Ala Glu Thr Ala Ala Gly Ile
                405                 410                 415

Asp Ser Lys Leu Ala Lys Gln Glu Ser Leu Ser His Lys Leu Gly Ala
            420                 425                 430
```

| | | | | | | | | | | | |
|---|---|---|---|---|---|---|---|---|---|---|---|
|Lys|Lys|Thr|Asp|Leu|Pro|Ser|Ser|Asp|Arg|Glu|Phe|Tyr|Asn|Lys|Ala|
| | |435| | | |440| | | |445| |

Tyr Asp Leu Leu Ala Arg Ile His Gln Asp Leu Leu Asp Asn Lys Gly
450             455             460

Arg Gln Val Asp Phe Glu Ala Leu Asp Asn Leu Leu Glu Arg Leu Lys
465             470             475             480

Asp Val Ser Ser Asp Lys Val Lys Leu Val Asp Asp Ile Leu Ala Phe
        485             490             495

Leu Ala Pro Ile Arg His Pro Glu Arg Leu Gly Lys Pro Asn Ala Gln
            500             505             510

Ile Thr Tyr Thr Asp Asp Glu Ile Gln Val Ala Lys Leu Ala Gly Lys
        515             520             525

Tyr Thr Thr Glu Asp Gly Tyr Ile Phe Asp Pro Arg Asp Ile Thr Ser
        530             535             540

Asp Glu Gly Asp Ala Tyr Val Thr Pro His Met Thr His Ser His Trp
545             550             555             560

Ile Lys Lys Asp Ser Leu Ser Glu Ala Glu Arg Ala Ala Gln Ala
            565             570             575

Tyr Ala Lys Glu Lys Gly Leu Thr Pro Pro Ser Thr Asp His Gln Asp
            580             585             590

Ser Gly Asn Thr Glu Ala Lys Gly Ala Glu Ala Ile Tyr Asn Arg Val
        595             600             605

Lys Ala Ala Lys Lys Val Pro Leu Asp Arg Met Pro Tyr Asn Leu Gln
            610             615             620

Tyr Thr Val Glu Val Lys Asn Gly Ser Leu Ile Ile Pro His Tyr Asp
625             630             635             640

His Tyr His Asn Ile Lys Phe Glu Trp Phe Asp Glu Gly Leu Tyr Glu
            645             650             655

Ala Pro Lys Gly Tyr Thr Leu Glu Asp Leu Leu Ala Thr Val Lys Tyr
            660             665             670

Tyr Val Glu His Pro Asn Glu Arg Pro His Ser Asp Asn Gly Phe Gly
        675             680             685

Asn Ala
    690

```
<210> SEQ ID NO 80
<211> LENGTH: 2469
<212> TYPE: DNA
<213> ORGANISM: S. pneumoniae

<400> SEQUENCE: 80
gtgaagaaaa catatggtta tatcggctca gttgctgcca ttttactagc tactcatatt      60
ggaagttacc aacttggtaa gcatcatatg ggtctagcaa caaaggacaa tcagattgcc     120
tatattgatg acagcaaagg taaggcaaaa gcccctaaaa caaacaaaac gatggatcaa     180
atcagtgctg aagaaggcat ctctgctgaa cagatcgtag tcaaaattac tgaccaaggc     240
tatgtgacct cacacggtga ccattatcat ttttacaatg ggaaagttcc ttatgatgcg     300
attattagtg aagagttgtt gatgacggat cctaattacc gttttaaaca atcagacgtt     360
atcaatgaaa tcttagacgg ttacgttatt aaagtcaatg caactatta tgtttacctc     420 aagccaggta gtaagcgcaa aaacattcga accaaacaac aaattgctga gcaagtagcc     480
aaaggaacta agaagctaaa gaaaaaggt ttagctcaag tggcccatct cagtaaagaa     540
gaagttgcgg cagtcaatga agcaaaaaga caaggacgct atactacaga cgatggctat     600
```

```
attttttagtc cgacagatat cattgatgat ttaggagatg cttatttagt acctcatggt    660
aatcactatc attatattcc taaaaaggat ttgtctccaa gtgagctagc tgctgcacaa    720
gcctactgga gtcaaaaaca aggtcgaggt gctagaccgt ctgattaccg cccgacacca    780
gccccaggtc gtaggaaagc cccaattcct gatgtgacgc ctaaccctgg acaaggtcat    840
cagccagata acgtggcta tcatccagcg cctcctaggc caaatgatgc gtcacaaaac    900
aaacaccaaa gagatgagtt taaaggaaaa acctttaagg aacttttaga tcaactacac    960
cgtcttgatt tgaaataccg tcatgtggaa gaagatgggt tgattttga accgactcaa   1020
gtgatcaaat caaacgcttt tgggtatgtg gtgcctcatg gagatcatta tcatattatc   1080
ccaagaagtc agttatcacc tcttgaaatg gaattagcag atcgatactt agctggccaa   1140
actgaggaca atgactcagg ttcagagcac tcaaaaccat cagataaaga agtgacacat   1200
accttttcttg gtcatcgcat caaagcttac ggaaaaggct tagatggtaa accatatgat   1260
acgagtgatg cttatgtttt tagtaaagaa tccattcatt cagtgataa atcaggagtt   1320
acagctaaac acggagatca tttccactat ataggatttg agaacttga acaatatgag   1380
ttggatgagg tcgctaactg ggtgaaagca aaggtcaag ctgatgagct tgctgctgct   1440
ttggatcagg aacaaggcaa agaaaaacca ctctttgaca ctaaaaaagt gagtcgcaaa   1500
gtaacaaaag atggtaaagt gggctatatg atgccaaaag atggtaagga ctatttctat   1560
gctcgtgatc aacttgattt gactcagatt gcctttgccg aacaagaact aatgcttaaa   1620
gataagaagc attaccgtta tgacattgtt gacacaggta ttgagccacg acttgctgta   1680
gatgtgtcaa gtctgccgat gcatgctggt aatgctactt acgatactgg aagttcgttt   1740
gttatcccac atattgatca tatccatgtc gttccgtatt catggttgac gcgcgatcag   1800
attgcaacag tcaagtatgt gatgcaacac cccgaagttc gtccggatgt atggtctaag   1860
ccagggcatg aagagtcagg ttcggtcatt ccaaatgtta cgcctcttga taaacgtgct   1920
ggtatgccaa actggcaaat tatccattct gctgaagaag ttcaaaaagc cctagcagaa   1980
ggtcgttttg caacaccaga cggctatatt ttcgatccac gagatgtttt ggccaaagaa   2040
acttttgtat ggaaagatgg ctcctttagc atcccaagag cagatggcag ttcattgaga   2100
accattaata aatctgatct atcccaagct gagtggcaac aagctcaaga gttattggca   2160
aagaaaaata ctggtgatgc tactgatacg gataaaccca agaaaagca acaggcagat   2220
aagagcaatg aaaaccaaca gccaagtgaa gccagtaaag aagaaaaaga atcagatgac   2280
tttatagaca gtttaccaga ctatggtcta gatagagcaa ccctagaaga tcatatcaat   2340
caattagcac aaaaagctaa tatcgatcct aagtatctca ttttccaacc agaaggtgtc   2400
caatttata taaaaatgg tgaattggta acttatgata tcaagacact tcaacaaata   2460
aacccttaa                                                          2469
```

<210> SEQ ID NO 81
<211> LENGTH: 823
<212> TYPE: PRT
<213> ORGANISM: S. pneumoniae

<400> SEQUENCE: 81

Val Lys Lys Thr Tyr Gly Tyr Ile Gly Ser Val Ala Ala Ile Leu Leu
1               5                   10                  15

Ala Thr His Ile Gly Ser Tyr Gln Leu Gly Lys His His Met Gly Leu
            20                  25                  30

Ala Thr Lys Asp Asn Gln Ile Ala Tyr Ile Asp Asp Ser Lys Gly Lys

-continued

```
           35                  40                  45
Ala Lys Ala Pro Lys Thr Asn Lys Thr Met Asp Gln Ile Ser Ala Glu
50                  55                  60

Glu Gly Ile Ser Ala Glu Gln Ile Val Val Lys Ile Thr Asp Gln Gly
65                  70                  75                  80

Tyr Val Thr Ser His Gly Asp His Tyr His Phe Tyr Asn Gly Lys Val
                    85                  90                  95

Pro Tyr Asp Ala Ile Ile Ser Glu Glu Leu Leu Met Thr Asp Pro Asn
                100                 105                 110

Tyr Arg Phe Lys Gln Ser Asp Val Ile Asn Glu Ile Leu Asp Gly Tyr
            115                 120                 125

Val Ile Lys Val Asn Gly Asn Tyr Tyr Val Tyr Leu Lys Pro Gly Ser
130                 135                 140

Lys Arg Lys Asn Ile Arg Thr Lys Gln Gln Ile Ala Glu Gln Val Ala
145                 150                 155                 160

Lys Gly Thr Lys Glu Ala Lys Glu Lys Gly Leu Ala Gln Val Ala His
                165                 170                 175

Leu Ser Lys Glu Glu Val Ala Ala Val Asn Glu Ala Lys Arg Gln Gly
                180                 185                 190

Arg Tyr Thr Thr Asp Asp Gly Tyr Ile Phe Ser Pro Thr Asp Ile Ile
            195                 200                 205

Asp Asp Leu Gly Asp Ala Tyr Leu Val Pro His Gly Asn His Tyr His
            210                 215                 220

Tyr Ile Pro Lys Lys Asp Leu Ser Pro Ser Glu Leu Ala Ala Ala Gln
225                 230                 235                 240

Ala Tyr Trp Ser Gln Lys Gln Gly Arg Gly Ala Arg Pro Ser Asp Tyr
                245                 250                 255

Arg Pro Thr Pro Ala Pro Gly Arg Arg Lys Ala Pro Ile Pro Asp Val
            260                 265                 270

Thr Pro Asn Pro Gly Gln Gly His Gln Pro Asp Asn Gly Gly Tyr His
            275                 280                 285

Pro Ala Pro Pro Arg Pro Asn Asp Ala Ser Gln Asn Lys His Gln Arg
290                 295                 300

Asp Glu Phe Lys Gly Lys Thr Phe Lys Glu Leu Leu Asp Gln Leu His
305                 310                 315                 320

Arg Leu Asp Leu Lys Tyr Arg His Val Glu Glu Asp Gly Leu Ile Phe
                325                 330                 335

Glu Pro Thr Gln Val Ile Lys Ser Asn Ala Phe Gly Tyr Val Val Pro
            340                 345                 350

His Gly Asp His Tyr His Ile Ile Pro Arg Ser Gln Leu Ser Pro Leu
            355                 360                 365

Glu Met Glu Leu Ala Asp Arg Tyr Leu Ala Gly Gln Thr Glu Asp Asn
370                 375                 380

Asp Ser Gly Ser Glu His Ser Lys Pro Ser Asp Lys Glu Val Thr His
385                 390                 395                 400

Thr Phe Leu Gly His Arg Ile Lys Ala Tyr Gly Lys Gly Leu Asp Gly
                405                 410                 415

Lys Pro Tyr Asp Thr Ser Asp Ala Tyr Val Phe Ser Lys Glu Ser Ile
            420                 425                 430

His Ser Val Asp Lys Ser Gly Val Thr Ala Lys His Gly Asp His Phe
            435                 440                 445

His Tyr Ile Gly Phe Gly Glu Leu Glu Gln Tyr Glu Leu Asp Glu Val
450                 455                 460
```

```
Ala Asn Trp Val Lys Ala Lys Gly Gln Ala Asp Glu Leu Ala Ala Ala
465                 470                 475                 480

Leu Asp Gln Glu Gln Gly Lys Glu Lys Pro Leu Phe Asp Thr Lys Lys
                485                 490                 495

Val Ser Arg Lys Val Thr Lys Asp Gly Lys Val Gly Tyr Met Met Pro
            500                 505                 510

Lys Asp Gly Lys Asp Tyr Phe Tyr Ala Arg Asp Gln Leu Asp Leu Thr
        515                 520                 525

Gln Ile Ala Phe Ala Glu Gln Glu Leu Met Leu Lys Asp Lys Lys His
    530                 535                 540

Tyr Arg Tyr Asp Ile Val Asp Thr Gly Ile Glu Pro Arg Leu Ala Val
545                 550                 555                 560

Asp Val Ser Ser Leu Pro Met His Ala Gly Asn Ala Thr Tyr Asp Thr
                565                 570                 575

Gly Ser Ser Phe Val Ile Pro His Ile Asp His Ile His Val Val Pro
            580                 585                 590

Tyr Ser Trp Leu Thr Arg Asp Gln Ile Ala Thr Val Lys Tyr Val Met
        595                 600                 605

Gln His Pro Glu Val Arg Pro Asp Val Trp Ser Lys Pro Gly His Glu
    610                 615                 620

Glu Ser Gly Ser Val Ile Pro Asn Val Thr Pro Leu Asp Lys Arg Ala
625                 630                 635                 640

Gly Met Pro Asn Trp Gln Ile Ile His Ser Ala Glu Glu Val Gln Lys
                645                 650                 655

Ala Leu Ala Glu Gly Arg Phe Ala Thr Pro Asp Gly Tyr Ile Phe Asp
            660                 665                 670

Pro Arg Asp Val Leu Ala Lys Glu Thr Phe Val Trp Lys Asp Gly Ser
        675                 680                 685

Phe Ser Ile Pro Arg Ala Asp Gly Ser Ser Leu Arg Thr Ile Asn Lys
    690                 695                 700

Ser Asp Leu Ser Gln Ala Glu Trp Gln Gln Ala Gln Glu Leu Leu Ala
705                 710                 715                 720

Lys Lys Asn Thr Gly Asp Ala Thr Asp Thr Asp Lys Pro Lys Glu Lys
                725                 730                 735

Gln Gln Ala Asp Lys Ser Asn Glu Asn Gln Gln Pro Ser Glu Ala Ser
            740                 745                 750

Lys Glu Glu Lys Glu Ser Asp Asp Phe Ile Asp Ser Leu Pro Asp Tyr
        755                 760                 765

Gly Leu Asp Arg Ala Thr Leu Glu Asp His Ile Asn Gln Leu Ala Gln
    770                 775                 780

Lys Ala Asn Ile Asp Pro Lys Tyr Leu Ile Phe Gln Pro Glu Gly Val
785                 790                 795                 800

Gln Phe Tyr Asn Lys Asn Gly Glu Leu Val Thr Tyr Asp Ile Lys Thr
                805                 810                 815

Leu Gln Gln Ile Asn Pro Pro
            820

<210> SEQ ID NO 82
<211> LENGTH: 2472
<212> TYPE: DNA
<213> ORGANISM: S. pneumoniae

<400> SEQUENCE: 82
gtgaagaaaa catatggtta tatcggctca gttgctgcca ttttactagc tactcatatt    60
```

-continued

```
ggaagttacc aacttggtaa gcatcatatg ggtctagcaa caaaggacaa tcagattgcc      120
tatattgatg atagcaaagg taaggcaaaa gcccctaaaa caaacaaaac gatggatcaa      180
atcagtgctg aagaaggcat ctctgctgaa cagatcgtag tcaaaattac tgaccaaggt      240
tatgtgacct cacacggtga ccattatcat ttttacaatg ggaaagttcc ttatgatgcg      300
attattagtg aagagttgtt gatgacggat cctaattacc attttaaaca atcagacgtt      360
atcaatgaaa tcttagacgg ttacgttatt aaagtcaatg gcaactatta tgtttacctc      420
aagccaggta gtaagcgcaa aaacattcga accaaacaac aaattgctga gcaagtagcc      480
aaaggaacta agaagctaa agaaaaaggt ttagctcaag tggcccatct cagtaaagaa      540
gaagttgcgg cagtcaatga agcaaaaaga caaggacgct atactacaga cgatggctat      600 attttagtc cgacagatat cattgatgat ttaggagacg cttatttagt acctcatggt      660
aatcactatc attatattcc taaaaaagat ttgtctccaa gtgagctagc tgctgcacaa      720
gcttactgga gtcaaaaaca aggtcgaggt gctagaccgt ctgattaccg cccgacacca      780
gccccaggtc gtaggaaagc tccaattcct gatgtgacgc taacccctgg acaaggtcat      840
cagccagata acggtggcta tcatccagcg cctcctaggc caaatgatgc gtcacaaaac      900
aaacaccaaa gagatgagtt taaaggaaaa acctttaagg aacttttaga tcaactacac      960
cgtcttgatt tgaaataccg tcatgtggaa gaagatgggt tgattttga accgactcaa     1020 gtgatcaaat caaacgcttt tgggtatgtg gtgcctcatg gagatcatta tcatattatc     1080
ccaagaagtc agttatcacc tcttgaaatg gaattagcag atcgatactt agccggtcaa     1140
actgaggaca atgattcagg ttcagatcac tcaaaaccat cagataaaga agtgacacat     1200 accttttcttg gtcatcgcat caaagcttac ggaaaaggct tagatggtaa accatatgat     1260
acgagtgatg cttatgtttt tagtaaagaa tccattcatt cagtggataa atcaggagtt     1320
acagctaaac acggagatca tttccactat ataggatttg gagaacttga acaatatgag     1380
ttggatgagg tcgctaactg ggtgaaagca aaggtcaag ctgatgagct tgctgctgct     1440
ttggatcagg aacaaggcaa agaaaaacca ctctttgaca ctaaaaaagt gagtcgcaaa     1500
gtaacaaaag atggtaaagt gggctatatt atgccaaaag atggcaagga ctatttctat     1560
gctcgtgatc aacttgattt gactcagatt gcctttgccg aacaagaact aatgcttaaa     1620
gataagaacc attaccgtta tgacattgtt gacacaggta ttgagccacg acttgctgta     1680
gatgtgtcaa gtctgccgat gcatgctggt aatgctactt cgatactgg aagttcgttt     1740 gttatccctc atattgatca tatccatgtc gttccgtatt catggttgac gcgcgatcag     1800
attgcaacaa tcaagtatgt gatgcaacac cccgaagttc gtccagatgt atggtctaag     1860
ccagggcatg aagagtcagg ttcggtcatt ccaaatgtta cgcctcttga taaacgtgct     1920
ggtatgccaa attggcaaat catccattct gctgaagaag ttcaaaaagc cctagcagaa     1980
ggtcgttttg caacaccaga cggctatatt ttcgatccac gagatgtttt ggccaaagaa     2040
acttttgtat ggaaagatgg ctcctttagc atcccaagag cagatggcag ttcattgaga     2100
accattaata aatctgatct atcccaagct gagtggcaac aagctcaaga gttattggca     2160
aagaaaaacg ctggtgatgc tactgatacg gataaaccca agaaaagca acaggcagat     2220 aagagcaatg aaaaccaaca gccaagtgaa gccagtaaag aagaagaaaa agaatcagat     2280
gactttatag acagtttacc agactatggt ctagatagag caaccctaga agatcatatc     2340
aatcaattag cacaaaaagc taatatcgat cctaagtatc tcattttcca accagaaggt     2400
```

-continued

```
gtccaatttt ataataaaaa tggtgaatta gtaacttatg atatcaagac gcttcaacaa   2460
ataaaccctt aa                                                       2472
```

<210> SEQ ID NO 83
<211> LENGTH: 824
<212> TYPE: PRT
<213> ORGANISM: S. pneumoniae

<400> SEQUENCE: 83

```
Val Lys Lys Thr Tyr Gly Tyr Ile Gly Ser Val Ala Ala Ile Leu Leu
1               5                   10                  15

Ala Thr His Ile Gly Ser Tyr Gln Leu Gly Lys His His Met Gly Leu
            20                  25                  30

Ala Thr Lys Asp Asn Gln Ile Ala Tyr Ile Asp Asp Ser Lys Gly Lys
        35                  40                  45

Ala Lys Ala Pro Lys Thr Asn Lys Thr Met Asp Gln Ile Ser Ala Glu
    50                  55                  60

Glu Gly Ile Ser Ala Glu Gln Ile Val Val Lys Ile Thr Asp Gln Gly
65                  70                  75                  80

Tyr Val Thr Ser His Gly Asp His Tyr His Phe Tyr Asn Gly Lys Val
                85                  90                  95

Pro Tyr Asp Ala Ile Ile Ser Glu Glu Leu Leu Met Thr Asp Pro Asn
            100                 105                 110

Tyr His Phe Lys Gln Ser Asp Val Ile Asn Glu Ile Leu Asp Gly Tyr
        115                 120                 125

Val Ile Lys Val Asn Gly Asn Tyr Tyr Val Tyr Leu Lys Pro Gly Ser
    130                 135                 140

Lys Arg Lys Asn Ile Arg Thr Lys Gln Gln Ile Ala Glu Gln Val Ala
145                 150                 155                 160

Lys Gly Thr Lys Glu Ala Lys Glu Lys Gly Leu Ala Gln Val Ala His
                165                 170                 175

Leu Ser Lys Glu Glu Val Ala Ala Val Asn Glu Ala Lys Arg Gln Gly
            180                 185                 190

Arg Tyr Thr Thr Asp Asp Gly Tyr Ile Phe Ser Pro Thr Asp Ile Ile
        195                 200                 205

Asp Asp Leu Gly Asp Ala Tyr Leu Val Pro His Gly Asn His Tyr His
    210                 215                 220

Tyr Ile Pro Lys Lys Asp Leu Ser Pro Ser Glu Leu Ala Ala Ala Gln
225                 230                 235                 240

Ala Tyr Trp Ser Gln Lys Gly Arg Gly Ala Arg Pro Ser Asp Tyr
                245                 250                 255

Arg Pro Thr Pro Ala Pro Gly Arg Arg Lys Ala Pro Ile Pro Asp Val
            260                 265                 270

Thr Pro Asn Pro Gly Gln Gly His Gln Pro Asp Asn Gly Gly Tyr His
        275                 280                 285

Pro Ala Pro Pro Arg Pro Asn Asp Ala Ser Gln Asn Lys His Gln Arg
    290                 295                 300

Asp Glu Phe Lys Gly Lys Thr Phe Lys Glu Leu Leu Asp Gln Leu His
305                 310                 315                 320

Arg Leu Asp Leu Lys Tyr Arg His Val Glu Glu Asp Gly Leu Ile Phe
                325                 330                 335

Glu Pro Thr Gln Val Ile Lys Ser Asn Ala Phe Gly Tyr Val Val Pro
            340                 345                 350

His Gly Asp His Tyr His Ile Ile Pro Arg Ser Gln Leu Ser Pro Leu
```

-continued

```
                355                 360                 365
Glu Met Glu Leu Ala Asp Arg Tyr Leu Ala Gly Gln Thr Glu Asp Asn
    370                 375                 380
Asp Ser Gly Ser Asp His Ser Lys Pro Ser Asp Lys Glu Val Thr His
385                 390                 395                 400
Thr Phe Leu Gly His Arg Ile Lys Ala Tyr Gly Lys Gly Leu Asp Gly
                405                 410                 415
Lys Pro Tyr Asp Thr Ser Asp Ala Tyr Val Phe Ser Lys Glu Ser Ile
            420                 425                 430
His Ser Val Asp Lys Ser Gly Val Thr Ala Lys His Gly Asp His Phe
        435                 440                 445
His Tyr Ile Gly Phe Gly Glu Leu Glu Gln Tyr Glu Leu Asp Glu Val
    450                 455                 460
Ala Asn Trp Val Lys Ala Lys Gly Gln Ala Asp Glu Leu Ala Ala Ala
465                 470                 475                 480
Leu Asp Gln Glu Gln Gly Lys Glu Lys Pro Leu Phe Asp Thr Lys Lys
                485                 490                 495
Val Ser Arg Lys Val Thr Lys Asp Gly Lys Val Gly Tyr Ile Met Pro
            500                 505                 510
Lys Asp Gly Lys Asp Tyr Phe Tyr Ala Arg Asp Gln Leu Asp Leu Thr
        515                 520                 525
Gln Ile Ala Phe Ala Glu Gln Glu Leu Met Leu Lys Asp Lys Asn His
    530                 535                 540
Tyr Arg Tyr Asp Ile Val Asp Thr Gly Ile Glu Pro Arg Leu Ala Val
545                 550                 555                 560
Asp Val Ser Ser Leu Pro Met His Ala Gly Asn Ala Thr Tyr Asp Thr
                565                 570                 575
Gly Ser Ser Phe Val Ile Pro His Ile Asp His Ile His Val Val Pro
            580                 585                 590
Tyr Ser Trp Leu Thr Arg Asp Gln Ile Ala Thr Ile Lys Tyr Val Met
        595                 600                 605
Gln His Pro Glu Val Arg Pro Asp Val Trp Ser Lys Pro Gly His Glu
    610                 615                 620
Glu Ser Gly Ser Val Ile Pro Asn Val Thr Pro Leu Asp Lys Arg Ala
625                 630                 635                 640
Gly Met Pro Asn Trp Gln Ile Ile His Ser Ala Glu Glu Val Gln Lys
                645                 650                 655
Ala Leu Ala Glu Gly Arg Phe Ala Thr Pro Asp Gly Tyr Ile Phe Asp
            660                 665                 670
Pro Arg Asp Val Leu Ala Lys Glu Thr Phe Val Trp Lys Asp Gly Ser
        675                 680                 685
Phe Ser Ile Pro Arg Ala Asp Gly Ser Ser Leu Arg Thr Ile Asn Lys
    690                 695                 700
Ser Asp Leu Ser Gln Ala Glu Trp Gln Gln Ala Gln Glu Leu Leu Ala
705                 710                 715                 720
Lys Lys Asn Ala Gly Asp Ala Thr Asp Thr Asp Lys Pro Lys Glu Lys
                725                 730                 735
Gln Gln Ala Asp Lys Ser Asn Glu Asn Gln Gln Pro Ser Glu Ala Ser
            740                 745                 750
Lys Glu Glu Glu Lys Glu Ser Asp Asp Phe Ile Asp Ser Leu Pro Asp
        755                 760                 765
Tyr Gly Leu Asp Arg Ala Thr Leu Glu Asp His Ile Asn Gln Leu Ala
    770                 775                 780
```

```
Gln Lys Ala Asn Ile Asp Pro Lys Tyr Leu Ile Phe Gln Pro Glu Gly
785                 790                 795                 800

Val Gln Phe Tyr Asn Lys Asn Gly Glu Leu Val Thr Tyr Asp Ile Lys
                805                 810                 815

Thr Leu Gln Gln Ile Asn Pro Pro
            820

<210> SEQ ID NO 84
<211> LENGTH: 1019
<212> TYPE: PRT
<213> ORGANISM: S. pneumoniae

<400> SEQUENCE: 84

Cys Ala Tyr Ala Leu Asn Gln His Arg Ser Gln Glu Asn Lys Asp Asn
1               5                   10                  15

Asn Arg Val Ser Tyr Val Asp Gly Ser Gln Ser Gln Lys Ser Glu
            20                  25                  30

Asn Leu Thr Pro Asp Gln Val Ser Gln Lys Glu Gly Ile Gln Ala Glu
            35                  40                  45

Gln Ile Val Ile Lys Ile Thr Asp Gln Gly Tyr Val Thr Ser His Gly
50                  55                  60

Asp His Tyr His Tyr Asn Gly Lys Val Pro Tyr Asp Ala Leu Phe
65                  70                  75                  80

Ser Glu Glu Leu Leu Met Lys Asp Pro Asn Tyr Gln Leu Lys Asp Ala
                85                  90                  95

Asp Ile Val Asn Glu Val Lys Gly Gly Tyr Ile Ile Lys Val Asp Gly
            100                 105                 110

Lys Tyr Tyr Val Tyr Leu Lys Asp Ala Ala His Ala Asp Asn Val Arg
            115                 120                 125

Thr Lys Asp Glu Ile Asn Arg Gln Lys Gln Glu His Val Lys Asp Asn
130                 135                 140

Glu Lys Val Asn Ser Asn Val Ala Val Ala Arg Ser Gln Gly Arg Tyr
145                 150                 155                 160

Thr Thr Asn Asp Gly Tyr Val Phe Asn Pro Ala Asp Ile Ile Glu Asp
                165                 170                 175

Thr Gly Asn Ala Tyr Ile Val Pro His Arg Gly His Tyr His Tyr Ile
            180                 185                 190

Pro Lys Ser Asp Leu Ser Ala Ser Glu Leu Ala Ala Lys Ala His
            195                 200                 205

Leu Ala Gly Lys Asn Met Gln Pro Ser Gln Leu Ser Tyr Ser Ser Thr
210                 215                 220

Ala Ser Asp Asn Asn Thr Gln Ser Val Ala Lys Gly Ser Thr Ser Lys
225                 230                 235                 240

Pro Ala Asn Lys Ser Glu Asn Leu Gln Ser Leu Leu Lys Glu Leu Tyr
                245                 250                 255

Asp Ser Pro Ser Ala Gln Arg Tyr Ser Glu Ser Asp Gly Leu Val Phe
            260                 265                 270

Asp Pro Ala Lys Ile Ile Ser Arg Thr Pro Asn Gly Val Ala Ile Pro
            275                 280                 285

His Gly Asp His Tyr His Phe Ile Pro Tyr Ser Lys Leu Ser Ala Leu
        290                 295                 300

Glu Glu Lys Ile Ala Arg Met Val Pro Ile Ser Gly Thr Gly Ser Thr
305                 310                 315                 320

Val Ser Thr Asn Ala Lys Pro Asn Glu Val Val Ser Ser Leu Gly Ser
```

```
                    325                 330                 335
Leu Ser Ser Asn Pro Ser Ser Leu Thr Thr Ser Lys Glu Leu Ser Ser
                340                 345                 350
Ala Ser Asp Gly Tyr Ile Phe Asn Pro Lys Asp Ile Val Glu Glu Thr
                355                 360                 365
Ala Thr Ala Tyr Ile Val Arg His Gly Asp His Phe His Tyr Ile Pro
            370                 375                 380
Lys Ser Asn Gln Ile Gly Gln Pro Thr Leu Pro Asn Asn Ser Leu Ala
385                 390                 395                 400
Thr Pro Ser Pro Ser Leu Pro Ile Asn Pro Gly Thr Ser His Glu Lys
                405                 410                 415
His Glu Glu Asp Gly Tyr Gly Phe Asp Ala Asn Arg Ile Ile Ala Glu
                420                 425                 430
Asp Glu Ser Gly Phe Val Met Ser His Gly Asp His Asn His Tyr Phe
            435                 440                 445
Phe Lys Lys Asp Leu Thr Glu Gln Ile Lys Ala Ala Gln Lys His
            450                 455                 460
Leu Glu Glu Val Lys Thr Ser His Asn Gly Leu Asp Ser Leu Ser Ser
465                 470                 475                 480
His Glu Gln Asp Tyr Pro Ser Asn Ala Lys Glu Met Lys Asp Leu Asp
                485                 490                 495
Lys Lys Ile Glu Glu Lys Ile Ala Gly Ile Met Lys Gln Tyr Gly Val
                500                 505                 510
Lys Arg Glu Ser Ile Val Val Asn Lys Glu Lys Asn Ala Ile Ile Tyr
            515                 520                 525
Pro His Gly Asp His His His Ala Asp Pro Ile Asp Glu His Lys Pro
            530                 535                 540
Val Gly Ile Gly His Ser His Ser Asn Tyr Glu Leu Phe Lys Pro Glu
545                 550                 555                 560
Glu Gly Val Ala Lys Glu Gly Asn Lys Val Tyr Thr Gly Glu Glu
                565                 570                 575
Leu Thr Asn Val Val Asn Leu Leu Lys Asn Ser Thr Phe Asn Asn Gln
                580                 585                 590
Asn Phe Thr Leu Ala Asn Gly Gln Lys Arg Val Ser Phe Ser Phe Pro
            595                 600                 605
Pro Glu Leu Glu Lys Lys Leu Gly Ile Asn Met Leu Val Lys Leu Ile
            610                 615                 620
Thr Pro Asp Gly Lys Val Leu Gly Lys Val Ser Gly Lys Val Phe Gly
625                 630                 635                 640
Glu Gly Val Gly Asn Ile Ala Asn Phe Glu Leu Asp Gln Pro Tyr Leu
                645                 650                 655
Pro Gly Gln Thr Phe Lys Tyr Thr Ile Ala Ser Lys Asp Tyr Pro Glu
                660                 665                 670
Val Ser Tyr Asp Gly Thr Phe Thr Val Pro Thr Ser Leu Ala Tyr Lys
            675                 680                 685
Met Ala Ser Gln Thr Ile Phe Tyr Pro Phe His Ala Gly Asp Thr Tyr
            690                 695                 700
Leu Arg Val Asn Pro Gln Phe Ala Val Pro Lys Gly Thr Asp Ala Leu
705                 710                 715                 720
Val Arg Val Phe Asp Glu Phe His Gly Asn Ala Tyr Leu Glu Asn Asn
                725                 730                 735
Tyr Lys Val Gly Glu Ile Lys Leu Pro Ile Pro Lys Leu Asn Gln Gly
            740                 745                 750
```

```
Thr Thr Arg Thr Ala Gly Asn Lys Ile Pro Val Thr Phe Met Ala Asn
        755                 760                 765

Ala Tyr Leu Asp Asn Gln Ser Thr Tyr Ile Val Glu Val Pro Ile Leu
        770                 775                 780

Glu Lys Glu Asn Gln Thr Asp Lys Pro Ser Ile Leu Pro Gln Phe Lys
785                 790                 795                 800

Arg Asn Lys Ala Gln Glu Asn Ser Lys Phe Asp Glu Lys Val Glu Glu
                805                 810                 815

Pro Lys Thr Ser Glu Lys Val Glu Lys Glu Lys Leu Ser Glu Thr Gly
                820                 825                 830

Asn Ser Thr Ser Asn Ser Thr Leu Glu Glu Val Pro Thr Val Asp Pro
            835                 840                 845

Val Gln Glu Lys Val Ala Lys Phe Ala Glu Ser Tyr Gly Met Lys Leu
        850                 855                 860

Glu Asn Val Leu Phe Asn Met Asp Gly Thr Ile Glu Leu Tyr Leu Pro
865                 870                 875                 880

Ser Gly Glu Val Ile Lys Lys Asn Met Ala Asp Phe Thr Gly Glu Ala
                885                 890                 895

Pro Gln Gly Asn Gly Glu Asn Lys Pro Ser Glu Asn Gly Lys Val Ser
                900                 905                 910

Thr Gly Thr Val Glu Asn Gln Pro Thr Glu Asn Lys Pro Ala Asp Ser
            915                 920                 925

Leu Pro Glu Ala Pro Asn Glu Lys Pro Val Lys Pro Glu Asn Ser Thr
        930                 935                 940

Asp Asn Gly Met Leu Asn Pro Glu Gly Asn Val Gly Ser Asp Pro Met
945                 950                 955                 960

Leu Asp Pro Ala Leu Glu Ala Pro Ala Val Asp Pro Val Gln Glu
                965                 970                 975

Lys Leu Glu Lys Phe Thr Ala Ser Tyr Gly Leu Gly Leu Asp Ser Val
            980                 985                 990

Ile Phe Asn Met Asp Gly Thr Ile Glu Leu Arg Leu Pro Ser Gly Glu
        995                 1000                1005

Val Ile Lys Lys Asn Leu Ser Asp Leu Ile Ala
    1010                1015

<210> SEQ ID NO 85
<211> LENGTH: 1019
<212> TYPE: PRT
<213> ORGANISM: S. pneumoniae

<400> SEQUENCE: 85

Cys Ala Tyr Ala Leu Asn Gln His Arg Ser Gln Glu Asn Lys Asp Asn
1               5                   10                  15

Asn Arg Val Ser Tyr Val Asp Gly Ser Gln Ser Ser Gln Lys Ser Glu
            20                  25                  30

Asn Leu Thr Pro Asp Gln Val Ser Gln Lys Glu Gly Ile Gln Ala Glu
        35                  40                  45

Gln Ile Val Ile Lys Ile Thr Asp Gln Gly Tyr Val Thr Ser His Gly
    50                  55                  60

Asp His Tyr His Tyr Tyr Asn Gly Lys Val Pro Tyr Asp Ala Leu Phe
65              70                  75                  80

Ser Glu Glu Leu Leu Met Lys Asp Pro Asn Tyr Gln Leu Lys Asp Ala
            85                  90                  95

Asp Ile Val Asn Glu Val Lys Gly Gly Tyr Ile Ile Lys Val Asp Gly
```

```
            100                 105                 110
Lys Tyr Tyr Val Tyr Leu Lys Asp Ala Ala His Ala Asp Asn Val Arg
        115                 120                 125

Thr Lys Asp Glu Ile Asn Arg Gln Lys Gln Glu His Val Lys Asp Asn
    130                 135                 140

Glu Lys Val Asn Ser Asn Val Ala Val Ala Arg Ser Gln Gly Arg Tyr
145                 150                 155                 160

Thr Thr Asn Asp Gly Tyr Val Phe Asn Pro Ala Asp Ile Ile Glu Asp
                165                 170                 175

Thr Gly Asn Ala Tyr Ile Val Pro His Gly His Tyr His Tyr Ile
            180                 185                 190

Pro Lys Ser Asp Leu Ser Ala Ser Glu Leu Ala Ala Lys Ala His
        195                 200                 205

Leu Ala Gly Lys Asn Met Gln Pro Ser Gln Leu Ser Tyr Ser Ser Thr
    210                 215                 220

Ala Ser Asp Asn Asn Thr Gln Ser Val Ala Lys Gly Ser Thr Ser Lys
225                 230                 235                 240

Pro Ala Asn Lys Ser Glu Asn Leu Gln Ser Leu Leu Lys Glu Leu Tyr
                245                 250                 255

Asp Ser Pro Ser Ala Gln Arg Tyr Ser Glu Ser Asp Gly Leu Val Phe
            260                 265                 270

Asp Pro Ala Lys Ile Ile Ser Arg Thr Pro Asn Gly Val Ala Ile Pro
        275                 280                 285

His Gly Asp His Tyr His Phe Ile Pro Tyr Ser Lys Leu Ser Ala Leu
    290                 295                 300

Glu Glu Lys Ile Ala Arg Arg Val Pro Ile Ser Gly Thr Gly Ser Thr
305                 310                 315                 320

Val Ser Thr Asn Ala Lys Pro Asn Glu Val Val Ser Ser Leu Gly Ser
                325                 330                 335

Leu Ser Ser Asn Pro Ser Ser Leu Thr Thr Ser Lys Glu Leu Ser Ser
            340                 345                 350

Ala Ser Asp Gly Tyr Ile Phe Asn Pro Lys Asp Ile Val Glu Glu Thr
        355                 360                 365

Ala Thr Ala Tyr Ile Val Arg His Gly Asp His Phe His Tyr Ile Pro
    370                 375                 380

Lys Ser Asn Gln Ile Gly Gln Pro Thr Leu Pro Asn Asn Ser Leu Ala
385                 390                 395                 400

Thr Pro Ser Pro Ser Leu Pro Ile Asn Pro Gly Ile Ser His Glu Lys
                405                 410                 415

His Glu Glu Asp Gly Tyr Gly Phe Asp Ala Asn Arg Ile Ile Ala Glu
            420                 425                 430

Asp Glu Ser Gly Phe Ile Met Ser His Gly Asn His Asn His Tyr Phe
        435                 440                 445

Phe Lys Lys Asp Leu Thr Glu Glu Gln Ile Lys Ala Ala Gln Lys His
    450                 455                 460

Leu Glu Glu Val Lys Thr Ser His Asn Gly Leu Asp Ser Leu Ser Ser
465                 470                 475                 480

His Glu Gln Asp Tyr Pro Gly Asn Ala Lys Glu Met Lys Asp Leu Asp
                485                 490                 495

Lys Lys Ile Glu Glu Lys Ile Ala Gly Ile Met Lys Gln Tyr Gly Val
            500                 505                 510

Lys Arg Glu Ser Ile Val Val Asn Lys Glu Lys Asn Ala Ile Ile Tyr
        515                 520                 525
```

```
Pro His Gly Asp His His Ala Asp Pro Ile Asp Glu His Lys Pro
    530                 535                 540

Val Gly Ile Gly His Ser His Ser Asn Tyr Glu Leu Phe Lys Pro Glu
545                 550                 555                 560

Glu Gly Val Ala Lys Lys Gly Asn Lys Val Tyr Thr Gly Glu Glu
                565                 570                 575

Leu Thr Asn Val Val Asn Leu Leu Lys Asn Ser Thr Phe Asn Asn Gln
            580                 585                 590

Asn Phe Thr Leu Ala Asn Gly Gln Lys Arg Val Ser Phe Ser Phe Pro
        595                 600                 605

Pro Glu Leu Glu Lys Lys Leu Gly Ile Asn Met Leu Val Lys Leu Ile
    610                 615                 620

Thr Pro Asp Gly Lys Val Leu Glu Lys Val Ser Gly Lys Val Phe Gly
625                 630                 635                 640

Glu Gly Val Gly Asn Ile Ala Asn Phe Glu Leu Asp Gln Pro Tyr Leu
                645                 650                 655

Pro Gly Gln Thr Phe Lys Tyr Thr Ile Ala Ser Lys Asp Tyr Pro Glu
            660                 665                 670

Val Ser Tyr Asp Gly Thr Phe Thr Val Pro Thr Ser Leu Ala Tyr Lys
        675                 680                 685

Met Ala Ser Gln Thr Ile Phe Tyr Pro Phe His Ala Gly Asp Thr Tyr
    690                 695                 700

Leu Arg Val Asn Pro Gln Phe Ala Val Pro Lys Gly Thr Asp Ala Leu
705                 710                 715                 720

Val Arg Val Phe Asp Glu Phe His Gly Asn Ala Tyr Leu Glu Asn Asn
                725                 730                 735

Tyr Lys Val Gly Glu Ile Lys Leu Pro Ile Pro Lys Leu Asn Gln Gly
            740                 745                 750

Thr Thr Arg Thr Ala Gly Asn Lys Ile Pro Val Thr Phe Met Ala Asn
        755                 760                 765

Ala Tyr Leu Asp Asn Gln Ser Thr Tyr Ile Val Glu Val Pro Ile Leu
    770                 775                 780

Glu Lys Glu Asn Gln Thr Asp Lys Pro Ser Ile Leu Pro Gln Phe Lys
785                 790                 795                 800

Arg Asn Lys Ala Gln Glu Asn Ser Lys Leu Asp Glu Lys Val Glu Glu
                805                 810                 815

Pro Lys Thr Ser Glu Lys Val Glu Lys Glu Lys Leu Ser Glu Thr Gly
            820                 825                 830

Asn Ser Thr Ser Asn Ser Thr Leu Glu Glu Val Pro Thr Val Asp Pro
        835                 840                 845

Val Gln Glu Lys Val Ala Lys Phe Ala Glu Ser Tyr Gly Met Lys Leu
    850                 855                 860

Glu Asn Val Leu Phe Asn Met Asp Gly Thr Ile Glu Leu Tyr Leu Pro
865                 870                 875                 880

Ser Gly Glu Val Ile Lys Lys Asn Met Ala Asp Phe Thr Gly Glu Ala
                885                 890                 895

Pro Gln Gly Asn Gly Glu Asn Lys Pro Ser Glu Asn Gly Lys Val Ser
            900                 905                 910

Thr Gly Thr Val Glu Asn Gln Pro Thr Glu Asn Lys Pro Ala Asp Ser
        915                 920                 925

Leu Pro Glu Ala Pro Asn Glu Lys Pro Val Lys Pro Glu Asn Ser Thr
    930                 935                 940
```

```
Asp Asn Gly Met Leu Asn Pro Glu Gly Asn Val Gly Ser Asp Pro Met
945                 950                 955                 960

Leu Asp Pro Ala Leu Glu Ala Pro Ala Val Asp Pro Val Gln Glu
            965                 970                 975

Lys Leu Glu Lys Phe Thr Ala Ser Tyr Gly Leu Gly Leu Asp Ser Val
            980                 985                 990

Ile Phe Asn Met Asp Gly Thr Ile Glu Leu Arg Leu Pro Ser Gly Glu
            995                 1000                1005

Val Ile Lys Lys Asn Leu Ser Asp Leu Ile Ala
    1010                1015

<210> SEQ ID NO 86
<211> LENGTH: 1019
<212> TYPE: PRT
<213> ORGANISM: S. pneumoniae

<400> SEQUENCE: 86

Cys Ala Tyr Ala Leu Asn Gln His Arg Ser Gln Glu Asn Lys Asp Asn
1               5                   10                  15

Asn Arg Val Ser Tyr Val Asp Gly Ser Gln Ser Ser Gln Lys Ser Glu
            20                  25                  30

Asn Leu Thr Pro Asp Gln Val Ser Gln Lys Glu Gly Ile Gln Ala Glu
            35                  40                  45

Gln Ile Val Ile Lys Ile Thr Asp Gln Gly Tyr Val Thr Ser His Gly
50                  55                  60

Asp His Tyr His Tyr Tyr Asn Gly Lys Val Pro Tyr Asp Ala Leu Phe
65                  70                  75                  80

Ser Glu Glu Leu Leu Met Lys Asp Pro Asn Tyr Gln Leu Lys Asp Ala
            85                  90                  95

Asp Ile Val Asn Glu Val Lys Gly Gly Tyr Ile Ile Lys Val Asp Gly
            100                 105                 110

Lys Tyr Tyr Val Tyr Leu Lys Asp Ala Ala His Ala Asp Asn Val Arg
            115                 120                 125

Thr Lys Asp Glu Ile Asn Arg Gln Lys Gln Glu His Val Lys Asp Asn
130                 135                 140

Glu Lys Val Asn Ser Asn Val Ala Val Ala Arg Ser Gln Gly Arg Tyr
145                 150                 155                 160

Thr Thr Asn Asp Gly Tyr Val Phe Asn Pro Ala Asp Ile Ile Glu Asp
            165                 170                 175

Thr Gly Asn Ala Tyr Ile Val Pro His Gly Gly His Tyr His Tyr Ile
            180                 185                 190

Pro Lys Ser Asp Leu Ser Ala Ser Glu Leu Ala Ala Lys Ala His
            195                 200                 205

Leu Ala Gly Lys Asn Met Gln Pro Ser Gln Leu Ser Tyr Ser Ser Thr
210                 215                 220

Ala Ser Asp Asn Asn Thr Gln Ser Val Ala Lys Gly Ser Thr Ser Lys
225                 230                 235                 240

Pro Ala Asn Lys Ser Glu Asn Leu Gln Ser Leu Leu Lys Glu Leu Tyr
            245                 250                 255

Asp Ser Pro Ser Ala Gln Arg Tyr Ser Glu Ser Asp Gly Leu Val Phe
            260                 265                 270

Asp Pro Ala Lys Ile Ile Ser Arg Thr Pro Asn Gly Val Ala Ile Pro
            275                 280                 285

His Gly Asp His Tyr His Phe Ile Pro Tyr Ser Lys Leu Ser Ala Leu
            290                 295                 300
```

```
Glu Glu Lys Ile Ala Arg Met Val Pro Ile Ser Gly Thr Gly Ser Thr
305                 310                 315                 320

Val Ser Thr Asn Ala Lys Pro Asn Glu Val Val Ser Ser Leu Gly Ser
                325                 330                 335

Leu Ser Ser Asn Pro Ser Ser Leu Thr Thr Ser Lys Glu Leu Ser Ser
                340                 345                 350

Ala Ser Asp Gly Tyr Ile Phe Asn Pro Lys Asp Ile Val Glu Glu Thr
        355                 360                 365

Ala Thr Ala Tyr Ile Val Arg His Gly Asp His Phe His Tyr Ile Pro
    370                 375                 380

Lys Ser Asn Gln Ile Gly Gln Pro Thr Leu Pro Asn Asn Ser Leu Ala
385                 390                 395                 400

Thr Pro Ser Pro Ser Leu Pro Ile Asn Pro Gly Thr Ser His Glu Lys
                405                 410                 415

His Glu Glu Asp Gly Tyr Gly Phe Asp Ala Asn Arg Ile Ile Ala Glu
                420                 425                 430

Asp Glu Ser Gly Phe Val Met Ser His Gly Asp His Asn His Tyr Phe
        435                 440                 445

Phe Lys Lys Asp Leu Thr Glu Glu Gln Ile Lys Ala Ala Gln Lys His
    450                 455                 460

Leu Glu Glu Val Lys Thr Ser His Asn Gly Leu Asp Ser Leu Ser Ser
465                 470                 475                 480

His Glu Gln Asp Tyr Pro Ser Asn Ala Lys Glu Met Lys Asp Leu Asp
                485                 490                 495

Lys Lys Ile Glu Glu Lys Ile Ala Gly Ile Met Lys Gln Tyr Gly Val
                500                 505                 510

Lys Arg Glu Ser Ile Val Val Asn Lys Glu Lys Asn Ala Ile Ile Tyr
            515                 520                 525

Pro His Gly Asp His His Ala Asp Pro Ile Asp Glu His Lys Pro
        530                 535                 540

Val Gly Ile Gly His Ser His Ser Asn Tyr Glu Leu Phe Lys Pro Glu
545                 550                 555                 560

Glu Gly Val Ala Lys Lys Gly Asn Lys Val Tyr Thr Gly Glu Glu
                565                 570                 575

Leu Thr Asn Val Val Asn Leu Leu Lys Asn Ser Thr Phe Asn Asn Gln
            580                 585                 590

Asn Phe Thr Leu Ala Asn Gly Gln Lys Arg Val Ser Phe Ser Phe Pro
        595                 600                 605

Pro Glu Leu Glu Lys Lys Leu Gly Ile Asn Met Leu Val Lys Leu Ile
    610                 615                 620

Thr Pro Asp Gly Lys Val Leu Glu Lys Val Ser Gly Lys Val Phe Gly
625                 630                 635                 640

Glu Gly Val Gly Asn Ile Ala Asn Phe Glu Leu Asp Gln Pro Tyr Leu
                645                 650                 655

Pro Gly Gln Thr Phe Lys Tyr Thr Ile Ala Ser Lys Asp Tyr Pro Glu
                660                 665                 670

Val Ser Tyr Asp Gly Thr Phe Thr Val Pro Thr Ser Leu Ala Tyr Lys
            675                 680                 685

Met Ala Ser Gln Thr Ile Phe Tyr Pro Phe His Ala Gly Asp Thr Tyr
        690                 695                 700

Leu Arg Val Asn Pro Gln Phe Ala Val Pro Lys Gly Thr Asp Ala Leu
705                 710                 715                 720
```

```
Val Arg Val Phe Asp Glu Phe His Gly Asn Ala Tyr Leu Glu Asn Asn
            725                 730                 735

Tyr Lys Val Gly Glu Ile Lys Leu Pro Ile Pro Lys Leu Asn Gln Gly
            740                 745                 750

Thr Thr Arg Thr Ala Gly Asn Lys Ile Pro Val Thr Phe Met Ala Asn
            755                 760                 765

Ala Tyr Leu Asp Asn Gln Ser Thr Tyr Ile Val Glu Val Pro Ile Leu
            770                 775                 780

Glu Lys Glu Asn Gln Thr Asp Lys Pro Ser Ile Leu Pro Gln Phe Lys
785                 790                 795                 800

Arg Asn Lys Ala Gln Glu Asn Leu Lys Leu Asp Glu Lys Val Glu Glu
                805                 810                 815

Pro Lys Thr Ser Glu Lys Val Glu Lys Glu Lys Leu Ser Glu Thr Gly
            820                 825                 830

Asn Ser Thr Ser Asn Ser Thr Leu Glu Glu Val Pro Thr Val Asp Pro
            835                 840                 845

Val Gln Glu Lys Val Ala Lys Phe Ala Glu Ser Tyr Gly Met Lys Leu
            850                 855                 860

Glu Asn Val Leu Phe Asn Met Asp Gly Thr Ile Glu Leu Tyr Leu Pro
865                 870                 875                 880

Ser Gly Glu Val Ile Lys Lys Asn Met Ala Asp Phe Thr Gly Glu Ala
                885                 890                 895

Pro Gln Gly Asn Gly Glu Asn Lys Pro Ser Glu Asn Gly Lys Val Ser
            900                 905                 910

Thr Gly Thr Val Glu Asn Gln Pro Thr Glu Asn Lys Pro Ala Asp Ser
            915                 920                 925

Leu Pro Glu Ala Pro Asn Glu Lys Pro Val Lys Pro Glu Asn Ser Thr
            930                 935                 940

Asp Asn Gly Met Leu Asn Pro Glu Gly Asn Val Gly Ser Asp Pro Met
945                 950                 955                 960

Leu Asp Pro Ala Leu Glu Ala Pro Ala Val Asp Pro Val Gln Glu
                965                 970                 975

Lys Leu Glu Lys Phe Thr Ala Ser Tyr Gly Leu Gly Leu Asp Ser Val
            980                 985                 990

Ile Phe Asn Met Asp Gly Thr Ile Glu Leu Arg Leu Pro Ser Gly Glu
                995                 1000                1005

Val Ile Lys Lys Asn Leu Ser Asp Leu Ile Ala
    1010                1015

<210> SEQ ID NO 87
<211> LENGTH: 1019
<212> TYPE: PRT
<213> ORGANISM: S. pneumoniae

<400> SEQUENCE: 87

Cys Ala Tyr Ala Leu Asn Gln His Arg Ser Gln Glu Asn Lys Asp Asn
1               5                   10                  15

Asn Arg Val Ser Tyr Val Asp Gly Ser Gln Ser Ser Gln Lys Ser Glu
            20                  25                  30

Asn Leu Thr Pro Asp Gln Val Ser Gln Lys Glu Gly Ile Gln Ala Glu
            35                  40                  45

Gln Ile Val Ile Lys Ile Thr Asp Gln Gly Tyr Val Thr Ser His Gly
        50                  55                  60

Asp His Tyr His Tyr Tyr Asn Gly Lys Val Pro Tyr Asp Ala Leu Phe
65              70                  75                  80
```

```
Ser Glu Glu Leu Leu Met Lys Asp Pro Asn Tyr Gln Leu Lys Asp Ala
                85                  90                  95

Asp Ile Val Asn Glu Val Lys Gly Gly Tyr Ile Ile Lys Val Asp Gly
            100                 105                 110

Lys Tyr Tyr Val Tyr Leu Lys Asp Ala Ala His Ala Asp Asn Val Arg
            115                 120                 125

Thr Lys Asp Glu Ile Asn Arg Gln Lys Gln His Val Lys Asp Asn
130                 135                 140

Glu Lys Val Asn Ser Asn Val Ala Val Ala Arg Ser Gln Gly Arg Tyr
145                 150                 155                 160

Thr Thr Asn Asp Gly Tyr Val Phe Asn Pro Ala Asp Ile Ile Glu Asp
                165                 170                 175

Thr Gly Asn Ala Tyr Ile Val Pro His Gly Gly His Tyr His Tyr Ile
                180                 185                 190

Pro Lys Ser Asp Leu Ser Ala Ser Glu Leu Ala Ala Lys Ala His
            195                 200                 205

Leu Ala Gly Lys Asn Met Gln Pro Ser Gln Leu Ser Tyr Ser Ser Thr
    210                 215                 220

Ala Ser Asp Asn Asn Thr Gln Ser Val Ala Lys Gly Ser Thr Ser Lys
225                 230                 235                 240

Pro Ala Asn Lys Ser Glu Asn Leu Gln Ser Leu Leu Lys Glu Leu Tyr
                245                 250                 255

Asp Ser Pro Ser Ala Gln Arg Tyr Ser Glu Ser Asp Gly Leu Val Phe
            260                 265                 270

Asp Pro Ala Lys Ile Ile Ser Arg Thr Pro Asn Gly Val Ala Ile Pro
            275                 280                 285

His Gly Asp His Tyr His Phe Ile Pro Tyr Ser Lys Leu Ser Ala Leu
    290                 295                 300

Glu Lys Ile Ala Arg Met Val Pro Ile Ser Gly Thr Gly Ser Thr
305                 310                 315                 320

Val Ser Thr Asn Ala Lys Pro Asn Glu Val Val Ser Ser Leu Gly Ser
                325                 330                 335

Leu Ser Ser Asn Pro Ser Ser Leu Thr Thr Ser Lys Glu Leu Ser Ser
                340                 345                 350

Ala Ser Asp Gly Tyr Ile Phe Asn Pro Lys Asp Ile Val Glu Glu Thr
            355                 360                 365

Ala Thr Ala Tyr Ile Val Arg His Gly Asp His Phe His Tyr Ile Pro
    370                 375                 380

Lys Ser Asn Gln Ile Gly Gln Pro Thr Leu Pro Asn Asn Ser Leu Ala
385                 390                 395                 400

Thr Pro Ser Pro Ser Leu Pro Ile Asn Pro Gly Thr Ser His Glu Lys
            405                 410                 415

His Glu Glu Asp Gly Tyr Gly Phe Asp Ala Asn Arg Ile Ile Ala Glu
            420                 425                 430

Asp Glu Ser Gly Phe Val Met Ser His Gly Asp His Asn His Tyr Phe
    435                 440                 445

Phe Lys Lys Asp Leu Thr Glu Glu Gln Ile Lys Ala Ala Gln Lys His
    450                 455                 460

Leu Glu Glu Val Lys Thr Ser His Asn Gly Leu Asp Ser Leu Ser Ser
465                 470                 475                 480

His Glu Gln Asp Tyr Pro Gly Asn Ala Lys Glu Met Lys Asp Leu Asp
                485                 490                 495
```

```
Lys Lys Ile Glu Glu Lys Ile Ala Gly Ile Met Lys Gln Tyr Gly Val
            500                 505                 510

Lys Arg Glu Ser Ile Val Val Asn Lys Glu Lys Asn Ala Ile Ile Tyr
        515                 520                 525

Pro His Gly Asp His His Ala Asp Pro Ile Asp Glu His Lys Pro
    530                 535                 540

Val Gly Ile Gly His Ser His Ser Asn Tyr Glu Leu Phe Lys Pro Glu
545                 550                 555                 560

Glu Gly Val Ala Lys Lys Gly Asn Lys Val Tyr Thr Gly Glu Glu
                565                 570                 575

Leu Thr Asn Val Val Asn Leu Leu Lys Asn Ser Thr Phe Asn Asn Gln
            580                 585                 590

Asn Phe Thr Leu Ala Asn Gly Gln Lys Arg Val Ser Phe Ser Phe Pro
        595                 600                 605

Pro Glu Leu Glu Lys Lys Leu Gly Ile Asn Met Leu Val Lys Leu Ile
    610                 615                 620

Thr Pro Asp Gly Lys Val Leu Glu Lys Val Ser Gly Lys Val Phe Gly
625                 630                 635                 640

Glu Gly Val Gly Asn Ile Ala Asn Phe Glu Leu Asp Gln Pro Tyr Leu
                645                 650                 655

Pro Gly Gln Thr Phe Lys Tyr Thr Ile Ala Ser Lys Asp Tyr Pro Glu
            660                 665                 670

Val Ser Tyr Asp Gly Thr Phe Thr Val Pro Thr Ser Leu Ala Tyr Lys
        675                 680                 685

Met Ala Ser Gln Thr Ile Phe Tyr Pro Phe His Ala Gly Asp Thr Tyr
    690                 695                 700

Leu Arg Val Asn Pro Gln Phe Ala Val Pro Lys Gly Thr Asp Ala Leu
705                 710                 715                 720

Val Arg Val Phe Asp Glu Phe His Gly Asn Ala Tyr Leu Glu Asn Asn
                725                 730                 735

Tyr Lys Val Gly Glu Ile Lys Leu Pro Ile Pro Lys Leu Asn Gln Gly
            740                 745                 750

Thr Thr Arg Thr Ala Gly Asn Lys Ile Pro Val Thr Phe Met Ala Asn
        755                 760                 765

Ala Tyr Leu Asp Asn Gln Ser Thr Tyr Ile Val Glu Val Pro Ile Leu
    770                 775                 780

Glu Lys Glu Asn Gln Thr Asp Lys Pro Ser Ile Leu Pro Gln Phe Lys
785                 790                 795                 800

Arg Asn Lys Ala Gln Glu Asn Ser Lys Leu Asp Glu Lys Val Glu Glu
                805                 810                 815

Pro Lys Thr Ser Glu Lys Val Lys Glu Lys Leu Ser Glu Thr Gly
            820                 825                 830

Asn Ser Thr Ser Asn Ser Thr Leu Glu Glu Val Pro Thr Val Asp Pro
        835                 840                 845

Val Gln Glu Lys Val Ala Lys Phe Ala Glu Ser Tyr Gly Met Lys Leu
    850                 855                 860

Glu Asn Val Leu Phe Asn Met Asp Gly Thr Ile Glu Leu Tyr Leu Pro
865                 870                 875                 880

Ser Gly Glu Val Ile Lys Lys Asn Met Ala Asp Phe Thr Gly Glu Ala
                885                 890                 895

Pro Gln Gly Asn Gly Glu Asn Lys Pro Ser Glu Asn Gly Lys Val Ser
            900                 905                 910

Thr Gly Thr Val Glu Asn Gln Pro Thr Glu Asn Lys Pro Ala Asp Ser
```

```
                    915                 920                 925
Leu Pro Glu Ala Pro Asn Glu Lys Pro Val Lys Pro Glu Asn Ser Thr
    930                 935                 940

Asp Asn Gly Met Leu Asn Pro Glu Gly Asn Val Gly Ser Asp Pro Met
945                 950                 955                 960

Leu Asp Pro Ala Leu Glu Glu Ala Pro Ala Val Asp Pro Val Gln Glu
                965                 970                 975

Lys Leu Glu Lys Phe Thr Ala Ser Tyr Gly Leu Gly Leu Asp Ser Val
            980                 985                 990

Ile Phe Asn Met Asp Gly Thr Ile Glu Leu Arg Leu Pro Ser Gly Glu
        995                1000                1005

Val Ile Lys Lys Asn Leu Ser Asp Phe Ile Ala
    1010                1015

<210> SEQ ID NO 88
<211> LENGTH: 1019
<212> TYPE: PRT
<213> ORGANISM: S. pneumoniae

<400> SEQUENCE: 88

Cys Ala Tyr Ala Leu Asn Gln His Arg Ser Gln Glu Asn Lys Asp Asn
 1               5                  10                  15

Asn Arg Val Ser Tyr Val Asp Gly Ser Gln Ser Gln Lys Ser Glu
            20                  25                  30

Asn Leu Thr Pro Asp Gln Val Ser Gln Lys Glu Gly Ile Gln Ala Glu
        35                  40                  45

Gln Ile Val Ile Lys Ile Thr Asp Gln Gly Tyr Val Thr Ser His Gly
    50                  55                  60

Asp His Tyr His Tyr Tyr Asn Gly Lys Val Pro Tyr Asp Ala Leu Phe
65                  70                  75                  80

Ser Glu Glu Leu Leu Met Lys Asp Pro Asn Tyr Gln Leu Lys Asp Ala
                85                  90                  95

Asp Ile Val Asn Glu Val Lys Gly Gly Tyr Ile Ile Lys Val Asp Gly
            100                 105                 110

Lys Tyr Tyr Val Tyr Leu Lys Asp Ala Ala His Ala Asp Asn Val Arg
        115                 120                 125

Thr Lys Asp Glu Ile Asn Arg Gln Lys Gln Glu His Val Lys Asp Asn
    130                 135                 140

Glu Lys Val Asn Ser Asn Val Ala Val Ala Arg Ser Gln Gly Arg Tyr
145                 150                 155                 160

Thr Thr Asn Asp Gly Tyr Val Phe Asn Pro Ala Asp Ile Ile Glu Asp
                165                 170                 175

Thr Gly Asn Ala Tyr Ile Val Pro His Arg Gly His Tyr His Tyr Ile
            180                 185                 190

Pro Lys Ser Asp Leu Ser Ala Ser Glu Leu Ala Ala Lys Ala His
        195                 200                 205

Leu Ala Gly Lys Asn Met Gln Pro Ser Gln Leu Ser Tyr Ser Ser Thr
    210                 215                 220

Ala Ser Asp Asn Asn Thr Gln Ser Val Ala Lys Gly Ser Thr Ser Lys
225                 230                 235                 240

Pro Ala Asn Lys Ser Glu Asn Leu Gln Ser Leu Leu Lys Glu Leu Tyr
                245                 250                 255

Asp Ser Pro Ser Ala Gln Arg Tyr Ser Glu Ser Asp Gly Leu Val Phe
            260                 265                 270
```

```
Asp Pro Ala Lys Ile Ile Ser Arg Thr Pro Asn Gly Val Ala Ile Pro
        275                 280                 285

His Gly Asp His Tyr His Phe Ile Pro Tyr Ser Lys Leu Ser Ala Leu
        290                 295                 300

Glu Glu Lys Ile Ala Arg Met Val Pro Ile Ser Gly Thr Gly Ser Thr
305                 310                 315                 320

Val Ser Thr Asn Ala Lys Pro Asn Glu Val Val Ser Ser Leu Gly Ser
                325                 330                 335

Leu Ser Ser Asn Pro Ser Ser Leu Thr Thr Ser Lys Glu Leu Ser Ser
                340                 345                 350

Ala Ser Asp Gly Tyr Ile Phe Asn Pro Lys Asp Ile Val Glu Glu Thr
                355                 360                 365

Ala Thr Ala Tyr Ile Val Arg His Gly Asp His Phe His Tyr Ile Pro
        370                 375                 380

Lys Ser Asn Gln Ile Gly Gln Pro Thr Leu Pro Asn Asn Ser Leu Ala
385                 390                 395                 400

Thr Pro Ser Pro Ser Leu Pro Ile Asn Pro Gly Thr Ser His Glu Lys
                405                 410                 415

His Glu Glu Asp Gly Tyr Gly Phe Asp Ala Asn Arg Ile Ile Ala Glu
                420                 425                 430

Asp Glu Ser Gly Phe Val Met Ser His Gly Asp His Asn His Tyr Phe
        435                 440                 445

Phe Lys Lys Asp Leu Thr Glu Glu Gln Ile Lys Ala Ala Gln Lys His
450                 455                 460

Leu Glu Glu Val Lys Thr Ser His Asn Gly Leu Asp Ser Leu Ser Ser
465                 470                 475                 480

His Glu Gln Asp Tyr Pro Ser Asn Ala Lys Glu Met Lys Asp Leu Asp
                485                 490                 495

Lys Lys Ile Glu Glu Lys Ile Ala Gly Ile Met Lys Gln Tyr Gly Val
                500                 505                 510

Lys Arg Glu Ser Ile Val Val Asn Lys Glu Lys Asn Ala Ile Ile Tyr
        515                 520                 525

Pro His Gly Asp His His Ala Asp Pro Ile Asp Glu His Lys Pro
        530                 535                 540

Val Gly Ile Gly His Ser His Ser Asn Tyr Glu Leu Phe Lys Pro Glu
545                 550                 555                 560

Glu Gly Val Ala Lys Lys Glu Gly Asn Lys Val Tyr Thr Gly Glu Glu
                565                 570                 575

Leu Thr Asn Val Val Asn Leu Leu Lys Asn Ser Thr Phe Asn Asn Gln
                580                 585                 590

Asn Phe Thr Leu Ala Asn Gly Gln Lys Arg Val Ser Phe Ser Phe Pro
        595                 600                 605

Pro Glu Leu Glu Lys Lys Leu Gly Ile Asn Met Leu Val Lys Leu Ile
        610                 615                 620

Thr Pro Asp Gly Lys Val Leu Glu Lys Val Ser Gly Lys Val Phe Gly
625                 630                 635                 640

Glu Gly Val Gly Asn Ile Ala Asn Phe Glu Leu Asp Gln Pro Tyr Leu
                645                 650                 655

Pro Gly Gln Thr Phe Lys Tyr Thr Ile Ala Ser Lys Asp Tyr Pro Glu
                660                 665                 670

Val Ser Tyr Asp Gly Thr Phe Thr Val Pro Thr Ser Leu Ala Tyr Lys
        675                 680                 685

Met Ala Ser Gln Thr Ile Phe Tyr Pro Phe His Ala Gly Asp Thr Tyr
```

-continued

```
              690                 695                 700
Leu Arg Val Asn Pro Gln Phe Ala Val Pro Lys Gly Thr Asp Ala Leu
705                 710                 715                 720

Val Arg Val Phe Asp Glu Phe His Gly Asn Ala Tyr Leu Glu Asn Asn
                    725                 730                 735

Tyr Lys Val Gly Glu Ile Lys Leu Pro Ile Pro Lys Leu Asn Gln Gly
                740                 745                 750

Thr Thr Arg Thr Ala Gly Asn Lys Ile Pro Val Thr Phe Met Ala Asn
            755                 760                 765

Ala Tyr Leu Asp Asn Gln Ser Thr Tyr Ile Val Glu Val Pro Ile Leu
770                 775                 780

Glu Lys Glu Asn Gln Thr Asp Lys Pro Ser Ile Leu Pro Gln Phe Lys
785                 790                 795                 800

Arg Asn Lys Ala Gln Glu Asn Ser Lys Phe Asp Glu Lys Val Glu Glu
                    805                 810                 815

Pro Lys Thr Ser Glu Lys Val Glu Lys Leu Ser Glu Thr Gly
                820                 825                 830

Asn Ser Thr Ser Asn Ser Thr Leu Glu Glu Val Pro Thr Val Asp Pro
                835                 840                 845

Val Gln Glu Lys Val Ala Lys Phe Ala Glu Ser Tyr Gly Met Lys Leu
850                 855                 860

Glu Asn Val Leu Phe Asn Met Asp Gly Thr Ile Glu Leu Tyr Leu Pro
865                 870                 875                 880

Ser Gly Glu Val Ile Lys Lys Asn Met Ala Asp Phe Thr Gly Glu Ala
                    885                 890                 895

Pro Gln Gly Asn Gly Glu Asn Lys Pro Ser Glu Asn Gly Lys Val Ser
                900                 905                 910

Thr Gly Thr Val Glu Asn Gln Pro Thr Glu Asn Lys Pro Ala Asp Ser
            915                 920                 925

Leu Pro Glu Ala Pro Asn Glu Lys Pro Val Lys Pro Glu Asn Ser Thr
            930                 935                 940

Asp Asn Gly Met Leu Asn Pro Glu Gly Asn Val Gly Ser Asp Pro Met
945                 950                 955                 960

Leu Asp Pro Ala Leu Glu Glu Ala Pro Ala Val Asp Pro Val Gln Glu
                965                 970                 975

Lys Leu Glu Lys Phe Thr Ala Ser Tyr Gly Leu Gly Leu Asp Ser Val
                980                 985                 990

Ile Phe Asn Met Asp Gly Thr Ile Glu Leu Arg Leu Pro Ser Gly Glu
                995                 1000                1005

Val Ile Lys Lys Asn Leu Ser Asp Leu Ile Ala
    1010                1015
```

<210> SEQ ID NO 89
<211> LENGTH: 1019
<212> TYPE: PRT
<213> ORGANISM: S. pneumoniae

<400> SEQUENCE: 89

```
Cys Ala Tyr Ala Leu Asn Gln His Arg Ser Gln Glu Asn Lys Asp Asn
1               5                   10                  15

Asn Arg Val Ser Tyr Val Asp Gly Ser Gln Ser Gln Lys Ser Glu
                20                  25                  30

Asn Leu Thr Pro Asp Gln Val Ser Gln Lys Glu Gly Ile Gln Ala Glu
            35                  40                  45
```

-continued

```
Gln Ile Val Ile Lys Ile Thr Asp Gln Gly Tyr Val Thr Ser His Gly
     50                  55                  60

Asp His Tyr His Tyr Tyr Asn Gly Lys Val Pro Tyr Asp Ala Leu Phe
 65                  70                  75                  80

Ser Glu Glu Leu Leu Met Lys Asp Pro Asn Tyr Gln Leu Lys Asp Ala
                 85                  90                  95

Asp Ile Val Asn Glu Val Lys Gly Gly Tyr Ile Ile Lys Val Asp Gly
                100                 105                 110

Lys Tyr Tyr Val Tyr Leu Lys Asp Ala Ala His Ala Asp Asn Val Arg
             115                 120                 125

Thr Lys Asp Glu Ile Asn Arg Gln Lys Gln Glu His Val Lys Asp Asn
    130                 135                 140

Glu Lys Val Asn Ser Asn Val Ala Val Ala Arg Ser Gln Gly Arg Tyr
145                 150                 155                 160

Thr Thr Asn Asp Gly Tyr Val Phe Asn Pro Ala Asp Ile Ile Glu Asp
                165                 170                 175

Thr Gly Asn Ala Tyr Ile Val Pro His Arg Gly His Tyr His Tyr Ile
                180                 185                 190

Pro Lys Ser Asp Leu Ser Ala Ser Glu Leu Ala Ala Lys Ala His
             195                 200                 205

Leu Ala Gly Lys Asn Met Gln Pro Ser Gln Leu Ser Tyr Ser Ser Thr
    210                 215                 220

Ala Ser Asp Asn Asn Thr Gln Ser Val Ala Lys Gly Ser Thr Ser Lys
225                 230                 235                 240

Pro Ala Asn Lys Ser Glu Asn Leu Gln Ser Leu Leu Lys Glu Leu Tyr
                245                 250                 255

Asp Ser Pro Ser Ala Gln Arg Tyr Ser Glu Ser Asp Gly Leu Val Phe
                260                 265                 270

Asp Pro Ala Lys Ile Ile Ser Arg Thr Pro Asn Gly Val Ala Ile Pro
            275                 280                 285

His Gly Asp His Tyr His Phe Ile Pro Tyr Ser Lys Leu Ser Ala Leu
    290                 295                 300

Glu Glu Lys Ile Ala Arg Met Val Pro Ile Ser Gly Thr Gly Ser Thr
305                 310                 315                 320

Val Ser Thr Asn Ala Lys Pro Asn Glu Val Val Ser Ser Leu Gly Ser
                325                 330                 335

Leu Ser Ser Asn Pro Ser Ser Leu Thr Thr Ser Lys Glu Leu Ser Ser
                340                 345                 350

Ala Ser Asp Gly Tyr Ile Phe Asn Pro Lys Asp Ile Val Glu Glu Thr
            355                 360                 365

Ala Thr Ala Tyr Ile Val Arg His Gly Asp His Phe His Tyr Ile Pro
    370                 375                 380

Lys Ser Asn Gln Ile Gly Gln Pro Thr Leu Pro Asn Asn Ser Leu Ala
385                 390                 395                 400

Thr Pro Ser Pro Ser Leu Pro Ile Asn Pro Gly Thr Ser His Glu Lys
                405                 410                 415

His Glu Glu Asp Gly Tyr Gly Phe Asp Ala Asn Arg Ile Ile Ala Glu
            420                 425                 430

Asp Glu Ser Gly Phe Val Met Ser His Gly Asp His Asn His Tyr Phe
    435                 440                 445

Phe Lys Lys Asp Leu Thr Glu Glu Gln Ile Lys Ala Ala Gln Lys His
450                 455                 460

Leu Glu Glu Val Lys Thr Ser His Asn Gly Leu Asp Ser Leu Ser Ser
```

-continued

```
              465                 470                 475                 480
His Glu Gln Asp Tyr Pro Ser Asn Ala Lys Glu Met Lys Asp Leu Asp
                    485                 490                 495
Lys Lys Ile Glu Glu Lys Ile Ala Gly Ile Met Lys Gln Tyr Gly Val
                500                 505                 510
Lys Arg Glu Ser Ile Val Val Asn Lys Glu Lys Asn Ala Ile Ile Tyr
            515                 520                 525
Pro His Gly Asp His His Ala Asp Pro Ile Asp Glu His Lys Pro
        530                 535                 540
Val Gly Ile Gly His Ser His Ser Asn Tyr Glu Leu Phe Lys Pro Glu
545                 550                 555                 560
Glu Gly Val Ala Lys Lys Glu Gly Asn Lys Val Tyr Thr Gly Glu Glu
                565                 570                 575
Leu Thr Asn Val Val Asn Leu Leu Lys Asn Ser Thr Phe Asn Asn Gln
                580                 585                 590
Asn Phe Thr Leu Ala Asn Gly Gln Lys Arg Val Ser Phe Ser Phe Pro
        595                 600                 605
Pro Glu Leu Glu Lys Lys Leu Gly Ile Asn Met Leu Val Lys Leu Ile
    610                 615                 620
Thr Pro Asp Gly Lys Val Leu Glu Lys Val Ser Gly Lys Val Phe Gly
625                 630                 635                 640
Glu Gly Val Gly Asn Ile Ala Asn Phe Glu Leu Asp Gln Pro Tyr Leu
                645                 650                 655
Pro Gly Gln Thr Phe Lys Tyr Thr Ile Ala Ser Lys Asp Tyr Pro Glu
                660                 665                 670
Val Ser Tyr Asp Gly Thr Phe Thr Val Pro Thr Ser Leu Ala Tyr Lys
            675                 680                 685
Met Ala Ser Gln Thr Ile Phe Tyr Pro Phe His Ala Gly Asp Thr Tyr
        690                 695                 700
Leu Arg Val Asn Pro Gln Phe Ala Val Pro Lys Gly Thr Asp Ala Leu
705                 710                 715                 720
Val Arg Val Phe Asp Glu Phe His Gly Asn Ala Tyr Leu Glu Asn Asn
                725                 730                 735
Tyr Lys Val Gly Glu Ile Lys Leu Pro Ile Pro Lys Leu Asn Gln Gly
                740                 745                 750
Thr Thr Arg Thr Ala Gly Asn Lys Ile Pro Val Thr Phe Met Ala Asn
            755                 760                 765
Ala Tyr Leu Asp Asn Gln Ser Thr Tyr Ile Val Glu Val Pro Ile Leu
        770                 775                 780
Glu Lys Glu Asn Gln Thr Asp Lys Pro Ser Ile Leu Pro Gln Phe Lys
785                 790                 795                 800
Arg Asn Lys Ala Gln Glu Asn Ser Lys Phe Asp Glu Lys Val Glu Glu
                805                 810                 815
Pro Lys Thr Ser Glu Lys Val Glu Lys Leu Ser Glu Thr Gly
                820                 825                 830
Asn Ser Thr Ser Asn Ser Thr Leu Glu Glu Val Pro Thr Val Asp Pro
            835                 840                 845
Val Gln Glu Lys Val Ala Lys Phe Ala Glu Ser Tyr Gly Met Lys Leu
        850                 855                 860
Glu Asn Val Leu Phe Asn Met Asp Gly Thr Ile Glu Leu Tyr Leu Pro
865                 870                 875                 880
Ser Gly Glu Val Ile Lys Lys Asn Met Ala Asp Phe Thr Gly Glu Ala
                885                 890                 895
```

-continued

```
Pro Gln Gly Asn Gly Glu Asn Lys Pro Ser Glu Asn Gly Lys Val Ser
            900                 905                 910

Thr Gly Thr Val Glu Asn Gln Pro Thr Glu Asn Lys Pro Ala Asp Ser
            915                 920                 925

Leu Pro Glu Ala Pro Asn Glu Lys Pro Val Lys Pro Glu Asn Ser Thr
            930                 935                 940

Asp Asn Gly Met Leu Asn Pro Glu Gly Asn Val Gly Ser Asp Pro Met
945                 950                 955                 960

Leu Asp Pro Ala Leu Glu Glu Ala Pro Ala Val Asp Pro Val Gln Glu
            965                 970                 975

Lys Leu Glu Lys Phe Thr Ala Ser Tyr Gly Leu Gly Leu Asp Ser Val
            980                 985                 990

Ile Phe Asn Met Asp Gly Thr Ile Glu Leu Arg Leu Pro Ser Gly Glu
            995                 1000                1005

Val Ile Lys Lys Asn Leu Ser Asp Leu Ile Ala
            1010                1015

<210> SEQ ID NO 90
<211> LENGTH: 819
<212> TYPE: PRT
<213> ORGANISM: S. pneumoniae

<400> SEQUENCE: 90

Cys Ser Tyr Glu Leu Gly Arg His Gln Ala Gly Gln Val Lys Lys Glu
1               5                   10                  15

Ser Asn Arg Val Ser Tyr Ile Asp Gly Asp Gln Ala Gly Gln Lys Ala
            20                  25                  30

Glu Asn Leu Thr Pro Asp Glu Val Ser Lys Arg Glu Gly Ile Asn Ala
        35                  40                  45

Glu Gln Ile Val Ile Lys Ile Thr Asp Gln Gly Tyr Val Thr Ser His
    50                  55                  60

Gly Asp His Tyr His Tyr Tyr Asn Gly Lys Val Pro Tyr Asp Ala Ile
65                  70                  75                  80

Ile Ser Glu Glu Leu Leu Met Lys Asp Pro Asn Tyr Gln Leu Lys Asp
                85                  90                  95

Ser Asp Ile Val Asn Glu Ile Lys Gly Gly Tyr Val Ile Lys Val Asp
            100                 105                 110

Gly Lys Tyr Tyr Val Tyr Leu Lys Asp Ala Ala His Ala Asp Asn Ile
        115                 120                 125

Arg Thr Lys Glu Glu Ile Lys Arg Gln Lys Gln Glu His Ser His Asn
    130                 135                 140

His Asn Ser Arg Ala Asp Asn Ala Val Ala Ala Arg Ala Gln Gly Arg
145                 150                 155                 160

Arg Tyr Thr Thr Asp Asp Gly Tyr Ile Phe Asn Ala Ser Asp Ile Ile
                165                 170                 175

Glu Asp Thr Gly Asp Ala Tyr Ile Val Pro His Gly Asp His Tyr His
            180                 185                 190

Tyr Ile Pro Lys Asn Glu Leu Ser Ala Ser Glu Leu Ala Ala Ala Glu
        195                 200                 205

Ala Tyr Trp Asn Gly Lys Gln Gly Ser Arg Pro Ser Ser Ser Ser Ser
    210                 215                 220

Tyr Asn Ala Asn Pro Val Gln Pro Arg Leu Ser Glu Asn His Asn Leu
225                 230                 235                 240

Thr Val Thr Pro Thr Tyr His Gln Asn Gln Gly Glu Asn Ile Ser Ser
```

-continued

```
            245                 250                 255
Leu Leu Arg Glu Leu Tyr Ala Lys Pro Leu Ser Glu Arg His Val Glu
            260                 265                 270
Ser Asp Gly Leu Ile Phe Asp Pro Ala Gln Ile Thr Ser Arg Thr Ala
            275                 280                 285
Arg Gly Val Ala Val Pro His Gly Asn His Tyr His Phe Ile Pro Tyr
            290                 295                 300
Glu Gln Met Ser Glu Leu Glu Lys Arg Ile Ala Arg Ile Ile Pro Leu
305                 310                 315                 320
Arg Tyr Arg Ser Asn His Trp Val Pro Asp Ser Arg Pro Glu Gln Pro
                325                 330                 335
Ser Pro Gln Ser Thr Pro Glu Pro Ser Pro Ser Leu Gln Pro Ala Pro
                340                 345                 350
Asn Pro Gln Pro Ala Pro Ser Asn Pro Ile Asp Glu Lys Leu Val Lys
                355                 360                 365
Glu Ala Val Arg Lys Val Gly Asp Gly Tyr Val Phe Glu Glu Asn Gly
                370                 375                 380
Val Ser Arg Tyr Ile Pro Ala Lys Asp Leu Ser Ala Glu Thr Ala Ala
385                 390                 395                 400
Gly Ile Asp Ser Lys Leu Ala Lys Gln Glu Ser Leu Ser His Lys Leu
                405                 410                 415
Gly Ala Lys Lys Thr Asp Leu Pro Ser Ser Asp Arg Glu Phe Tyr Asn
                420                 425                 430
Lys Ala Tyr Asp Leu Leu Ala Arg Ile His Gln Asp Leu Leu Asp Asn
                435                 440                 445
Lys Gly Arg Gln Val Asp Phe Glu Val Leu Asp Asn Leu Leu Glu Arg
                450                 455                 460
Leu Lys Asp Val Ser Ser Asp Lys Val Lys Leu Val Asp Asp Ile Leu
465                 470                 475                 480
Ala Phe Leu Ala Pro Ile Arg His Pro Glu Arg Leu Gly Lys Pro Asn
                485                 490                 495
Ala Gln Ile Thr Tyr Thr Asp Asp Glu Ile Gln Val Ala Lys Leu Ala
                500                 505                 510
Gly Lys Tyr Thr Thr Glu Asp Gly Tyr Ile Phe Asp Pro Arg Asp Ile
                515                 520                 525
Thr Ser Asp Glu Gly Asp Ala Tyr Val Thr Pro His Met Thr His Ser
530                 535                 540
His Trp Ile Lys Lys Asp Ser Leu Ser Glu Ala Glu Arg Ala Ala Ala
545                 550                 555                 560
Gln Ala Tyr Ala Lys Glu Lys Gly Leu Thr Pro Pro Ser Thr Asp His
                565                 570                 575
Gln Asp Ser Gly Asn Thr Glu Ala Lys Gly Ala Glu Ala Ile Tyr Asn
                580                 585                 590
Arg Val Lys Ala Ala Lys Lys Val Pro Leu Asp Arg Met Pro Tyr Asn
                595                 600                 605
Leu Gln Tyr Thr Val Glu Val Lys Asn Gly Ser Leu Ile Ile Pro His
                610                 615                 620
Tyr Asp His Tyr His Asn Ile Lys Phe Glu Trp Phe Asp Glu Gly Leu
625                 630                 635                 640
Tyr Glu Ala Pro Lys Gly Tyr Ser Leu Glu Asp Leu Leu Ala Thr Val
                645                 650                 655
Lys Tyr Tyr Val Glu His Pro Asn Glu Arg Pro His Ser Asp Asn Gly
                660                 665                 670
```

-continued

```
Phe Gly Asn Ala Ser Asp His Val Arg Lys Asn Lys Ala Asp Gln Asp
            675                 680                 685

Ser Lys Pro Asp Glu Lys Glu His Asp Glu Val Ser Glu Pro Thr
    690                 695                 700

His Pro Glu Ser Asp Glu Lys Glu Asn His Ala Gly Leu Asn Pro Ser
705                 710                 715                 720

Ala Asp Asn Leu Tyr Lys Pro Ser Thr Asp Thr Glu Thr Glu Glu
                725                 730                 735

Glu Ala Glu Asp Thr Thr Asp Glu Ala Glu Ile Pro Gln Val Glu Asn
            740                 745                 750

Ser Val Ile Asn Ala Lys Ile Ala Asp Ala Glu Ala Leu Leu Glu Lys
            755                 760                 765

Val Thr Asp Pro Ser Ile Arg Gln Asn Ala Met Glu Thr Leu Thr Gly
            770                 775                 780

Leu Lys Ser Ser Leu Leu Leu Gly Thr Lys Asp Asn Asn Thr Ile Ser
785                 790                 795                 800

Ala Glu Val Asp Ser Leu Leu Ala Leu Leu Lys Glu Ser Gln Pro Ala
                805                 810                 815

Pro Ile Gln

<210> SEQ ID NO 91
<211> LENGTH: 820
<212> TYPE: PRT
<213> ORGANISM: S. pneumoniae

<400> SEQUENCE: 91

Cys Ser Tyr Glu Leu Gly Arg His Gln Ala Gly Gln Val Lys Lys Glu
1               5                   10                  15

Ser Asn Arg Val Ser Tyr Ile Asp Gly Asp Gln Ala Gly Gln Lys Ala
            20                  25                  30

Glu Asn Leu Thr Pro Asp Glu Val Ser Lys Arg Glu Gly Ile Asn Ala
        35                  40                  45

Glu Gln Ile Val Ile Lys Ile Thr Asp Gln Gly Tyr Val Thr Ser His
    50                  55                  60

Gly Asp His Tyr His Tyr Tyr Asn Gly Lys Val Pro Tyr Asp Ala Ile
65                  70                  75                  80

Ile Ser Glu Glu Leu Leu Met Lys Asp Pro Asn Tyr Gln Leu Lys Asp
                85                  90                  95

Ser Asp Ile Val Asn Glu Ile Lys Gly Gly Tyr Val Ile Lys Val Asp
            100                 105                 110

Gly Lys Tyr Tyr Val Tyr Leu Lys Asp Ala Ala His Ala Asp Asn Ile
        115                 120                 125

Arg Thr Lys Glu Glu Ile Lys Arg Gln Lys Gln Glu His Ser His Asn
    130                 135                 140

His Gly Gly Gly Ser Asn Asp Gln Ala Val Val Ala Ala Arg Ala Gln
145                 150                 155                 160

Gly Arg Tyr Thr Thr Asp Asp Gly Tyr Ile Phe Asn Ala Ser Asp Ile
                165                 170                 175

Ile Glu Asp Thr Gly Asp Ala Tyr Ile Val Pro His Gly Asp His Tyr
            180                 185                 190

His Tyr Ile Pro Lys Asn Glu Leu Ser Ala Ser Glu Leu Ala Ala Ala
        195                 200                 205

Glu Ala Tyr Trp Asn Gly Lys Gln Gly Ser Arg Pro Ser Ser Ser Ser
    210                 215                 220
```

```
Ser Tyr Asn Ala Asn Pro Ala Gln Pro Arg Leu Ser Glu Asn His Asn
225                 230                 235                 240

Leu Thr Val Thr Pro Thr Tyr His Gln Asn Gln Gly Glu Asn Ile Ser
            245                 250                 255

Ser Leu Leu Arg Glu Leu Tyr Ala Lys Pro Leu Ser Glu Arg His Val
            260                 265                 270

Glu Ser Asp Gly Leu Ile Phe Asp Pro Ala Gln Ile Thr Ser Arg Thr
            275                 280                 285

Ala Arg Gly Val Ala Val Pro His Gly Asn His Tyr His Phe Ile Pro
        290                 295                 300

Tyr Glu Gln Met Ser Glu Leu Glu Lys Arg Ile Ala Arg Ile Ile Pro
305                 310                 315                 320

Leu Arg Tyr Arg Ser Asn His Trp Val Pro Asp Ser Arg Pro Glu Gln
                325                 330                 335

Pro Ser Pro Gln Ser Thr Pro Glu Pro Ser Pro Ser Pro Gln Pro Ala
                340                 345                 350

Pro Asn Pro Gln Pro Ala Pro Ser Asn Pro Ile Asp Glu Lys Leu Val
            355                 360                 365

Lys Glu Ala Val Arg Lys Val Gly Asp Gly Tyr Val Phe Glu Glu Asn
370                 375                 380

Gly Val Ser Arg Tyr Ile Pro Ala Lys Asp Leu Ser Ala Glu Thr Ala
385                 390                 395                 400

Ala Gly Ile Asp Ser Lys Leu Ala Lys Gln Glu Ser Leu Ser His Lys
                405                 410                 415

Leu Gly Ala Lys Lys Thr Asp Leu Pro Ser Ser Asp Arg Glu Phe Tyr
            420                 425                 430

Asn Lys Ala Tyr Asp Leu Leu Ala Arg Ile His Gln Asp Leu Leu Asp
        435                 440                 445

Asn Lys Gly Arg Gln Val Asp Phe Glu Ala Leu Asp Asn Leu Leu Glu
450                 455                 460

Arg Leu Lys Asp Val Pro Ser Asp Lys Val Lys Leu Val Asp Asp Ile
465                 470                 475                 480

Leu Ala Phe Leu Ala Pro Ile Arg His Pro Glu Arg Leu Gly Lys Pro
                485                 490                 495

Asn Ala Gln Ile Thr Tyr Thr Asp Asp Glu Ile Gln Val Ala Lys Leu
            500                 505                 510

Ala Gly Lys Tyr Thr Thr Glu Asp Gly Tyr Ile Phe Asp Pro Arg Asp
        515                 520                 525

Ile Thr Ser Asp Glu Gly Asp Ala Tyr Val Thr Pro His Met Thr His
530                 535                 540

Ser His Trp Ile Lys Lys Asp Ser Leu Ser Glu Ala Glu Arg Ala Ala
545                 550                 555                 560

Ala Gln Ala Tyr Ala Lys Glu Lys Gly Leu Thr Pro Pro Ser Thr Asp
            565                 570                 575

His Gln Asp Ser Gly Asn Thr Glu Ala Lys Gly Ala Glu Ala Ile Tyr
            580                 585                 590

Asn Arg Val Lys Ala Ala Lys Lys Val Pro Leu Asp Arg Met Pro Tyr
        595                 600                 605

Asn Leu Gln Tyr Thr Val Glu Val Lys Asn Gly Ser Leu Ile Ile Pro
            610                 615                 620

His Tyr Asp His Tyr His Asn Ile Lys Phe Glu Trp Phe Asp Glu Gly
625                 630                 635                 640
```

```
Leu Tyr Glu Ala Pro Lys Gly Tyr Thr Leu Glu Asp Leu Leu Ala Thr
                645                 650                 655
Val Lys Tyr Tyr Val Glu His Pro Asn Glu Arg Pro His Ser Asp Asn
            660                 665                 670
Gly Phe Gly Asn Ala Ser Asp His Val Arg Lys Asn Lys Val Asp Gln
        675                 680                 685
Asp Ser Lys Pro Asp Glu Asp Lys Glu His Asp Glu Val Ser Glu Pro
    690                 695                 700
Thr His Pro Glu Ser Asp Glu Lys Glu Asn His Ala Gly Leu Asn Pro
705                 710                 715                 720
Ser Ala Asp Asn Leu Tyr Lys Pro Ser Thr Asp Glu Glu Thr Glu
                725                 730                 735
Glu Glu Ala Glu Asp Thr Thr Asp Glu Ala Glu Ile Pro Gln Val Glu
            740                 745                 750
Asn Ser Val Ile Asn Ala Lys Ile Ala Asp Ala Glu Ala Leu Leu Glu
        755                 760                 765
Lys Val Thr Asp Pro Ser Ile Arg Gln Asn Ala Met Glu Thr Leu Thr
    770                 775                 780
Gly Leu Lys Ser Ser Leu Leu Gly Thr Lys Asp Asn Asn Thr Ile
785                 790                 795                 800
Ser Ala Glu Val Asp Ser Leu Leu Ala Leu Leu Lys Glu Ser Gln Pro
                805                 810                 815
Ala Pro Ile Gln
            820

<210> SEQ ID NO 92
<211> LENGTH: 816
<212> TYPE: PRT
<213> ORGANISM: S. pneumoniae

<400> SEQUENCE: 92

Cys Ser Tyr Glu Leu Gly Arg His Gln Ala Gly Gln Asp Lys Lys Glu
1               5                   10                  15
Ser Asn Arg Val Ala Tyr Ile Asp Gly Asp Gln Ala Gly Gln Lys Ala
            20                  25                  30
Glu Asn Leu Thr Pro Asp Glu Val Ser Lys Arg Glu Gly Ile Asn Ala
        35                  40                  45
Glu Gln Ile Val Ile Lys Ile Thr Asp Gln Gly Tyr Val Thr Ser His
    50                  55                  60
Gly Asp His Tyr His Tyr Tyr Asn Gly Lys Val Pro Tyr Asp Ala Ile
65                  70                  75                  80
Ile Ser Glu Glu Leu Leu Met Lys Asp Pro Asn Tyr Gln Leu Lys Asp
                85                  90                  95
Ser Asp Ile Val Asn Glu Ile Lys Gly Gly Tyr Val Ile Lys Val Asn
            100                 105                 110
Gly Lys Tyr Tyr Val Tyr Leu Lys Asp Ala Ala His Ala Asp Asn Ile
        115                 120                 125
Arg Thr Lys Glu Glu Ile Lys Arg Gln Lys Gln Glu His Ser His Asn
    130                 135                 140
His Gly Gly Gly Ser Asn Asp Gln Ala Val Val Ala Ala Arg Ala Gln
145                 150                 155                 160
Gly Arg Tyr Thr Thr Asp Asp Gly Tyr Ile Phe Asn Ala Ser Asp Ile
                165                 170                 175
Ile Glu Asp Thr Gly Asp Ala Tyr Ile Val Pro His Gly Asn His Phe
            180                 185                 190
```

```
His Tyr Ile Pro Lys Ser Asp Leu Ser Ala Ser Glu Leu Ala Ala Ala
        195                 200                 205

Gln Ala Tyr Trp Asn Gly Lys Gln Gly Ser Arg Pro Ser Ser Ser Ser
        210                 215                 220

Ser His Asn Ala Asn Pro Ala Gln Pro Arg Leu Ser Glu Asn His Asn
225                 230                 235                 240

Leu Thr Val Thr Pro Thr Tyr His Gln Asn Gln Gly Glu Asn Ile Ser
                245                 250                 255

Ser Leu Leu Arg Glu Leu Tyr Ala Lys Pro Leu Ser Glu Arg His Val
                260                 265                 270

Glu Ser Asp Gly Leu Ile Phe Asp Pro Ala Gln Ile Thr Ser Arg Thr
        275                 280                 285

Ala Arg Gly Val Ala Val Pro His Gly Asn His Tyr His Phe Ile Pro
        290                 295                 300

Tyr Glu Gln Met Ser Glu Leu Glu Arg Ile Ala Arg Ile Ile Pro
305                 310                 315                 320

Leu Arg Tyr Arg Ser Asn His Trp Val Pro Asp Ser Arg Pro Glu Gln
                325                 330                 335

Pro Ser Pro Gln Pro Ser Pro Ser Pro Gln Pro Ala Pro Asn Pro Gln
                340                 345                 350

Pro Ala Pro Ser Asn Pro Ile Asp Glu Lys Leu Val Lys Glu Ala Val
        355                 360                 365

Arg Lys Val Gly Asp Gly Tyr Val Phe Glu Glu Asn Gly Val Ser Arg
        370                 375                 380

Tyr Ile Pro Ala Lys Asp Leu Ser Ala Glu Thr Ala Ala Gly Ile Asp
385                 390                 395                 400

Ser Lys Leu Ala Lys Gln Glu Ser Leu Ser His Lys Leu Gly Thr Lys
                405                 410                 415

Lys Thr Asp Leu Pro Ser Ser Asp Arg Glu Phe Tyr Asn Lys Ala Tyr
                420                 425                 430

Asp Leu Leu Ala Arg Ile His Gln Asp Leu Leu Asp Asn Lys Gly Arg
                435                 440                 445

Gln Val Asp Phe Glu Ala Leu Asp Asn Leu Leu Glu Arg Leu Lys Asp
        450                 455                 460

Val Ser Ser Asp Lys Val Lys Leu Val Glu Asp Ile Leu Ala Phe Leu
465                 470                 475                 480

Ala Pro Ile Arg His Pro Glu Arg Leu Gly Lys Pro Asn Ser Gln Ile
                485                 490                 495

Thr Tyr Thr Asp Asp Glu Ile Gln Val Ala Lys Leu Ala Gly Lys Tyr
                500                 505                 510

Thr Thr Glu Asp Gly Tyr Ile Phe Asp Pro Arg Asp Ile Thr Ser Asp
        515                 520                 525

Glu Gly Asp Ala Tyr Val Thr Pro His Met Thr His Ser His Trp Ile
        530                 535                 540

Lys Lys Asp Ser Leu Ser Glu Ala Arg Ala Ala Gln Ala Tyr
545                 550                 555                 560

Ala Lys Glu Lys Gly Leu Thr Pro Ser Thr Asp His Arg Asp Ser
                565                 570                 575

Gly Asn Thr Glu Ala Lys Gly Ala Glu Ala Ile Tyr Asn Arg Val Lys
                580                 585                 590

Ala Ala Lys Lys Val Pro Leu Asp Arg Met Pro Tyr Asn Leu Gln Tyr
        595                 600                 605
```

```
Thr Val Glu Val Lys Asn Gly Ser Leu Ile Ile Pro His Tyr Asp His
    610                 615                 620

Tyr His Asn Ile Lys Phe Glu Trp Phe Asp Glu Gly Leu Tyr Glu Ala
625                 630                 635                 640

Pro Lys Gly Tyr Thr Leu Glu Asp Leu Leu Ala Thr Val Lys Tyr Tyr
                645                 650                 655

Val Glu His Pro Asn Glu Arg Pro His Ser Asp Asn Gly Phe Gly Asn
                660                 665                 670

Ala Ser Asp His Val Arg Lys Asn Lys Ala Asp Gln Asp Ser Lys Pro
            675                 680                 685

Asp Glu Asp Lys Gly His Asp Glu Val Ser Glu Pro Thr His Pro Glu
    690                 695                 700

Ser Asp Glu Lys Glu Asn His Ala Gly Leu Asn Pro Ser Ala Asp Asn
705                 710                 715                 720

Leu Tyr Lys Pro Ser Thr Asp Thr Glu Thr Glu Glu Ala Glu
                725                 730                 735

Asp Thr Thr Asp Glu Ala Glu Ile Pro Gln Val Glu His Ser Val Ile
                740                 745                 750

Asn Ala Lys Ile Ala Asp Ala Glu Ala Leu Leu Glu Lys Val Thr Asp
            755                 760                 765

Pro Ser Ile Arg Gln Asn Ala Met Glu Thr Leu Thr Gly Leu Lys Ser
770                 775                 780

Ser Leu Leu Leu Gly Thr Lys Asp Asn Asn Thr Ile Ser Ala Glu Val
785                 790                 795                 800

Asp Ser Leu Leu Ala Leu Leu Lys Lys Ser Gln Pro Ala Pro Ile Gln
                805                 810                 815

<210> SEQ ID NO 93
<211> LENGTH: 816
<212> TYPE: PRT
<213> ORGANISM: S. pneumoniae

<400> SEQUENCE: 93

Cys Ser Tyr Glu Leu Gly Arg His Gln Ala Gly Gln Asp Lys Lys Glu
1               5                   10                  15

Ser Asn Arg Val Ala Tyr Ile Asp Gly Asp Gln Ala Gly Gln Lys Ala
            20                  25                  30

Glu Asn Leu Thr Pro Asp Glu Val Ser Lys Arg Glu Gly Ile Asn Ala
        35                  40                  45

Glu Gln Ile Val Ile Lys Ile Thr Asp Gln Gly Tyr Val Thr Ser His
    50                  55                  60

Gly Asp His Tyr His Tyr Tyr Asn Gly Lys Val Pro Tyr Asp Ala Ile
65                  70                  75                  80

Ile Ser Glu Glu Leu Leu Met Lys Asp Pro Asn Tyr Gln Leu Lys Asp
                85                  90                  95

Ser Asp Ile Val Asn Glu Ile Lys Gly Gly Tyr Val Ile Lys Val Asn
            100                 105                 110

Gly Lys Tyr Tyr Val Tyr Leu Lys Asp Ala Ala His Ala Asp Asn Ile
        115                 120                 125

Arg Thr Lys Glu Glu Ile Lys Arg Gln Arg Gln Glu His Ser His Asn
    130                 135                 140

His Gly Gly Gly Ser Asn Asp Gln Ala Val Val Ala Ala Arg Ala Gln
145                 150                 155                 160

Gly Arg Tyr Thr Thr Asp Asp Gly Tyr Ile Phe Asn Ala Ser Asp Ile
                165                 170                 175
```

-continued

```
Ile Glu Asp Thr Gly Asp Ala Tyr Ile Val Pro His Gly Asn His Phe
            180                 185                 190

His Tyr Ile Pro Lys Ser Asp Leu Ser Ala Ser Glu Leu Ala Ala Ala
        195                 200                 205

Gln Ala Tyr Trp Asn Gly Lys Gln Gly Ser Arg Pro Ser Ser Ser Ser
    210                 215                 220

Ser His Asn Ala Asn Pro Ala Gln Pro Arg Leu Ser Glu Asn His Asn
225                 230                 235                 240

Leu Thr Val Thr Pro Thr Tyr His Gln Asn Gln Gly Glu Asn Ile Ser
                245                 250                 255

Ser Leu Leu Arg Glu Leu Tyr Ala Lys Pro Leu Ser Glu Arg His Val
                260                 265                 270

Glu Ser Asp Gly Leu Ile Phe Asp Pro Ala Gln Ile Thr Ser Arg Thr
            275                 280                 285

Ala Arg Gly Val Ala Val Pro His Gly Asn His Tyr His Phe Ile Pro
        290                 295                 300

Tyr Glu Gln Met Ser Glu Leu Glu Glu Arg Ile Ala Arg Ile Ile Pro
305                 310                 315                 320

Leu Arg Tyr Arg Ser Asn His Trp Val Pro Asp Ser Arg Pro Glu Gln
                325                 330                 335

Pro Ser Pro Gln Pro Ser Pro Ser Pro Gln Pro Ala Pro Asn Pro Gln
                340                 345                 350

Pro Ala Pro Ser Asn Pro Ile Asp Glu Lys Leu Val Lys Glu Ala Val
            355                 360                 365

Arg Lys Val Gly Asp Gly Tyr Val Phe Glu Glu Asn Gly Val Ser Arg
        370                 375                 380

Tyr Ile Pro Ala Lys Asp Leu Ser Ala Glu Thr Ala Ala Gly Ile Asp
385                 390                 395                 400

Ser Lys Leu Ala Lys Gln Glu Ser Leu Ser His Lys Leu Gly Thr Lys
                405                 410                 415

Lys Thr Asp Leu Pro Ser Ser Asp Arg Glu Phe Tyr Asn Lys Ala Tyr
            420                 425                 430

Asp Leu Leu Ala Arg Ile His Gln Asp Leu Leu Asp Asn Lys Gly Arg
        435                 440                 445

Gln Val Asp Phe Glu Ala Leu Asp Asn Leu Leu Glu Arg Leu Lys Asp
    450                 455                 460

Val Ser Ser Asp Lys Val Lys Leu Val Glu Asp Ile Leu Ala Phe Leu
465                 470                 475                 480

Ala Pro Ile Arg His Pro Glu Arg Leu Gly Lys Pro Asn Ser Gln Ile
                485                 490                 495

Thr Tyr Thr Asp Asp Glu Ile Gln Val Ala Lys Leu Ala Gly Lys Tyr
            500                 505                 510

Thr Thr Glu Asp Gly Tyr Ile Phe Asp Pro Arg Asp Ile Thr Ser Asp
        515                 520                 525

Glu Gly Asp Ala Tyr Val Thr Pro His Met Thr His Ser His Trp Ile
    530                 535                 540

Lys Lys Asp Ser Leu Ser Glu Ala Glu Arg Ala Ala Ala Gln Ala Tyr
545                 550                 555                 560

Ala Lys Glu Lys Gly Leu Thr Pro Pro Ser Thr Asp His Gln Asp Ser
                565                 570                 575

Gly Asn Thr Glu Ala Lys Gly Ala Glu Ala Ile Tyr Asn Arg Val Lys
            580                 585                 590
```

-continued

```
Ala Ala Lys Lys Val Pro Leu Asp Arg Met Pro Tyr Asn Leu Gln Tyr
        595                 600                 605

Thr Val Glu Val Lys Asn Gly Ser Leu Ile Ile Pro His Tyr Asp His
    610                 615                 620

Tyr His Asn Ile Lys Phe Glu Trp Phe Asp Gly Leu Tyr Glu Ala
625                 630                 635                 640

Pro Lys Gly Tyr Thr Leu Glu Asp Leu Leu Ala Thr Val Lys Tyr Tyr
                645                 650                 655

Val Glu His Pro Asn Glu Arg Pro His Ser Asp Asn Gly Phe Gly Asn
            660                 665                 670

Ala Ser Asp His Val Arg Lys Asn Lys Ala Asp Gln Asp Ser Lys Pro
        675                 680                 685

Asp Glu Asp Lys Gly His Asp Glu Val Ser Glu Pro Thr His Pro Glu
    690                 695                 700

Ser Asp Glu Lys Glu Asn His Ala Gly Leu Asn Pro Ser Ala Asp Asn
705                 710                 715                 720

Leu Tyr Lys Pro Ser Thr Asp Thr Glu Glu Thr Glu Glu Ala Glu
                725                 730                 735

Asp Thr Thr Asp Glu Ala Glu Ile Pro Gln Val Glu His Ser Val Ile
            740                 745                 750

Asn Ala Lys Ile Ala Asp Ala Glu Ala Leu Leu Glu Lys Val Thr Asp
        755                 760                 765

Pro Ser Ile Arg Gln Asn Ala Met Glu Thr Leu Thr Gly Leu Lys Ser
    770                 775                 780

Ser Leu Leu Leu Gly Thr Lys Asp Asn Asn Thr Ile Ser Ala Glu Val
785                 790                 795                 800

Asp Ser Leu Leu Ala Leu Leu Lys Lys Ser Gln Pro Ala Pro Ile Gln
                805                 810                 815

<210> SEQ ID NO 94
<211> LENGTH: 816
<212> TYPE: PRT
<213> ORGANISM: S. pneumoniae

<400> SEQUENCE: 94

Cys Ser Tyr Glu Leu Gly Arg His Gln Ala Gly Gln Asp Lys Lys Glu
1               5                   10                  15

Ser Asn Arg Val Ala Tyr Ile Asp Gly Asp Gln Ala Gly Gln Lys Ala
            20                  25                  30

Glu Asn Leu Thr Pro Asp Glu Val Ser Lys Arg Glu Gly Ile Asn Ala
        35                  40                  45

Glu Gln Ile Val Ile Lys Ile Thr Asp Gln Gly Tyr Val Thr Ser His
    50                  55                  60

Gly Asp His Tyr His Tyr Tyr Asn Gly Lys Val Pro Tyr Asp Ala Ile
65                  70                  75                  80

Ile Ser Glu Glu Leu Leu Met Lys Asp Pro Asn Tyr Gln Leu Lys Asp
                85                  90                  95

Ser Asp Ile Val Asn Glu Ile Lys Gly Gly Tyr Val Ile Lys Val Asn
            100                 105                 110

Gly Lys Tyr Tyr Val Tyr Leu Lys Asp Ala Ala His Ala Asp Asn Ile
        115                 120                 125

Arg Thr Lys Glu Glu Ile Lys Arg Gln Lys Gln Glu His Ser His Asn
    130                 135                 140

His Gly Gly Gly Ser Asn Asp Gln Ala Val Val Ala Ala Arg Ala Gln
145                 150                 155                 160
```

-continued

```
Gly Arg Tyr Thr Thr Asp Asp Gly Tyr Ile Phe Asn Ala Ser Asp Ile
            165                 170                 175
Ile Glu Asp Thr Gly Asp Ala Tyr Ile Val Pro Arg Gly Asn His Phe
        180                 185                 190
His Tyr Ile Pro Lys Ser Asp Leu Ser Ala Ser Glu Leu Ala Ala Ala
    195                 200                 205
Gln Ala Tyr Trp Asn Gly Lys Gln Gly Ser Arg Pro Ser Ser Ser Ser
210                 215                 220
Ser His Asn Ala Asn Pro Ala Gln Pro Arg Leu Ser Glu Asn His Asn
225                 230                 235                 240
Leu Thr Val Thr Pro Thr Tyr His Gln Asn Gln Gly Glu Asn Ile Ser
                245                 250                 255
Ser Leu Leu Arg Glu Leu Tyr Ala Lys Pro Leu Ser Glu Arg Arg Val
            260                 265                 270
Glu Ser Asp Gly Leu Ile Phe Asp Pro Ala Gln Ile Thr Ser Arg Thr
        275                 280                 285
Ala Arg Gly Val Ala Val Pro His Gly Asn His Tyr His Phe Ile Pro
    290                 295                 300
Tyr Glu Gln Met Ser Glu Leu Glu Glu Arg Ile Ala Arg Ile Ile Pro
305                 310                 315                 320
Leu Arg Tyr Arg Ser Asn His Trp Val Pro Asp Ser Arg Pro Glu Gln
                325                 330                 335
Pro Ser Pro Gln Pro Ser Pro Ser Pro Gln Pro Ala Pro Asn Pro Gln
            340                 345                 350
Pro Ala Pro Ser Asn Pro Ile Asp Glu Lys Leu Val Lys Glu Ala Val
        355                 360                 365
Arg Lys Val Gly Asp Gly Tyr Val Phe Glu Glu Asn Gly Val Ser Arg
    370                 375                 380
Tyr Ile Pro Ala Lys Asp Leu Ser Ala Glu Thr Ala Ala Gly Ile Asp
385                 390                 395                 400
Ser Lys Leu Ala Lys Gln Glu Ser Leu Ser His Lys Leu Gly Thr Lys
                405                 410                 415
Lys Thr Asp Leu Pro Ser Ser Asp Arg Glu Phe Tyr Asn Lys Ala Tyr
            420                 425                 430
Asp Leu Leu Ala Arg Ile His Gln Asp Leu Leu Asp Asn Lys Gly Arg
        435                 440                 445
Gln Val Asp Phe Glu Ala Leu Asp Asn Leu Leu Glu Arg Leu Lys Asp
    450                 455                 460
Val Ser Ser Asp Lys Val Lys Leu Val Glu Asp Ile Leu Ala Phe Leu
465                 470                 475                 480
Ala Pro Ile Arg His Pro Glu Arg Leu Gly Lys Pro Asn Ser Gln Ile
                485                 490                 495
Thr Tyr Thr Asp Asp Glu Ile Gln Val Ala Lys Leu Ala Gly Lys Tyr
            500                 505                 510
Thr Thr Glu Asp Gly Tyr Ile Phe Asp Pro Arg Asp Ile Thr Ser Asp
        515                 520                 525
Glu Gly Asp Ala Tyr Val Thr Pro His Met Thr His Ser His Trp Ile
    530                 535                 540
Lys Lys Asp Ser Leu Ser Glu Ala Glu Arg Ala Ala Gln Ala Tyr
545                 550                 555                 560
Ala Lys Glu Lys Gly Leu Thr Pro Pro Ser Thr Asp His Gln Asp Ser
                565                 570                 575
```

```
Gly Asn Thr Glu Ala Lys Gly Ala Glu Ala Ile Tyr Asn Arg Val Lys
            580                 585                 590

Ala Ala Lys Lys Val Pro Leu Asp Arg Met Pro Tyr Asn Leu Gln Tyr
        595                 600                 605

Thr Val Glu Val Lys Asn Gly Ser Leu Ile Ile Pro His Tyr Asp His
    610                 615                 620

Tyr His Asn Ile Lys Phe Glu Trp Phe Asp Glu Gly Leu Tyr Glu Ala
625                 630                 635                 640

Pro Lys Gly Tyr Thr Leu Glu Asp Leu Leu Ala Thr Val Lys Tyr Tyr
                645                 650                 655

Val Glu His Pro Asn Glu Arg Pro His Ser Asp Asn Gly Phe Gly Asn
            660                 665                 670

Ala Ser Asp His Val Arg Lys Asn Lys Ala Asp Gln Asp Ser Lys Pro
        675                 680                 685

Asp Glu Asp Lys Gly His Asp Glu Val Ser Glu Pro Thr His Pro Glu
    690                 695                 700

Ser Asp Glu Lys Glu Asn His Ala Gly Leu Asn Pro Ser Ala Asp Asn
705                 710                 715                 720

Leu Tyr Lys Pro Ser Thr Asp Thr Glu Glu Thr Glu Glu Glu Ala Glu
                725                 730                 735

Asp Thr Thr Asp Glu Ala Glu Ile Pro Gln Val Glu His Ser Val Ile
            740                 745                 750

Asn Ala Lys Ile Ala Asp Ala Glu Ala Leu Leu Glu Lys Val Thr Asp
        755                 760                 765

Pro Ser Ile Arg Gln Asn Ala Met Glu Thr Leu Thr Gly Leu Lys Ser
    770                 775                 780

Ser Leu Leu Leu Gly Thr Lys Asp Asn Asn Thr Ile Ser Ala Glu Val
785                 790                 795                 800

Asp Ser Leu Leu Ala Leu Leu Lys Lys Ser Gln Pro Ala Pro Ile Gln
                805                 810                 815

<210> SEQ ID NO 95
<211> LENGTH: 834
<212> TYPE: PRT
<213> ORGANISM: S. pneumoniae

<400> SEQUENCE: 95

Cys Ser Tyr Glu Leu Gly Arg His Gln Ala Gly Gln Val Lys Lys Glu
1               5                   10                  15

Ser Asn Arg Val Ser Tyr Ile Asp Gly Asp Gln Ala Gly Gln Lys Ala
            20                  25                  30

Glu Asn Leu Thr Pro Asp Glu Val Ser Lys Arg Glu Gly Ile Asn Ala
        35                  40                  45

Glu Gln Ile Val Ile Lys Ile Thr Asp Gln Gly Tyr Val Thr Ser His
    50                  55                  60

Gly Asp His Tyr His Tyr Asn Gly Lys Val Pro Tyr Asp Ala Ile
65                  70                  75                  80

Ile Ser Glu Glu Leu Leu Met Lys Asp Pro Asn Tyr Gln Leu Lys Asp
                85                  90                  95

Ser Asp Ile Val Asn Glu Ile Lys Gly Gly Tyr Val Ile Lys Val Asp
            100                 105                 110

Gly Lys Tyr Tyr Val Tyr Leu Lys Asp Ala Ala His Ala Asp Asn Ile
        115                 120                 125

Arg Thr Lys Glu Glu Ile Lys Arg Gln Lys Gln Glu Arg Ser His Asn
    130                 135                 140
```

-continued

```
His Asn Ser Arg Ala Asp Asn Ala Val Ala Ala Arg Ala Gln Gly
145                 150                 155                 160

Arg Tyr Thr Thr Asp Asp Gly Tyr Ile Phe Asn Ala Ser Asp Ile Ile
            165                 170                 175

Glu Asp Thr Gly Asp Ala Tyr Ile Val Pro His Gly Asp His Tyr His
        180                 185                 190

Tyr Ile Pro Lys Ser Asp Leu Ser Ala Ser Glu Leu Ala Ala Ala Gln
    195                 200                 205

Ala Tyr Trp Asn Gly Lys Gln Gly Ser Arg Pro Ser Ser Ser Ser Ser
210                 215                 220

His Asn Ala Asn Pro Ala Gln Pro Arg Leu Ser Glu Asn His Asn Leu
225                 230                 235                 240

Thr Val Thr Pro Thr Tyr His Gln Asn Gln Gly Glu Asn Ile Ser Ser
                245                 250                 255

Leu Leu Arg Glu Leu Tyr Ala Lys Pro Leu Ser Glu Arg His Val Glu
            260                 265                 270

Ser Asp Gly Leu Ile Phe Asp Pro Ala Gln Ile Thr Ser Arg Thr Ala
        275                 280                 285

Asn Gly Val Ala Val Pro His Gly Asp His Tyr His Phe Ile Pro Tyr
    290                 295                 300

Ser Gln Leu Ser Pro Leu Glu Glu Lys Leu Ala Arg Ile Ile Pro Leu
305                 310                 315                 320

Arg Tyr Arg Ser Asn His Trp Val Pro Asp Ser Arg Pro Glu Gln Pro
                325                 330                 335

Ser Pro Gln Ser Thr Pro Glu Pro Ser Pro Ser Pro Gln Pro Ala Pro
            340                 345                 350

Asn Pro Gln Pro Ala Pro Ser Asn Pro Ile Asp Glu Lys Leu Val Lys
        355                 360                 365

Glu Ala Val Arg Lys Val Gly Asp Gly Tyr Val Phe Glu Glu Asn Gly
    370                 375                 380

Val Pro Arg Tyr Ile Pro Ala Lys Asp Leu Ser Ala Glu Thr Ala Ala
385                 390                 395                 400

Gly Ile Asp Ser Lys Leu Ala Lys Gln Glu Ser Leu Ser His Lys Leu
                405                 410                 415

Gly Ala Lys Lys Thr Asp Leu Pro Ser Ser Asp Arg Glu Phe Tyr Asn
            420                 425                 430

Lys Ala Tyr Asp Leu Leu Ala Arg Ile His Gln Asp Leu Leu Asp Asn
        435                 440                 445

Lys Gly Arg Gln Val Asp Phe Glu Ala Leu Asp Asn Leu Leu Glu Arg
    450                 455                 460

Leu Lys Asp Val Ser Ser Asp Lys Val Lys Leu Val Asp Ile Leu
465                 470                 475                 480

Ala Phe Leu Ala Pro Ile Arg His Pro Glu Arg Leu Gly Lys Pro Asn
                485                 490                 495

Ala Gln Ile Thr Tyr Thr Asp Asp Glu Ile Gln Val Ala Lys Leu Ala
            500                 505                 510

Gly Lys Tyr Thr Thr Glu Asp Gly Tyr Ile Phe Asp Pro Arg Asp Ile
        515                 520                 525

Thr Ser Asp Glu Gly Asp Ala Tyr Val Thr Pro His Met Thr His Ser
    530                 535                 540

His Trp Ile Lys Lys Asp Ser Leu Ser Glu Ala Glu Arg Ala Ala Ala
545                 550                 555                 560
```

```
Gln Ala Tyr Ala Lys Glu Lys Gly Leu Thr Pro Pro Ser Thr Asp His
                565                 570                 575

Gln Asp Ser Gly Asn Thr Glu Ala Lys Gly Ala Glu Ala Ile Tyr Asn
            580                 585                 590

Arg Val Lys Ala Ala Lys Lys Val Pro Leu Asp Arg Met Pro Tyr Asn
        595                 600                 605

Leu Gln Tyr Thr Val Glu Val Lys Asn Gly Ser Leu Ile Ile Pro His
    610                 615                 620

Tyr Asp His Tyr His Asn Ile Lys Phe Glu Trp Phe Asp Glu Gly Leu
625                 630                 635                 640

Tyr Glu Ala Pro Lys Gly Tyr Ser Leu Glu Asp Leu Leu Ala Thr Val
                645                 650                 655

Lys Tyr Tyr Val Glu His Pro Asn Glu Arg Pro His Ser Asp Asn Gly
            660                 665                 670

Phe Gly Asn Ala Ser Asp His Val Gln Arg Asn Lys Asn Gly Gln Ala
        675                 680                 685

Asp Thr Asn Gln Thr Glu Lys Pro Asn Glu Glu Lys Pro Gln Thr Glu
    690                 695                 700

Lys Pro Glu Glu Asp Lys Glu His Asp Glu Val Ser Glu Pro Thr His
705                 710                 715                 720

Pro Glu Ser Asp Glu Lys Glu Asn His Val Gly Leu Asn Pro Ser Ala
                725                 730                 735

Asp Asn Leu Tyr Lys Pro Ser Thr Asp Thr Glu Glu Thr Glu Glu Glu
            740                 745                 750

Ala Glu Asp Thr Thr Asp Glu Ala Glu Ile Pro Gln Val Glu Tyr Ser
        755                 760                 765

Val Ile Asn Ala Lys Ile Ala Glu Ala Glu Leu Leu Glu Lys Val
    770                 775                 780

Thr Asp Ser Ser Ile Arg Gln Asn Ala Val Glu Thr Leu Thr Gly Leu
785                 790                 795                 800

Lys Ser Ser Leu Leu Leu Gly Thr Lys Asp Asn Asn Thr Ile Ser Ala
                805                 810                 815

Glu Val Asp Ser Leu Leu Ala Leu Leu Lys Ser Gln Pro Ala Pro
            820                 825                 830

Ile Gln

<210> SEQ ID NO 96
<211> LENGTH: 811
<212> TYPE: PRT
<213> ORGANISM: S. pneumoniae

<400> SEQUENCE: 96

Cys Ser Tyr Glu Leu Gly Arg His Gln Ala Gly Gln Asp Lys Lys Glu
1               5                   10                  15

Ser Asn Arg Val Ala Tyr Ile Asp Gly Asp Gln Ala Gly Gln Lys Ala
            20                  25                  30

Glu Asn Leu Thr Pro Asp Glu Val Ser Lys Arg Glu Gly Ile Asn Ala
        35                  40                  45

Glu Gln Ile Val Ile Lys Ile Thr Asp Gln Gly Tyr Val Thr Ser His
    50                  55                  60

Gly Asp His Tyr His Tyr Tyr Asn Gly Lys Val Pro Tyr Asp Ala Ile
65                  70                  75                  80

Ile Ser Glu Glu Leu Leu Met Lys Asp Pro Asn Tyr Gln Leu Lys Asp
                85                  90                  95
```

-continued

```
Ser Asp Ile Val Asn Glu Ile Lys Gly Gly Tyr Val Ile Lys Val Asn
                100                 105                 110

Gly Lys Tyr Tyr Val Tyr Leu Lys Asp Ala Ala His Ala Asp Asn Ile
            115                 120                 125

Arg Thr Lys Glu Glu Ile Lys Arg Gln Lys Gln Glu His Ser His Asn
        130                 135                 140

His Gly Gly Ser Asn Asp Gln Ala Val Ala Ala Arg Ala Gln
145                 150                 155                 160

Gly Arg Tyr Thr Thr Asp Asp Gly Tyr Ile Phe Asn Ala Ser Asp Ile
                165                 170                 175

Ile Glu Asp Thr Gly Asp Ala Tyr Ile Val Pro His Gly Asn His Phe
            180                 185                 190

His Tyr Ile Pro Lys Ser Asp Leu Ser Ala Ser Glu Leu Ala Ala Ala
        195                 200                 205

Gln Ala Tyr Trp Asn Gly Lys Gln Gly Ser Arg Pro Ser Ser Ser Ser
    210                 215                 220

Ser His Asn Ala Asn Pro Ala Gln Pro Arg Leu Ser Glu Asn His Asn
225                 230                 235                 240

Leu Thr Val Thr Pro Thr Tyr His Gln Asn Gln Gly Glu Asn Ile Ser
                245                 250                 255

Ser Leu Leu Arg Glu Leu Tyr Ala Lys Pro Leu Ser Glu Arg His Val
            260                 265                 270

Glu Ser Asp Gly Leu Ile Phe Asp Pro Ala Gln Ile Thr Ser Arg Thr
        275                 280                 285

Ala Arg Gly Val Ala Val Pro His Gly Asn His Tyr His Phe Ile Pro
    290                 295                 300

Tyr Glu Gln Met Ser Glu Leu Glu Glu Arg Ile Ala Arg Ile Ile Pro
305                 310                 315                 320

Leu Arg Tyr Arg Ser Asn His Trp Val Pro Asp Ser Arg Pro Glu Gln
                325                 330                 335

Pro Ser Pro Gln Pro Ser Pro Gln Pro Ala Pro Asn Pro Gln
            340                 345                 350

Pro Ala Pro Ser Asn Pro Ile Asp Glu Lys Leu Val Lys Glu Ala Val
        355                 360                 365

Arg Lys Val Gly Asp Gly Tyr Val Phe Glu Glu Asn Gly Val Ser Arg
    370                 375                 380

Tyr Ile Pro Ala Lys Asp Leu Ser Ala Glu Thr Ala Ala Gly Ile Asp
385                 390                 395                 400

Ser Lys Leu Ala Lys Gln Glu Ser Leu Ser His Lys Leu Gly Thr Lys
                405                 410                 415

Lys Thr Asp Leu Pro Ser Ser Asp Arg Glu Phe Tyr Asn Lys Ala Tyr
            420                 425                 430

Asp Leu Leu Ala Arg Ile His Gln Asp Leu Leu Asp Asn Lys Gly Arg
        435                 440                 445

Gln Val Asp Phe Glu Ala Leu Asp Asn Leu Leu Glu Arg Leu Lys Asp
    450                 455                 460

Val Ser Ser Asp Lys Val Lys Leu Val Glu Asp Ile Leu Ala Phe Leu
465                 470                 475                 480

Ala Pro Ile Arg His Pro Glu Arg Leu Gly Lys Pro Asn Ser Gln Ile
                485                 490                 495

Thr Tyr Thr Asp Asp Glu Ile Gln Val Ala Lys Leu Ala Gly Lys Tyr
            500                 505                 510

Thr Thr Glu Asp Gly Tyr Ile Phe Asp Pro Arg Asp Ile Thr Ser Asp
```

```
                515                 520                 525
Glu Gly Asp Ala Tyr Val Thr Pro His Met Thr His Ser His Trp Ile
            530                 535                 540
Lys Lys Asp Ser Leu Ser Glu Ala Glu Arg Ala Ala Gln Ala Tyr
545                 550                 555                 560
Ala Lys Glu Lys Gly Leu Thr Pro Pro Ser Thr Asp His Gln Asp Ser
                565                 570                 575
Gly Asn Thr Glu Ala Lys Gly Ala Glu Ala Ile Tyr Asn Arg Val Lys
            580                 585                 590
Ala Ala Lys Lys Val Pro Leu Asp Arg Met Pro Tyr Asn Leu Gln Tyr
            595                 600                 605
Thr Val Glu Val Lys Asn Gly Ser Leu Ile Ile Pro His Tyr Asp His
            610                 615                 620
Tyr His Asn Ile Lys Phe Glu Trp Phe Asp Glu Gly Leu Tyr Glu Ala
625                 630                 635                 640
Pro Lys Gly Tyr Thr Leu Glu Asp Leu Leu Ala Thr Val Lys Tyr Tyr
                645                 650                 655
Val Glu His Pro Asn Glu Arg Pro His Ser Asp Asn Gly Phe Gly Asn
            660                 665                 670
Ala Ser Asp His Val Arg Lys Asn Lys Ala Asp Gln Asp Ser Lys Pro
            675                 680                 685
Asp Glu Asp Lys Gly His Asp Glu Val Ser Glu Pro Thr His Pro Glu
            690                 695                 700
Ser Asp Glu Lys Glu Asn His Ala Gly Leu Asn Pro Ser Ala Asp Asn
705                 710                 715                 720
Leu Tyr Lys Pro Ser Thr Asp Thr Glu Glu Thr Glu Glu Glu Ala Glu
                725                 730                 735
Asp Thr Thr Asp Glu Ala Glu Ile Pro Gln Val Glu His Ser Val Ile
            740                 745                 750
Asn Ala Lys Ile Ala Asp Ala Glu Ala Leu Leu Glu Lys Val Thr Asp
            755                 760                 765
Pro Ser Ile Arg Gln Asn Ala Met Glu Thr Leu Thr Gly Leu Lys Ser
            770                 775                 780
Ser Leu Leu Leu Gly Thr Lys Asp Asn Asn Thr Ile Ser Ala Glu Val
785                 790                 795                 800
Asp Ser Leu Leu Ala Leu Leu Lys Glu Ser Lys
                805                 810

<210> SEQ ID NO 97
<211> LENGTH: 811
<212> TYPE: PRT
<213> ORGANISM: S. pneumoniae

<400> SEQUENCE: 97

Cys Ser Tyr Glu Leu Gly Arg His Gln Ala Gly Gln Asp Lys Lys Glu
1               5                   10                  15
Ser Asn Arg Val Ala Tyr Ile Asp Gly Asp Gln Ala Gly Gln Lys Ala
            20                  25                  30
Glu Asn Leu Thr Pro Asp Glu Val Ser Lys Arg Glu Gly Ile Asn Ala
        35                  40                  45
Glu Gln Ile Val Ile Lys Ile Thr Asp Gln Gly Tyr Val Thr Ser His
    50                  55                  60
Gly Asp His Tyr His Tyr Tyr Asn Gly Lys Val Pro Tyr Asp Ala Ile
65                  70                  75                  80
```

-continued

```
Ile Ser Glu Glu Leu Leu Met Lys Asp Pro Asn Tyr Gln Leu Lys Asp
                85                  90                  95
Ser Asp Ile Val Asn Glu Ile Lys Gly Gly Tyr Val Ile Lys Val Asn
            100                 105                 110
Gly Lys Tyr Tyr Gly Tyr Leu Lys Asp Ala Ala His Ala Asp Asn Ile
        115                 120                 125
Arg Thr Lys Glu Glu Ile Lys Arg Gln Lys Gln Glu His Ser His Asn
    130                 135                 140
His Gly Gly Gly Ser Asn Asp Gln Ala Val Val Ala Ala Arg Ala Gln
145                 150                 155                 160
Gly Arg Tyr Thr Thr Asp Asp Gly Tyr Ile Phe Asn Ala Ser Asp Ile
                165                 170                 175
Ile Glu Asp Thr Gly Asp Ala Tyr Ile Val Pro His Gly Asn His Phe
            180                 185                 190
His Tyr Ile Pro Lys Ser Asp Leu Ser Ala Ser Glu Leu Ala Ala Ala
        195                 200                 205
Gln Ala Tyr Trp Asn Gly Lys Gln Gly Ser Arg Pro Ser Ser Ser Ser
    210                 215                 220
Ser His Asn Ala Asn Pro Ala Gln Pro Arg Leu Ser Glu Asn His Asn
225                 230                 235                 240
Leu Thr Val Thr Pro Thr Tyr His Gln Asn Gln Gly Glu Asn Ile Ser
                245                 250                 255
Ser Leu Leu Arg Glu Leu Tyr Ala Lys Pro Leu Ser Glu Arg His Val
            260                 265                 270
Glu Ser Asp Gly Leu Ile Phe Asp Pro Ala Gln Ile Thr Ser Arg Thr
        275                 280                 285
Ala Arg Gly Val Ala Val Pro His Gly Asn His Tyr His Phe Ile Pro
    290                 295                 300
Tyr Glu Gln Met Ser Glu Leu Glu Glu Arg Ile Ala Arg Ile Ile Pro
305                 310                 315                 320
Leu Arg Tyr Arg Ser Asn His Trp Val Pro Asp Ser Arg Pro Glu Gln
                325                 330                 335
Pro Ser Pro Gln Pro Ser Pro Ser Gln Pro Ala Pro Asn Pro Gln
            340                 345                 350
Pro Ala Pro Ser Asn Pro Ile Asp Glu Lys Leu Val Lys Glu Ala Val
        355                 360                 365
Arg Lys Val Gly Asp Gly Tyr Val Phe Glu Glu Asn Gly Val Ser Arg
    370                 375                 380
Tyr Ile Pro Ala Lys Asp Leu Ser Ala Glu Thr Ala Ala Gly Ile Asp
385                 390                 395                 400
Ser Lys Leu Ala Lys Gln Glu Ser Leu Ser His Lys Leu Gly Thr Lys
                405                 410                 415
Lys Thr Asp Leu Pro Ser Ser Asp Arg Glu Phe Tyr Asn Lys Ala Tyr
            420                 425                 430
Asp Leu Leu Ala Arg Ile His Gln Asp Leu Leu Asp Asn Lys Gly Arg
        435                 440                 445
Gln Val Asp Phe Glu Ala Leu Asp Asn Leu Leu Glu Arg Leu Lys Asp
    450                 455                 460
Val Ser Ser Asp Lys Val Lys Leu Val Glu Asp Ile Leu Ala Phe Leu
465                 470                 475                 480
Ala Pro Ile Arg His Pro Glu Arg Leu Gly Lys Pro Asn Ser Gln Ile
                485                 490                 495
Thr Tyr Thr Asp Asp Glu Ile Gln Val Ala Lys Leu Ala Gly Lys Tyr
```

```
            500                 505                 510
Thr Thr Glu Asp Gly Tyr Ile Phe Asp Pro Arg Asp Ile Thr Ser Asp
        515                 520                 525

Glu Gly Asp Ala Tyr Val Thr Pro His Met Thr His Ser His Trp Ile
530                 535                 540

Lys Lys Asp Ser Leu Ser Glu Ala Glu Arg Ala Ala Gln Ala Tyr
545             550                 555                 560

Ala Lys Glu Lys Gly Leu Thr Pro Ser Thr Asp His Gln Asp Ser
            565                 570                 575

Gly Asn Thr Glu Ala Lys Gly Ala Glu Ala Ile Tyr Asn Arg Val Lys
        580                 585                 590

Ala Ala Lys Lys Val Pro Leu Asp Arg Met Pro Tyr Asn Leu Gln Tyr
            595                 600                 605

Thr Val Glu Val Lys Asn Gly Ser Leu Ile Ile Pro His Tyr Asp His
        610                 615                 620

Tyr His Asn Ile Lys Phe Glu Trp Phe Asp Gly Leu Tyr Glu Ala
625                 630                 635                 640

Pro Lys Gly Tyr Thr Leu Glu Asp Leu Leu Ala Thr Val Lys Tyr Tyr
            645                 650                 655

Val Glu His Pro Asn Glu Arg Pro His Ser Asp Asn Gly Phe Gly Asn
        660                 665                 670

Ala Ser Asp His Val Arg Lys Asn Lys Ala Asp Gln Asp Ser Lys Pro
            675                 680                 685

Asp Glu Asp Lys Gly His Asp Glu Val Ser Glu Pro Thr His Pro Glu
690                 695                 700

Ser Asp Glu Lys Glu Asn His Ala Gly Leu Asn Pro Ser Ala Asp Asn
705                 710                 715                 720

Leu Tyr Lys Pro Ser Thr Asp Thr Glu Glu Thr Glu Glu Ala Glu
            725                 730                 735

Asp Thr Thr Asp Glu Ala Glu Ile Pro Gln Val Glu His Ser Val Ile
            740                 745                 750

Asn Ala Lys Ile Ala Asp Ala Glu Ala Leu Leu Glu Lys Val Thr Asp
            755                 760                 765

Pro Ser Ile Arg Gln Asn Ala Met Glu Thr Leu Thr Gly Leu Lys Ser
770                 775                 780

Ser Leu Leu Leu Gly Thr Lys Asp Asn Asn Thr Ile Ser Ala Glu Val
785                 790                 795                 800

Asp Ser Leu Leu Ala Leu Leu Lys Glu Ser Lys
                805                 810

<210> SEQ ID NO 98
<211> LENGTH: 811
<212> TYPE: PRT
<213> ORGANISM: S. pneumoniae

<400> SEQUENCE: 98

Cys Ser Tyr Glu Leu Gly Arg His Gln Ala Gly Gln Asp Lys Lys Glu
1               5                   10                  15

Ser Asn Arg Val Ala Tyr Ile Asp Gly Asp Gln Ala Gly Gln Lys Ala
            20                  25                  30

Glu Asn Leu Thr Pro Asp Glu Val Ser Lys Arg Glu Gly Ile Asn Ala
        35                  40                  45

Glu Gln Ile Val Ile Lys Ile Thr Asp Gln Gly Tyr Val Thr Ser His
    50                  55                  60
```

-continued

```
Gly Asp His Tyr His Tyr Tyr Asn Gly Lys Val Pro Tyr Asp Ala Ile
 65                  70                  75                  80

Ile Ser Glu Glu Leu Leu Met Lys Asp Pro Asn Tyr Gln Leu Lys Asp
                 85                  90                  95

Ser Asp Ile Val Asn Glu Ile Lys Gly Gly Tyr Val Ile Lys Val Asn
            100                 105                 110

Gly Lys Tyr Tyr Val Tyr Leu Lys Asp Ala Ala His Ala Asp Asn Ile
        115                 120                 125

Arg Thr Lys Glu Glu Ile Lys Arg Gln Lys Gln His Ser His Asn
    130                 135                 140

His Gly Gly Gly Ser Asn Asp Gln Ala Val Val Ala Ala Arg Ala Gln
145                 150                 155                 160

Gly Arg Tyr Thr Thr Asp Asp Gly Tyr Ile Phe Asn Ala Ser Asp Ile
                165                 170                 175

Ile Glu Asp Thr Gly Asp Ala Tyr Ile Val Pro His Gly Asn His Phe
            180                 185                 190

His Tyr Ile Pro Lys Ser Asp Leu Ser Ala Ser Glu Leu Ala Ala Ala
        195                 200                 205

Gln Ala Tyr Trp Asn Gly Lys Gln Gly Ser Arg Pro Ser Ser Ser Ser
    210                 215                 220

Ser His Asn Ala Asn Pro Ala Gln Pro Arg Leu Ser Glu Asn His Asn
225                 230                 235                 240

Leu Thr Val Thr Pro Thr Tyr His Gln Asn Gln Gly Glu Asn Ile Ser
                245                 250                 255

Ser Leu Leu Arg Glu Leu Tyr Ala Lys Pro Leu Ser Glu Arg His Val
            260                 265                 270

Glu Ser Asp Gly Leu Ile Phe Asp Pro Ala Gln Ile Thr Ser Arg Thr
        275                 280                 285

Ala Arg Gly Val Ala Val Pro His Gly Asn His Tyr His Phe Ile Pro
    290                 295                 300

Tyr Glu Gln Met Ser Glu Leu Glu Glu Arg Ile Ala Arg Ile Ile Pro
305                 310                 315                 320

Leu Arg Tyr Arg Ser Asn His Trp Val Pro Asp Ser Arg Pro Glu Gln
                325                 330                 335

Pro Ser Pro Gln Pro Ser Pro Ser Pro Gln Pro Ala Pro Asn Pro Gln
            340                 345                 350

Pro Ala Pro Ser Asn Pro Ile Asp Glu Lys Leu Val Lys Glu Ala Val
        355                 360                 365

Arg Lys Val Gly Asp Gly Tyr Val Phe Glu Glu Asn Gly Val Ser Arg
    370                 375                 380

Tyr Ile Pro Ala Lys Asp Leu Ser Ala Glu Thr Ala Ala Gly Ile Asp
385                 390                 395                 400

Ser Lys Leu Ala Lys Gln Glu Ser Leu Ser His Lys Leu Gly Thr Lys
                405                 410                 415

Lys Thr Asp Leu Pro Ser Ser Asp Arg Glu Phe Tyr Asn Lys Ala Tyr
            420                 425                 430

Asp Leu Leu Ala Arg Ile His Gln Asp Leu Leu Asp Asn Lys Gly Arg
        435                 440                 445

Gln Val Asp Phe Glu Ala Leu Asp Asn Leu Leu Glu Arg Leu Lys Asp
    450                 455                 460

Val Ser Ser Asp Lys Val Lys Leu Val Glu Asp Ile Leu Ala Phe Leu
465                 470                 475                 480

Ala Pro Ile Arg His Pro Glu Arg Leu Gly Lys Pro Asn Ser Gln Ile
```

-continued

```
                485                 490                 495
Thr Tyr Thr Asp Asp Glu Ile Gln Val Ala Lys Leu Ala Gly Lys Tyr
            500                 505                 510
Thr Thr Glu Asp Gly Tyr Ile Phe Asp Pro Arg Asp Ile Thr Ser Asp
            515                 520                 525
Glu Gly Asp Ala Tyr Val Thr Pro His Met Thr His Ser His Trp Ile
            530                 535                 540
Lys Lys Asp Ser Leu Ser Glu Ala Glu Arg Ala Ala Gln Ala Tyr
545                 550                 555                 560
Ala Lys Glu Lys Gly Leu Thr Pro Pro Ser Thr Asp His Gln Asp Ser
                565                 570                 575
Gly Asn Thr Glu Ala Lys Gly Ala Glu Ala Ile Tyr Asn Arg Val Lys
                580                 585                 590
Ala Ala Lys Lys Val Pro Leu Asp Arg Met Pro Tyr Asn Leu Gln Tyr
            595                 600                 605
Thr Val Glu Val Lys Asn Gly Ser Leu Ile Ile Pro His Tyr Asp His
            610                 615                 620
Tyr His Asn Ile Lys Phe Glu Trp Phe Asp Glu Gly Leu Tyr Glu Ala
625                 630                 635                 640
Pro Lys Gly Tyr Thr Leu Glu Asp Leu Leu Ala Thr Val Lys Tyr Tyr
                645                 650                 655
Val Glu His Pro Asn Glu Arg Pro His Ser Asp Asn Gly Phe Gly Asn
            660                 665                 670
Ala Ser Asp His Val Arg Lys Asn Lys Ala Asp Gln Asp Ser Lys Pro
            675                 680                 685
Asp Glu Asp Lys Gly His Asp Glu Val Ser Glu Pro Thr His Pro Glu
            690                 695                 700
Ser Asp Glu Lys Glu Asn His Ala Gly Leu Asn Pro Ser Ala Asp Asn
705                 710                 715                 720
Leu Tyr Lys Pro Ser Thr Asp Thr Glu Glu Thr Glu Glu Glu Ala Glu
                725                 730                 735
Asp Thr Thr Asp Glu Ala Glu Ile Pro Gln Val Glu His Ser Val Ile
            740                 745                 750
Asn Ala Lys Ile Ala Asp Ala Glu Ala Leu Leu Glu Lys Val Thr Asp
            755                 760                 765
Pro Ser Ile Arg Gln Asn Ala Met Glu Thr Leu Thr Gly Leu Lys Ser
            770                 775                 780
Ser Leu Leu Leu Gly Thr Lys Asp Asn Asn Thr Ile Ser Ala Glu Val
785                 790                 795                 800
Asp Ser Leu Leu Ala Leu Leu Lys Glu Ser Lys
                805                 810

<210> SEQ ID NO 99
<211> LENGTH: 811
<212> TYPE: PRT
<213> ORGANISM: S. pneumoniae

<400> SEQUENCE: 99

Cys Ser Tyr Glu Leu Gly Arg His Gln Ala Gly Gln Val Lys Lys Glu
1               5                   10                  15
Ser Asn Arg Val Ser Tyr Ile Asp Gly Asp Gln Ala Gly Gln Lys Ala
                20                  25                  30
Glu Asn Leu Thr Pro Asp Glu Val Ser Lys Arg Glu Gly Ile Asn Ala
            35                  40                  45
```

```
Glu Gln Ile Val Ile Lys Ile Thr Asp Gln Gly Tyr Val Thr Ser His
    50                  55                  60

Gly Asp His Tyr His Tyr Asn Gly Lys Val Pro Tyr Asp Ala Ile
65                  70                  75                  80

Ile Ser Glu Glu Leu Leu Met Lys Asp Pro Asn Tyr Gln Leu Lys Asp
                85                  90                  95

Ser Asp Ile Val Asn Glu Ile Lys Gly Gly Tyr Val Ile Lys Val Asp
            100                 105                 110

Gly Lys Tyr Tyr Val Tyr Leu Lys Asp Ala Ala His Ala Asp Asn Ile
            115                 120                 125

Arg Thr Lys Glu Glu Ile Lys Arg Gln Lys Gln Glu Arg Ser His Asn
    130                 135                 140

His Asn Ser Arg Ala Asp Asn Ala Val Ala Ala Arg Ala Gln Gly
145                 150                 155                 160

Arg Tyr Thr Thr Asp Asp Gly Tyr Ile Phe Asn Ala Ser Asp Ile Ile
                165                 170                 175

Glu Asp Thr Gly Asp Ala Tyr Ile Val Pro His Gly Asp His Tyr His
            180                 185                 190

Tyr Ile Pro Lys Ser Asp Leu Ser Ala Ser Glu Leu Ala Ala Ala Gln
            195                 200                 205

Ala Tyr Trp Asn Gly Lys Gln Gly Ser Arg Pro Ser Ser Ser Ser Ser
    210                 215                 220

His Asn Ala Asn Pro Ala Gln Pro Arg Leu Ser Glu Asn His Asn Leu
225                 230                 235                 240

Thr Val Thr Pro Thr Tyr His Gln Asn Gln Gly Glu Asn Ile Ser Ser
                245                 250                 255

Leu Leu Arg Glu Leu Tyr Ala Lys Pro Leu Ser Glu Arg His Val Glu
            260                 265                 270

Ser Asp Gly Leu Ile Phe Asp Pro Ala Gln Ile Thr Ser Arg Thr Ala
    275                 280                 285

Asn Gly Val Ala Val Pro His Gly Asp His Tyr His Phe Ile Pro Tyr
290                 295                 300

Ser Gln Leu Ser Pro Leu Glu Glu Lys Leu Ala Arg Ile Ile Pro Leu
305                 310                 315                 320

Arg Tyr Arg Ser Asn His Trp Val Pro Asp Ser Arg Pro Glu Gln Pro
                325                 330                 335

Ser Pro Gln Ser Thr Pro Glu Pro Ser Pro Ser Gln Pro Ala Pro
            340                 345                 350

Asn Pro Gln Pro Ala Pro Ser Asn Pro Ile Asp Glu Lys Leu Val Lys
    355                 360                 365

Glu Ala Val Arg Lys Val Gly Asp Gly Tyr Val Phe Glu Glu Asn Gly
    370                 375                 380

Val Pro Arg Tyr Ile Pro Ala Lys Asp Leu Ser Ala Glu Thr Ala Ala
385                 390                 395                 400

Gly Ile Asp Ser Lys Leu Ala Lys Gln Glu Ser Leu Ser His Lys Leu
                405                 410                 415

Gly Ala Lys Lys Thr Asp Leu Pro Ser Ser Asp Arg Glu Phe Tyr Asn
            420                 425                 430

Lys Ala Tyr Asp Leu Leu Ala Arg Ile His Gln Asp Leu Leu Asp Asn
            435                 440                 445

Lys Gly Arg Gln Val Asp Phe Glu Ala Leu Asp Asn Leu Leu Glu Arg
    450                 455                 460

Leu Lys Asp Val Ser Ser Asp Lys Val Lys Leu Val Asp Asp Ile Leu
```

```
                465                 470                 475                 480

Ala Phe Leu Ala Pro Ile Arg His Pro Glu Arg Leu Gly Lys Pro Asn
                    485                 490                 495

Ala Gln Ile Thr Tyr Thr Asp Asp Glu Ile Gln Val Ala Lys Leu Ala
                500                 505                 510

Gly Lys Tyr Thr Thr Glu Asp Gly Tyr Ile Phe Asp Pro Arg Asp Ile
                515                 520                 525

Thr Ser Asp Glu Gly Asp Ala Tyr Val Thr Pro His Met Thr His Ser
            530                 535                 540

His Trp Ile Lys Lys Asp Ser Leu Ser Glu Ala Glu Arg Ala Ala Ala
545                 550                 555                 560

Gln Ala Tyr Ala Lys Glu Lys Gly Leu Thr Pro Pro Ser Thr Asp His
                565                 570                 575

Gln Asp Ser Gly Asn Thr Glu Ala Lys Gly Ala Glu Ala Ile Tyr Asn
                580                 585                 590

Arg Val Lys Ala Ala Lys Lys Val Pro Leu Asp Arg Met Pro Tyr Asn
                595                 600                 605

Leu Gln Tyr Thr Val Glu Val Lys Asn Gly Ser Leu Ile Ile Pro His
            610                 615                 620

Tyr Asp His Tyr His Asn Ile Lys Phe Glu Trp Phe Asp Glu Gly Leu
625                 630                 635                 640

Tyr Glu Ala Pro Lys Gly Tyr Ser Leu Glu Asp Leu Leu Ala Thr Val
                645                 650                 655

Lys Tyr Tyr Val Glu His Pro Asn Glu Arg Pro His Ser Asp Asn Gly
                660                 665                 670

Phe Gly Asn Ala Ser Asp His Val Gln Arg Asn Lys Asn Gly Gln Ala
                675                 680                 685

Asp Thr Asn Gln Thr Glu Lys Pro Asn Glu Lys Pro Gln Thr Glu
            690                 695                 700

Lys Pro Glu Glu Glu Thr Pro Arg Glu Glu Lys Pro Gln Ser Glu Lys
705                 710                 715                 720

Pro Glu Ser Pro Lys Pro Thr Glu Glu Pro Glu Glu Ser Pro Glu
                725                 730                 735

Glu Ser Pro Glu Glu Ser Glu Glu Pro Gln Val Glu Thr Glu Lys Val
            740                 745                 750

Lys Glu Lys Leu Arg Glu Ala Glu Asp Leu Leu Gly Lys Ile Gln Asn
            755                 760                 765

Pro Ile Ile Lys Ser Asn Ala Lys Glu Thr Leu Thr Gly Leu Lys Asn
            770                 775                 780

Asn Leu Leu Phe Gly Thr Gln Asp Asn Asn Thr Ile Met Ala Glu Ala
785                 790                 795                 800

Glu Lys Leu Leu Ala Leu Leu Lys Glu Ser Lys
                805                 810

<210> SEQ ID NO 100
<211> LENGTH: 805
<212> TYPE: PRT
<213> ORGANISM: S. pneumoniae

<400> SEQUENCE: 100

Cys Ser Tyr Glu Leu Gly Arg His Gln Ala Gly Gln Asp Lys Lys Glu
1               5                   10                  15

Ser Asn Arg Val Ala Tyr Ile Asp Gly Asp Gln Ala Gly Gln Lys Ala
            20                  25                  30
```

-continued

```
Glu Asn Leu Thr Pro Asp Glu Val Ser Lys Arg Glu Gly Ile Asn Ala
        35                  40                  45
Glu Gln Ile Val Ile Lys Ile Thr Asp Gln Gly Tyr Val Thr Ser His
    50                  55                  60
Gly Asp His Tyr His Tyr Tyr Asn Gly Lys Val Pro Tyr Asp Ala Ile
65                  70                  75                  80
Ile Ser Glu Glu Leu Leu Met Lys Asp Pro Asn Tyr Gln Leu Lys Asp
                85                  90                  95
Ser Asp Ile Val Asn Glu Ile Lys Gly Gly Tyr Val Ile Lys Val Asn
            100                 105                 110
Gly Lys Tyr Tyr Val Tyr Leu Lys Asp Ala Ala His Ala Asp Asn Ile
        115                 120                 125
Arg Thr Lys Glu Glu Ile Lys Arg Gln Lys Gln Glu Arg Ser His Asn
    130                 135                 140
His Asn Ser Arg Ala Asp Asn Ala Val Ala Ala Arg Ala Gln Gly
145                 150                 155                 160
Arg Tyr Thr Thr Asp Asp Gly Tyr Ile Phe Asn Ala Ser Asp Ile Ile
                165                 170                 175
Glu Asp Thr Gly Asp Ala Tyr Ile Val Pro His Gly Asp His Tyr His
            180                 185                 190
Tyr Ile Pro Lys Asn Glu Leu Ser Ala Ser Glu Leu Ala Ala Ala Glu
        195                 200                 205
Ala Tyr Trp Asn Gly Lys Gln Gly Ser Arg Pro Ser Ser Ser Ser Ser
    210                 215                 220
Tyr Asn Ala Asn Pro Ala Gln Pro Arg Leu Ser Glu Asn His Asn Leu
225                 230                 235                 240
Thr Val Thr Pro Thr Tyr His Gln Asn Gln Gly Glu Asn Ile Ser Ser
                245                 250                 255
Leu Leu Arg Glu Leu Tyr Ala Lys Pro Leu Ser Glu Arg His Val Glu
            260                 265                 270
Ser Asp Gly Leu Ile Phe Asp Pro Ala Gln Ile Thr Ser Arg Thr Ala
        275                 280                 285
Arg Gly Val Ala Val Pro His Gly Asn His Tyr His Phe Ile Pro Tyr
    290                 295                 300
Glu Gln Met Ser Glu Leu Glu Lys Arg Ile Ala Arg Ile Ile Pro Leu
305                 310                 315                 320
Arg Tyr Arg Ser Asn His Trp Val Pro Asp Ser Arg Pro Glu Glu Pro
                325                 330                 335
Ser Pro Gln Pro Thr Pro Glu Pro Ser Pro Ser Pro Gln Pro Ala Pro
            340                 345                 350
Ser Asn Pro Ile Asp Glu Lys Leu Val Lys Glu Ala Val Arg Lys Val
        355                 360                 365
Gly Asp Gly Tyr Val Phe Glu Glu Asn Gly Val Ser Arg Tyr Ile Pro
    370                 375                 380
Ala Lys Asp Leu Ser Ala Glu Thr Ala Ala Gly Ile Asp Ser Lys Leu
385                 390                 395                 400
Ala Lys Gln Glu Ser Leu Ser His Lys Leu Gly Ala Lys Lys Thr Asp
                405                 410                 415
Leu Pro Ser Ser Asp Arg Glu Phe Tyr Asn Lys Ala Tyr Asp Leu Leu
            420                 425                 430
Ala Arg Ile His Gln Asp Leu Leu Asp Asn Lys Gly Arg Gln Val Asp
        435                 440                 445
Phe Glu Ala Leu Asp Asn Leu Leu Glu Arg Leu Lys Asp Val Ser Ser
```

```
                450                 455                 460
Asp Lys Val Lys Leu Val Asp Asp Ile Leu Ala Phe Leu Ala Pro Ile
465                 470                 475                 480

Arg His Pro Glu Arg Leu Gly Lys Pro Asn Ala Gln Ile Thr Tyr Thr
                485                 490                 495

Asp Asp Glu Ile Gln Val Ala Lys Leu Ala Gly Lys Tyr Thr Thr Glu
            500                 505                 510

Asp Gly Tyr Ile Phe Asp Pro Arg Asp Ile Thr Ser Asp Glu Gly Asp
            515                 520                 525

Ala Tyr Val Thr Pro His Met Thr His Ser His Trp Ile Lys Lys Asp
530                 535                 540

Ser Leu Ser Glu Ala Glu Arg Ala Ala Gln Ala Tyr Ala Lys Glu
545                 550                 555                 560

Lys Gly Leu Thr Pro Pro Ser Thr Asp His Gln Asp Ser Gly Asn Thr
                565                 570                 575

Glu Ala Lys Gly Ala Glu Ala Ile Tyr Asn Arg Val Lys Ala Ala Lys
            580                 585                 590

Lys Val Pro Leu Asp Arg Met Pro Tyr Asn Leu Gln Tyr Thr Val Glu
            595                 600                 605

Val Lys Asn Gly Ser Leu Ile Ile Pro His Tyr Asp His Tyr His Asn
610                 615                 620

Ile Lys Phe Glu Trp Phe Asp Glu Gly Leu Tyr Glu Ala Pro Lys Gly
625                 630                 635                 640

Tyr Ser Leu Glu Asp Leu Leu Ala Thr Val Lys Tyr Tyr Val Glu His
                645                 650                 655

Pro Asn Glu Arg Pro His Ser Asp Asn Gly Phe Gly Asn Ala Ser Asp
                660                 665                 670

His Val Gln Arg Asn Lys Asn Gly Gln Ala Asp Thr Asn Gln Thr Glu
            675                 680                 685

Lys Pro Asn Glu Glu Lys Pro Gln Thr Glu Lys Pro Glu Glu Thr
            690                 695                 700

Pro Arg Glu Glu Lys Pro Gln Ser Glu Lys Pro Glu Ser Pro Lys Pro
705                 710                 715                 720

Thr Glu Glu Pro Glu Glu Ser Pro Glu Glu Ser Pro Glu Glu Ser
                725                 730                 735

Glu Glu Pro Gln Val Glu Thr Glu Lys Val Lys Glu Lys Leu Arg Glu
            740                 745                 750

Ala Glu Asp Leu Leu Gly Lys Ile Gln Asn Pro Ile Ile Lys Ser Asn
                755                 760                 765

Ala Lys Glu Thr Leu Thr Gly Leu Lys Asn Asn Leu Leu Phe Gly Thr
770                 775                 780

Gln Asp Asn Asn Thr Ile Met Ala Glu Ala Glu Lys Leu Leu Ala Leu
785                 790                 795                 800

Leu Lys Glu Ser Lys
            805

<210> SEQ ID NO 101
<211> LENGTH: 807
<212> TYPE: PRT
<213> ORGANISM: S. pneumoniae

<400> SEQUENCE: 101

Cys Ser Tyr Glu Leu Gly Arg His Gln Ala Gly Gln Val Lys Lys Glu
1               5                   10                  15
```

```
Ser Asn Arg Val Ser Tyr Ile Asp Gly Asp Gln Ala Gly Gln Lys Ala
             20                  25                  30

Glu Asn Leu Thr Pro Asp Glu Val Ser Lys Arg Gly Ile Asn Ala
         35                  40                  45

Glu Gln Ile Val Ile Lys Ile Thr Asp Gln Gly Tyr Val Thr Ser His
 50                      55                  60

Gly Asp His Tyr His Tyr Tyr Asn Gly Lys Val Pro Tyr Asp Ala Ile
65                   70                  75                  80

Ile Ser Glu Glu Leu Leu Met Lys Asp Pro Asn Tyr Gln Leu Lys Asp
                 85                  90                  95

Ser Asp Ile Val Asn Glu Ile Lys Gly Gly Tyr Ile Lys Val Asp
            100                 105                 110

Gly Lys Tyr Tyr Val Tyr Leu Lys Asp Ala Ala His Ala Asp Asn Ile
            115                 120                 125

Arg Thr Lys Glu Glu Ile Lys Arg Gln Lys Gln Glu Arg Ser His Asn
    130                 135                 140

His Asn Ser Arg Ala Asp Asn Ala Val Ala Ala Arg Ala Gln Gly
145                 150                 155                 160

Arg Tyr Thr Thr Asp Asp Gly Tyr Ile Phe Asn Ala Ser Asp Ile Ile
                165                 170                 175

Glu Asp Thr Gly Asp Ala Tyr Ile Val Pro His Gly Asn His Phe His
            180                 185                 190

Tyr Ile Pro Lys Ser Asp Leu Ser Ala Ser Glu Leu Ala Ala Ala Gln
                195                 200                 205

Ala Tyr Trp Asn Gly Lys Gln Gly Ser Arg Pro Ser Ser Ser Ser Ser
    210                 215                 220

His Asn Ala Asn Pro Ala Gln Pro Arg Leu Ser Glu Asn His Asn Leu
225                 230                 235                 240

Thr Val Thr Pro Thr Tyr His Gln Asn Gln Gly Glu Asn Ile Ser Ser
                245                 250                 255

Leu Leu Arg Glu Leu Tyr Ala Lys Pro Leu Ser Glu Arg His Val Glu
            260                 265                 270

Ser Asp Gly Leu Ile Phe Asp Pro Ala Gln Ile Thr Ser Arg Thr Ala
        275                 280                 285

Arg Gly Val Ala Val Pro His Gly Asn His Tyr His Phe Ile Pro Tyr
    290                 295                 300

Ser Gln Met Ser Glu Leu Glu Arg Ile Ala Arg Ile Ile Pro Leu
305                 310                 315                 320

Arg Tyr Arg Ser Asn His Trp Val Pro Asp Ser Arg Pro Glu Gln Pro
                325                 330                 335

Ser Pro Gln Ser Thr Pro Glu Pro Ser Pro Gln Ser Ala Pro
            340                 345                 350

Asn Pro Gln Pro Ala Pro Ser Asn Pro Ile Asp Glu Lys Leu Val Lys
            355                 360                 365

Glu Val Val Arg Lys Val Gly Asp Gly Tyr Val Phe Glu Lys Asn Gly
            370                 375                 380

Val Ser Arg Tyr Ile Pro Ala Lys Asn Leu Ser Ala Glu Thr Ala Ala
385                 390                 395                 400

Gly Ile Asp Ser Lys Leu Ala Lys Gln Glu Ser Leu Ser His Lys Leu
                405                 410                 415

Gly Ala Lys Lys Thr Asp Leu Pro Ser Ser Asp Arg Glu Phe Tyr Asn
            420                 425                 430

Lys Ala Tyr Asp Leu Leu Ala Arg Ile His Gln Asp Leu Leu Asp Asn
```

```
                435                 440                 445
Lys Gly Arg Gln Val Asp Phe Glu Ala Leu Asp Asn Leu Leu Glu Arg
450                 455                 460

Leu Glu Asp Val Pro Ser Asp Lys Val Lys Leu Val Asp Asp Ile Leu
465                 470                 475                 480

Ala Phe Leu Ala Pro Ile Arg His Pro Glu Arg Leu Gly Lys Pro Asn
                485                 490                 495

Ala Gln Ile Thr Tyr Thr Asp Asp Glu Ile Gln Val Ala Lys Leu Ala
                500                 505                 510

Gly Lys Tyr Thr Thr Glu Asp Gly Tyr Ile Phe Asp Pro Arg Asp Ile
                515                 520                 525

Thr Ser Asp Glu Gly Asp Ala Tyr Val Thr Pro His Met Thr His Ser
530                 535                 540

His Trp Ile Lys Lys Asp Ser Leu Ser Glu Ala Glu Arg Ala Ala Ala
545                 550                 555                 560

Gln Ala Tyr Ala Lys Glu Lys Gly Leu Thr Pro Pro Ser Thr Asp His
                565                 570                 575

Gln Asp Ser Gly Asn Thr Glu Ala Lys Gly Ala Glu Ala Ile Tyr Asn
                580                 585                 590

Arg Val Lys Ala Ala Lys Val Pro Leu Asp Arg Met Pro Tyr Asn
                595                 600                 605

Leu Gln Tyr Thr Val Glu Val Lys Asn Gly Ser Leu Ile Ile Pro His
                610                 615                 620

Tyr Asp His Tyr His Asn Ile Lys Phe Glu Trp Phe Asp Glu Gly Leu
625                 630                 635                 640

Tyr Glu Ala Pro Lys Gly Tyr Thr Leu Glu Asp Leu Leu Ala Thr Val
                645                 650                 655

Lys Tyr Tyr Val Glu His Pro Asn Glu Arg Pro His Ser Asp Asn Gly
                660                 665                 670

Phe Gly Asn Ala Ser Asp His Val Gln Arg Asn Lys Asn Gly Gln Ala
                675                 680                 685

Asp Thr Asn Gln Thr Glu Lys Pro Ser Glu Lys Pro Gln Thr Glu
690                 695                 700

Lys Pro Glu Glu Glu Thr Pro Arg Glu Glu Lys Pro Gln Ser Glu Lys
705                 710                 715                 720

Pro Glu Ser Pro Lys Pro Thr Glu Glu Pro Glu Glu Ser Pro Glu
                725                 730                 735

Glu Ser Glu Glu Pro Gln Val Glu Thr Glu Lys Val Glu Glu Lys Leu
                740                 745                 750

Arg Glu Ala Glu Asp Leu Leu Gly Lys Ile Gln Asp Pro Ile Ile Lys
                755                 760                 765

Ser Asn Ala Lys Glu Thr Leu Thr Gly Leu Lys Asn Asn Leu Leu Phe
770                 775                 780

Gly Thr Gln Asp Asn Asn Thr Ile Met Ala Glu Ala Lys Leu Leu
785                 790                 795                 800

Ala Leu Leu Lys Glu Ser Lys
                805
```

<210> SEQ ID NO 102
<211> LENGTH: 821
<212> TYPE: PRT
<213> ORGANISM: S. pneumoniae

<400> SEQUENCE: 102

-continued

```
Cys Ala Tyr Glu Leu Gly Leu His Gln Ala Gln Thr Val Lys Glu Asn
 1               5                  10                  15

Asn Arg Val Ser Tyr Ile Asp Gly Lys Gln Ala Thr Gln Lys Thr Glu
             20                  25                  30

Asn Leu Thr Pro Asp Glu Val Ser Lys Arg Gly Ile Asn Ala Glu
             35                  40                  45

Gln Ile Val Ile Lys Ile Thr Asp Gln Gly Tyr Val Thr Ser His Gly
 50                  55                  60

Asp His Tyr His Tyr Tyr Asn Gly Lys Val Pro Tyr Asp Ala Ile Ile
 65              70                  75                  80

Ser Glu Glu Leu Leu Met Lys Asp Pro Asn Tyr Gln Leu Lys Asp Ser
                 85                  90                  95

Asp Ile Val Asn Glu Ile Lys Gly Gly Tyr Val Ile Lys Val Asn Gly
             100                 105                 110

Lys Tyr Tyr Val Tyr Leu Lys Asp Ala Ala His Ala Asp Asn Val Arg
             115                 120                 125

Thr Lys Glu Glu Ile Asn Arg Gln Lys Gln Glu His Ser Gln His Arg
130                 135                 140

Glu Gly Gly Thr Ser Ala Asn Asp Gly Ala Val Ala Phe Ala Arg Ser
145                 150                 155                 160

Gln Gly Arg Tyr Thr Thr Asp Asp Gly Tyr Ile Phe Asn Ala Ser Asp
             165                 170                 175

Ile Ile Glu Asp Thr Gly Asp Ala Tyr Ile Val Pro His Gly Asp His
             180                 185                 190

Tyr His Tyr Ile Pro Lys Asn Glu Leu Ser Ala Ser Glu Leu Ala Ala
             195                 200                 205

Ala Glu Ala Phe Leu Ser Gly Arg Glu Asn Leu Ser Asn Leu Arg Thr
210                 215                 220

Tyr Arg Arg Gln Asn Ser Asp Asn Thr Pro Arg Thr Asn Trp Val Pro
225                 230                 235                 240

Ser Val Ser Asn Pro Gly Thr Thr Asn Thr Asn Thr Ser Asn Asn Ser
             245                 250                 255

Asn Thr Asn Ser Gln Ala Ser Gln Ser Asn Asp Ile Asp Ser Leu Leu
             260                 265                 270

Lys Gln Leu Tyr Lys Leu Pro Leu Ser Gln Arg His Val Glu Ser Asp
             275                 280                 285

Gly Leu Ile Phe Asp Pro Ala Gln Ile Thr Ser Arg Thr Ala Arg Gly
290                 295                 300

Val Ala Val Pro His Gly Asn His Tyr His Phe Ile Pro Tyr Glu Gln
305                 310                 315                 320

Met Ser Glu Leu Glu Lys Arg Ile Ala Arg Ile Ile Pro Leu Arg Tyr
             325                 330                 335

Arg Ser Asn His Trp Val Pro Asp Ser Arg Pro Glu Glu Pro Ser Pro
             340                 345                 350

Gln Pro Thr Pro Glu Pro Ser Pro Ser Pro Gln Pro Ala Pro Asn Pro
             355                 360                 365

Gln Pro Ala Pro Ser Asn Pro Ile Asp Glu Lys Leu Val Lys Glu Ala
             370                 375                 380

Val Arg Lys Val Gly Asp Gly Tyr Val Phe Glu Glu Asn Gly Val Ser
385                 390                 395                 400

Arg Tyr Ile Pro Ala Lys Asn Leu Ser Ala Glu Thr Ala Ala Gly Ile
             405                 410                 415

Asp Ser Lys Leu Ala Lys Gln Glu Ser Leu Ser His Lys Leu Gly Ala
```

-continued

```
                420              425              430
Lys Lys Thr Asp Leu Pro Ser Ser Asp Arg Glu Phe Tyr Asn Lys Ala
            435              440              445
Tyr Asp Leu Leu Ala Arg Ile His Gln Asp Leu Leu Asp Asn Lys Gly
            450              455              460
Arg Gln Val Asp Phe Glu Ala Leu Asp Asn Leu Leu Glu Arg Leu Lys
465              470              475              480
Asp Val Ser Ser Asp Lys Val Lys Leu Val Asp Asp Ile Leu Ala Phe
                485              490              495
Leu Ala Pro Ile Arg His Pro Glu Arg Leu Gly Lys Pro Asn Ala Gln
            500              505              510
Ile Thr Tyr Thr Asp Asp Glu Ile Gln Val Ala Lys Leu Ala Gly Lys
            515              520              525
Tyr Thr Thr Glu Asp Gly Tyr Ile Phe Asp Pro Arg Asp Ile Thr Ser
            530              535              540
Asp Glu Gly Asp Ala Tyr Val Thr Pro His Met Thr His Ser His Trp
545              550              555              560
Ile Lys Lys Asp Ser Leu Ser Glu Ala Glu Arg Ala Ala Gln Ala
            565              570              575
Tyr Ala Lys Glu Lys Gly Leu Thr Pro Pro Ser Thr Asp His Gln Asp
            580              585              590
Ser Gly Asn Thr Glu Ala Lys Gly Ala Glu Ala Ile Tyr Asn Arg Val
            595              600              605
Lys Ala Ala Lys Lys Val Pro Leu Asp Arg Met Pro Tyr Asn Leu Gln
610              615              620
Tyr Thr Val Glu Val Lys Asn Gly Ser Leu Ile Ile Pro His Tyr Asp
625              630              635              640
His Tyr His Asn Ile Lys Phe Glu Trp Phe Asp Gly Leu Tyr Glu
                645              650              655
Ala Pro Lys Gly Tyr Thr Leu Glu Asp Leu Leu Ala Thr Val Lys Tyr
            660              665              670
Tyr Val Glu His Pro Asn Glu Arg Pro His Ser Asp Asn Gly Phe Gly
            675              680              685
Asn Ala Ser Asp His Val Gln Arg Asn Lys Asn Gly Gln Ala Asp Thr
            690              695              700
Asn Gln Thr Glu Lys Pro Ser Glu Glu Lys Pro Gln Thr Glu Lys Pro
705              710              715              720
Glu Glu Glu Thr Pro Arg Glu Glu Lys Pro Gln Ser Glu Lys Pro Glu
                725              730              735
Ser Pro Lys Pro Thr Glu Glu Pro Glu Glu Ser Pro Glu Glu Ser
            740              745              750
Glu Glu Pro Gln Val Glu Thr Glu Lys Val Glu Glu Lys Leu Arg Glu
            755              760              765
Ala Glu Asp Leu Leu Gly Lys Ile Gln Asp Pro Ile Ile Lys Ser Asn
            770              775              780
Ala Lys Glu Thr Leu Thr Gly Leu Lys Asn Asn Leu Leu Phe Gly Thr
785              790              795              800
Gln Asp Asn Asn Thr Ile Met Ala Glu Ala Glu Lys Leu Leu Ala Leu
                805              810              815
Leu Lys Glu Ser Lys
            820
```